US012594323B2

(12) United States Patent
Wong et al.

(10) Patent No.: US 12,594,323 B2
(45) Date of Patent: Apr. 7, 2026

(54) METHODS OF REDUCING NEUROINFLAMMATION

(71) Applicant: ImmunityBio, Inc., San Diego, CA (US)

(72) Inventors: Hing C. Wong, Miramar, FL (US); Varghese George, Miramar, FL (US); Niraj Shrestha, Miramar, FL (US); Pallavi Chaturvedi, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 473 days.

(21) Appl. No.: 18/300,354

(22) Filed: Apr. 13, 2023

(65) Prior Publication Data

US 2023/0372444 A1 Nov. 23, 2023

Related U.S. Application Data

(60) Provisional application No. 63/330,639, filed on Apr. 13, 2022, provisional application No. 63/330,660, filed on Apr. 13, 2022.

(51) Int. Cl.
| | |
|---|---|
| *A61K 38/17* | (2006.01) |
| *A61K 38/20* | (2006.01) |
| *A61P 25/16* | (2006.01) |

(52) U.S. Cl.
CPC .......... *A61K 38/1793* (2013.01); *A61K 38/20* (2013.01); *A61P 25/16* (2018.01)

(58) Field of Classification Search
CPC .. A61K 38/1793; A61K 38/20; A61K 38/179; A61K 38/2086; A61K 38/36; A61K 38/1841; A61P 25/28; A61P 25/00
See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,475,792 | B2 | 7/2013 | Dall'Acqua et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,741,604 | B2 | 6/2014 | Campbell et al. |

| | | | |
|---|---|---|---|
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 11,401,324 | B2 | 8/2022 | Wong |
| 11,518,792 | B2 | 12/2022 | Wong |
| 11,672,826 | B2 | 6/2023 | Wong |
| 11,730,762 | B2 | 8/2023 | Wong |
| 11,738,052 | B2 | 8/2023 | Wong |
| 12,018,071 | B2 | 6/2024 | Wong |
| 12,024,545 | B2 | 7/2024 | Wong et al. |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Wells, 1990, Biochemistry 29:8509-8517.*
U.S. Appl. No. 16/556,040, filed Aug. 29, 2019, Wong.
U.S. Appl. No. 16/557,822, filed Aug. 30, 2019, Wong.
U.S. Appl. No. 16/557,875, filed Aug. 30, 2019, Wong.
[No Author Listed], "CN Br-activated Sepharose 4 Fast Flow," 1999, Affinity Chromatography, 4 pages.
Abbott et al., "Genomic organization, exact localization, and tissue expression of the human CD26 (dipeptidyl peptidase IV) gene," Immunogenetics, Sep. 1994, 40(5):331-338.
Abdul-Aziz et al., "Acute myeloid leukemia induces protumoral p16INK4a-driven senescence in the bone marrow microenvironment," Blood, Jan. 31, 2019, 133(5):446-456.

(Continued)

*Primary Examiner* — Gyan Chandra
(74) *Attorney, Agent, or Firm* — Sheridan Ross P.C.

(57) ABSTRACT

Provided herein are multi-chain chimeric polypeptides and use thereof in reducing neuroinflammation in a subject.

26 Claims, 75 Drawing Sheets
(18 of 75 Drawing Sheet(s) Filed in Color)
Specification includes a Sequence Listing.

(56) References Cited

U.S. PATENT DOCUMENTS

| | | | |
|---|---|---|---|
| 2014/0242077 A1 | 8/2014 | Choi | |
| 2015/0218274 A1 | 8/2015 | Sabatos-Peyton et al. | |
| 2015/0259429 A1 | 9/2015 | Benaroch et al. | |
| 2016/0175397 A1 | 6/2016 | Umana et al. | |
| 2016/0340413 A1 | 11/2016 | Duerner et al. | |
| 2016/0367664 A1 | 12/2016 | Wang et al. | |
| 2017/0051063 A1 | 2/2017 | Baum et al. | |
| 2017/0198042 A1 | 7/2017 | Williams et al. | |
| 2017/0283499 A1 | 10/2017 | Delhem et al. | |
| 2018/0200366 A1 | 7/2018 | Wong | |
| 2019/0078082 A1 | 3/2019 | Amorese et al. | |
| 2019/0092846 A1 | 3/2019 | Ibebunjo et al. | |
| 2019/0177406 A1 | 6/2019 | Ledbetter et al. | |
| 2019/0315850 A1 | 10/2019 | Bedinger et al. | |
| 2020/0071374 A1 | 3/2020 | Wong | |
| 2020/0123607 A1 | 4/2020 | Serrano Marugan et al. | |
| 2020/0190174 A1 | 6/2020 | Wong | |
| 2020/0392221 A1 | 12/2020 | Van Snick et al. | |
| 2020/0399358 A1 | 12/2020 | Shapiro et al. | |
| 2021/0060064 A1 | 3/2021 | Wong | |
| 2021/0061897 A1 | 3/2021 | Ledbetter et al. | |
| 2021/0070825 A1 | 3/2021 | Wong | |
| 2021/0070826 A1 | 3/2021 | Wong | |
| 2021/0100840 A1 | 4/2021 | Wong et al. | |
| 2021/0137981 A1 | 5/2021 | Wong | |
| 2021/0268022 A1 | 9/2021 | Wong et al. | |
| 2021/0277054 A1 | 9/2021 | Wong et al. | |
| 2021/0338724 A1 | 11/2021 | Wong | |
| 2021/0355204 A1 | 11/2021 | Bedinger et al. | |
| 2021/0403545 A1 | 12/2021 | Van Snick et al. | |
| 2022/0073578 A1 | 3/2022 | Wong et al. | |
| 2023/0023389 A1 | 1/2023 | Wong | |
| 2023/0039157 A1 | 2/2023 | Wong | |
| 2023/0128292 A1 | 4/2023 | Wong | |
| 2023/0174666 A1 | 6/2023 | Wong et al. | |
| 2023/0272027 A1 | 8/2023 | Wong | |
| 2023/0372399 A1 | 11/2023 | Wong | |
| 2023/0381238 A1 | 11/2023 | Wong | |
| 2023/0398151 A1 | 12/2023 | Wong | |
| 2024/0124543 A1 | 4/2024 | Wong | |
| 2024/0124544 A1 | 4/2024 | Wong | |
| 2024/0132561 A1 | 4/2024 | Wong | |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Aertgeerts et al., "Crystal structure of human dipeptidyl peptidase IV in complex with a decapeptide reveals details on substrate specificity and tetrahedral intermediate formation, " Protein Science, Feb. 2004, 13(2):412-421.

Ait-Oufella et al., "Natural regulatory T cells control the development of atherosclerosis in mice," Nature Medicine, Feb. 5, 2006, 12:178-180.

Akbari, et al., "Design, expression and evaluation of a novel humanized single chain antibody against epidermal growth factor receptor (EGFR)," Protein Expr. Purif., 2016, 127:8-15.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.

Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.

Baker et al., "Effects of conjugated linoleic acid (CLA) on tissue composition parameters in a murine cachexia model," The FASEB Journal, Mar. 2006, 20(4), 2 pages (Abstract Only).

Baker, et al., "Clearance of p16Ink4a-positive senescent cells delays ageing-associated disorders," Nature, 2011, 479(7372): 232-236.

Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.

Bennett et al., "Erratum: Killing the old: cell senescence in atherosclerosis," Nature Reviews Cardiology, Jan. 12, 2017, 14(3):132.

Bennett et al., "Killing the old: cell senescence in atherosclerosis," Nature Reviews Cardiology, Dec. 12, 2016, 14(1):8-9, 2 pages.

Bentebibel et al., "A First-in-Human Study and Biomarker Analysis of NKTR-214, a Novel IL2Raf Biased Cytokine, in Patients with Advanced or Metastatic Solid Tumors, " Cancer Discovery, Jun. 2019, 9(6):711-721.

Berry et al., "Cancer Anorexia and Cachexia: Screening in an Ambulatory Infusion Service and Nutrition Consultation," Clin J Oncol Nurs., 2018, 22(1):63-68.

(56) References Cited

OTHER PUBLICATIONS

Bhat et al., "Astrocyte Senescence as a Component of Alzheimer's Disease," PLoS One, Sep. 12, 2012, 7(9):e45069, 10 pages.

Biran et al., "Senescent cells communicate via intercellular protein transfer," Genes & Development, Apr. 8, 2015, 29(8):791-802, 13 pages.

Bird et al., "TGFβ inhibition restores a regenerative response in acute liver injury by suppressing paracrine senescence," Science translational medicine, Aug. 15, 2018, 10(454):eaan 1230, 15 pages.

Borea et al., "Pharmacology of Adenosine Receptors: The State of the Art," Physiological Reviews, May 30, 2018, 98(3):1591-1625.

Borgerding et al., "B-lymphoma cells escape rituximab-triggered elimination by NK cells through increased HLA class I expression," Experimental Hematology, Mar. 1, 2010, 38(3):213-21.

Bork, "Powers and Pitfalls in Sequence Analysis: The 70% Hurdle," Genome Research, 2000, 10:398-400.

Bourgeois et al., "Regulation of cellular senescence via the FOXO4-p53 axis, " FEBS Lett., 2018, 592(12): 2083-2097.

Bowie et al., "Deciphering the Message in Protein Sequences: Tolerance to Amino Acid Substitutions," Science, 1990, 247:1306-1310.

Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.

Boyman et al., "Selective Stimulation of T Cell Subsets with Antibody-Cytokine Immune Complexes," Science, Mar. 31, 2006, 311(5769):1924-1927.

Brämer et al., "Membrane adsorber for the fast purification of a monoclonal antibody using protein a chromatography," Membranes, Nov. 27, 2019, 9(12):159, 15 pages.

Brennan et al., "Structural determination of lipid antigens captured at the CD1d-T-cell receptor interface," PNAS, 2017, 114(31):8348-8353.

Brighton et al., "Clearance of senescent decidual cells by uterine natural killer cells in cycling human endometrium," Elife, Dec. 11, 2017, 6:e31274, 23 pages.

Brooks et al., "Combined inhibition of PD1 and CD96 checkpoints improves survival in a resectable murine model of pancreatic cancer," European Journal of Cancer, Jul. 1, 2016, 61:S189, 1 page.

Broxmeyer et al., "Modulation of Hematopoietic Chemokine Effects In Vitro and In Vivo by DPP-4/CD26," Stem Cells and Development, Mar. 4, 2016, 25(8):575-585.

Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.

Brunstein et al., "Umbilical cord blood-derived T regulatory cells to prevent GVHD:kinetics, toxicity profile, and clinical effect," Blood, Feb. 25, 2016, 127(8):1044-1051.

Buhling et al., "Functional role of CD26 on human B lymphocytes," Immunology Letters, Feb. 1995, 45(1-2):47-51.

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.

Bussian et al., "Clearance of senescent glial cells prevents tau-dependent pathology and cognitive decline," Nature, Sep. 19, 2018, 562(7728):578-582, 21 pages.

Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.

Cai et al., "Quercetin inhibits transforming growth factor β1-induced epithelial- mesenchymal transition in human retinal pigment epithelial cells via the Smad pathway," Drug design, development and therapy, Dec. 6, 2018, 12:4149-4161.

Cao et al., "Expression and characterization of recombinant humanized anti-HER2 single-chain antibody in Pichia pastoris for targeted cancer therapy," Biotechnology Letters, Jul. 1, 2015, 37(7):1347-54.

Cao, "Self-regulation and cross-regulation of pattern-recognition receptor signaling in health and disease," Nature Reviews Immunology, Dec. 29, 2015, 16(1):35-50.

Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.

Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.

Cavinato et al., "Molecular mechanisms of UVB-induced senescence of dermal fibroblasts and its relevance for photoaging of the human skin," Experimental Gerontology. Aug. 2017, 94:78-82.

Chabannon et al., "Manufacturing natural killer cells as medicinal products," Frontiers in Immunology, Nov. 15, 2016, 7(504):1-9.

Chalan et al., "Expression of Lectin-Like Transcript 1, the Ligand for CD161, in Rheumatoid Arthritis," PLoS ONE, 2015, 10(7):e0132436.

Chambers et al., "Can blocking inflammation enhance immunity during aging?" Journal of Allergy and Clinical Immunology, May 2020, 145(5):1323-1331.

Chan et al., "Molecular mechanisms of natural killer cell activation in response to cellular stress," Cell Death & Differentiation, Jan. 2014, 21(1):5-14.

Chance et al., "A simple and rapid assay of oxidative phosphorylation," Nature, Jun. 1955, 175(4469):1120-1121.

Chandrudu et al., "Chemical methods for peptide and protein production," Molecules, 2013, 18(4):4373-4388.

Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.

Chang et al., "The dock and lock method: a novel platform technology for building multivalent, multifunctional structures of defined composition with retained bioactivity," Clinical cancer research, Sep. 15, 2007, 13(18):5586s-5591s.

Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.

Chen et al., "A novel idea for establishing Parkinson's disease mouse model by intranasal administration of paraquat" Neurological Research, 43(4):267-277, 2021.

Chen et al., "Circulating levels of resistin and risk of type 2 diabetes in men and women: results from two prospective cohorts," Diabetes Care, Feb. 2009, 32(2):329-334.

Chen et al., "Sterile inflammation: sensing and reacting to damage," Nature Reviews Immunology, Nov. 19, 2010, 10(12):826-837.

Chichili et al., "Linkers in the structural biology of protein—protein interactions," Protein Science, Feb. 2013, 22(2): 153-67.

Childs et al., "Senescent cells: an emerging target for diseases of ageing," Nature Reviews Drug Discovery, Jul. 21, 2017, 16(10):718-735, 18 pages.

Childs et al., "Senescent intimal foam cells are deleterious at all stages of atherosclerosis," Science, Oct. 28, 2016, 354(6311):472-477.

Chinta, et al., "Cellular senescence is induced by the environmental neurotoxin paraquat and contributes to neuropathology linked to Parkinson's Disease," Cell Rep., 2018, 22(4): 930-940.

Chong et al., "CD36 initiates the secretory phenotype during the establishment of cellular senescence, " EMBO Rep., May 18, 2018, 19(6):e45274, 13 pages.

Ciaglia et al., "Recognition by natural killer cells of N6-isopentenyladensoine-treated human glioma cell lines," Int. J. Cancer, 2018 142(1):176-190.

Cichocki et al., "GSK3 inhibition drives maturation of NK cells and enhances their antitumor activity," Cancer Research, Oct. 15, 2017, 77(20):5664-75.

Cifaldi et al., "Boosting Natural Killer Cell-Based Immunotherapy with Anticancer Drugs: a Perspective," Trends Molecular Medicine, Dec. 2017, 23(12):1156-1175, 20 pages.

(56) References Cited

OTHER PUBLICATIONS

Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.

Clayton et al., "Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.

Collado et al., "Senescence in tumours: evidence from mice and humans," Nature Reviews Cancer, Jan. 2010, 10(1):51-57.

Conarello et al., "Mice lacking dipeptidyl peptidase IV are protected against obesity and insulin resistance," Proc. Natl. Acad. Sci. U.S.A., May 27, 2003, 100(11):6825-6830.

Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl. ):CT082, Jul. 1, 2019, 2 pages.

Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42):36396-36403.

Cosgrove et al., "Usher protein functions in hair cells and photoreceptors," Int J Biochem Cell Biol., Jan. 2014, 46:80-89.

Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.

Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.

Crews et al., "Molecular mechanisms of neurodegeneration in Alzheimer's disease," Human Molecular Genetics, Apr. 22, 2010, 19(R1):R12-R20, 9 pages.

Cromie et al., "Nanobodies and their use in GPCR drug discovery," Current Topics in Medicinal Chemistry, Dec. 1, 2015, 15(24):2543-57.

Czaja et al., "A comprehensive analysis of the binding of anti-KIR antibodies to activating KIRs," Genes and Immunity, Jan. 2014, 15(1), 15 pages.

Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.

Dall'Era et al., "Adoptive Regulatory T Cell Therapy in a Patient with Systemic Lupus Erythematosus," Arthritis Rheumatology, Mar. 2019, 71(3):431-440.

De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.

De Genst et al., "Antibody repertoire development in camelids," Developmental & Comparative Immunology, Jan. 1, 2006, 30(1-2):187-98.

De Meyer et al., "Nanobody-based products as research and diagnostic tools," Trends in Biotechnology, May 1, 2014, 32(5):263-70.

De Stefano et al., "Establishing pathological cut-offs of brain atrophy rates in multiple sclerosis," Journal of Neurology, Neurosurgery, and Psychiatry, Jan. 2016, 87(1):93-99.

Deacon, "Physiology and Pharmacology of DPP-4 in Glucose Homeostasis and the Treatment of Type 2 Diabetes," Frontiers in Endocrinology, Feb. 2019, 10:80, 14 pages.

Deaglio et al., "Adenosine generation catalyzed by CD39 and CD73 expressed on regulatory T cells mediates immune suppression," Journal of Experimental Medicine, May 14, 2007, 204(6):1257-1265.

Demaria et al., "An Essential Role for Senescent Cells in Optimal Wound Healing through Secretion of PDGF-AA," Developmental Cell, Dec. 22, 2014, 31(6):722-733.

Deyev et al., "Design of multivalent complexes using the barnase-barstar module," Nature Biotechnology, Dec. 2003, 21(12):1486-92.

Di Ianni et al., "Tregs prevent GVHD and promote immune reconstitution inHLA-haploidentical transplantation," Blood, Apr. 7, 2011, 117(14):3921-3928.

Dietel et al., "Decreased Nos. of regulatory T cells are associated with human atherosclerotic lesion vulnerability and inversely correlate with infiltrated mature dendritic cells," Atherosclerosis, Sep. 2013, 230:92-99.

DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.

Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).

Dimri et al., "A biomarker that identifies senescent human cells in culture and in aging skin in vivo," Proceedings of the National Academy of Sciences, Sep. 29, 1995, 92(20):9363-9367.

Dinarello, "Interleukin 1 and interleukin 18 as mediators of inflammation and the aging process," The American Journal of Clinical Nutrition, Feb. 1, 2006, 83(2):447S-455S.

Docagne et al., "A soluble transforming growth factor-β (TGF-β) type I receptor mimics TGF-β responses," Journal of Biological Chemistry, Dec. 7, 2001, 276(49):46243-50.

Dong et al., "Characterization of adenosine deaminase binding to human CD26 on T cells and its biologic role in immune response," Journal of Immunology, Feb. 15, 1996, 156(4):1349-1355.

Dong et al., "Determination of adenosine deaminase binding domain on CD26 and its immunoregulatory effect on T cell activation," Journal of Immunology, Dec. 15, 1997, 159(12):6070-6076.

Dong et al., "Loss of methylation at the IFNG promoter and CNS-1 is associated with the development of functional IFN-γ memory in human CD4+T lymphocytes," European Journal of Immunology, 2013, 43(3), 793-804.

Dou et al., "Cytoplasmic chromatin triggers inflammation in senescence and cancer," Nature, Oct. 4, 2017, 550(7676):402-406, 21 pages.

Drees et al., "Soluble production of a biologically active single-chain antibody against murine PD-L1 in Escherichia coli," Protein Express. Purif., 2014, 94:60-66.

Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.

Edwardraja et al., "Redesigning of anti-c-met single chain Fv antibody for the cytoplasmic folding and its structural analysis," Biotechnology and Bioengineering, Jun. 15, 2010, 106(3):367-75.

Eisenhut et al., "Ion Channels in Inflammation," Pflugers Archive, Jan. 29, 2011, 461(4):401-421.

Elgueta et al., "Molecular mechanism and function of CD40/CD40L engagement in the immune system," Immunological Reviews, 2009, 229(1):152-172 doi.org/10.1111/j.1600-065X.2009.00782.x.

Elpek et al., "Mature natural killer cells with phenotypic and functional alterations accumulate upon sustained stimulation with IL-15/IL-15Rα complexes," Proceedings of the National Academy of Science, Dec. 14, 2010, 107:21647-21652.

Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.

Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.

Esensten et al., "Regulatory T-cell therapy for autoimmune and autoinflammatory diseases: The next frontier," The Journal of Allergy and Clinical Immunology, Dec. 1, 2018, 142(6):1710-1718.

Farr et al., "Targeting cellular senescence prevents age-related bone loss in mice," Nat. Med., 2017, 23(9):1072-1079.

(56)                        References Cited

OTHER PUBLICATIONS

Fehniger et al., "A Phase 1 Trial of CNDO-109—Activated Natural Killer Cells in Patients with High-Risk Acute Myeloid Leukemia," Biology of Blood and Marrow Transplantation, Aug. 2018, 24(8):1581-1589.

Feng et al., "The yin and yang functions of extracellular ATP and adenosine in tumor immunity," Cancer Cell International, Apr. 7, 2020, 20:110, 11 pages.

Fernando et al., "Targeting tumor endothelial marker 8 in the tumor vasculature of colorectal carcinomas in mice," Cancer research, Jun. 15, 2009, 69(12):5126-5132.

Ferreira et al., "Next-generation regulatory T cell therapy," Nature Reviews Drug Discovery, Sep. 20, 2019, 18(10):749-769, 21 pages.

Ferrucci et al., "The origins of age-related proinflammatory state," Blood, Mar. 15, 2005, 105(6):2294-2299.

Finkelman et al., "Anti-cytokine antibodies as carrier proteins. Prolongation of in vivo effects of exogenous cytokines by injection of cytokine-anti-cytokine antibody complexes, " The Journal of Immunology, Aug. 1, 1993, 151:1235-1244.

Finkelstein et al., "Obesity and Severe Obesity Forecasts Through 2030," American Journal of Preventative Medicine, Jun. 2012, 42(6):563-570.

Ford et al., "TREM and TREM-like receptors in inflammation and disease," Current Opinion in Immunology, Feb. 21, 2009, 21(1):38-46.

Franceschi et al., "Inflamm-aging. An evolutionary perspective on immunosenescence," Annals of the New York Academy of Sciences, Jun. 2000, 908:244-254.

Frutoso et al., "Emergence of NK Cell Hyporesponsiveness after Two IL-15 Stimulation Cycles," Journal of Immunology, May 30, 2018, 201:493-506.

Ganesh et al., "TGF-β Inhibition and Immunotherapy: Checkmate," Immunity, Apr. 17, 2018, 48(4):626-628.

Garber, "Bispecific antibodies rise again," Nat. Rev. Drug Discov., 2014, 13:799-801.

Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.

Gejima et al., "Human single-chain Fv (scFv) antibody specific to human IL-6 with the inhibitory activity on IL-6-signaling," Human Antibodies, Jan. 1, 2002, 11(4):121-9.

Geng et al., "A novel anti-TNF scFv constructed with human antibody frameworks and antagonistic peptides," Immunol. Res. 62(3):377-385, 2015.

Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.

Ghosh et al., "The Senescence-Associated Secretory Phenotype: Critical Effector in SkinCancer and Aging," Journal of Investigative Dermatology, Nov. 2016, 136(11):2133-2139.

Gibbs et al., "Identification of the factor VIIa binding site on tissue factor by homologous loop swap and alanine scanning mutagenesis," Biochemistry, Nov. 1, 1994, 33(47):14003-10.

Gong et al., "DAMP-sensing receptors in sterile inflammation and inflammatory diseases," Nature Reviews Immunology, Sep. 26, 2019, 20(2):95-112.

Gorrell et al., "Expression of the rat CD26 Antigen (dipeptidyl peptidase IV) on subpopulations of rat lymphocytes," Cellular Immunology, Apr. 15, 1991, 134(1):205-215.

Greenspan et al., "Defining epitopes: It's not as easy as it seems," Nature Biotechnology, 1999, 17:936-937.

Grupp et al., "Chimeric Antigen Receptor-Modified T Cells for Acute Lymphoid Leukemia," The New England Journal of Medicine, Apr. 18, 2013, 368(16):1509-1518.

Gu et al., "Human CD39hi regulatory T cells present stronger stability and function under inflammatory conditions," Cellular and Molecular Immunology, Jul. 4, 2016, 14(6):521-528.

Guha et al., "Affinity purification of human tissue factor: interaction of factor VII and tissue factor in detergent micelles," Proceedings of the National Academy of Sciences, Jan. 1986, 83(2):299-302.

Guo et al., "Immunobiology of the IL-15-IL-15R complex as an antitumor and antiviral agent," 2017, Cytokine & Growth Factor Reviews, 38:10-21.

Gutschmidt et al., "A quantitative histochemical study of dipeptidyl peptidase IV (DPP IV), " Histochemistry, 1981, 73(2):285-304.

Haile et al., "Soluble CD80 Restores T Cell Activation and Overcomes Tumor Cell Programmed Death Ligand 1-Mediated Immune Suppression," J. Immunol., 2013, 191(5):2829-2836.

Hayflick et al., "The serial cultivation of human diploid cell strains," Experimental Cell Research, Dec. 1961, 25:585-621.

He et al., "Senescence in Health and Disease," Cell, Jun. 1, 2017, 169(6):1000-1011.

Hebbar et al., "Detection of circulating soluble CD28 in patients with systemic lupus erythematosus, primary Sjögren's syndrome and systemic sclerosis," Clinical & Experimental Immunology, May 2004, 136(2):388-92.

Helfrich et al., "A rapid and versatile method for harnessing scFv antibody fragments with various biological effector functions," Journal of Immunological methods, 2000, 237(1-2):131-145.

Hélie et al., "Application of the Protein Maker as a platform purification system for therapeutic antibody research and development," Computational and Structural Biotechnology Journal, Jan. 1, 2016, 14:238-244.

Helman et al., "Effects of ageing and senescence on pancreatic β-cell function," Diabetes Obes Metab., Sep. 2016, 18(Suppl. 1):58-62.

Heneka et al., "Inflammasome signaling in brain function and neurodegenerative disease," Nature Reviews Neuroscience, Sep. 11, 2018, 19(10):610-621.

Heneka et al., "NLRP3 is activated in Alzheimer's disease and contributes to pathology in APP/PS1 mice," Nature, Jan. 31, 2013, 493(7434):674-678, 8 pages.

Heng et al., "G Protein-Coupled Receptors Revisited: Therapeutic Applications Inspired by Synthetic Biology," Annual Review of Pharmacology and Toxicology, Jan. 2014, 54:227-249.

Heng et al., "Multiple soluble TGF-β receptors in addition to soluble endoglin are elevated in preeclamptic serum and they synergistically inhibit TGF-β signalling. " Placenta, 2017 57:320 (1 page).

Highfill et al., "Overcoming Challenges in Process Development of Cellular Therapies," Current Hematologic Malignancy Reports, Jul. 6, 2019, 14(4):269-277, 9 pages.

Hoare et al., "The Power Behind the Throne: Senescence and the Hallmarks of Cancer," Annual Review of Cancer Biology, 2018, 2:175-194.

Hoffmann et al., "Large-scale in vitro expansion of polyclonal human CD4+CD25high regulatory T Cells," Blood, Aug. 2004, 104(3):895-903.

Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.

Hombach et al., "Generation of the single chain antibody fragment conserves the idiotypic profile of the anti-CD30 monoclonal antibody HRS3," Scandinavian Journal of Immunology, Nov. 1998, 48(5):497-501.

Hu et al., "Discovery of a novel IL-15 based protein with improved developability and efficacy for cancer immunotherapy," Scientific Reports, 2018, 8:7675, 11 pages.

Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.

Huang et al., "Targeting the vasculature of colorectal carcinoma with a fused protein of (RGD) 3-tTF" The Scientific World Journal, 2013(637086):1-11, 2013.

Hudak et al., "Glycocalyx engineering reveals a Siglec-based mechanism for NK cell immunoevasion," Nature Chemical Biology, Jan. 2014, 10(1), 20 pages.

(56) References Cited

OTHER PUBLICATIONS

Hudson et al., "Targeting RAGE Signaling in Inflammatory Disease," Annual Review of Medicine, Jan. 2018, 69:349-364, 16 pages.

Huell et al., "Interleukin-6 is present in early stages of plaque formation and is restricted to the brains of Alzheimer's disease patients," Acta Neuropathologica, Nov. 1995, 89(6):544-551.

Hughes et al., "Transfer of a TCR gene derived from a patient with a marked antitumor response conveys highly active T-cell effector functions," Hum. Gene Ther., 2005, 16:457-72.

Hui et al., "Butyrate inhibit collagen-induced arthritis via Treg/IL-10/Th17 axis," International immunopharmacology, Mar. 1, 2019, 68: Abstract 1 page.

Hynes et al., "In vitro analysis of cell metabolism using a long-decay pH-sensitive lanthanide probe and extracellular acidification assay," Analytical biochemistry, Jul. 1, 2009, 390(1):21-28.

Iannello et al., "p53-dependent chemokine production by senescent tumor cells supports NKG2D-dependent tumor elimination by natural killer cells," Journal of Experimental Medicine, Sep. 23, 2013, 210(10):2057-69.

Igarashi et al., "VEGF-C and TGF-β reciprocally regulate mesenchymal stem cell commitment to differentiation into lymphatic endothelial or osteoblastic phenotypes," International journal of molecular medicine, Apr. 1, 2016, 37(4):1005-1013.

Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.

Infante-Duarte et al., "New developments in understanding and treating neuroinflammation," Journal of Molecular Medicine, Sep. 2008, 86:975-985.

Info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver=3&hsa_cam=737902488&hsa_kw=&hsa_ad=621736020174&hsa_tgt=dsa-460355902483&hsamt=&hsa_acc=6752996364&hsa_grp=92226101427&hsa_net=adwords&gclid=CjwKCAjw_ihBhADEiwAXEazJvXifVFgeRGV_W99XbY72eRROhWnHtdd695ydPgyh8qdvTwd9ikGIRoCdecQAvD_BwE>, 5 pages.

International Preliminary Report on Patentability in International Appln. No. PCT/US2019/048881, dated Mar. 11, 2021, 7 pages.

International Preliminary Report on Patentability in International Appln. No. PCT/US2019/048930, dated Mar. 11, 2021, 9 pages.

International Preliminary Report on Patentability in International Appln. No. PCT/US2019/049142, dated Mar. 11, 2021, 11 pages.

International Preliminary Report on Patentability in International Appln. No. PCT/US2019/049158, dated Mar. 11, 2021, 8 pages.

International Preliminary Report on Patentability in International Appln. No. PCT/US2020/035598, mailed Dec. 6, 2022, 7 pages.

International Preliminary Report on Patentability in International Appln. No. PCT/US2020/038717, dated Dec. 30, 2021, 9 pages.

International Preliminary Report on Patentability in International Appln. No. PCT/US2021/017620, dated Aug. 25, 2022, 12 pages.

International Preliminary Report on Patentability in International Appln. No. PCT/US2021/017621, dated Aug. 25, 2022, 8 pages.

International Preliminary Report on Patentability in International Appln. No. PCT/US2021/017714, dated Aug. 25, 2022, 12 pages.

International Preliminary Report on Patentability in International Appln. No. PCT/US2021/029920, dated Nov. 10, 2022, 11 pages.

International Preliminary Report on Patentability in International Appln. No. PCT/US2021/035285, mailed Dec. 15, 2022, 7 pages.

International Search Report and Written Opinion in International Appln. No. PCT/US2019/048881, dated Nov. 9, 2019, 16 pages.

International Search Report and Written Opinion in International Appln. No. PCT/US2019/048930, dated Nov. 20, 2019, 18 pages.

International Search Report and Written Opinion in International Appln. No. PCT/US2019/049142, dated Jun. 23, 2020, 20 pages.

International Search Report and Written Opinion in International Appln. No. PCT/US2019/049158, dated Jan. 20, 2020, 17 pages.

International Search Report and Written Opinion in International Appln. No. PCT/US2020/035598, dated Feb. 18, 2021, 12 pages.

International Search Report and Written Opinion in International Appln. No. PCT/US2020/038717, dated Oct. 16, 2020, 17 pages.

International Search Report and Written Opinion in International Appln. No. PCT/US2021/017620, dated Aug. 6, 2021, 22 pages.

International Search Report and Written Opinion in International Appln. No. PCT/US2021/017621, dated Jun. 9, 2021, 15 pages.

International Search Report and Written Opinion in International Appln. No. PCT/US2021/017714, dated Aug. 27, 2021, 22 pages.

International Search Report and Written Opinion in International Appln. No. PCT/US2021/029920, dated Oct. 6, 2021, 21 pages.

International Search Report and Written Opinion in International Appln. No. PCT/US2021/035285, dated Oct. 18, 2021, 14 pages.

International Search Report and Written Opinion in International Appln. No. PCT/US2023/065745, mailed on Jun. 26, 2023, 14 pages.

Inzucchi et al., "New Drugs for the Treatment of Diabetes, Part II: Incretin-Based Therapy and Beyond, " Circulation, Jan. 29, 2008, 117(4):574-584, 21 pages.

Jain et al., "Mitochondrial Reactive Oxygen Species Regulate Transforming Growth Factor-β Signaling," Journal of Biological Chemistry, Jan. 11, 2013, 288(2):770-777.

Jakob et al., "Structure reveals function of the dual variable domain immunoglobulin (DVD-Ig™) molecule," Mabs, May 1, 2013, Taylor & Francis, 5(3):358-63.

Janeway et al., "The interaction of the antibody molecule with specific antigen" In Immunobiology: The Immune System in Health and Disease, 5th edition, 5 p. 2001.

Janeway, "Approaching the Asymptote? Evolution and Revolution in Immunology," Cold Spring Harbor Symposia on Quantitative Biology, 1989, 54 Pt 1:1-13.

Jeannin et al., "Soluble CD86 Is a Costimulatory Molecule for Human T Lymphocytes," Immunity, 2000, 13(3):303-312.

Jeon et al., "Local clearance of senescent cells attenuates the development of post-traumatic osteoarthritis and creates a pro-regenerative environment," Nat Med., Jun. 2017, 23(6):775-781.

Jin et al., "Novel Insights Into the NLRP3 Inflammasome in Atherosclerosis," Journal of the American Heart Association, Jun. 11, 2019, 8(12):e012219, 12 pages.

Justice et al., "Senolytics in idiopathic pulmonary fibrosis: Results from a first-in- human, open-label, pilot study," EBioMedicine, Feb. 2019, 40:554-563.

Kain et al., "The identification of the endogenous ligands of natural killer T cells reveals the presence of mammalian α-linked glycosylceramides," Immunity, Oct. 16, 2014, 41(4):543-54.

Karin et al., "Senescent cell turnover slows with age providing an explanation for the Gompertz law," Nature Communications, Dec. 2, 2019, 10:5495, 9 pages.

Karkera et al., "The anti-interleukin-6 antibody siltuximab down-regulates genes implicated in tumorigenesis in prostate cancer patients from a phase I study," The Prostate, Feb. 14, 2011, 71(13):1455-1465.

Katsuumi et al., "Vascular Senescence in Cardiovascular and Metabolic Diseases," Frontiers in Cardiovascular Medicine, Mar. 5, 2018, 5:18, 13 pages.

Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.

Kijanka et al., "Nanobody-based cancer therapy of solid tumors," Nanomedicine, Jan. 2015, 10(1):161-74.

Kim et al., "Experimental malaria infection triggers early expansion of natural killer cells," Infection and Immunity, Dec. 1, 2008, 76(12):5873-82.

Kim et al., "Identification of senescent cell surface targetable protein DPP4," Genes & Development, 2017, 31(15):1529-1534.

(56) References Cited

OTHER PUBLICATIONS

Kim et al., "Insulin resistance, inflammation, and nonalcoholic fatty liver disease in non-obese adults without metabolic syndrome components," Hepatol Int., Jun. 2013, 7(2):586-591.

Kim et al., "SCAMP4 enhances the senescent cell secretome," Genes & Development, 2018, 32(13-14):909-914.

Kirchhofer et al., "The tissue factor region that interacts with substrates factor IX and factor X," Biochemistry, Jun. 27, 2000, 39(25):7380-7.

Kirkland et al., "Cellular Senescence: A Translational Perspective," EBioMedicine, Jul. 2017, 21:21-28.

Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017, 6(3):e1277306, 15 pages.

Klein et al., "Design and characterization of structured protein linkers with differing flexibilities," Protein Engineering, Design & Selection, 2014, 27(10):325-30.

Klemann et al., "Cut to the chase: a review of CD26/dipeptidyl peptidase-4's (DPP4) entanglement in the immune system," Clinical and Experimental Immunology, Feb. 25, 2016, 185(1):1-21.

Klingemann et al., "Natural killer cells for immunotherapy—advantages of the NK-92 cell line over blood NK cells," Frontiers in immunology, Mar. 14, 2016, 7(91):1-7.

Klingenberg et al., "Depletion of FOXP3+ regulatory T cells promotes hypercholesterolemia and atherosclerosis," The Journal of Clinical Investigation, Feb. 15, 2013, 123:1323-1334.

Kondo et al., "Requirements for the functional expression of OX40 ligand on human activated CD4+ and CD8+ T cells," Human Immunology, 2007, 68(7):563-571.

Kovaleva et al., "Shark variable new antigen receptor biologics—a novel technology platform for therapeutic drug development," Expert Opinion on Biological Therapy, Oct. 1, 2014, 14(10):1527-39.

Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.

Krah et al., "Single-domain antibodies for biomedical applications," Immunopharmacology and Immunotoxicology, Jan. 2, 2016, 38(1):21-8.

Kritsilis et al., "Ageing, Cellular Senescence and Neurodegenerative Disease," International Journal of Molecular Sciences, Sep. 27, 2018, 19(10):2937, 37 pages.

Krizhanovsky et al., "Senescence of activated stellate cells limits liver fibrosis, " Cell, Aug. 22, 2008, 134(4):657-67.

Kumagai et al., "Monitoring of glutamate-induced excitotoxicity by mitochondrial oxygen consumption," Synapse, Jan. 2019, 73(1):e22067, 24 Pages.

Kuyinu et al., "Animal models of osteoarthritis: classification, update, and measurement of outcomes," J Orthop Surg Res., Feb. 2, 2016, 11:19, 27 pages.

Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.

Lamkanfi et al., "Mechanisms and Functions of Inflammasomes," Cell, May 22, 2014, 157(5): 1013-1022.

Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).

Latz et al., "Activation and regulation of the inflammasomes," Nature Reviews Immunology, May 24, 2013, 13(6):397-411.

Latz et al., "NLRP3 inflammasome activation in inflammaging," Seminars in Immunology, Dec. 2018, 40:61-73, 13 pages.

Lau et al., "RNA-associated autoantigens activate B cells by combined B cell antigen receptor/Toll-like receptor 7 engagement," The Journal of Experimental Medicine, Oct. 31, 2005, 202(9):1171-1177.

Lazar et al., "Transforming Growth Factor Alpha: Mutation of Aspartic Acid 47 and Leucine 48 Results in Different Biological Activities, " Mol. Cell. Biol., 1988, 8:1247-1252.

Li et al., "A Novel I L2-based Irrmunotherapeutic Protein Prevents the Development of Atherosclerosis in ApoE-/mice and LDLR-/-mice," Journal of Immunology, May 1, 2020, 204(1): Supplement (Abstract Only), 2 pages.

Li et al., "Adoptive transfer of natural killer cells in combination with chemotherapy improves outcomes of patients with locally advanced colon carcinoma," Cytotherapy, Jan. 2018, 20(1):134-148, 15 pages.

Li et al., "Lipid metabolism fuels cancer's spread," Cell metabolism, Feb. 7, 2017, 25(2):228-230.

Li et al., "The cGAS-cGAMP-STING pathway connects DNA damage to inflammation, senescence, and cancer," Journal of Experimental Medicine, Apr. 5, 2018, 215(5):1287-1299.

Li et al., "Transforming Growth Factor-β Regulation of Immune Responses," Annu. Rev. Immunol., 2006, 24:99-146.

Liton et al., "Cellular senescence in the glaucomatous outflow pathway," Experimental Gerontology, Aug.-Sep. 2005, 40(8-9):745-748.

Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.

Liu et al., "Evaluation of the biological activities of the IL-15 superagonist complex, ALT-803, following intravenous versus subcutaneous administration in murine models," Cytokine, Jul. 2018, 107:105-112, 8 pages.

Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.

Lu et al., "Molecular basis of binding between novel human coronavirus MERS-CoV and its receptor CD26," Nature, Jul. 7, 2013, 500(7461):227-231.

Lujambio et al., "Non-Cell-Autonomous Tumor Suppression by p53," Cell, Apr. 11, 2013, 153(2):449-460.

Maeda et al., "Original Ligand for LTβR Is LIGHT: Insight into Evolution of the LT/LTBR System," J Immunol., 2018, 201(1):202-214.

Maganto-García et al., "Dynamic Changes in Regulatory T Cells Are Linked to Levels of Diet-Induced Hypercholesterolemia," Circulation, Jun. 20, 2011, 124:185-195.

Mandelboim et al., "Recognition of haemagglutinins on virus-infected cells by NKp46 activates lysis by human NK cells," Nature, Feb. 2001, 409(6823):1055.

Marguet et al., "Enhanced insulin secretion and improved glucose tolerance in mice lacking CD26, " Proc. Natl. Acad. Sci. U.S.A., Jun. 6, 2000, 97(12):6874-6879.

Martelli et al., "HLA-haploidentical transplantation with regulatory and conventional T-cell adoptive immunotherapy prevents acute leukemia relapse," Blood, Jul. 24, 2014, 124(4):638-644.

Masoumi et al., "The role of hypoxia as the driving force for non-erythroid production of globin chains in preeclamptic placentas," Placenta. 2017;57:320.

Matsuura et al., "Pole test is a useful method for evaluating the mouse movement disorder caused by striatal dopamine depletion" Journal of neuroscience methods, 73(1):45-48, 1997.

McCarron et al., "TGF-β prevents T follicular helper cell accumulation and B cell autoreactivity," J Clin Invest., 2014, 124(10):4375-4386.

McHugh et al., "Senescence and aging: Causes, consequences, and therapeutic avenues," Journal of Cellular Biology, Nov. 7, 2017, 217(1):65-77.

Mehta et al., "Why do trials for Alzheimer's disease drugs keep failing? A discontinued drug perspective for 2010-2015," Expert Opinion on Investigational Drugs, May 2017, 26(6):735-739.

Melk et al., "Expression of p16INK4a and other cell cycle regulator and senescence associated genes in aging human kidney," Kidney Int., Feb. 2004, 65(2):510-520.

(56)          References Cited

OTHER PUBLICATIONS

Melk et al., "Senescence of renal cells: molecular basis and clinical implications," Nephrology Dialysis Transplantation, Dec. 2003, 18(12):2474-2478.

Menshawy et al., "CD58; leucocyte function adhesion-3 (LFA-3) could be used as a differentiating marker between immune and non-immune thyroid disorders," Comparative Clinical Pathology, 2018, 27(3), 721-727.

Mentlein et al., "Dipeptidyl-peptidase IV (CD26)-role in the inactivation of regulatory peptides," Regulatory Peptides, Nov. 30, 1999, 85(1):9-24.

Miah et al., "KIR2DL4 differentially signals downstream functions in human NK cells through distinct structural modules," The Journal of Immunology, Mar. 1, 2008, 180(5):2922-32.

Michelet et al., "Metabolic reprogramming of natural killer cells in obesity limits antitumor responses," Nature Immunology, Nov. 12, 2018, 19(12):1330-1340.

Mikayama et al., "Molecular cloning and functional expression of a cDNA encoding glycosylation-inhibiting factor," Proc. Natl. Acad. Sci. USA, Nov. 1, 1993, 90(21):10056-10060.

Milanovic et al., "Senescence-associated reprogramming promotes cancer stemness," Nature, Dec. 20, 2017, 553(7686):96-100.

Milanovic et al., "The Senescence-Stemness Alliance—A Cancer-Hijacked Regeneration Principle," Trends in Cellular Biology, Dec. 2018, 28(12):1049-1061, 13 pages.

Miller et al., "Soluble CD70: a novel immunotherapeutic agent for experimental glioblastoma," J Neurosurg., 2010, 113(2):280-285.

Miller et al., "Successful adoptive transfer and in vivo expansion of human haploidentical NK cells in patients with cancer," Blood, Apr. 15, 2005, 105(8):3051-3057.

Minamino et al., "A crucial role for adipose tissue p53 in the regulation of insulin resistance," Nature Medicine, Aug. 30, 2009, 15(9):1082-1087.

Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.

Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.

Moesta et al., "Targeting CD39 in cancer," Nature Reviews Immunology, Jul. 29, 2020, 20(12):739-755, 17 pages.

Moiseeva et al., "Metformin inhibits the senescence-associated secretory phenotype by interfering with IKK/NF-κB activation," Aging Cell, Mar. 23, 2013, 12(3):489-498.

Molema et al., "The use of bispecific antibodies in tumor cell and tumor vasculature directed immunotherapy," Journal of Controlled Release, 2000, 64(1-3):229-239.

Molgora et al., "Regulatory role of IL-1R8 in immunity and disease," Frontiers in Immunology, Apr. 20, 2016, 7:149.

Mookerjee et al., "Measurement and Analysis of Extracellular Acid Production to Determine Glycolytic Rate," Journal of Visualized Experiments, Jove, Dec. 2015, (106):e53464, 9 Pages.

Moore et al., "Macrophages in atherosclerosis: a dynamic balance," Nature Reviews Immunology, Sep. 2, 2013, 13:709-721, 13 pages.

Moreno et al., "Molecular Evidence of Adenosine Deaminase Linking Adenosine A2A Receptor and CD26 Proteins," Frontiers in Pharmacology, Feb. 15, 2018, 9:106, 18 pages.

Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.

Mortier et al., "Soluble interleukin-15 receptor a (IL-15Rα)-sushi as a selective and potent agonist of IL-15 action through IL-15Rβ/γ: hyperagonist IL-15. IL-15Rα fusion proteins," Journal of Biological Chemistry, Jan. 20, 2006, 281(3):1612-1619.

Mujić-Delić et al., "GPCR-targeting nanobodies: attractive research tools, diagnostics, and therapeutics," Trends in Pharmacological Sciences, May 1, 2014, 35(5):247-55.

Muller et al., "Antibody fusions with immunomodulatory proteins for cancer therapy," Pharmacology and Therapeutics, 2015, 154:57-66.

Mulvihill et al., "Pharmacology, Physiology, and Mechanisms of Action of Dipeptidyl Peptidase-4 Inhibitors," Endocrine Reviews, Dec. 1, 2014, 35(6):992-1019.

Munoz-Espin et al., "Cellular senescence: from physiology to pathology," Nature Reviews Molecular Cellular Biology, Jun. 23, 2014, 15(7):482-496.

Munoz-Espin et al., "Programmed Cell Senescence during Mammalian Embryonic Development," Cell, Nov. 21, 2013, 155(5):1104-1118.

Musi et al., "Tau protein aggregation is associated with cellular senescence in the brain," Aging Cell, Aug. 20, 2018, 17(6):e12840, 13 pages.

Must et al., "The Disease Burden Associated with Overweight and Obesity," Endotext, Feingold et al. (eds.), South Dartmouth, MA, 2000, 35 pages.

Muyldermans et al., "Recognition of antigens by single-domain antibody fragments: the superfluous luxury of paired domains," Trends in Biochemical Sciences, Apr. 1, 2001, 26(4):230-5.

Muyldermans, "Nanobodies: natural single-domain antibodies," Annual Review of Biochemistry, Jun. 2, 2013, 82:775-97.

Muyldermans, "Single domain camel antibodies: current status," Reviews in Molecular Biotechnology, Jun. 1, 2001, 74(4):277-302.

Myung et al., "Evidence of DNA damage in Alzheimer disease: phosphorylation of histone H2AX in astrocytes," Age, Apr. 23, 2008, 30(4):209-215.

Nag et al., "Soluble MHC II-peptide complexes induce antigen-specific apoptosis in T cells," Cellular Immunology, May 25, 1996, 170(1):25-33.

Nayyar et al., "Overcoming Resistance to Natural Killer Cell Based Immunotherapies for Solid Tumors," Frontiers in Oncology, 2019, 9: 28 pages.

Nelson et al., "A senescent cell bystander effect: senescence-induced senescence," Aging Cell, Feb. 9, 2012, 11(2):345-349.

Nilsson et al., "Targeted delivery of tissue factor to the ED-B domain of fibronectin, a marker of angiogenesis, mediates the infarction of solid tumors in mice," Cancer Research, American Association for Cancer Research, Proceedings: AACR 107th Annual Meeting, 2016, Apr. 16-20, 2016, New Orleans, LA 61(2):711-716.

Nishida et al., "CD26 is a potential therapeutic target by humanized monoclonal antibody for the treatment of multiple myeloma," Blood Cancer Journal, Oct. 22, 2018, 8(11):99, 17 pages.

O'Sullivan et al., "Natural Killer Cell Memory," Immunity, Oct. 20, 2015, 43(4):634-645.

Oberle et al., "Rapid Suppression of Cytokine Transcription in Human CD4+CD25—T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.

Ogrodnik et al., "Cellular senescence drives age-dependent hepatic steatosis," Nat Commun., Jun. 2017, 8:15691, 12 pages.

Ogrodnik et al., "Obesity-Induced Cellular Senescence Drives Anxiety and Impairs Neurogenesis," Cell Metabolism, May 2019, 29(5):1061-1077, 25 pages.

Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.

Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.

Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.

Ohnuma et al., "Role of CD26/dipeptidyl peptidase IV in human T cell activation and function," Frontiers in Bioscience, Jan. 1, 2008, 13:2299-2310.

(56) References Cited

OTHER PUBLICATIONS

Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.

Ovadya et al., "Strategies targeting cellular senescence," The Journal of Clinical Investigation, Apr. 2, 2018, 128(4):1247-54.

Owicki et al., "Biosensors based on the energy metabolism of living cells: the physical chemistry and cell biology of extracellular acidification," Biosensors and Bioelectronics, Jan. 1, 1992, 7(4):255-272.

Padutsch et al., "Superior Treg-Expanding Properties of a Novel Dual-Acting Cytokine Fusion Protein," Frontiers in Pharmacology, Dec. 18, 2019, 10:1490, 10 pages.

Palmer et al., "Cellular Senescence in Type 2 Diabetes: A Therapeutic Opportunity," Diabetes, Jul. 2015, 64(7):2289-2298.

Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.

Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.

Pittayapruek et al., "Role of Matrix Metalloproteinases in Photoaging and Photocarcinogenesis," International Journal of Molecular Sciences, 2016, 17(6):868, 20 pages.

Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.

Priyanka et al., "Linkers in the structural biology of protein-protein interactions," Protein Sci., 2013, 22(2):153-167.

Purohit et al., "Smad3-dependent regulation of type I collagen in human dermal fibroblasts: Impact on human skin connective tissue aging, " Journal of Dermatological Science, Jul. 2016, 83(1):80-83.

Putnam et al., "Clinical grade manufacturing of human alloantigen-reactive regulatory T cells for use in transplantation," American journal of transplantation, Nov. 1, 2013, 13(11):3010-3020.

Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.

Rafei et al., "Off-the-shelf virus specific T-cells for therapy of adenovirus disease in immunosuppressed patients," Journal of Clinical Oncology, May 26, 2019, 37(15 Suppl.):7008, 2 pages.

Rahbarizadeh et al., "Nanobody; an old concept and new vehicle for immunotargeting," Immunological Investigations, Jan. 1, 2011, 40(3):299-338.

Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.

Ranganathan et al., "Pinpointing the putative heparin/sialic acid-binding residues in the 'sushi' domain 7 of factor H: a molecular modeling study," Biocomputing 2000, 1999, 155-67.

Rao et al., "Purification and characterization of rabbit tissue factor," Thrombosis Research, Oct. 1, 1989, 56(1):109-118.

Rasmussen et al., "Crystal structure of human dipeptidyl peptidase IV/CD26 in complex with a substrate analog," Nature Structural and Molecular Biology, 2003, 10(1):19-25.

Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.

Reddy et al., "Linkers in the structural biology of protein—protein interactions" Protein science, 22(2):153-167, 2013.

Resta et al., "Ecto-enzyme and signaling functions of lymphocyte CD 7 3," Immunological Reviews, 1998, 161:95-109.

Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.

Rippmann et al., "Fusion of the Tissue Factor Extracellular Domain to a Tumor Stroma specific Single-Chain Fragment Variable Antibody Results in an Antigen-Specific Coagulation-Promoting Molecule," Biochemical Journal, 2000, 349(3):805-812.

Rittie et al., "Natural and Sun-Induced Aging of Human Skin," Cold Spring Harbor Perspective in Medicine, 2015, 5(1):a015370, 15 pages.

Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.

Rodier et al., "Persistent DNA damage signaling triggers senescence-associated inflammatory cytokine secretion," Nature Cell Biology, Jul. 13, 2009, 11(8), 15 pages.

Rogge et al., "Antibodies to the IL-12 receptor β2 chain mark human Th1 but not Th2 cells in vitro and in vivo," The Journal of Immunology, Apr. 1, 1999, 162(7):3926-32.

Roh et al., "Damage-Associated Molecular Patterns in Inflammatory Diseases," Immune Network, Aug. 2018, 18(4):e27, 14 pages.

Romano et al., "Past, Present, and Future of Regulatory T Cell Therapy in Transplantation and Autoimmunity," Frontiers in Immunology, Jan. 1, 2019, 10:43, 14 pages.

Romee et al., "Cytokine activation induces human memory-like NK cells," Blood, Dec. 6, 2012, 120(24):4751-4760.

Ross et al., "Signaling and function of interleukin-2 in T lymphocytes" Annual review of immunology, 2018, 36:411-433.

Rossi et al., "Complex and defined biostructures with the dock-and-lock method," Trends in Pharmacological Sciences, Sep. 1, 2012, 33(9):474-81.

Rossi et al., "Stably tethered multifunctional structures of defined composition made by the dock and lock method for use in cancer targeting," Proceedings of the National Academy of Sciences, May 2, 2006, 103(18):6841-6.

Rubinstein et al., "Converting IL-15 to a superagonist by binding to soluble IL-15Rα," Proceedings of the National Academy of Sciences U.S.A., Jun. 13, 2006, 103(24):9166-9171.

Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.

Ruf et al., "Tissue factor residues 157-167 are required for efficient proteolytic activation of factor X and factor VII," Journal of Biological Chemistry, Nov. 5, 1992, 267(31):22206-10.

Ruscetti et al., "NK cell—mediated cytotoxicity contributes to tumor control by a cytostatic drug combination," Science, Dec. 21, 2018, 362(6421):1416-1422, 8 pages.

Sagiv et al., "Granule exocytosis mediates immune surveillance of senescent cells," Oncogene, 2013, 32(15):1971-1977.

Sakaguchi et al., "Regulatory T Cells and Human Disease," Annual Review of Immunology, Apr. 26, 2020, 38:541-566.

Sakaguchi et al., "Regulatory T Cells and Immune Tolerance," Cell, May 30, 2008, 133(5):775-787.

Sakaguchi et al., "Regulatory T cells: how do they suppress immune responses?" International Immunology, Sep. 7, 2009, 21(10):1105-1111.

Sakamoto et al., "Phase I clinical trial of autologous NK cell therapy using novel expansion method in patients with advanced digestive cancer," Journal of Translational Medicine, Aug. 25, 2015, 13:277, 13 pages.

Sakamuri et al., "Measurement of respiratory function in isolated cardiac mitochondria using Seahorse XFe24 Analyzer: applications for aging research," Geroscience, Jun. 1, 2018, 40(3):347-356.

Salminen et al., "Emerging role of NF-κB signaling in the induction of senescence- associated secretory phenotype (SASP)," Cellular Signaling, Apr. 2012, 24(4):835-845.

Sandusky et al., "Regulation of 2B4 (CD244)-mediated NK cell activation by ligand-induced receptor modulation," European Journal of Immunology, Dec. 2006, 36(12):3268-76.

Sato et al., "Recombinant soluble murine IL-4 receptor can inhibit or enhance IgE responses in vivo," The Journal of Immunology, Apr. 1, 1993, 150:2717-2723.

Schafer et al., "Cellular senescence mediates fibrotic pulmonary disease," Nat Commun., Feb. 2017, 8:14532, 11 pages.

(56) References Cited

OTHER PUBLICATIONS

Schullek et al., "Key ligand interface residues in tissue factor contribute independently to factor VIIa binding," Journal of Biological Chemistry, Jul. 29, 1994, 269(30):19399-403.

Schwoppe et al., "Tissue-factor fusion proteins induce occlusion of tumor vessels," Thrombosis Research, Apr. 1, 2010, 125:S143-S150.

Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.

Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.

Sharma et al., "Regulatory T Cells License Macrophage Pro Resolving Functions During Atherosclerosis Regression," Circulation Research, Apr. 27, 2020, 127:335-353.

Smith et al., "Antigen Nature and Complexity Influence Human Antibody Light Chain Usage and Specificity," Vaccine, 2016, 34(25):2813-2820.

Smith et al., "Development and evaluation of an optimal human single-chain variable fragment-derived BCMA-targeted Car T cell vector," Molecular Therapy, Jun. 6, 2018, 26(6):1447-56.

Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.

Sondel et al., "Combination Therapy with Interleukin-2 and Anti-tumor Monoclonal Antibodies," Cancer Journal from Scientific American, Jan. 1, 1997, 3(Suppl. 1):S121-S127.

Sone et al., "Pancreatic beta cell senescence contributes to the pathogenesis of type 2 diabetes in high-fat diet-induced diabetic mice," Diabetologia, 2005, 48(1):58-67.

Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.

Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.

Sousa-Victor et al., "Geroconversion of aged muscle stem cells under regenerative pressure," Cell Cycle, Oct. 15, 2014, 13(20):3183-3190.

Spiess et al., "Alternative molecular formats and therapeutic applications for bispecific antibodies," Molecular Immunology, Oct. 1, 2015, 67(2):95-106.

Stoklasek et al., "Combined IL-15/IL-15Rα Immunotherapy Maximizes IL-15 Activity In Vivo," The Journal of Immunology, Nov. 1, 2006, 177(9):6072-6080.

Storer et al., "Senescence Is a Developmental Mechanism that Contributes to Embryonic Growth and Patterning," Cell, Nov. 21, 2013, 155(5):1119-1130.

Stryer, Biochemistry Fourth Edition, W. H. Freeman and Company, New York, 1995, pp. 18-23, 8 pages.

Swanson et al., "The NLRP3 inflammasome: molecular activation and regulation to therapeutics," Nature Reviews Immunology, Apr. 29, 2019, 19(8):477-489, 13 pages.

Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.

Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.

Takahashi et al., "Downregulation of cytoplasmic DNases is implicated in cytoplasmic DNA accumulation and SASP in senescent cells," Nature Communications, Mar. 28, 2018, 9:1249, 12 pages.

Takahashi et al., "Simple and inexpensive technique for measuring oxygen consumption rate in adherent cultured cells," The Journal of Physiological Sciences, Nov. 2017, 67(6):731-737.

Takeda et al., "Phase I study of YS110, a recombinant humanized monoclonal antibody to CD26, in Japanese patients with advanced malignant pleural mesothelioma," Lung Cancer, Nov. 2019, 137:64-70.

Tam et al., "Methods and strategies of peptide ligation," Peptide Science: Original Research on Biomolecules, 2001, 60(3):194-205.

Tanaka et al., "Cloning and functional expression of the T cell activation antigen CD26," Journal of Immunology, Jul. 15, 1992, 149(2):481-486.

Tang et al., "The Foxp3+ regulatory T cell: a jack of all trades, master of regulation," Nature Immunology, Feb. 19, 2008, 9(3):239-244.

Teissier et al., "The receptor for advanced glycation end-products (RAGE) is an important pattern recognition receptor (PRR) for inflammaging," Biogerontology, Apr. 9, 2019, 20(3):279-301, 23 pages.

Teng et al., "Structural assessment of the effects of amino acid substitutions on protein stability and protein-protein interaction," International journal of computational biology and drug design, Feb. 7, 2011, 3(4):334-349.

Theil et al., "Adoptive transfer of allogeneic regulatory T cells into patients with chronic graft-versus-host disease," Cytotherapy, Apr. 2015, 17(4):473-486, 14 pages.

ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.

Thonhoff et al., "Expanded autologous regulatory T-lymphocyte infusions in ALS," Neurology Neuroimmunology Neuroinflammation, May 18, 2018, 5(4):e465, 8 pages.

Tobin et al., "NK cells in childhood obesity are activated, metabolically stressed, and functionally deficient," JCI Insight, Dec. 21, 2017, 2(24):e94939, 9 pages.

Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.

Tominaga et al., "TGF-β Signaling in Cellular Senescence and Aging-Related Pathology," International Journal of Molecular Sciences, Oct. 10, 2019, 20(20):5002, 18 pages.

Trevani et al., "Extracellular acidification induces human neutrophil activation," The Journal of Immunology, Apr. 15, 1999, 162(8):4849-4857.

Tse et al., "ABT-263: A Potent and Orally Bioavailable Bcl-2 Family Inhibitor," Cancer Research, May 2008, 68(9):3421-3428.

Uppendahl et al., "Natural killer cell-based immunotherapy in gynecologic malignancy: a review," Frontiers in immunology, Jan. 5, 2018, 8(1825): 1-15.

Urh et al., "Affinity chromatography: general methods," Methods in enzymology, Jan. 1, 2009, 463: 23 pages.

Uryga et al., "Ageing induced vascular smooth muscle cell senescence in atherosclerosis," Journal of Physiology, Apr. 15, 2016, 594(8):2115-2124.

Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).

Van Audenhove et al., "Nanobodies as versatile tools to understand, diagnose, visualize and treat cancer," EBioMedicine, Jun. 1, 2016, 8:40-8.

Van Bockstaele et al., "The development of nanobodies for therapeutic applications" Current opinion in investigational drugs, 10(11):1212-1224, 2009.

(56) References Cited

OTHER PUBLICATIONS

Van den Bergh et al., "IL-15 receptor alpha as the magic wand to boost the success of IL-15 antitumor therapies: The upswing of IL-15 transpresentation," Pharmacology and Therapeutics, 2017, 170:73-79.

Van Deursen, "The role of senescent cells in ageing, " Nature, May 21, 2014, 509(7501):439-446.

Vankadari et al., "Emerging COVID-19 coronavirus: glycan shield and structure prediction of spike glycoprotein and its interaction with human CD26," Emerging Microbes and Infection, Mar. 17, 2020, 9(1):601-604.

Veluchamy et al., "The rise of allogeneic natural killer cells as a platform for cancer immunotherapy: recent innovations and future developments," Frontiers in immunology, May 31, 2017, 8(631): 1-20.

Vidarsson et al., "IgG subclasses and allotypes: from structure to effector functions," Frontiers in immunology, Oct. 20, 2014, 5:520, 17 Pages.

Vincke et al., "Introduction to heavy chain antibodies and derived Nanobodies," Single Domain Antibodies, Humana Press, Totowa, NJ, 2012, pp. 15-26.

Voelker et al., "Anti-TGF-β1 Antibody Therapy in Patients with Diabetic Nephropathy," J Am Soc Nephrol., 2017, 28:953-962.

Voet et al., Biochemistry, John Wiley & Sons, Inc., 1990, pp. 126-128 and 228-234, 12 pages.

Von Kobbe, "Cellular senescence: a view throughout organismal life," Cellular and Molecular Life Sciences, Jul. 20, 2018, 75:3553-3567, 15 pages.

Waaijer et al., "Do senescence markers correlate in vitro and in situ within individual human donors?" Aging, Feb. 2018, 10(2):278-289.

Wallace et al., "B lymphocytes confer immune tolerance via cell surface GARP-TGF-β complex," JCI Insight., 2018, 3(7):e99863, 19 pages.

Walsh et al., "Inflammasomes in the CNS," Nature Reviews Neuroscience, Jan. 8, 2014, 15(2):84-97, 14 pages.

Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565.

Wang et al., "Biomarkers of Cellular Senescence and Skin Aging," Frontiers in Genetics, Aug. 23, 2018, 9:247, 14 pages.

Wang et al., "Loss of lamin B1 is a biomarker to quantify cellular senescence in photoaged skin," Scientific Reports, Nov. 15, 2017, 7(1):15678, 8 pages.

Wang et al., "Recombinant human CD137L for cancer immunotherapy: effects of different fusions and linkers on its activity," Cancer Immunol Immunother., 2012, 61(4):489-495.

Washburn et al., "A potential role for shed soluble major histocompatibility class I molecules as modulators of neurite outgrowth," PLoS One, Mar. 31, 2011, 6(3):e18439.

Weber et al., "Specific low-affinity recognition of major histocompatibility complex plus peptide by soluble T-cell receptor," Nature, Apr. 1992, 356(6372):793.

Weihermann et al., "Elastin structure and its involvement in skin photoageing," International Journal of Cosmetic Science, Jun. 2017, 39(3):241-247.

Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.

Weiner et al., "Antibody-based immunotherapy of cancer," Cell, Mar. 16, 2012, 148(6):1081-4.

Weiss et al., "Formyl-Peptide Receptors in Infection, Inflammation, and Cancer," Trends in Immunology, Oct. 2018, 39(10):815-829, 15 pages.

Wesolowski et al., "Single domain antibodies: promising experimental and therapeutic tools in infection and immunity," Medical Microbiology and Immunology, Aug. 1, 2009, 198(3):157-74.

Wiemann et al., "Hepatocyte telomere shortening and senescence are general markers of human liver cirrhosis," The FASEB Journal, Jul. 2002, 16(9):935-942.

Wilchek et al., "Essentials of biorecognition: The (strept) avidin-biotin system as a model for protein-protein and protein-ligand interaction," Immunology letters, Feb. 28, 2006, 103(1):Abstract 2 pages.

Wiley et al., "Mitochondrial Dysfunction Induces Senescence with a Distinct Secretory Phenotype," Cell Metabolism, Feb. 9, 2016, 23(2):303-314.

Witkowsa et al., "Soluble intercellular adhesion molecule-1 (sICAM-1): an overview," Eur Cytokine Netw. 2004, 15(2):91-98.

Wong et al., "Interleukin-15: Interleukin-15 receptor a scaffold for creation of multivalent targeted immune molecules," Protein Engineering, Design & Selection, Apr. 1, 2011, 24(4):373-383.

Xiong et al., "Maternal uterine NK cell-activating receptor KIR2DS1 enhances placentation," The Journal of Clinical Investigation, Oct. 1, 2013, 123(10):4264-72.

Xu et al., "Celecoxib attenuates cachectic events in mice by modulating the expression of vascular endothelial growth factor," Mol Med Rep., Jan. 2015, 11(1):289-294.

Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.

Xu et al., "Senolytics improve physical function and increase lifespan in old age," Nature Medicine, Aug. 2018, 24(8):1246, 15 pages.

Xu et al., "Transplanted senescent cells induce an osteoarthritis-like condition in mice," The Journals of Gerontology: Series A, Jun. 1, 2017, 72(6):780-5.

Yamamoto et al., "Measurement of glucose uptake in cultured cells," Curr Protoc Pharmacol, Dec. 2011, Chapter 12:12.14.1-12.14.22.

Yamazaki et al., "Vascular Cell Senescence Contributes to Blood-Brain Barrier Breakdown," Stroke, Feb. 16, 2016, 47(4):1068-1077, 15 pages.

Yan et al., "Obesity- and aging-induced excess of central transforming growth factor-β potentiates diabetic development via an RNA stress response," Nature Medicine, Aug. 3, 2014, 20:1001-1008, 9 pages.

Yanai et al., "Cellular senescence-like features of lung fibroblasts derived from idiopathic pulmonary fibrosis patients," Aging (Albany NY), Sep. 2015, 7(9):664-672.

Yigit et al., "A combination of an anti-SLAMF6 antibody and ibrutinib efficiently abrogates expansion of chronic lymphocytic leukemia cells," Oncotarget, May 3, 2016, 7(18):26346.

Yousefzadeh et al., "An aged immune system drives senescence and ageing of solid organs," Nature, May 12, 2021, 594:100-105, 34 pages.

Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.

Yu et al., "The dipeptidyl peptidase IV family in cancer and cell biology," FEBS Journal, Feb. 5, 2010, 277(5):1126-1144.

Yun et al., "Recurrent turnover of senescent cells during regeneration of a complex structure," Elife, May 5, 2015, 4:e05505, 16 pages.

Yung et al., "A selective transforming growth factor-β ligand trap attenuates pulmonary hypertension," American Journal of Respiratory and Critical Care Medicine, Nov. 1, 2016, 194(9):1140-51.

Zhang et al., "AAED1 modulates proliferation and glycolysis in gastric cancer," Oncology Reports, Aug. 1, 2018, 40(2):1156-1164.

Zhang et al., "Depletion of NK cells improves cognitive function in the Alzheimer disease mouse model," The Journal of Immunology, Jul. 15, 2020, 205(2), 10 pages.

Zhang et al., "The bone anabolic effects of irisin are through preferential stimulation of aerobic glycolysis," Bone, Sep. 1, 2018, 114:150-160.

Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.

(56) References Cited

OTHER PUBLICATIONS

Zheng et al., "Acquisition of Suppressive Function by Activated Human CD4+CD25—T Cells Is Associated with the Expression of CTLA-4 Not FoxP3," The Journal of Immunology, Aug. 1, 2008, 181(3):1683-1691.

Zhong et al., "A Potential Role for Dendritic Cell/Macrophage-Expressing DPP4 in Obesity-Induced Visceral Inflammation," Diabetes, Jan. 2013, 62(1):149-157.

Zhou et al., "A novel chimeric antigen receptor redirecting T-cell specificity towards CD26cancer cells," Leukemia, Apr. 2020, 35(1):119-129, 11 pages.

Zhou, "Emerging mechanisms and applications of low-dose IL-2 therapy in autoimmunity," Cytokine & Growth Factor Reviews, Jun. 30, 2022, 67:80-88.

Zhu et al., "New agents that target senescent cells: the flavone, fisetin, and the BCL-XL inhibitors, A1331852 and A1155463," Aging (Albany NY), Mar. 2017, 9(3):955-963.

Zhu et al., "Novel Human Interleukin-15 Agonists," The Journal of Immunology, Sep. 15, 2009, 183(6):3598-3607.

Zou et al., "2-NBDG as a fluorescent indicator for direct glucose uptake measurement," Journal of biochemical and biophysical methods, Sep. 30, 2005, 64(3):207-215.

Zwaagstra et al., "Engineering and therapeutic application of single-chain bivalent TGF-β family traps," Molecular Cancer Therapeutics, Jul. 1, 2012, 11(7):1477-87.

Shen et al., "Engineering peptide linkers for scFv immunosensors," Anal Chem., Mar. 2008, 80(6):1910-1917.

\* cited by examiner

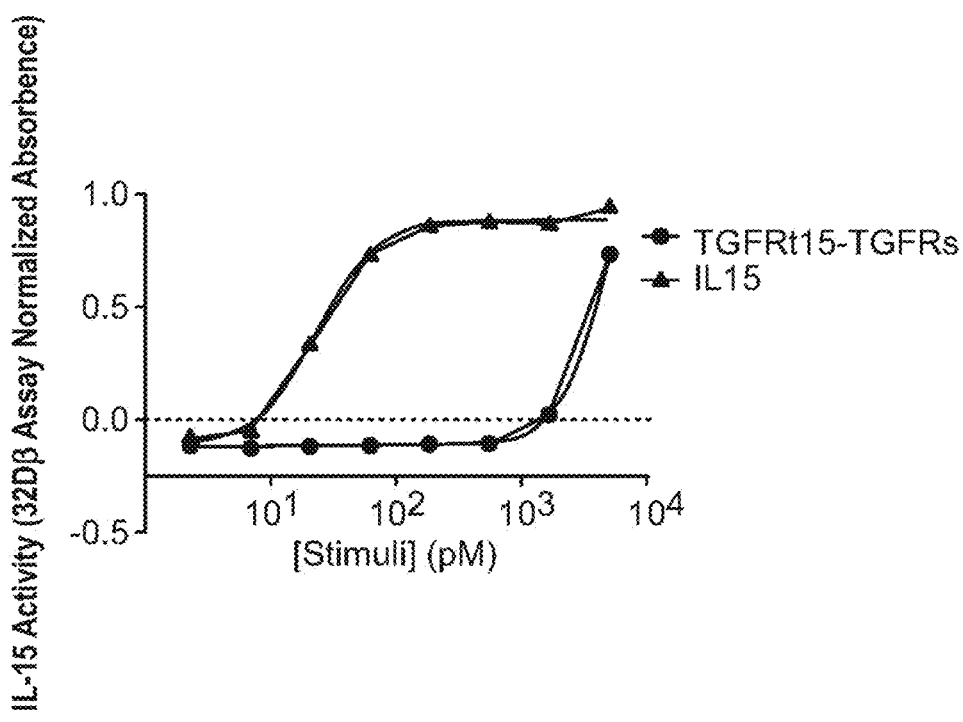
FIG. 6
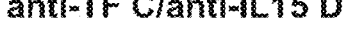
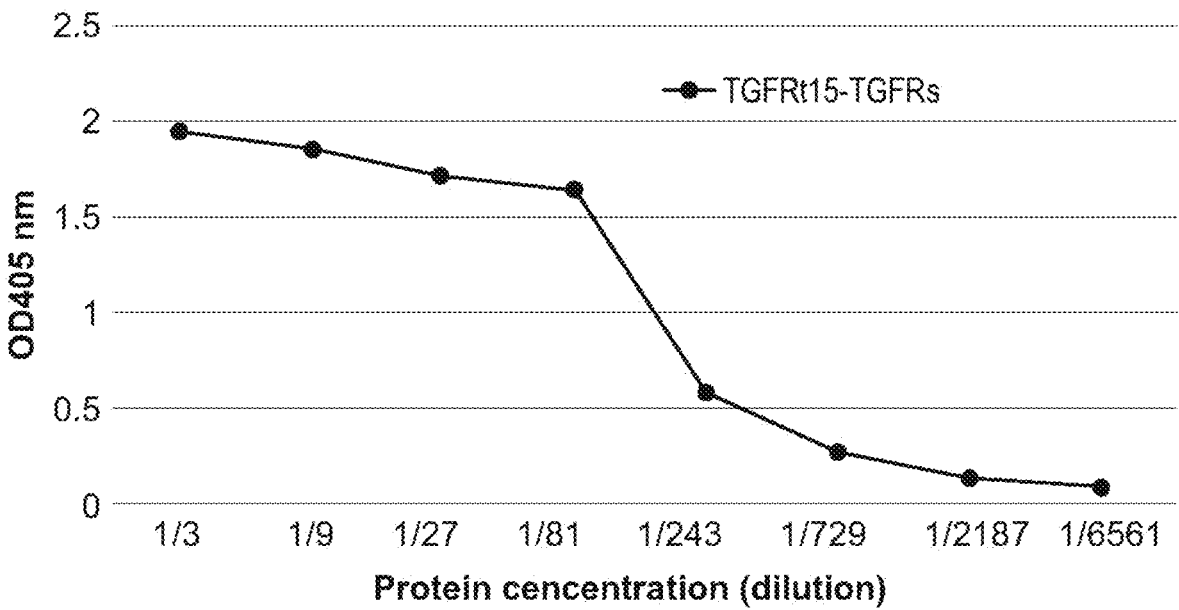
FIG. 7A anti-TF C/anti-TGFR D

10APR19SampleElution18-05 001

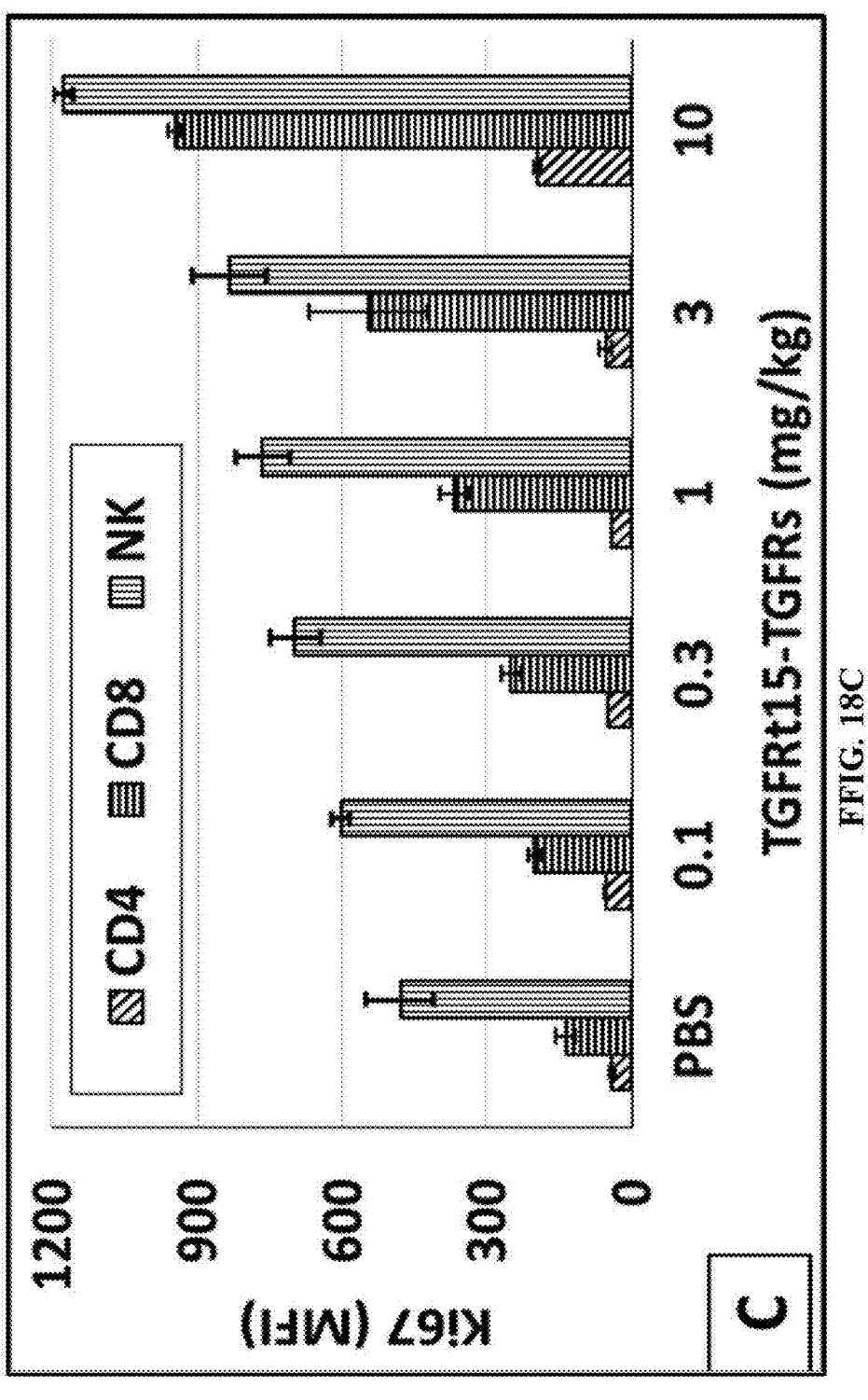
FFIG. 18C

DTX (10 mg/kg, TGFRt15-TGFRs (3 mg/kg), TA99 (200 μg)

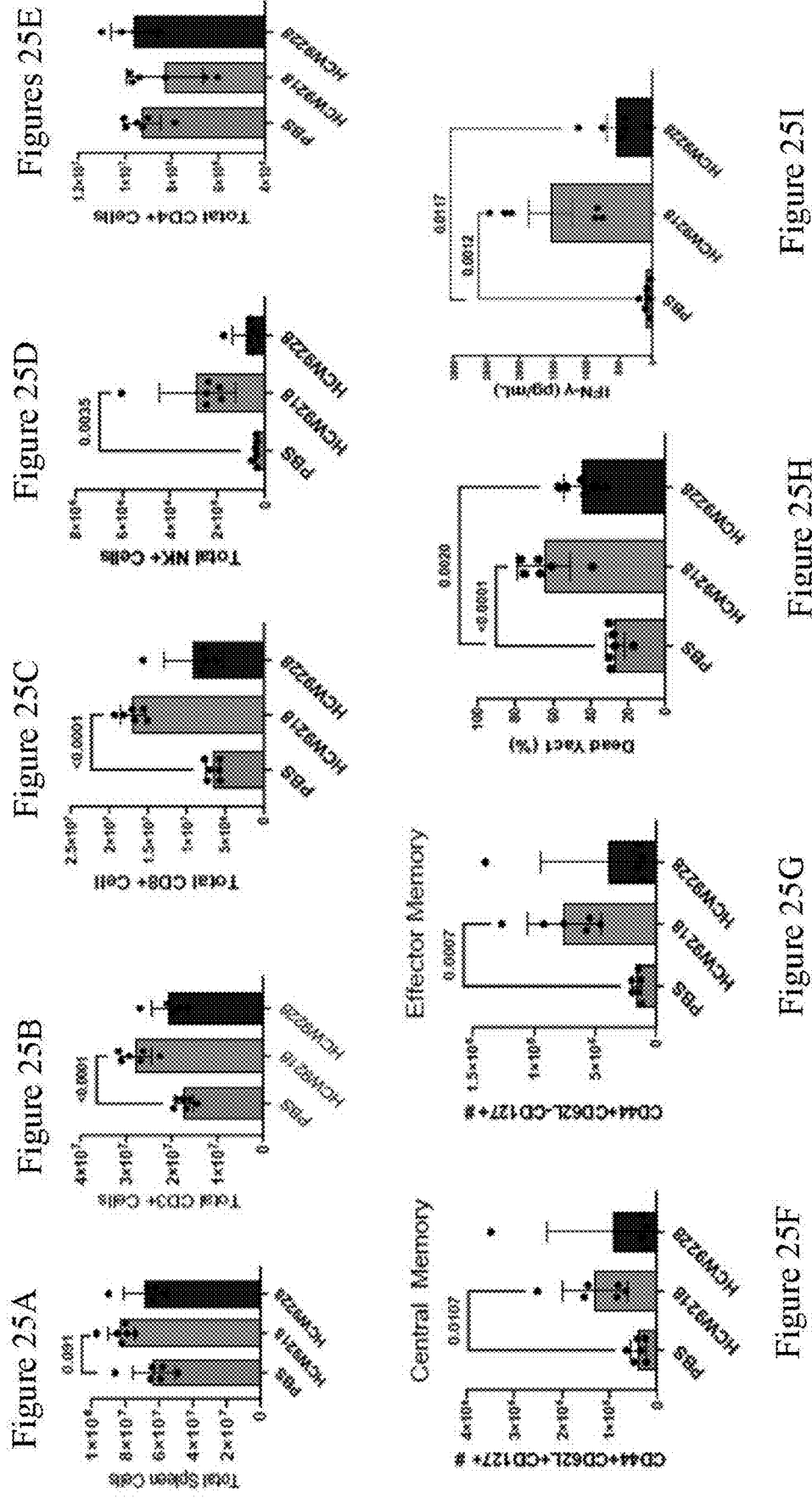

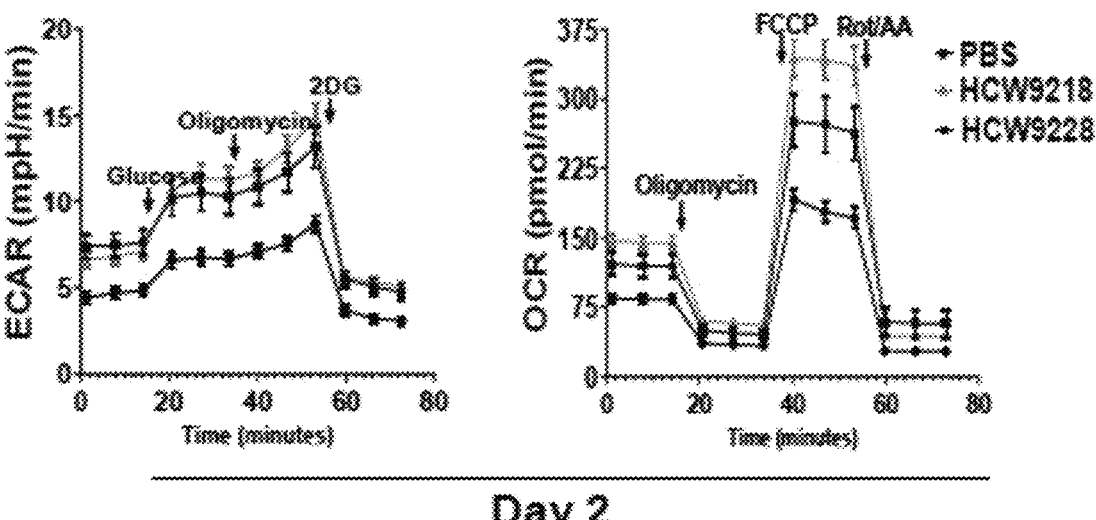
Day 2
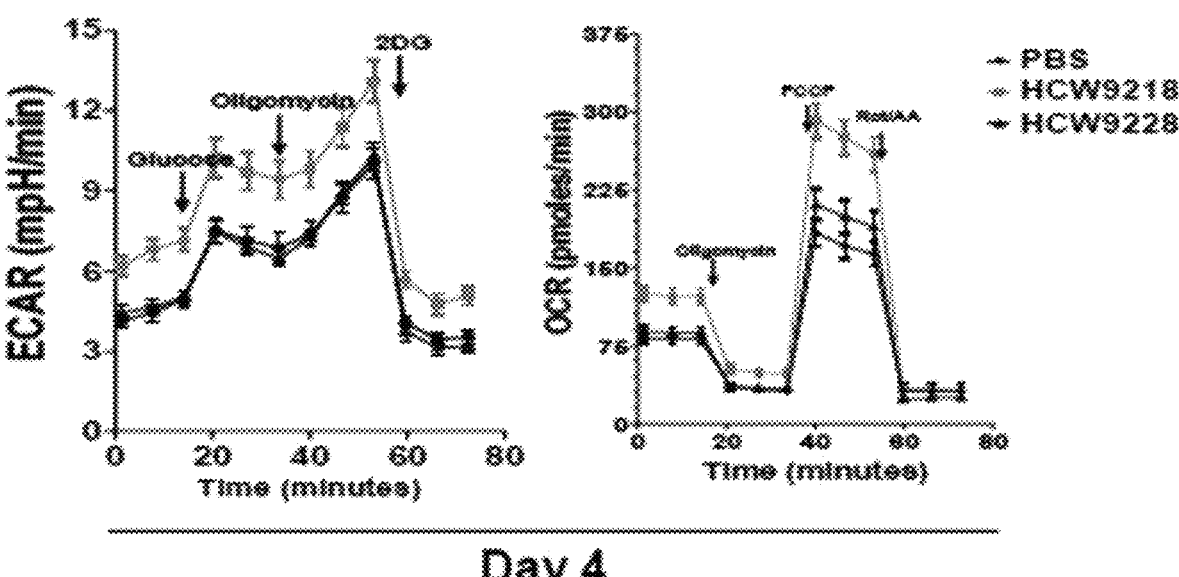
Day 4
FIG. 25J

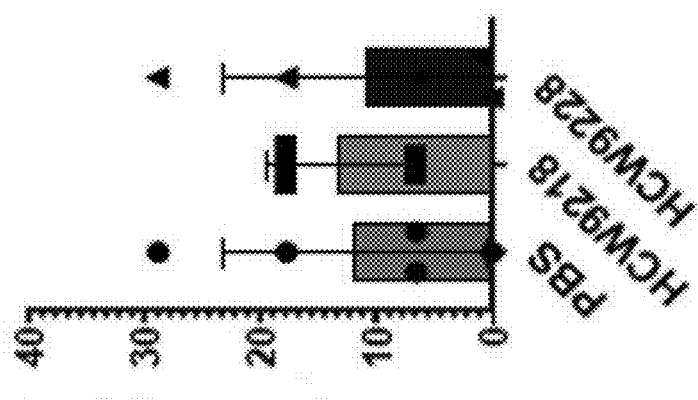
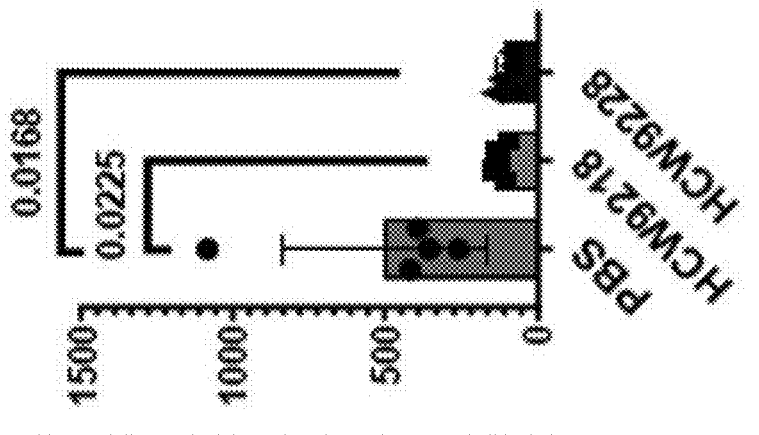
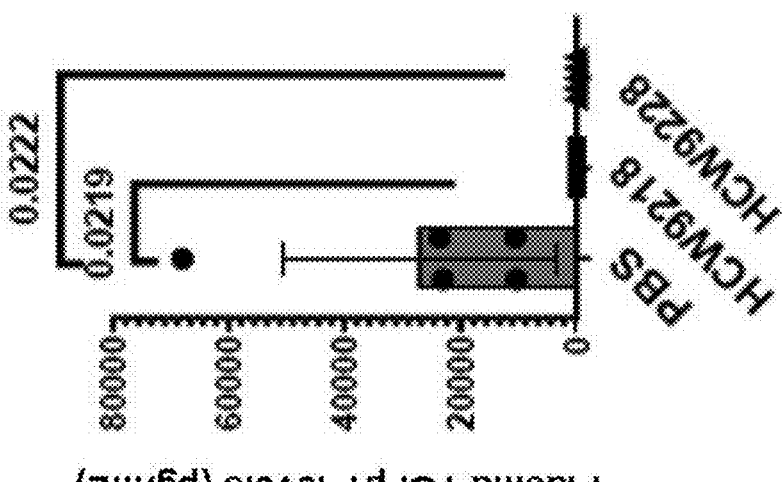
FIG. 25K

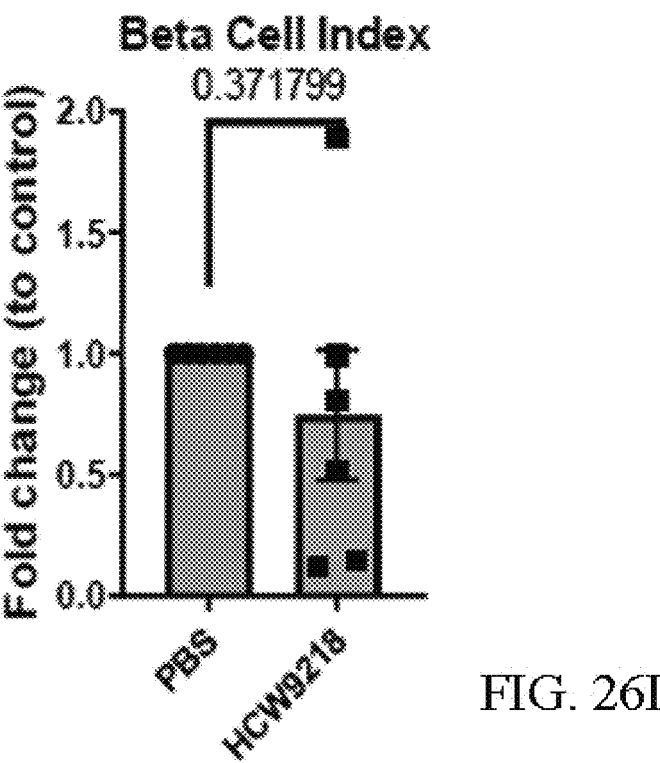
FIG. 26I
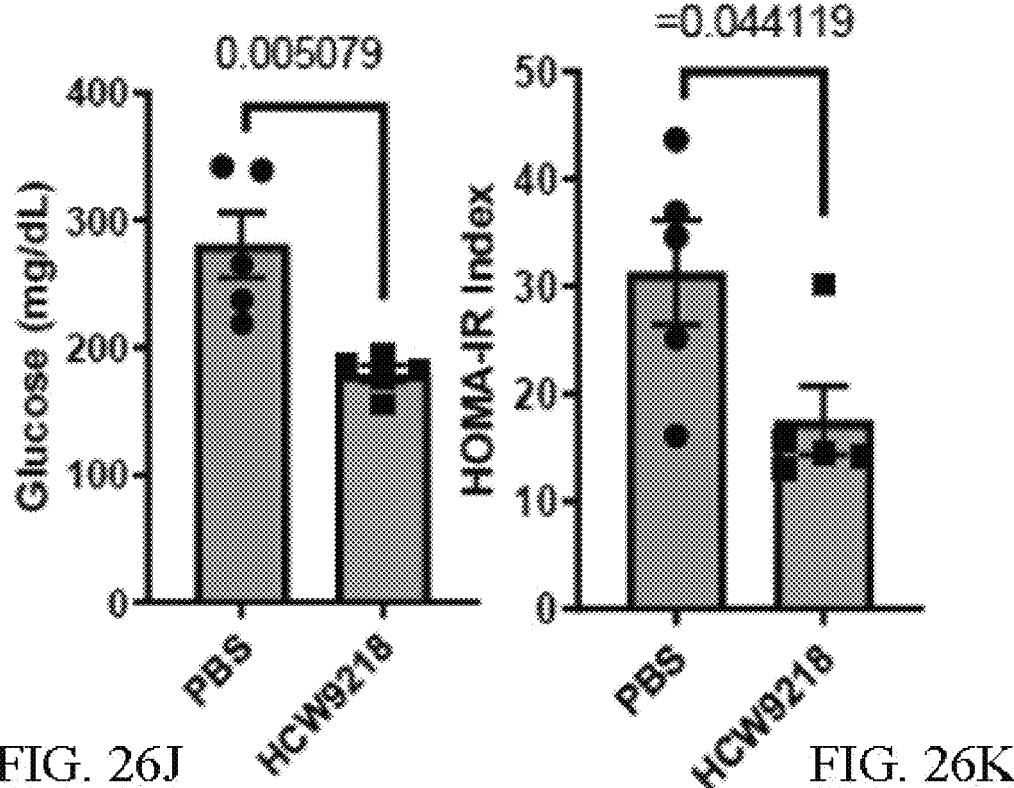
FIG. 26J                                    FIG. 26K

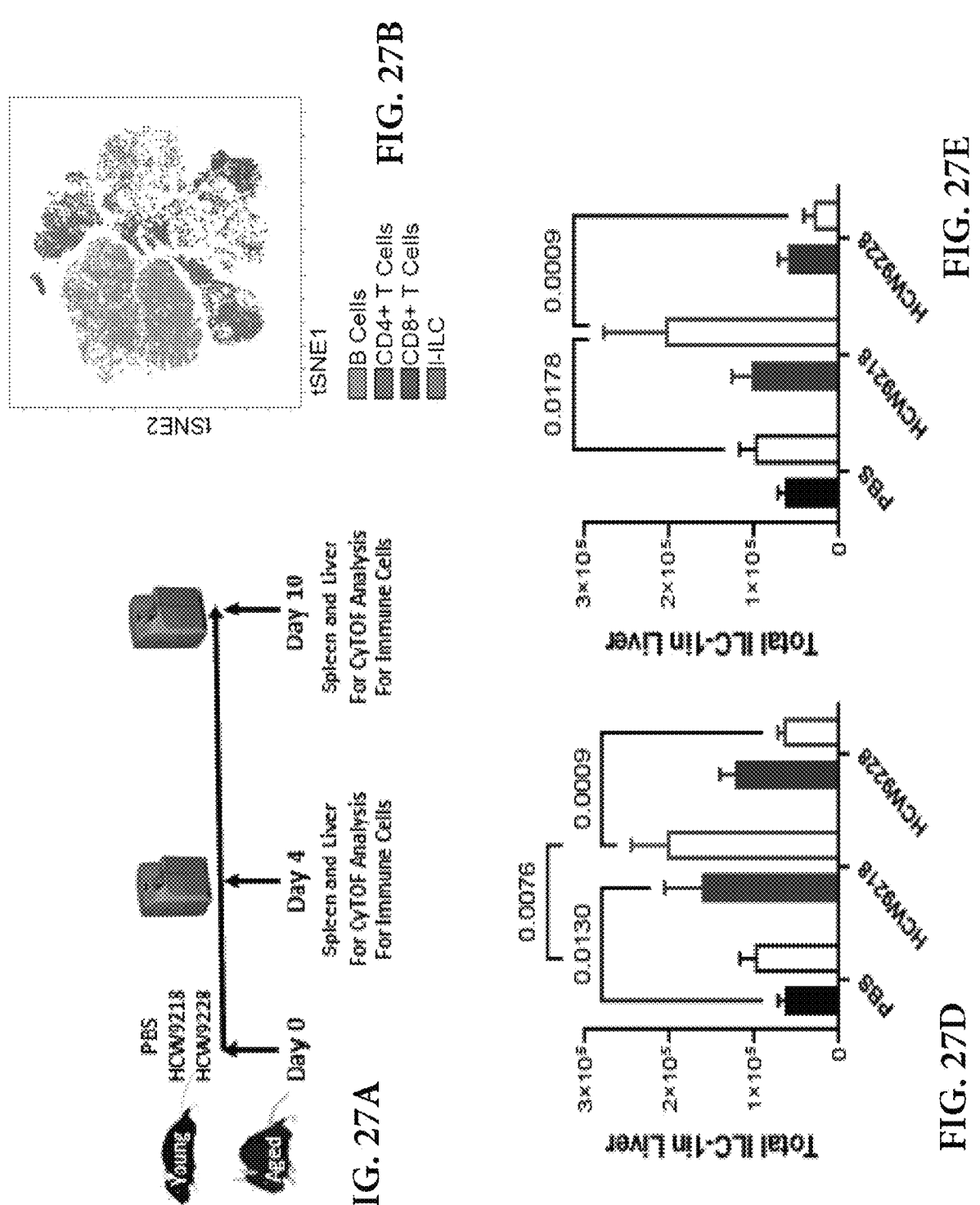

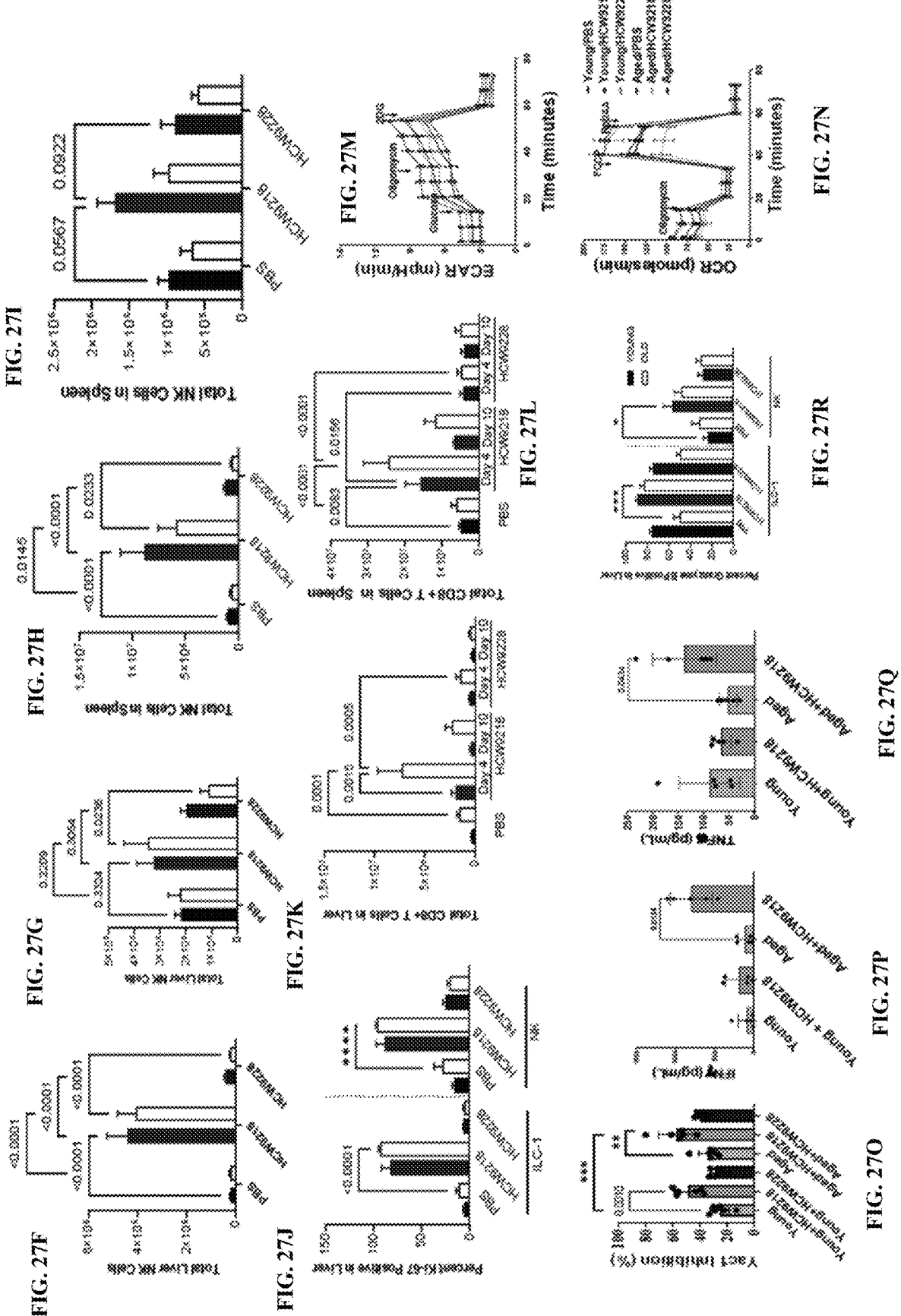

Senescence and
Inflammation genes

Gluconeogenesis and
fatty acid metabolism

Circadian Rhythm

FIG. 29A
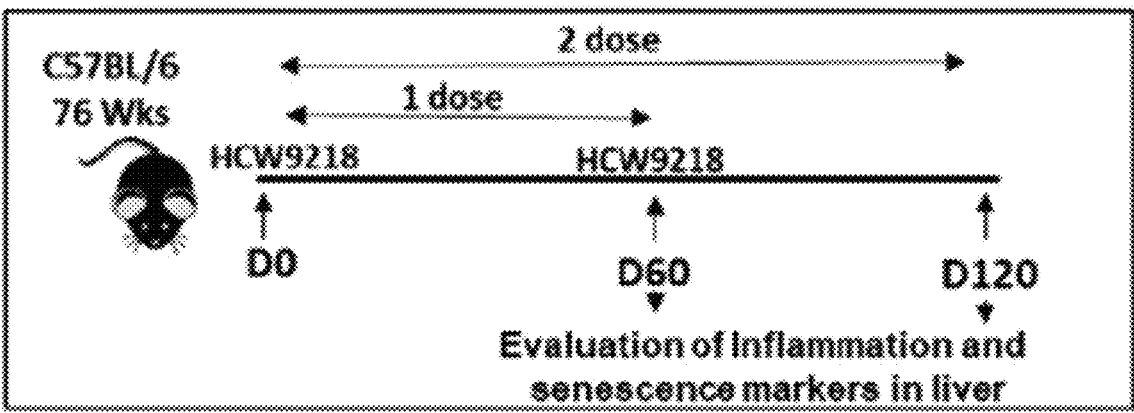
FIG. 29B
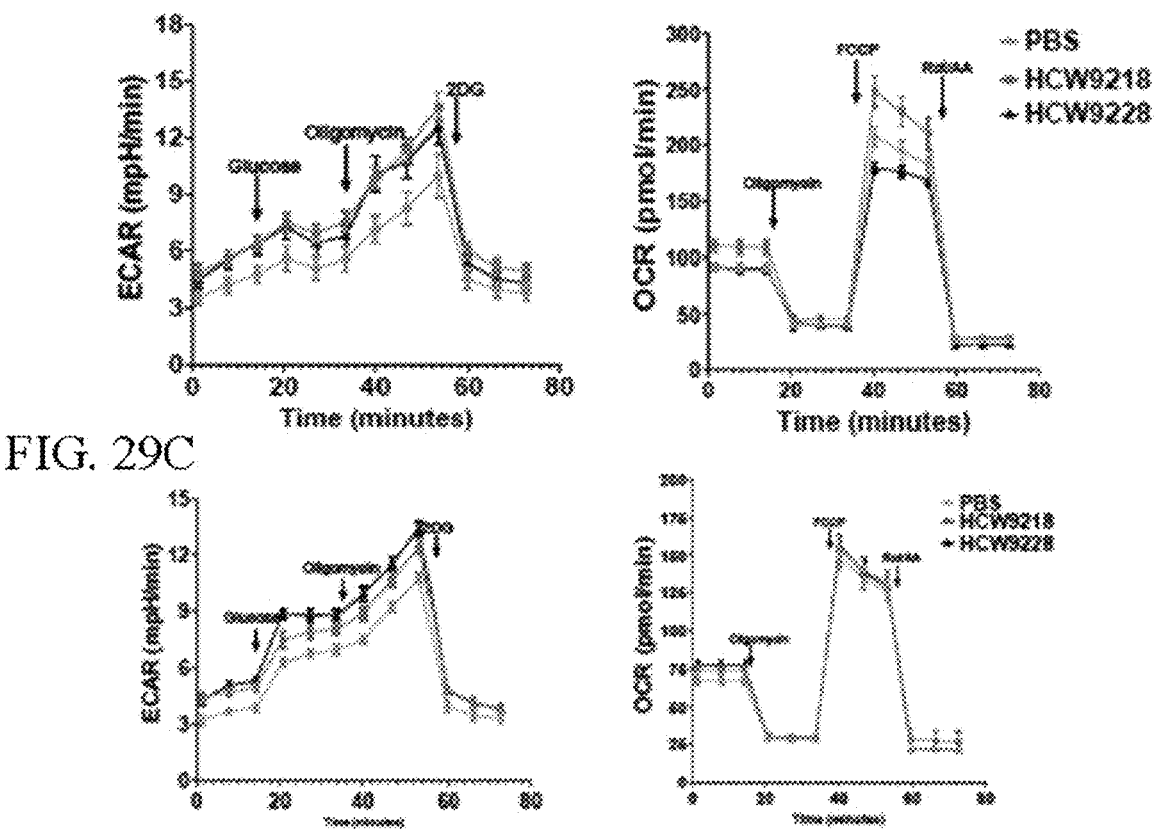
FIG. 29C

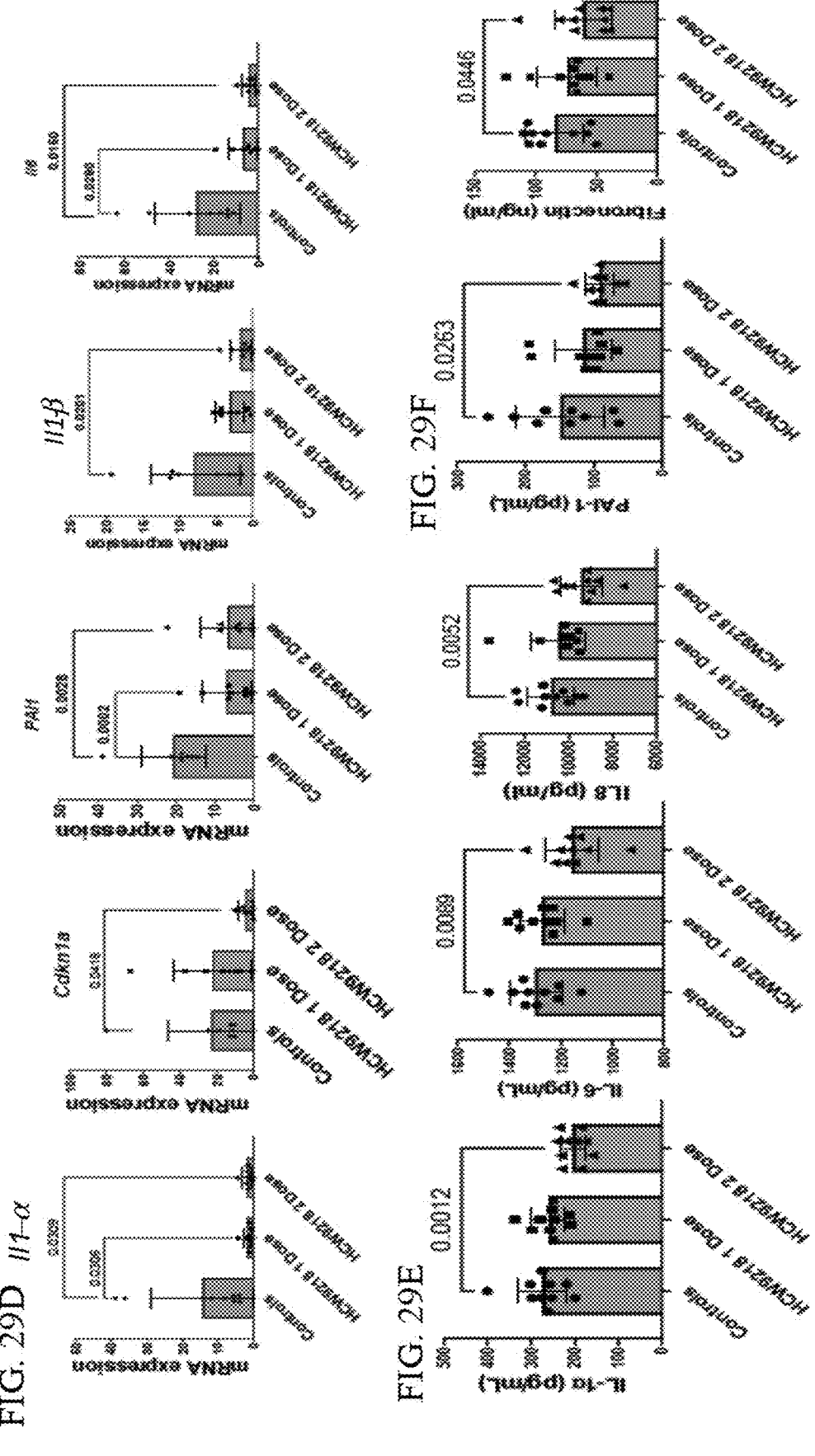

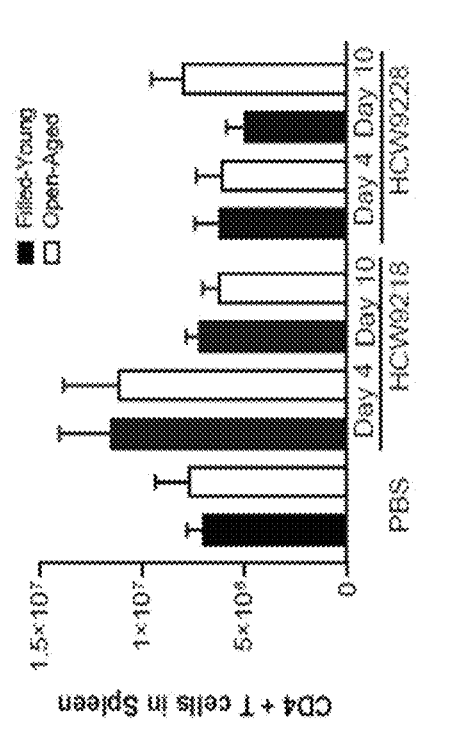
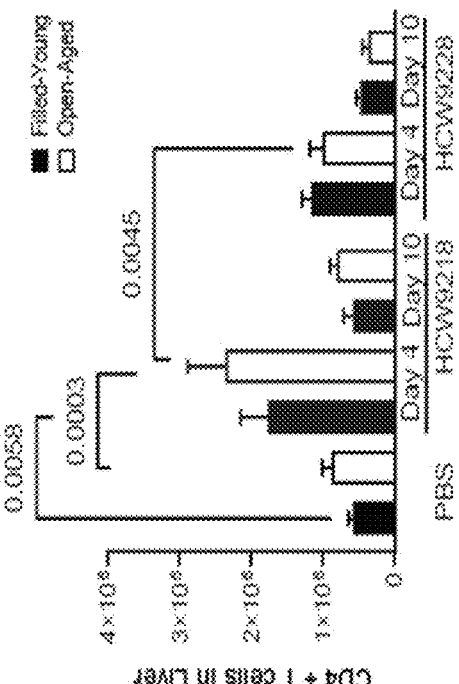
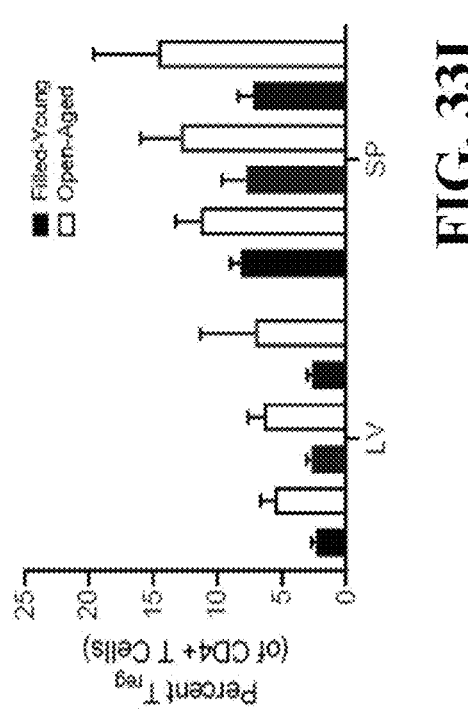
FIG. 33H
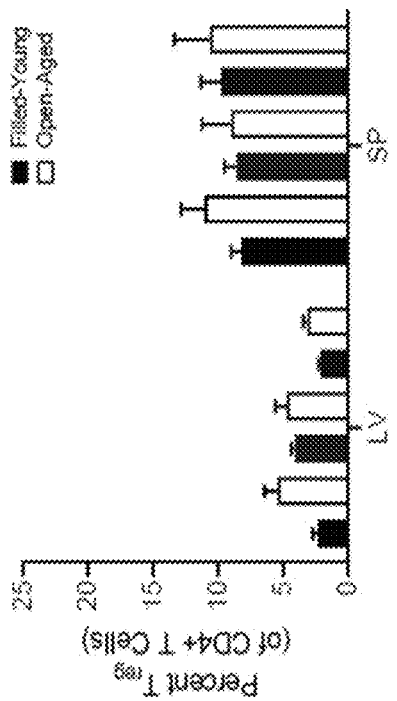
FIG. 33I

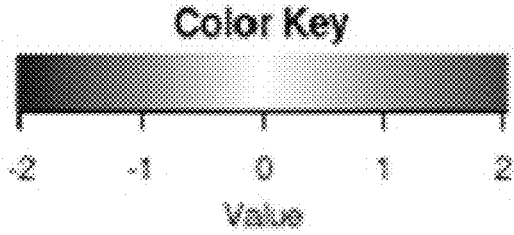
FIG. 34A

Senescence, Inflammation and
Circadian Rhythm Related
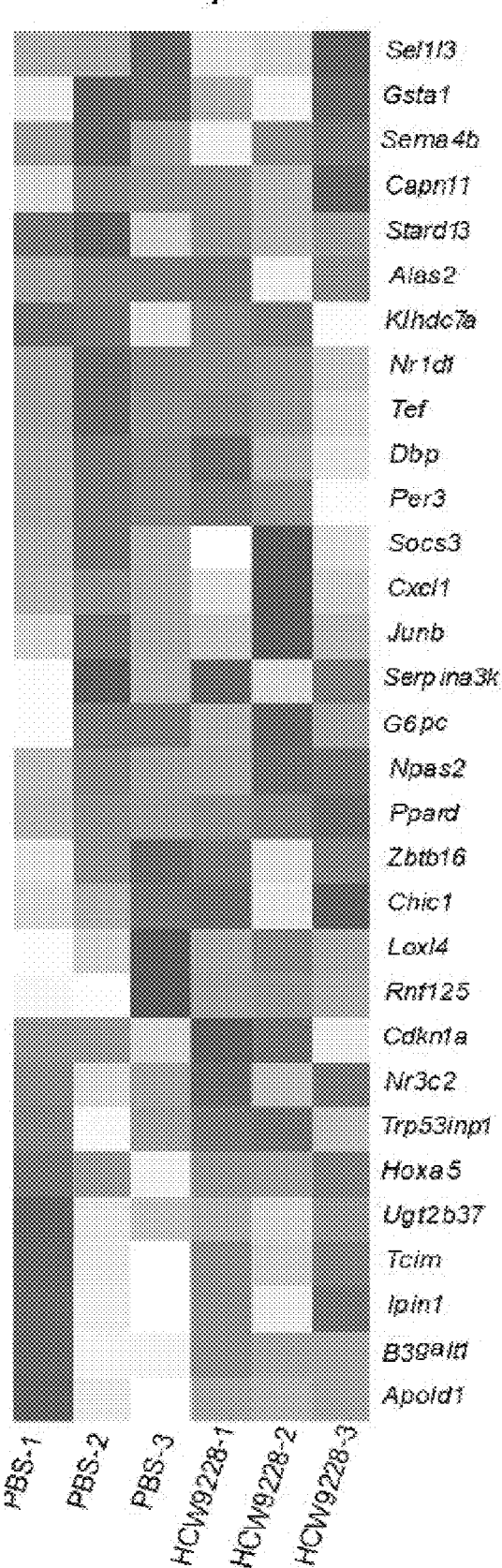
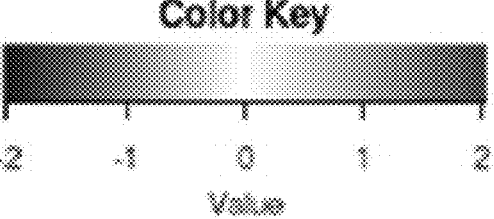
FIG. 34B

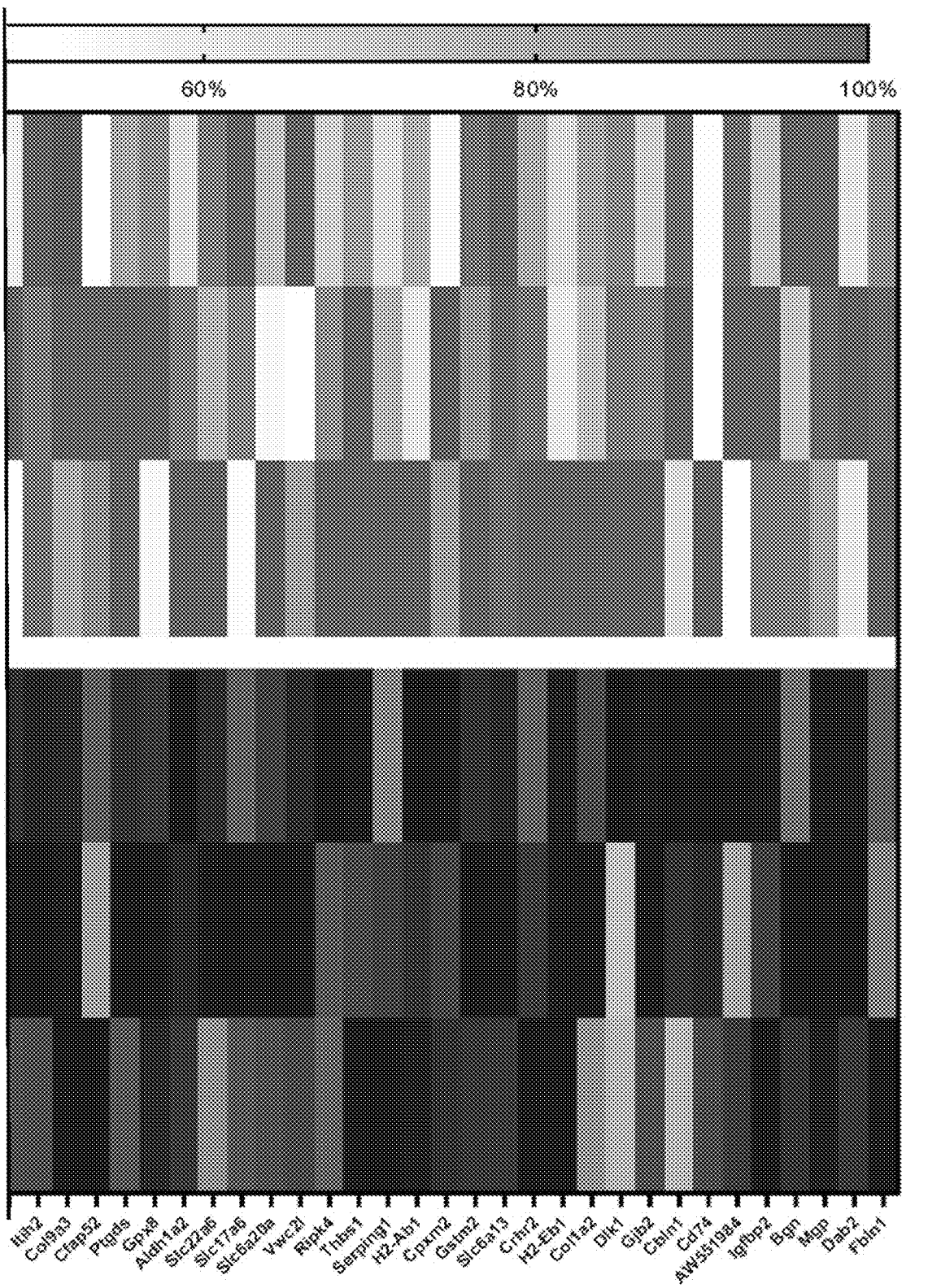
FIG. 35A (Con't)

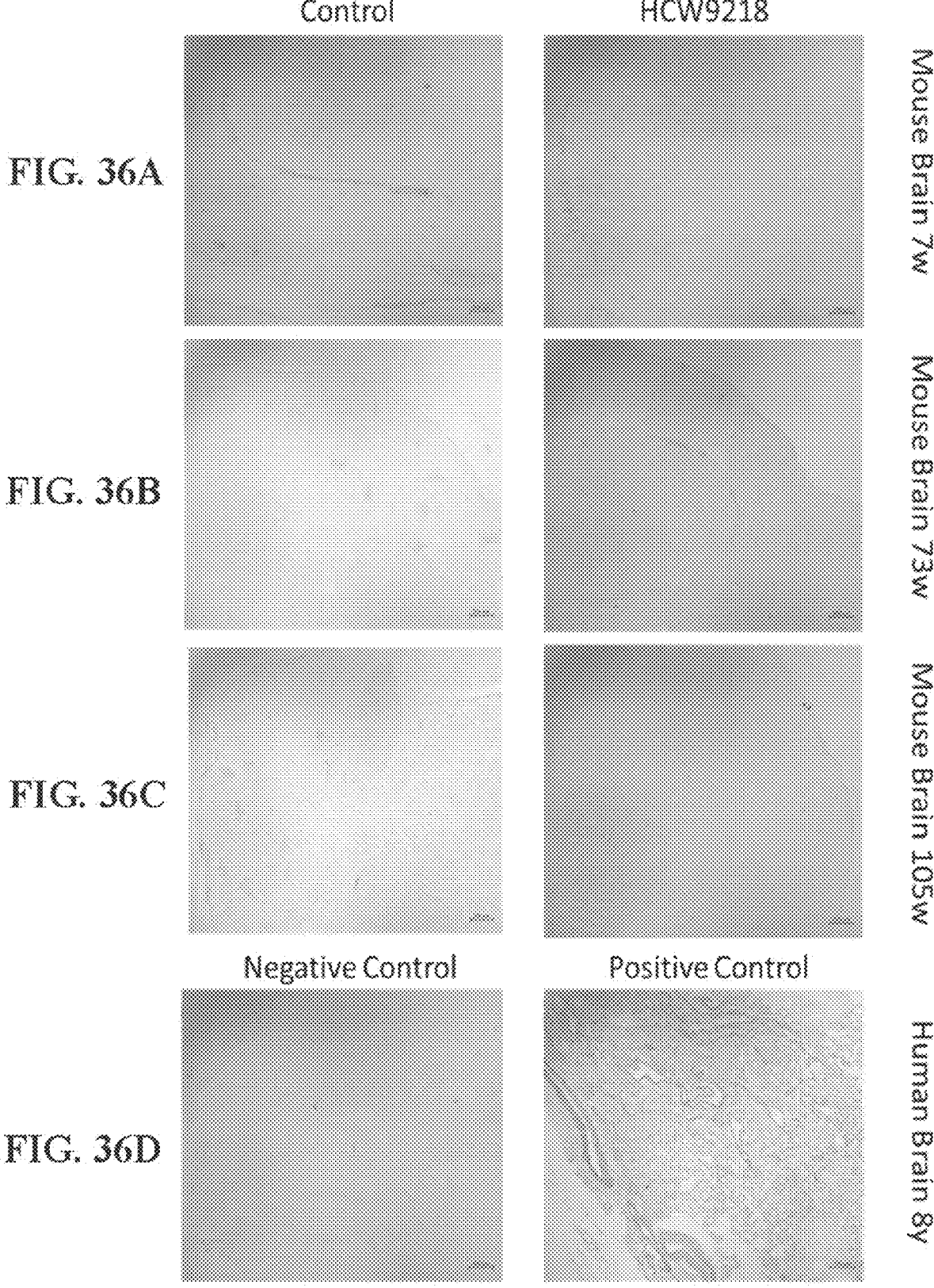

FIG. 38B

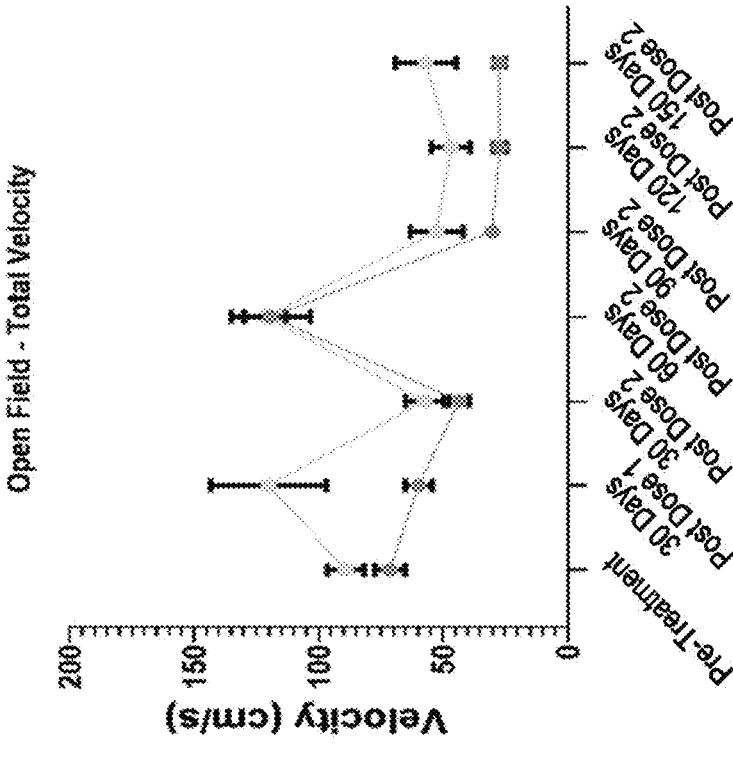
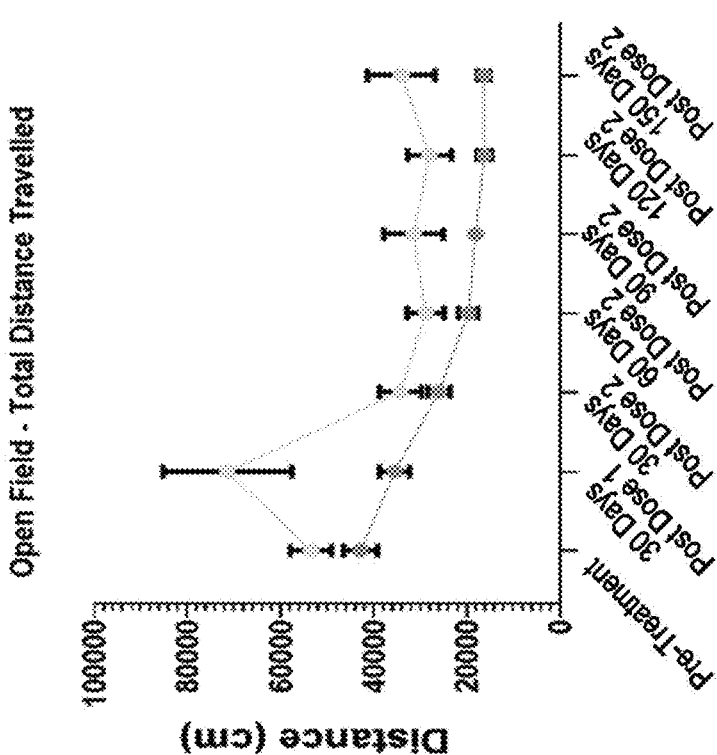
FIG. 38B (CONT)

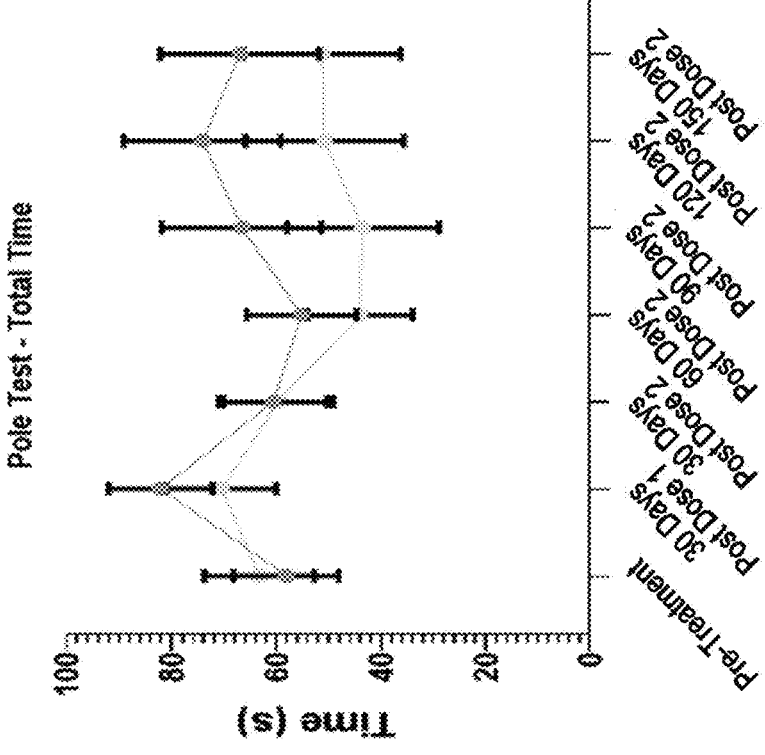
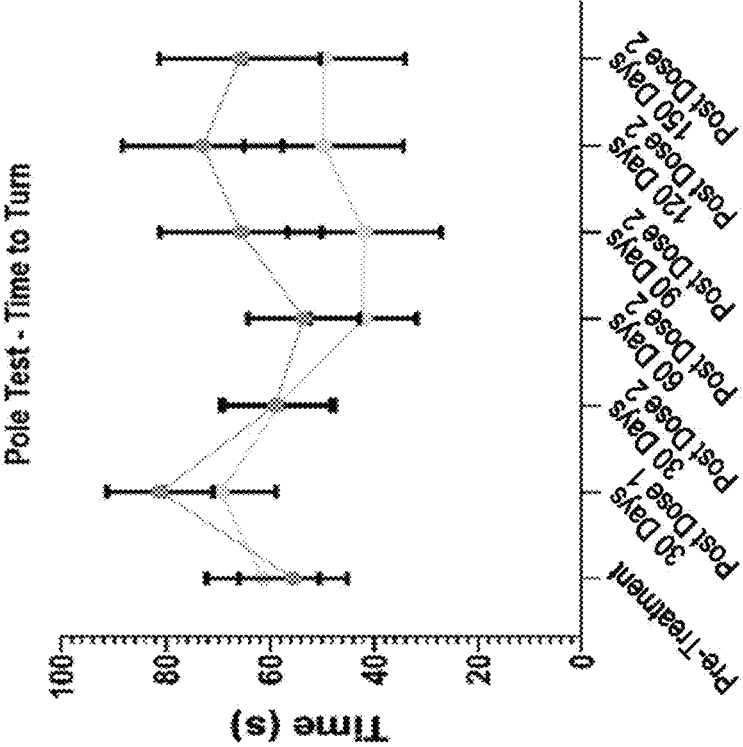
FIG. 38B (CONT)

SEQUENCE LISTING

```
Sequence total quantity: 71
SEQ ID NO: 1            moltype = AA  length = 219
FEATURE                 Location/Qualifiers
source                  1..219
                        mol_type = protein
                        organism = Homo sapiens
SEQUENCE: 1
SGTTNTVAAY NLTWKSTNFK TILEWEPKPV NQVYTVQIST KSGDWKSKCF YTTDTECDLT   60
DEIVKDVKQT YLARVFSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 2            moltype = AA  length = 136
FEATURE                 Location/Qualifiers
source                  1..136
                        mol_type = protein
                        organism = Homo sapiens
SEQUENCE: 2
IPPHVQKSVN NDMIVTDNNG AVKFPQLCKF CDVRFSTCDN QKSCMSNCSI TSICEKPQEV   60
CVAVWRKNDE NITLETVCHD PKLPYHDFIL EDAASPKCIM KEKKKPGETF FMCSCSSDEC  120
```

```
NDNIIFSEEY NTSNPD                                                     136

SEQ ID NO: 3                  moltype = AA   length = 15
FEATURE                       Location/Qualifiers
source                        1..15
                              mol_type = protein
                              organism = synthetic construct
SEQUENCE: 3
GGGGSGGGGS GGGGS                                                      15

SEQ ID NO: 4                  moltype = AA   length = 287
FEATURE                       Location/Qualifiers
source                        1..287
                              mol_type = protein
                              organism = synthetic construct
SEQUENCE: 4
IPPHVQKSVN NDMIVTDNNG AVKFPQLCKF CDVRFSTCDN QKSCMSNCSI TSICEKPQEV     60
CVAVWRKNDE NITLETVCHD PKLPYHDFIL EDAASPKCIM KEKKKPGETF FMCSCSSDEC    120
NDNIIFSEEY NTSNPDGGGG SGGGGSGGGG SIPPHVQKSV NNDMIVTDNN GAVKFPQLCK    180
FCDVRFSTCD NQKSCMSNCS ITSICEKPQE VCVAVWRKND ENITLETVCH DPKLPYHDFI    240
LEDAASPKCI MKEKKKPGET FFMCSCSSDE CNDNIIFSEE YNTSNPD                  287

SEQ ID NO: 5                  moltype = AA   length = 352
FEATURE                       Location/Qualifiers
source                        1..352
                              mol_type = protein
                              organism = synthetic construct
SEQUENCE: 5
IPPHVQKSVN NDMIVTDNNG AVKFPQLCKF CDVRFSTCDN QKSCMSNCSI TSICEKPQEV     60
CVAVWRKNDE NITLETVCHD PKLPYHDFIL EDAASPKCIM KEKKKPGETF FMCSCSSDEC    120
NDNIIFSEEY NTSNPDGGGG SGGGGSGGGG SIPPHVQKSV NNDMIVTDNN GAVKFPQLCK    180
FCDVRFSTCD NQKSCMSNCS ITSICEKPQE VCVAVWRKND ENITLETVCH DPKLPYHDFI    240
LEDAASPKCI MKEKKKPGET FFMCSCSSDE CNDNIIFSEE YNTSNPDITC PPPMSVEHAD    300
IWVKSYSLYS RERYICNSGF KRKAGTSSLT ECVLNKATNV AHWTTPSLKC IR           352

SEQ ID NO: 6                  moltype = AA   length = 620
FEATURE                       Location/Qualifiers
source                        1..620
                              mol_type = protein
                              organism = synthetic construct
SEQUENCE: 6
IPPHVQKSVN NDMIVTDNNG AVKFPQLCKF CDVRFSTCDN QKSCMSNCSI TSICEKPQEV     60
CVAVWRKNDE NITLETVCHD PKLPYHDFIL EDAASPKCIM KEKKKPGETF FMCSCSSDEC    120
NDNIIFSEEY NTSNPDGGGG SGGGGSGGGG SIPPHVQKSV NNDMIVTDNN GAVKFPQLCK    180
FCDVRFSTCD NQKSCMSNCS ITSICEKPQE VCVAVWRKND ENITLETVCH DPKLPYHDFI    240
LEDAASPKCI MKEKKKPGET FFMCSCSSDE CNDNIIFSEE YNTSNPDSGT TNTVAAYNLT    300
WKSTNFKTIL EWEPKPVNQV YTVQISTKSG DWKSKCFYTT DTECDLTDEI VKDVKQTYLA    360
RVFSYPAGNV ESTGSAGEPL YENSPEFTPY LETNLGQPTI QSFEQVGTKV NVTVEDERTL    420
VRRNNTFLSL RDVFGKDLIY TLYYWKSSSS GKKTAKTNTN EFLIDVDKGE NYCFSVQAVI    480
PSRTVNRKST DSPVECMGQE KGEFRENWVN VISDLKKIED LIQSMHIDAT LYTESDVHPS    540
CKVTAMKCFL LELQVISLES GDASIHDTVE NLIILANNSL SSNGNVTESG CKECEELEEK    600
NIKEFLQSFV HIVQMFINTS                                                620

SEQ ID NO: 7                  moltype = AA   length = 638
FEATURE                       Location/Qualifiers
source                        1..638
                              mol_type = protein
                              organism = synthetic construct
SEQUENCE: 7
MKWVTFISLL FLFSSAYSIP PHVQKSVNND MIVTDNNGAV KFPQLCKFCD VRFSTCDNQK     60
SCMSNCSITS ICEKPQEVCV AVWRKNDENI TLETVCHDPK LPYHDFILED AASPKCIMKE    120
KKKPGETFFM CSCSSDECND NIIFSEEYNT SNPDGGGGSG GGGSGGGGSI PPHVQKSVNN    180
DMIVTDNNGA VKFPQLCKFC DVRFSTCDNQ KSCMSNCSIT SICEKPQEVC VAVWRKNDEN    240
ITLETVCHDP KLPYHDFILE DAASPKCIMK EKKKPGETFF MCSCSSDECN DNIIFSEEYN    300
TSNPDSGTTN TVAAYNLTWK STNFKTILEW EPKPVNQVYT VQISTKSGDW KSKCFYTTDT    360
ECDLTDEIVK DVKQTYLARV FSYPAGNVES TGSAGEPLYE NSPEFTPYLE TNLGQPTIQS    420
FEQVGTKVNV TVEDERTLVR RNNTFLSLRD VFGKDLIYTL YYWKSSSSGK KTAKTNTNEF    480
LIDVDKGENY CFSVQAVIPS RTVNRKSTDS PVECMGQEKG EFRENWVNVI SDLKKIEDLI    540
QSMHIDATLY TESDVHPSCK VTAMKCFLLE LQVISLESGD ASIHDTVENL IILANNSLSS    600
NGNVTESGCK ECEELEEKNI KEFLQSFVHI VQMFINTS                            638

SEQ ID NO: 8                  moltype = AA   length = 370
FEATURE                       Location/Qualifiers
source                        1..370
                              mol_type = protein
                              organism = synthetic construct
SEQUENCE: 8
MKWVTFISLL FLFSSAYSIP PHVQKSVNND MIVTDNNGAV KFPQLCKFCD VRFSTCDNQK     60
SCMSNCSITS ICEKPQEVCV AVWRKNDENI TLETVCHDPK LPYHDFILED AASPKCIMKE    120
```

-continued

```
KKKPGETFFM CSCSSDECND NIIFSEEYNT SNPDGGGGSG GGGSGGGGSI PPHVQKSVNN   180
DMIVTDNNGA VKFPQLCKFC DVRFSTCDNQ KSCMSNCSIT SICEKPQEVC VAVWRKNDEN   240
ITLETVCHDP KLPYHDFILE DAASPKCIMK EKKKPGETFF MCSCSSDECN DNIIFSEEYN   300
TSNPDITCPP PMSVEHADIW VKSYSLYSRE RYICNSGFKR KAGTSSLTEC VLNKATNVAH   360
WTTPSLKCIR                                                         370

SEQ ID NO: 9              moltype = DNA  length = 657
FEATURE                   Location/Qualifiers
source                    1..657
                          mol_type = genomic DNA
                          organism = Homo sapiens
SEQUENCE: 9
agcggcacaa ccaacacagt cgctgcctat aacctcactt ggaagagcac caacttcaaa   60
accatcctcg aatgggaacc caaaccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtga gagcactgg ttccgctggc gagcctttat acgagaacag ccccgaattt   300
acccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480
tcttcctccg gcaagaagac agctaaaacc aacacaaacg agtttttaat cgacgtggat   540
aaaggcgaaa actactgttt cagcgtgcaa gctgtgatcc cctcccggac cgtgaatagg   600
aaaagcaccg atagccccgt tgagtgcatg ggccaagaaa agggcgagtt ccgggag      657

SEQ ID NO: 10             moltype = AA  length = 219
FEATURE                   Location/Qualifiers
source                    1..219
                          mol_type = protein
                          organism = Homo sapiens
SEQUENCE: 10
SGTTNTVAAY NLTWKSTNFA TALEWEPKPV NQVYTVQIST KSGDWKSKCF YTTDTECALT   60
DEIVKDVKQT YLARVFSYPA GNVESTGSAG EPLYENSPEF TPYLETNLGQ PTIQSFEQVG   120
TKVNVTVEDE RTLVARNNTA LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 11             moltype = AA  length = 219
FEATURE                   Location/Qualifiers
source                    1..219
                          mol_type = protein
                          organism = Homo sapiens
SEQUENCE: 11
SGTTNTVAAY NLTWKSTNFA TALEWEPKPV NQVYTVQIST KSGDAKSKCF YTTDTECALT   60
DEIVKDVKQT YLARVFSYPA GNVESTGSAG EPLAENSPEF TPYLETNLGQ PTIQSFEQVG   120
TKVNVTVEDE RTLVARNNTA LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 12             moltype = AA  length = 223
FEATURE                   Location/Qualifiers
source                    1..223
                          mol_type = protein
                          organism = Mus musculus
SEQUENCE: 12
AGIPEKAFNL TWISTDFKTI LEWQPKPTNY TYTVQISDRS RNWKNKCFST TDTECDLTDE   60
IVKDVTWAYE AKVLSVPRRN SVHGDGDQLV IHGEEPPFTN APKFLPYRDT NLGQPVIQQF   120
EQDGRKLNVV VKDSLTLVRK NGTFLTLRQV FGKDLGYIIT YRKGSSTGKK TNITNTNEFS   180
IDVEEGVSYC FFVQAMIFSR KTNQNSPGSS TVCTEQWKSF LGE                     223

SEQ ID NO: 13             moltype = AA  length = 224
FEATURE                   Location/Qualifiers
source                    1..224
                          mol_type = protein
                          organism = Rattus rattus
SEQUENCE: 13
AGTPPGKAFN LTWISTDFKT ILEWQPKPTN YTYTVQISDR SRNWKYKCTG TTDTECDLTD   60
EIVKDVNWTY EARVLSVPWR NSTHGKETLF GTHGEEPPFT NARKFLPYRD TKIGQPVIQK   120
YEQGGTKLKV TVKDSFTLVR KNGTFLTLRQ VFGNDLGYIL TYRKDSSTGR KTNTTHTNEF   180
LIDVEKGVSY CFFAQAVIFS RKTNHKSPES ITKCTEQWKS VLGE                    224

SEQ ID NO: 14             moltype = DNA  length = 45
FEATURE                   Location/Qualifiers
source                    1..45
                          mol_type = other DNA
                          organism = synthetic construct
SEQUENCE: 14
ggcggtggag gatccggagg aggtggctcc ggcggcggag gatct                    45

SEQ ID NO: 15             moltype = AA  length = 8
FEATURE                   Location/Qualifiers
source                    1..8
```

```
                              mol_type = protein
                              organism = synthetic construct
SEQUENCE: 15
GGGSGGGS                                                        8

SEQ ID NO: 16           moltype = AA   length = 65
FEATURE                 Location/Qualifiers
source                  1..65
                        mol_type = protein
                        organism = Homo sapiens
SEQUENCE: 16
ITCPPPMSVE HADIWVKSYS LYSRERYICN SGFKRKAGTS SLTECVLNKA TNVAHWTTPS  60
LKCIR                                                            65

SEQ ID NO: 17           moltype = DNA   length = 195
FEATURE                 Location/Qualifiers
source                  1..195
                        mol_type = genomic DNA
                        organism = Homo sapiens
SEQUENCE: 17
attacatgcc cccctcccat gagcgtggag cacgccgaca tctgggtgaa gagctatagc  60
ctctacagcc gggagaggta tatctgtaac agcggcttca agaggaaggc cggcaccagc 120
agcctcaccg agtgcgtgct gaataaggct accaacgtgg ctcactggac aacaccctct 180
ttaaagtgca tccgg                                                195

SEQ ID NO: 18           moltype = AA   length = 114
FEATURE                 Location/Qualifiers
source                  1..114
                        mol_type = protein
                        organism = Homo sapiens
SEQUENCE: 18
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 19           moltype = DNA   length = 342
FEATURE                 Location/Qualifiers
source                  1..342
                        mol_type = genomic DNA
                        organism = Homo sapiens
SEQUENCE: 19
aactgggtga acgtcatcag cgatttaaag aagatcgaag atttaattca gtccatgcat  60
atcgacgcca ctttatacac agaatccgac gtgcacccct cttgtaaggt gaccgccatg 120
aaatgttttt tactggagct gcaagttatc tctttagaga gcggagacgc tagcatccac 180
gacaccgtgg agaatttaat cattttagcc aataactctt tatccagcaa cggcaacgtg 240
acagagtccg gctgcaagga gtgcgaagag ctggaggaga agaacatcaa ggagtttctg 300
caatcctttg tgcacattgt ccagatgttc atcaatacct cc                   342

SEQ ID NO: 20           moltype = AA   length = 18
FEATURE                 Location/Qualifiers
source                  1..18
                        mol_type = protein
                        organism = synthetic construct
SEQUENCE: 20
MKWVTFISLL FLFSSAYS                                              18

SEQ ID NO: 21           moltype = DNA   length = 54
FEATURE                 Location/Qualifiers
source                  1..54
                        mol_type = other DNA
                        organism = synthetic construct
SEQUENCE: 21
atgaaatggg tgacctttat ttctttactg ttcctcttta gcagcgccta ctcc        54

SEQ ID NO: 22           moltype = DNA   length = 54
FEATURE                 Location/Qualifiers
source                  1..54
                        mol_type = other DNA
                        organism = synthetic construct
SEQUENCE: 22
atgaagtggg tcacatttat ctctttactg ttcctcttct ccagcgccta cagc        54

SEQ ID NO: 23           moltype = DNA   length = 54
FEATURE                 Location/Qualifiers
source                  1..54
                        mol_type = other DNA
                        organism = synthetic construct
SEQUENCE: 23
atgaaatggg tgacctttat ttctttactg ttcctcttta gcagcgccta ctcc        54
```

```
SEQ ID NO: 24          moltype = AA  length = 16
FEATURE                Location/Qualifiers
source                 1..16
                       mol_type = protein
                       organism = synthetic construct
SEQUENCE: 24
MKCLLYLAFL FLGVNC                                                        16

SEQ ID NO: 25          moltype = AA  length = 58
FEATURE                Location/Qualifiers
source                 1..58
                       mol_type = protein
                       organism = synthetic construct
SEQUENCE: 25
MGQIVTMFEA LPHIIDEVIN IVIIVLIIIT SIKAVYNFAT CGILALVSFL FLAGRSCG     58

SEQ ID NO: 26          moltype = AA  length = 97
FEATURE                Location/Qualifiers
source                 1..97
                       mol_type = protein
                       organism = synthetic construct
SEQUENCE: 26
MPNHQSGSPT GSSDLLLSGK KQRPHLALRR KRRREMRKIN RKVRRMNLAP IKEKTAWQHL     60
QALISEAEEV LKTSQTPQNS LTLFLALLSV LGPPVTG                             97

SEQ ID NO: 27          moltype = AA  length = 30
FEATURE                Location/Qualifiers
source                 1..30
                       mol_type = protein
                       organism = synthetic construct
SEQUENCE: 27
MDSKGSSQKG SRLLLLLVVS NLLLCQGVVS                                        30

SEQ ID NO: 28          moltype = AA  length = 16
FEATURE                Location/Qualifiers
source                 1..16
                       mol_type = protein
                       organism = synthetic construct
SEQUENCE: 28
MKCLLYLAFL FLGVNC                                                        16

SEQ ID NO: 29          moltype = AA  length = 15
FEATURE                Location/Qualifiers
source                 1..15
                       mol_type = protein
                       organism = synthetic construct
SEQUENCE: 29
GLNDIFEAQK IEWHE                                                         15

SEQ ID NO: 30          moltype = AA  length = 26
FEATURE                Location/Qualifiers
source                 1..26
                       mol_type = protein
                       organism = synthetic construct
SEQUENCE: 30
KRRWKKNFIA VSAANRFKKI SSSGAL                                            26

SEQ ID NO: 31          moltype = AA  length = 6
FEATURE                Location/Qualifiers
source                 1..6
                       mol_type = protein
                       organism = synthetic construct
SEQUENCE: 31
EEEEEE                                                                   6

SEQ ID NO: 32          moltype = AA  length = 13
FEATURE                Location/Qualifiers
source                 1..13
                       mol_type = protein
                       organism = synthetic construct
SEQUENCE: 32
GAPVPYPDPL EPR                                                          13

SEQ ID NO: 33          moltype = AA  length = 8
FEATURE                Location/Qualifiers
source                 1..8
                       mol_type = protein
                       organism = synthetic construct
SEQUENCE: 33
```

-continued

```
DYKDDDDK                                                          8

SEQ ID NO: 34         moltype = AA   length = 9
FEATURE               Location/Qualifiers
source                1..9
                      mol_type = protein
                      organism = synthetic construct
SEQUENCE: 34
YPYDVPDYA                                                         9

SEQ ID NO: 35         moltype = AA   length = 5
FEATURE               Location/Qualifiers
source                1..5
                      mol_type = protein
                      organism = synthetic construct
SEQUENCE: 35
HHHHH                                                             5

SEQ ID NO: 36         moltype = AA   length = 6
FEATURE               Location/Qualifiers
source                1..6
                      mol_type = protein
                      organism = synthetic construct
SEQUENCE: 36
HHHHHH                                                            6

SEQ ID NO: 37         moltype = AA   length = 7
FEATURE               Location/Qualifiers
source                1..7
                      mol_type = protein
                      organism = synthetic construct
SEQUENCE: 37
HHHHHHH                                                           7

SEQ ID NO: 38         moltype = AA   length = 8
FEATURE               Location/Qualifiers
source                1..8
                      mol_type = protein
                      organism = synthetic construct
SEQUENCE: 38
HHHHHHHH                                                          8

SEQ ID NO: 39         moltype = AA   length = 9
FEATURE               Location/Qualifiers
source                1..9
                      mol_type = protein
                      organism = synthetic construct
SEQUENCE: 39
HHHHHHHHH                                                         9

SEQ ID NO: 40         moltype = AA   length = 10
FEATURE               Location/Qualifiers
source                1..10
                      mol_type = protein
                      organism = synthetic construct
SEQUENCE: 40
HHHHHHHHHH                                                        10

SEQ ID NO: 41         moltype = AA   length = 10
FEATURE               Location/Qualifiers
source                1..10
                      mol_type = protein
                      organism = synthetic construct
SEQUENCE: 41
EQKLISEEDL                                                        10

SEQ ID NO: 42         moltype = AA   length = 18
FEATURE               Location/Qualifiers
source                1..18
                      mol_type = protein
                      organism = synthetic construct
SEQUENCE: 42
TKENPRSNQE ESYDDNES                                               18

SEQ ID NO: 43         moltype = AA   length = 15
FEATURE               Location/Qualifiers
source                1..15
                      mol_type = protein
                      organism = synthetic construct
```

```
SEQUENCE: 43
KETAAAKFER QHMDS                                                                15

SEQ ID NO: 44          moltype = AA  length = 38
FEATURE                Location/Qualifiers
source                 1..38
                       mol_type = protein
                       organism = synthetic construct
SEQUENCE: 44
MDEKTTGWRG GHVVEGLAGE LEQLRARLEH HPQGQREP                                        38

SEQ ID NO: 45          moltype = AA  length = 13
FEATURE                Location/Qualifiers
source                 1..13
                       mol_type = protein
                       organism = synthetic construct
SEQUENCE: 45
SLAELLNAGL GGS                                                                   13

SEQ ID NO: 46          moltype = AA  length = 8
FEATURE                Location/Qualifiers
source                 1..8
                       mol_type = protein
                       organism = synthetic construct
SEQUENCE: 46
TQDPSRVG                                                                         8

SEQ ID NO: 47          moltype = AA  length = 12
FEATURE                Location/Qualifiers
source                 1..12
                       mol_type = protein
                       organism = synthetic construct
SEQUENCE: 47
PDRVRAVSHW SS                                                                    12

SEQ ID NO: 48          moltype = AA  length = 8
FEATURE                Location/Qualifiers
source                 1..8
                       mol_type = protein
                       organism = synthetic construct
SEQUENCE: 48
WSHPQFEK                                                                         8

SEQ ID NO: 49          moltype = AA  length = 6
FEATURE                Location/Qualifiers
source                 1..6
                       mol_type = protein
                       organism = synthetic construct
SEQUENCE: 49
CCPGCC                                                                           6

SEQ ID NO: 50          moltype = AA  length = 10
FEATURE                Location/Qualifiers
source                 1..10
                       mol_type = protein
                       organism = synthetic construct
SEQUENCE: 50
EVHTNQDPLD                                                                       10

SEQ ID NO: 51          moltype = AA  length = 14
FEATURE                Location/Qualifiers
source                 1..14
                       mol_type = protein
                       organism = synthetic construct
SEQUENCE: 51
GKPIPNPLLG LDST                                                                  14

SEQ ID NO: 52          moltype = AA  length = 11
FEATURE                Location/Qualifiers
source                 1..11
                       mol_type = protein
                       organism = synthetic construct
SEQUENCE: 52
YTDIEMNRLG K                                                                     11

SEQ ID NO: 53          moltype = AA  length = 8
FEATURE                Location/Qualifiers
source                 1..8
                       mol_type = protein
```

-continued

```
                         organism = synthetic construct
SEQUENCE: 53
DLYDDDDK                                                      8

SEQ ID NO: 54          moltype = AA   length = 10
FEATURE                Location/Qualifiers
source                 1..10
                       mol_type = protein
                       organism = synthetic construct
SEQUENCE: 54
EQKLISEEDL                                                   10

SEQ ID NO: 55          moltype = DNA   length = 408
FEATURE                Location/Qualifiers
source                 1..408
                       mol_type = genomic DNA
                       organism = Homo sapiens
SEQUENCE: 55
atcccccccc atgtgcaaaa gagcgtgaac aacgatatga tcgtgaccga caacaacggc   60
gccgtgaagt ttcccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgat            408

SEQ ID NO: 56          moltype = DNA   length = 408
FEATURE                Location/Qualifiers
source                 1..408
                       mol_type = genomic DNA
                       organism = Homo sapiens
SEQUENCE: 56
attcctcccc acgtgcagaa gagcgtgaat aatgacatga tcgtgaccga taacaatggc   60
gccgtgaaat ttcccagct gtgcaaattc tgcgatgtga ggttttccac ctgcgacaac  120
cagaagtcct gtatgagcaa ctgctccatc acctccatct gtgagaagcc tcaggaggtg  180
tgcgtggctg tctggcggaa gaatgacgag aatatcaccc tggaaaccgt ctgccacgat  240
cccaagctgc cctaccacga tttcatcctg gaagacgccg ccagccctaa gtgcatcatg  300
aaagagaaaa agaagcctgg cgagacctt ttcatgtgct cctgcagcag cgacgaatgc  360
aacgacaata tcatctttag cgaggaatac aataccagca acccccgac            408

SEQ ID NO: 57          moltype = DNA   length = 861
FEATURE                Location/Qualifiers
source                 1..861
                       mol_type = other DNA
                       organism = synthetic construct
SEQUENCE: 57
atcccccccc atgtgcaaaa gagcgtgaac aacgatatga tcgtgaccga caacaacggc   60
gccgtgaagt ttcccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaacccga c                                        861

SEQ ID NO: 58          moltype = DNA   length = 1860
FEATURE                Location/Qualifiers
source                 1..1860
                       mol_type = other DNA
                       organism = synthetic construct
SEQUENCE: 58
atcccccccc atgtgcaaaa gagcgtgaac aacgatatga tcgtgaccga caacaacggc   60
gccgtgaagt ttcccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
```

```
gagaatatca ccctggaaac cgtctgccac gatcccaagc tgccctacca cgatttcatc   720
ctggaagacg ccgccagccc taagtgcatc atgaaagaga aaaagaagcc tggcgagacc   780
tttttcatgt gctcctgcag cagcgacgaa tgcaacgaca atatcatctt tagcgaggaa   840
tacaatacca gcaaccccga cagcggcaca accaacacag tcgctgccta taacctcact   900
tggaagagca ccaacttcaa aaccatcctc gaatgcgaac ccaaacccgt taaccaagtt   960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagcctta   1140
tacgagaaca gccccgaatt tacccttac ctcgagacca atttaggaca gcccaccatc   1200
caaagctttg agcaagttgg cacaaaggtg aatgtgacag tggaggacga gcggactta   1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagttttaa tcgacgtgga taaaggcgaa aactactgtt tcagcgtgca agctgtgatc  1440
ccctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcaccctct   1620
tgtaaggtga ccgccatgaa atgttttta ctggagctgc aagttatctc tttagagagc   1680
ggagacgcta gcatccacga caccgtggag aatttaatca ttttagccaa taactctta   1740
tccagcaacg gcaacgtgac agagtccggc tgcaaggagt gcgaagagct ggaggagaag  1800
aacatcaagg agtttctgca atcctttgtg cacattgtcc agatgttcat caataccttcc  1860
```

SEQ ID NO: 59            moltype = DNA  length = 1914
FEATURE                  Location/Qualifiers
source                   1..1914
                         mol_type = other DNA
                         organism = synthetic construct
SEQUENCE: 59

```
atgaagtggg tgaccttcat cagcctgctg ttcctgttct ccagcgccta ctccatcccc   60
ccccatgtgc aaaagagcgt gaacaacgat atgatcgtga ccgacaacaa cggcgccgtg   120
aagtttcccc agctctgcaa gttctgcgat gtcaggtca gcacctgcga taatcagaag   180
tcctgcatgt ccaactgcag catcacctcc atctgcgaga agccccaaga agtgtgcgtg   240
gccgtgtggc ggaaaaatga cgagaacatc accctggaga ccgtgtgtca cgaccccaag   300
ctcccttatc acgacttcat tctggaggac gctgcctccc ccaaatgcat catgaaggag   360
aagaagaagc ccggagagac cttctttatg tgttcctgta gcagcgacga gtgtaacgac   420
aacatcatct tcagcgaaga gtacaacacc agcaaccctg atggaggtgg cggatccgga   480
ggtggaggtt ctggtggagg tgggagtatt cctcccacg tgcagaagag cgtgaataat   540
gacatgatcg tgaccgataa caatggcgcc gtgaaatttc cccagctgtg caaattctgc   600
gatgtgaggt ttccacctg cgacaaccag aagtcctgta tgagcaactg ctccatcacc   660
tccatctgtg agaagcctca ggaggtgtgc gtggctgtct ggcggaagaa tgacgagaat   720
atcaccctgg aaaccgtctg ccacgatccc aagctgccct accacgattt catcctggaa   780
gacgccgcca gccctaagtg catcatgaaa gagaaaaaga agcctggcga gacctttttc   840
atgtgctcct gcagcagcga cgaatgcaac gacaatatca tctttagcga ggaatacaat   900
accagcaact caaaaccat cctcgaatgg gaacccaaac ccgttaacca gttatcacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccggtg   1140
tttagctacc ccgccggcaa tgtggagagc actggttccg ctggcgagcc tttatacag   1200
aacagccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat ctacacactg   1380
tattactgga agtcctcttc ctccggcaag aagacagcta aaaccaacac aaacgagttc   1440
ttaatcgacg tggataaagg cgaaaactac tgtttcagcg tgcaagctgt gatcccctcc   1500
cggaccgtga ataggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cacttttac acagaatccg acgtgcaccc tcttgtaag   1680
gtgaccgcca tgaaatgttt tttactggag ctgcaagtta tctctttaga gagcggagac   1740
gctagcatcc acgacaccgt ggagaattta atcattttag ccaataactc tttatccagc   1800
aacggcaacg tgacagagtc cggctgcaag gagtgcgaag agctggagga agaacatc   1860
aaggagtttc tgcaatcctt tgtgcacatt gtccagatgt tcatcaatac ctcc   1914
```

SEQ ID NO: 60            moltype = DNA  length = 1056
FEATURE                  Location/Qualifiers
source                   1..1056
                         mol_type = other DNA
                         organism = synthetic construct
SEQUENCE: 60

```
atcccccccc atgtgcaaaa gagcgtgaac aacgatatga tcgtgaccga caacaacggc   60
gccgtgaagt ttccccagct ctgcaagttc tgcgatgtca ggttcagcac ctgcgataat   120
cagaagtcct gcatgtccaa ctgcagcatc acctccatct gcgagaagcc ccaagaagtg   180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga gaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga aatttcccca gctgtgcaaa   540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaaagaagcc tggcgagacc   780
```

```
tttttcatgt gctcctgcag cagcgacgaa tgcaacgaca atatcatctt tagcgaggaa  840
tacaatacca gcaaccccga cattacatgc cccctccca tgagcgtgga gcacgccgac   900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccgg                            1056
```

```
SEQ ID NO: 61              moltype = DNA   length = 1110
FEATURE                    Location/Qualifiers
source                     1..1110
                           mol_type = other DNA
                           organism = synthetic construct
SEQUENCE: 61
atgaagtggg tgaccttcat cagcctgctg ttcctgttct ccagcgccta ctccatcccc   60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcag catcacctcc atctgcgaga agccccaaga agtgtgcgtg   240
gccgtgtggc ggaaaaatga cgagaacatc accctggaga ccgtgtgtca cgaccccaag   300
ctcccttatc acgacttcat tctggaggac gctgcctccc caaatgcat catgaaggag   360
aagaagaagc ccggagagac cttctttatg tgttcctgta gcagcgacga gtgtaacgac   420
aacatcatct tcagcgaaga gtacaacacc agcaaccctg atggaggtgg cggatccgga   480
ggtggaggtt ctggtggagg tgggagtatt cctccccacg tgcagaagag cgtgaataat   540
gacatgatcg tgaccgataa caatggcgcc gtgaaatttc cccagctgtg caaattctgc   600
gatgtgaggt tttccacctg cgacaaccag aagtcctgta tgagcaactg ctccatcacc   660
tccatctgtg agaagcctca ggaggtgtgc gtggctgtct ggcggaagaa tgacgagaat   720
atcaccctgg aaaccgtctg ccacgatccc aagctgccct accacgattt catcctggaa   780
gacgccgcca gccctaagtg catcatgaaa gagaaaaaga agcctggcga gacctttttc   840
atgtgctcct gcagcagcga cgaatgcaac gacaatatca tctttagcga ggaatacaat   900
accagcaacc ccgacattac atgcccccct cccatgagcg tggagcacgc cgacatctgg   960
gtgaagagct atagcctcta cagccgggag aggtatatct gtaacagcgg cttcaagagg   1020
aaggccggca ccagcagcct caccgagtgc gtgctgaata aggctaccaa cgtggctcac   1080
tggacaacac cctctttaaa gtgcatccgg                                   1110
```

```
SEQ ID NO: 62              moltype = AA   length = 114
FEATURE                    Location/Qualifiers
source                     1..114
                           mol_type = protein
                           organism = Homo sapiens
SEQUENCE: 62
NWVNVISNLK KIEDLIQSMH IDATLYTESD VHPSCKVTAM KCFLLELQVI SLESGDASIH   60
DTVENLIILA NNSLSSNGNV TESGCKECEE LEEKNIKEFL QSFVHIVQMF INTS          114
```

```
SEQ ID NO: 63              moltype = DNA   length = 342
FEATURE                    Location/Qualifiers
source                     1..342
                           mol_type = genomic DNA
                           organism = Homo sapiens
SEQUENCE: 63
aactgggtga atgtaataag taatttgaaa aaaattgaag atcttattca atctatgcat   60
attgatgcta cttatatac ggaaagtgat gttcacccca gttgcaaagt aacagcaatg   120
aagtgctttc tcttggagtt acaagttatt tcacttgagt ccggagatgc aagtattcat  180
gatacagtag aaaatctgat catcctagca aacaacagtt tgtcttctaa tgggaatgta  240
acagaatctg gatgcaaaga atgtgaggaa ctggaggaaa aaaatattaa agaatttttg  300
cagagttttg tacatattgt ccaaatgttc atcaacactt ct                     342
```

```
SEQ ID NO: 64              moltype = AA   length = 352
FEATURE                    Location/Qualifiers
source                     1..352
                           mol_type = protein
                           organism = synthetic construct
SEQUENCE: 64
IPPHVQKSVN NDMIVTDNNG AVKFPQLCKF CDVRFSTCDN QKSCMSNCSI TSICEKPQEV   60
CVAVWRKNDE NITLETVCHD PKLPYHDFIL EDAASPKCIM KEKKKPGETF FMCSCSSDEC   120
NDNIIFSEEY NTSNPDGGGG SGGGGSGGGG SIPPHVQKSV NNDMIVTDNN GAVKFPQLCK   180
FCDVRFSTCD NQKSCMSNCS ITSICEKPQE VCVAVWRKND ENITLETVCH DPKLPYHDFI   240
LEDAASPKCI MKEKKKPGET FFMCSCSSDE CNDNIIFSEE YNTSNPDITC PPPMSVEHAD   300
IWVKSYSLYS RERYICNSGF KRKAGTSSLT ECVLNKATNV AHWTTPSLKC IR           352
```

```
SEQ ID NO: 65              moltype = DNA   length = 1056
FEATURE                    Location/Qualifiers
source                     1..1056
                           mol_type = other DNA
                           organism = synthetic construct
SEQUENCE: 65
atcccccccc atgtgcaaaa gagcgtgaac aacgatatga tcgtgaccga caacaacggc   60
gccgtgaagt tccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
```

```
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga aatttcccca gctgtgcaaa   540
ttctgcgatg tgaggttttc cacctgcgac aaccagaagt cctgtatgag caactgctcc   600
atcacctcca tctgtgagaa gcctcaggag gtgtgcgtga ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaaagaagcc tggcgagacc   780
tttttcatgt gctcctgcag cagcgacgaa tgcaacgaca atatcatctt tagcgaggaa   840
tacaatacca gcaaccccga cattacatgc ccccctccca tgagcgtgga gcacgccgac   900
atctgggtga gagctatag cctctacagc cgggagaggt atatctgtaa cagcggcttc   960
aagaggaagg ccggcaccag cagcctcacc gagtgcgtgc tgaataaggc taccaacgtg  1020
gctcactgga caacccctc tttaaagtgc atccgg                             1056
```

SEQ ID NO: 66             moltype = AA  length = 370
FEATURE                   Location/Qualifiers
source                    1..370
                          mol_type = protein
                          organism = synthetic construct
SEQUENCE: 66
```
MKWVTFISLL FLFSSAYSIP PHVQKSVNND MIVTDNNGAV KFPQLCKFCD VRFSTCDNQK   60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                         370
```

SEQ ID NO: 67             moltype = DNA  length = 1110
FEATURE                   Location/Qualifiers
source                    1..1110
                          mol_type = other DNA
                          organism = synthetic construct
SEQUENCE: 67
```
atgaagtggg tgaccttcat cagcctgctg ttcctgttct ccagcgccta ctccatcccc   60
cccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga gccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc caaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctg aaaccgtctg ccacgatccc aagctgccct accacgattt catcctggaa  780
gacgccgcca gccctaagtg catcatgaaa gagaaaaaga agcctggcga gaccttttttc  840
atgtgctcct gcagcagcga cgaatgcaac gacaatatca tctttagcga ggaatacaat  900
accagcaacc ccgacattac atgcccccct cccatgagcg tggagcacgc cgacatctgg   960
gtgaagagct atagcctcta cagccggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg                                  1110
```

SEQ ID NO: 68             moltype = AA  length = 620
FEATURE                   Location/Qualifiers
source                    1..620
                          mol_type = protein
                          organism = synthetic construct
SEQUENCE: 68
```
IPPHVQKSVN NDMIVTDNNG AVKFPQLCKF CDVRFSTCDN QKSCMSNCSI TSICEKPQEV   60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISNLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620
```

SEQ ID NO: 69             moltype = DNA  length = 1860
FEATURE                   Location/Qualifiers
source                    1..1860
                          mol_type = other DNA
                          organism = synthetic construct
SEQUENCE: 69
```
atcccaccgc acgttcagaa gtcggtgaat aacgacatga tagtcactga caacaacggt   60
gcagtcaagt ttccacaact gtgtaaattt tgtgatgtga gattttccac ctgtgacaac  120
```

```
cagaaatcct gcatgagcaa ctgcagcatc acctccatct gtgagaagcc acaggaagtc    180
tgtgtggctg tatggagaaa gaatgacgag aacataacac tagagacagt ttgccatgac    240
cccaagctcc cctaccatga ctttattctg gaagatgctg cttctccaaa gtgcattatg    300
aaggaaaaaa aaaagcctgg tgagactttc ttcatgtgtt cctgtagctc tgatgagtgc    360
aatgcaacaa tcatcttctc agaagaatat aacaccagca atcctgacgg aggtggcgga    420
tccggaggtg gaggttctgg tggaggtggg agtattcctc cccacgtgca gaagagcgtg    480
aataatgaca tgatcgtgac cgataacaat ggcgccgtga aatttcccca gctgtgcaaa    540
ttctgcgatg tgaggttttc cacctgcgac aaccagaagt cctgtatgag caactgctcc    600
atcacctcca tctgtgagaa gcctcaggag gtgtgcgtgg ctgtctggcg gaagaatgac    660
gagaatatca ccctggaaac cgtctgccac gatcccaagc tgccctacca cgatttcatc    720
ctggaagacg ccgccagccc taagtgcatc atgaaagaga aaaagaagcc tggcgagacc    780
tttttcatgt gctcctgcag cagcgacgaa tgcaacgaca atatcatctt tagcgaggaa    840
tacaatacca gcaaccccga ctcaggcact acaaatactg tggcagcata taatttaact    900
tggaaatcaa ctaatttcaa gacaattttg gagtgggaaa ccaaacccgt caatcaagtc    960
tacactgttc aaataagcac taagtcagga gattgggaaa gcaaatgctt ttacacaaca    1020
gacacagagt gtgacctcac cgacgagatt gtgaaggatg tgaagcagac gtacttggca    1080
cgggtcttct cctacccggc agggaatgtg gagagcaccg gttctgctgg ggagcctctg    1140
tatgagaact ccccagagtt cacaccttac ctggagacaa acctcggaca gccaacaatt    1200
cagagttttg aacaggtggg aacaaaagtg aatgtgaccg tagaagatga acggacttta    1260
gtcagaagga acaacacttt cctaagcctc cgggatgttt ttggcaagga cttaatttat    1320
acactttatt attggaaatc ttcaagttca ggaaagaaaa cagccaaaac aaacactaat    1380
gagtttttga ttgatgtgga taaaggagaa aactactgtt tcagtgttca agcagtgatt    1440
ccctcccgaa cagttaaccg gaagagtaca gacagcccgg tagagtgtat gggccaggag    1500
aaaggggaat tcagagaaaa ctgggtgaat gtaataagta atttgaaaaa aattgaagat    1560
cttattcaat ctatgcatat tgatgctact ttatatacgg aaagtgatgt tcaccccagt    1620
tgcaaagtaa cagcaatgaa gtgctttctc ttggagttac aagttatttc acttgagtcc    1680
ggagatgcaa gtattcatga tacagtagaa aatctgatca tcctagcaaa caacagtttg    1740
tcttctaatg gaaatgtaac agaatctgga tgcaaagaat gtgaggaact ggaggaaaaa    1800
aatattaaag aatttttgca gagttttgta catattgtcc aaatgttcat caacacttct    1860
```

```
SEQ ID NO: 70           moltype = AA  length = 637
FEATURE                 Location/Qualifiers
source                  1..637
                        mol_type = protein
                        organism = synthetic construct
SEQUENCE: 70
MGVKVLFALI CIAVAEAIPP HVQKSVNNDM IVTDNNGAVK FPQLCKFCDV RFSTCDNQKS     60
CMSNCSITSI CEKPQEVCVA VWRKNDENIT LETVCHDPKL PYHDFILEDA ASPKCIMKEK    120
KKPGETFFMC SCSSDECNDN IIFSEEYNTS NPDGGGSGG GGSGGGGSIP PHVQKSVNND    180
MIVTDNNGAV KFPQLCKFCD VRFSTCDNQK SCMSNCSITS ICEKPQEVCV AVWRKNDENI    240
TLETVCHDPK LPYHDFILED AASPKCIMKE KKKPGETFFM CSCSSDECND NIIFSEEYNT    300
SNPDSGTTNT VAAYNLTWKS TNFKTILEWE PKPVNQVYTV QISTKSGDWK SKCFYTTDTE    360
CDLTDEIVKD VKQTYLARVF SYPAGNVEST GSAGEPLYEN SPEFTPYLET NLGQPTIQSF    420
EQVGTKVNVT VEDERTLVRR NNTFLSLRDV FGKDLIYTLY YWKSSSSGKK TAKTNTNEFL    480
IDVDKGENYC FSVQAVIPSR TVNRKSTDSP VECMGQEKGE FRENWVNVIS NLKKIEDLIQ    540
SMHIDATLYT ESDVHPSCKV TAMKCFLLEL QVISLESGDA SIHDTVENLI ILANNSLSSN    600
GNVTESGCKE CEELEEKNIK EFLQSFVHIV QMFINTS                             637
```

```
SEQ ID NO: 71           moltype = DNA  length = 1911
FEATURE                 Location/Qualifiers
source                  1..1911
                        mol_type = other DNA
                        organism = synthetic construct
SEQUENCE: 71
atgggagtga aagttctttt tgcccttatt tgtattgctg tggccgaggc catcccaccg     60
cacgttcaga agtcggtgaa taacgacatg atagtcactg acaacaacgg tgcagtcaag    120
tttcacaac tgtgtaaatt ttgtgatgtg agattttcca cctgtgacaa ccagaaatcc    180
tgcatgagca actgcagcat cacctccatc tgtgagaagc acaggaagt ctgtgtggct    240
gtatggagaa agaatgacga gaacataaca ctagagacag tttgccatga ccccaagctc    300
cctaccatg actttattct ggaagatgct gcttctccaa agtgcattat gaaggaaaaa    360
aaaaagcctg gtgagacttt cttcatgtgt cctgtagct ctgatgagtg caatgacaac    420
atcatcttct cagaagaata taacaccagc aatcctgacg gaggtggcgg atccggaggt    480
ggaggttctg gtggaggtgg gagtattcct ccccacgtgc agaagagcgt gaataatgac    540
atgatcgtga ccgataacaa tggcgccgtg aaatttcccc agctgtgcaa attctgcgat    600
gtgaggtttt ccacctgcga caaccagaag tcctgtatga gcaactgctc catcacctcc    660
atctgtgaga gcctcagga ggtgtgcgtg gctgtctggc ggaagaatga cgagaatatc    720
accctggaaa ccgtctgcca cgatcccaag ctgccctacc acgatttcat cctggaagac    780
gccgccagcc ctaagtgcat catgaaagag aaaaagaagc ctggcgagac cttttttcatg    840
tgctcctgca gcagcgacga atgcaacgac aatatcatct tagcgagga atacaatacc    900
agcaaccccg actcaggcac tacaaatact gtggcagcat ataatttaac ttggaaatca    960
actaatttca agacaatttt ggagtgggaa cccaaacccg tcaatcaagt ctacactgtt   1020
caaataagca ctaagtcagg agattggaaa agcaaatgct tttacacaac agacacagag   1080
tgtgacctca ccgacgagat tgtgaaggat gtgaagcaga cgtacttggc acgggtcttc   1140
tcctacccgg cagggaatgt ggagagcacc ggttctgctg gggagcctct gtatgagaac   1200
tccccagagt tcacacctta cctggagaca aacctcggac agccaacaat tcagagtttt   1260
gaacaggtgg gaacaaaagt gaatgtgacc gtagaagatg aacggacttt agtcagaagg   1320
aacaacactt tcctaagcct ccgggatgtt tttggcaagg acttaattta tacactttat   1380
tattggaaat cttcaagttc aggaaagaaa acagccaaaa caaacactaa tgagtttttg   1440
attgatgtgg ataaaggaga aaactactgt ttcagtgttc aagcagtgat tccctcccga   1500
```

-continued

```
acagttaacc ggaagagtac agacagcccg gtagagtgta tgggccagga gaaaggggaa  1560
ttcagagaaa actgggtgaa tgtaataagt aatttgaaaa aaattgaaga tcttattcaa  1620
tctatgcata ttgatgctac tttatatacg gaaagtgatg ttcaccccag ttgcaaagta  1680
acagcaatga agtgctttct cttggagtta caagttattt cacttgagtc cggagatgca  1740
agtattcatg atacagtaga aaatctgatc atcctagcaa acaacagttt gtcttctaat  1800
gggaatgtaa cagaatctgg atgcaaagaa tgtgaggaac tggaggaaaa aaatattaaa  1860
gaatttttgc agagttttgt acatattgtc caaatgttca tcaacacttc t           1911
```

METHODS OF REDUCING NEUROINFLAMMATION

CROSS-REFERENCE TO RELATED APPLICATIONS

This application claims priority to U.S. Provisional Patent Application Ser. No. 63/330,660, filed Apr. 13, 2022, and U.S. Provisional Patent Application Ser. No. 63/330,639, filed Apr. 13, 2022; the entire contents of which are herein incorporated by reference.

SEQUENCE LISTING

This application contains a Sequence Listing that has been submitted electronically as an XML file named 47039-0032001_SL_ST26.XML. This XML file, created on Apr. 10, 2023, is 83,459 bytes in size. The material in the XML file is hereby incorporated by reference in its entirety.

TECHNICAL FIELD

The present disclosure relates to the field of biotechnology, and more specifically, to antigen-binding molecules and the treatment of neuroinflammatory diseases.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

SUMMARY

Provided herein are methods of reducing the level of neuroinflammation in a tissue of a subject in need thereof that include administering to the subject a therapeutically effective amount of a multi-chain chimeric polypeptide comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

Also provided herein are methods of treating a neuroinflammatory disorder in a subject that include administering to the subject a therapeutically effective amount of a multi-chain chimeric polypeptide comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

Also provided herein are methods of reducing the rate of progression of a neuroinflammatory disorder in a subject that include administering to the subject a therapeutically effective amount of a multi-chain chimeric polypeptide comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

In some embodiments, the first target-binding domain and the soluble tissue factor domain directly abut each other in the first chimeric polypeptide. In some embodiments, the first chimeric polypeptide further comprises a linker sequence between the first target-binding domain and the soluble tissue factor domain in the first chimeric polypeptide. In some embodiments, the soluble tissue factor domain and the first domain of the pair of affinity domains directly abut each other in the first chimeric polypeptide. In some embodiments, the first chimeric polypeptide further comprises a linker sequence between the soluble tissue factor domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further comprises a linker sequence between the second domain of the pair of affinity domains and the second target-binding domain in the second chimeric polypeptide.

In some embodiments, the first target-binding domain and the second target-binding domain bind specifically to the same antigen. In some embodiments, the first target-binding domain and the second target-binding domain bind specifically to different antigens. In some embodiments, one or both of the first target-binding domain and the second target-binding domain is an antigen-binding domain. In some embodiments, one or both of the first target-binding domain and the second target-binding domain is a soluble TGF-β receptor II (TGF-βRII). In some embodiments, the first target-binding domain and the second target-binding domain are a soluble TGF-βRII.

In some embodiments, the first chimeric polypeptide further comprises one or more additional target-binding domain(s). In some embodiments, the second chimeric polypeptide further comprises one or more additional target-binding domains.

In some embodiments, the soluble tissue factor domain is a soluble human tissue factor domain. In some embodiments, the soluble human tissue factor domain comprises a sequence that is at least 80% identical to SEQ ID NO: 1.

In some embodiments, the pair of affinity domains is a sushi domain from an alpha chain of human IL-15 receptor (IL15Rα) and a soluble IL-15. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further comprises a signal sequence at its N-terminal end.

In some embodiments, the first target-binding domain comprises a first sequence that is at least 80% identical to SEQ ID NO: 2 and a second sequence that is at least 80% identical to SEQ ID NO: 2, wherein the first and second sequence are separated by a linker. In some embodiments, the first target-binding domain comprises a first sequence that is at least 90% identical to SEQ ID NO: 2 and a second sequence that is at least 90% identical to SEQ ID NO: 2. In some embodiments, the first target-binding domain comprises a first sequence of SEQ ID NO: 2 and a second sequence of SEQ ID NO: 2. In some embodiments, the linker comprises a sequence of SEQ ID NO: 3.

In some embodiments, the first target-binding domain comprises a sequence that is at least 80% identical to SEQ ID NO: 4. In some embodiments, the first target-binding domain comprises a sequence that is at least 90% identical to SEQ ID NO: 4. In some embodiments, the first target-binding domain comprises a sequence of SEQ ID NO: 4.

In some embodiments, the first chimeric polypeptide comprises a sequence that is at least 80% identical to SEQ ID NO: 6. In some embodiments, the first chimeric polypeptide comprises a sequence that is at least 90% identical to SEQ ID NO: 6. In some embodiments, the first chimeric polypeptide comprises a sequence of SEQ ID NO: 6.

In some embodiments, the first chimeric polypeptide comprises a sequence of SEQ ID NO: 7. In some embodiments, the first chimeric polypeptide comprises a sequence of SEQ ID NO: 68. In some embodiments, the first chimeric polypeptide comprises a sequence of SEQ ID NO: 70.

In some embodiments, the second target-binding domain comprises a first sequence that is at least 80% identical to SEQ ID NO: 2 and a second sequence that is at least 80% identical to SEQ ID NO: 2, wherein the first and second sequence are separated by a linker. In some embodiments, the second target-binding domain comprises a first sequence that is at least 90% identical to SEQ ID NO: 2 and a second sequence that is at least 90% identical to SEQ ID NO: 2. In some embodiments, the second target-binding domain comprises a first sequence of SEQ ID NO: 2 and a second sequence of SEQ ID NO: 2. In some embodiments, the linker comprises a sequence of SEQ ID NO: 3.

In some embodiments, the second target-binding domain comprises a sequence that is at least 80% identical to SEQ ID NO: 4. In some embodiments, the second target-binding domain comprises a sequence that is at least 90% identical to SEQ ID NO: 4. In some embodiments, the second target-binding domain comprises a sequence of SEQ ID NO: 4.

In some embodiments, the second chimeric polypeptide comprises a sequence that is at least 80% identical to SEQ ID NO: 5. In some embodiments, the second chimeric polypeptide comprises a sequence that is at least 90% identical to SEQ ID NO: 5. In some embodiments, the second chimeric polypeptide comprises a sequence of SEQ ID NO: 5. In some embodiments, the second chimeric polypeptide comprises a sequence of SEQ ID NO: 8.

In some embodiments, the tissue is one or more of the brain, spinal cord, skeletal muscle, or optic nerve. In some embodiments, the subject has been diagnosed or identified as having a neuroinflammatory disease. In some embodiments, the subject has been identified as having an increased risk of developing a neuroinflammatory disease. In some embodiments, the neuroinflammatory disease is selected from the group consisting of: Alzheimer's disease (AD), Parkinson's disease (PD), multiple sclerosis (MS), schizophrenia, autism, depression, major depressive disorder (MDD), dysthymia, bipolar disorders, mood disorders, anxiety, fibromyalgia, Huntington's disease, amyotrophic lateral sclerosis (ALS), acute disseminated encephalomyelitis (ADEM), acute optic neuritis (AON), transverse myelitis, neuromyelitis optica (NMO), Lewy body dementia (LBD), and sarcopenia.

As used herein, the term "neuroinflammation" refers an inflammatory response within the central nervous system (CNS) (e.g., brain and/or spinal cord) and can be characterized by a host of cellular and molecular changes within the brain or central nervous system (e.g., production of one or more of cytokines, chemokines, reactive oxygen species, and secondary messengers). In some embodiments, neuroinflammation can be a chronic inflammation that is caused by toxic metabolites, autoimmunity, aging, microbes, viruses, traumatic brain injury, or spinal cord injury.

As used herein, the term "neuroinflammatory disorder" refers to a condition where immune responses damages components of the nervous system (e.g., brain, spinal cord, and/or optic nerves). In some embodiments, neuroinflammatory disorders can be associated with aging or traumatic brain injury. For example, neuroinflammatory disorders can include neurodegenerative disorders (e.g., Alzheimer's disease, Parkinson's disease, and multiple sclerosis). In some examples, neuroinflammatory disorders can include, but are not limited to, fibromyalgia, Huntington's disease, Lewy body dementia (LBD), amyotrophic lateral sclerosis (ALS), acute disseminated encephalomyelitis (ADEM), acute optic neuritis (AON), transverse myelitis, or neuromyelitis optica (NMO). In some examples, a neuroinflammatory disorder can include various psychiatric illnesses (e.g., schizophrenia, autism, depression, and other mood disorders). In some embodiments, increased levels of neuroinflammation can accelerate brain aging and progression of certain diseases, including sarcopenia.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., an scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1 \times 10^{-7}$ M (e.g., less than $1 \times 10^{-8}$ M, less than $1 \times 10^{-9}$ M, less than $1 \times 10^{-10}$ M, or less than $1 \times 10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. Generally, the methods of treatment include administering a therapeutically effective amount of composition that reduces at least one symptom of a disorder to a subject who is in need of, or who has been determined to be in need of such treatment.

The phrase "rate of progression of a neuroinflammatory disorder" means the rate at which a neuroinflammatory disorder starts to get worse or result in gradual loss of neurons in areas of the CNS. For example, a neuroinflammatory disorder can progress at a rapid rate (e.g., days or weeks) or at a slower rate (e.g., months or years). In some embodiments, a rate of progression of a neuroinflammatory disorder can be measured by molecular imaging (e.g., positron emission tomography (PET)), monitoring microglial activation, or astrocytic responses (e.g., immunohistochemistry, immunocytochemistry), or magnetic resonance methods (e.g., magnetic resonance imaging (MRI) or magnetic resonance spectroscopy (MRS)) or through cognitive assessments.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

The patent or application file contains at least one drawing executed in color. Copies of the patent or patent application publication with color drawing(s) will be provided by the Office upon request and payment of the necessary fee.

FIG. 6 shows results of 32Dβ cell proliferation assay with TGFRt15-TGFRs or recombinant IL-15

FIGS. 7A and 7B show results of detecting IL-15 and TGFβRII in TGFRt15-TGFRs with corresponding antibodies using ELISA.

FIG. 11A shows spleen weight in mice treated with TGFRt15-TGFRs as compared to PBS control. FIG. 11B shows the percentage of CD4+ T cells, CD8+ T cells, and NK cells in mice treated with TGFRt15-TGFRs as compared to PBS control.

FIG. 12A shows spleen weight of mice treated with TGFRt15-TGFRs at 16, 24, 48, 72, and 92 hours after treatment. FIG. 12B shows the percentages of immune cells in mice treated with TGFRt15-TGFRs at 16, 24, 48, 72, and 92 hours after treatment.

FIGS. 18A-18C show immunostimulation in C57BL/6 mice following treatment with TGFRt15-TGFRs.

FIGS. 25A-25K show TGFRt15-TGFRs (HCW9218) enhances immune-mediated biological activities in diabetic db/db mouse. FIGS. 25A-25E show representative flow cytometry data showing increase in immune cell surface makers on splenocytes of TGFRt15-TGFRs (HCW9218)-treated mice at day 4 compared to controls. FIGS. 25F-25G show representative flow cytometry data showing increase in central memory cells and effector memory cells number in splenocytes population compared to control with TGFRt15-TGFRs (HCW9218) at day 4. FIG. 25H shows killing of Yac1 target cells by in vivo TGFRt15-TGFRs (HCW9218) treated as compared to control splenocytes. FIG. 25I shows increase in interferon (IFN)-γ release by CD3+ cells upon antigen-independent stimulation by in vivo TGFRt15-TGFRs (HCW9218) treated and ex vivo −CD3/a-CD28 beads stimulated splenocytes compared to control. FIG. 25J shows representative data for increase in extracellular acidification rates (ECAR) and oxygen consumption rates (OCR) data from in vivo either treated with PBS or TGFRt15-TGFRs (HCW9218) or TGFRt15*-TGFRs (HCW9228) splenocytes and analyzed by Seahorse XFe Bioanalyzer (Agilent). FIG. 25K shows ELISA data showing decrease in TGFβ1 and TGFβ2 but not TGFβ3 in plasma after TGFRt15-TGFRs (HCW9218) or TGFRt15*-TGFRs (HCW9228).

FIGS. 26A-26P show TGFRt15-TGFRs (HCW9218) treatment reduces senescent pancreatic R islet cells and SASP factors to improve type-2 diabetes of db/db mice. FIG. 26A shows schema of TGFRt15-TGFRs (HCW9218) treatment in db/db mice model. FIGS. 26G-26I show Aging, SASP, and Beta Cell index in pancreas by quantitative PCR. FIG. 26J shows Fasting Blood glucose after TGFRt15-TGFRs (HCW9218) treatment. FIG. 26K shows HOMA-IR index after TGFRt15-TGFRs (HCW9218) treatment. FIGS. 26M-26P show Heat Map for Metabolic, Senescence, Inflammation and Vasculature genes.

FIGS. 27A-27R show TGFRt15-TGFRs (HCW9218) stimulates immune cell activity and metabolic functions in liver of chronologically aged mice. FIG. 27A shows schema of TGFRt15-TGFRs (HCW9218) and TGFRt15*-TGFRs (HCW9228) treatment in young and aged mice model for day 4 and day 10. FIG. 27B shows composite unbiased t-SNE identifying B cells, T cells, and group 1 ILCs. FIGS. 27D-27E show summary data from N=3 independent experiments, with N=6 mice/group demonstrating the increased total ILC-1 cell frequency in the liver at day 4 (FIG. 27D) and day 10 (FIG. 27E). FIGS.

27F-27I show total NK cell frequency in the liver at day 4 (FIG. 27F) and day 10 (FIG. 27G) and in the spleen at day 4 (FIG. 27H) and day 10 (FIG. 27I). FIG. 27J shows percentage positive of Ki-67 proliferation makers in liver. FIGS. 27K-27L show total CD8+ T cell frequency in the liver (FIG. 27K) and spleen (FIG. 27L) at day 4 and day 10. FIGS. 27M-27N show representative data for increase in Extracellular acidification rates (ECAR) (FIG. 27M) and oxygen consumption rates (OCR) (FIG. 27N) data from splenocytes stimulated in vivo with TGFRt15-TGFRs (HCW9218) from young and aged mouse by Seahorse XFe bioanalyzer compared to control. FIG. 27O show measuring the ex vivo cytotoxic activity on Yac1 target cells by in vivo TGFRt15-TGFRs (HCW9218)-stimulated splenocytes from young and aged mice compared to controls (PBS or TGFRt15*-TGFRs (HCW9228)) by flow cytometry. FIGS. 27P-27Q show increase in interferon (IFN)-γ and (TNF)-α release by CD3+ cells upon antigen independent stimulation by in vivo TGFRt15-TGFRs (HCW9218) treated and ex vivo α-CD3/CD28 beads stimulated splenocytes compared to control aged and young mice measured by MAGPIXX multiplexing system. FIG. 27R shows representative flow cytometry data showing increase in percentage of intracellular granzyme B levels.

FIG. 28A shows 60 Days of TGFRt15-TGFRs (HCW9218) treated aged mice liver cells total RNASeq difference compared to control treatment in volcano plots. FIGS. 28B-28D show heat maps of the differentially expressed senescence and inflammation, glucogenesis and fatty acid metabolism and circadian rhythm associated genes in liver after treatment with TGFRt15-TGFRs (HCW9218) compared to control treatment (adjusted p value<0.05). FIGS. 28E-28F show relative mRNA expression of IL1ca, PAI-1, 116 and Tnfα in kidney and Il1β, Il1α, PAI-1, Il6 and Tnfα in liver was analyzed by quantitative PCR after treatment with TGFRt15-TGFRs (HCW9218) compared to control at day and/or day 60.

FIGS. 29A-29I show two-doses of TGFRt15-TGFRs (HCW9218) stimulates metabolic functions and reduces inflammation (SASP) and cellular senescence markers in chronologically aged mice liver for extended time. FIG. 29A shows schema of two dose TGFRt15-TGFRs (HCW9218) treatment in chronologically aged (76 weeks) female aged C57BL/6J mice that were subcutaneously injected with 3 mg/kg of TGFRt15-TGFRs (HCW9218) (n=5-8) or saline. Mice received second dose of TGFRt15-TGFRs (HCW9218) at day 60 and were euthanized at day 120. FIGS. 29B-29C show representative data for increase in extracellular acidification rates (ECAR) and oxygen consumption rates (OCR) data from splenocytes stimulated in vivo with two doses of TGFRt15-TGFRs (HCW9218) measured by Seahorse XFe bioanalyzer compared to control. FIG. 29D shows relative mRNA expression Il1α, Cdkn1a, Pai-1, Il1b, and Il6 in liver after treatment with TGFRt15-TGFRs (HCW9218) one or two doses compared to control at day 120 determined by quantitative PCR. FIGS. 29E-29F show ELISA data showing protein levels of IL-1α, IL-6, IL-8, PAI-1 and Fibronectin in liver tissue by ELISA liver after treatment with TGFRt15-TGFRs (HCW9218) one or two doses compared to control at day 120. FIGS. 29G-29H show immunofluorescent staining of liver tissue cells expressing p21+(yellow) after treatment with two doses of TGFRt15-TGFRs (HCW9218). FIG. 29I shows heat maps of the differentially expressed senescence, inflammation, and circadian rhythm associated genes in liver after treatment with TGFRt15-TGFRs (HCW9218) compared to control treatment (adjusted p value<0.05).

FIG. 30A shows relative mRNA expression of senescence associated genes Cdkn1a, Il6, Il1α, cdkn2a, Il1β, Tnfα and Il8 in hippocampus of young and aged mice 120 determined using quantitative PCR. FIG. 30B shows relative mRNA expression senescence associated genes Cdkn1a, Il1α, Il6, Tnfα, Il1β and Il18 genes in hippocampus of aged mice after 60 days of treatment with TGFRt15-TGFRs (HCW9218) and compared to control determined using quantitative PCR. 18S rRNA was used for normalization. FIG. 30C shows total RNASeq volcano plots on hippocampus of aged mice 60 days after TGFRt15-TGFRs (HCW9218) compared to control treatment. FIGS. 30D-30E show heat maps of the differentially expressed neuronal and circadian rhythm and neuroinflammatory associated genes in hippocampus after treatment with TGFRt15-TGFRs (HCW9218) compared to control treatment (adjusted p value<0.05).

FIGS. 31A-31I show significant maintenance of physical performance over time by both TGFRt15-TGFRs (HCW9218) and TGFRt15*-TGFRs (HCW9228) treated aged mice and TGFRt15-TGFRs (HCW9218) is well tolerated by mice and non-human primate and not long-term adverse effects on naturally aged mice. FIG. 31A shows grip strength test performed in aged mice treated with TGFRt15-TGFRs (HCW9218) and TGFRt15*-TGFRs (HCW9228) compared to controls. FIG. 31B shows Rotarod performance in mice treated with saline, TGFRt15-TGFRs (HCW9218) and TGFRt15*-TGFRs (HCW9228), FIG. 31C shows Open Field test in the same mice mentioned above to measure total distance travelled. FIGS. 31D-31E show flow cytometric analysis of Ki67 expression (FIG. 31D) and absolute numbers (FIG. 31E) of CD4, CD8, Treg and CD16+NK cells in blood from Cynomolgus monkeys (10/group) following two dose treatment (study days 1 and 15) with TGFRt15-TGFRs (HCW9218) or saline. FIG. 31F shows probability of survival-monitored for survival and analyzed using the log-rank test. FIG. 31G shows weight was measured after 5 months. FIGS. 31H-31I show representative flow cytometry data showing percentage of CD8+ T cells and NK cells in blood.

FIGS. 32A-32D show representative data for increase in metabolic parameters from splenocytes from db/db mouse stimulated in vivo with one dose of TGFRt15-TGFRs (HCW9218) by Seahorse XFe bioanalyzer compared to control at day 2 (FIGS. 32A-32B) and day 4 (FIGS. 32C-32D).

FIGS. 33A-33I show TGFRt15-TGFRs (HCW9218) enhance immune-mediated biological activities in aged mouse. FIGS. 33A-33B show representative data by flow cytometry showing increase in immune cell surface makers compared to controls at day 4 after treatment with TGFRt15-TGFRs (HCW9218) in blood (FIG. 33A) and spleen (FIG. 33B) of young and aged mice. FIGS. 33C-33D show immune cells proliferation marker Ki67 in NK cells in blood (FIG. 33C) and spleen (FIG. 33D) by flow cytometry at day 4 of young and aged mice. FIGS. 33E-33G show representative flow cytometry data showing increase in immune cell surface makers on liver immune cells compared to controls at day 4 after treatment with TGFRt15-TGFRs (HCW9218) in young and aged mice. FIGS. 33H-33I show summary data from N=2 independent experiments, with N=6 mice/group demonstrating the increased in frequency of total CD4+ T cells in liver at day 4 and day 10 after treatment with TGFRt15-TGFRs (HCW9218) compared to control treatment (FIG. 33H) and in spleen at day 4 and 10 (FIG. 33I).

FIGS. 34A-34C show TGFRt15-TGFRs (HCW9218) stimulates immune cell activity and metabolic functions and reduces inflammation (SASP) and cellular senescence markers of chronologically aged mice. FIG. 34A shows heat maps of the differentially expressed immune pathway associated genes in liver after treatment with TGFRt15-TGFRs (HCW9218) compared to control treatment (adjusted p value<0.05). FIG. 34B show heat maps of the differentially expressed Senescence, Inflammation and Circadian Rhythm associated genes associated genes in liver after treatment with TGFRt15*-TGFRs (HCW9228) compared to control treatment (adjusted p value<0.05). FIG. 34C shows heat maps of the differentially expressed Senescence, Inflammation and Circadian Rhythm associated genes associated genes in liver after treatment with TGFRt15-TGFRs (HCW9218) compared to TGFRt15*-TGFRs (HCW9228) treatment after 120 days (adjusted p value<0.05).

FIGS. 36A-36D show blood brain barrier study immunohistostaining. FIGS. 36A-36D show mice received subcutaneous injections of either PBS or TGFRt15-TGFRs (HCW9218) (3 mg/kg) and euthanized next day. The cryosections of the brains from 7-week-old (FIG. 36A), 73-week-old (FIG. 36B), or 105-week-old (FIG. 36C) mice in either control group or treatment group were processed for immunohistostaining with an anti-human tissue factor (TF) specific antibody. No positive staining was detected in mouse brains. FIG. 36D shows the antibody shows a specific staining to human TF in human brain section.

FIG. 37A shows grip strength, FIG. 37B shows Rotarod test and FIG. 37C shows Open field test performed in aged mice treated with TGFRt15-TGFRs (HCW9218) and TGFRt15*-TGFRs (HCW9228) to measure acute effect on the peak force value 30 days after the first dose of each respective treatment.

FIG. 38B is a graph showing the latency to fall in a Rotarod test, speed in a Rotarod test, total distance travelled in an open field, total velocity in an open field, time to turn in a Pole Test, and total time in a Pole Test in a chemically-induced Parkinson's disease mouse model untreated or treated with TGFRt15-TGFRs (HCW9218) as described in Example 16.

DETAILED DESCRIPTION

Provided herein are methods of reducing the level of neuroinflammation in a tissue of a subject in need thereof; methods of treating a neuroinflammatory disorder in a subject; and methods of reducing the rate of progression of a neuroinflammatory disorder in a subject, that include administering to the subject a therapeutically effective amount of a multi-chain chimeric polypeptide comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

Figure 1:
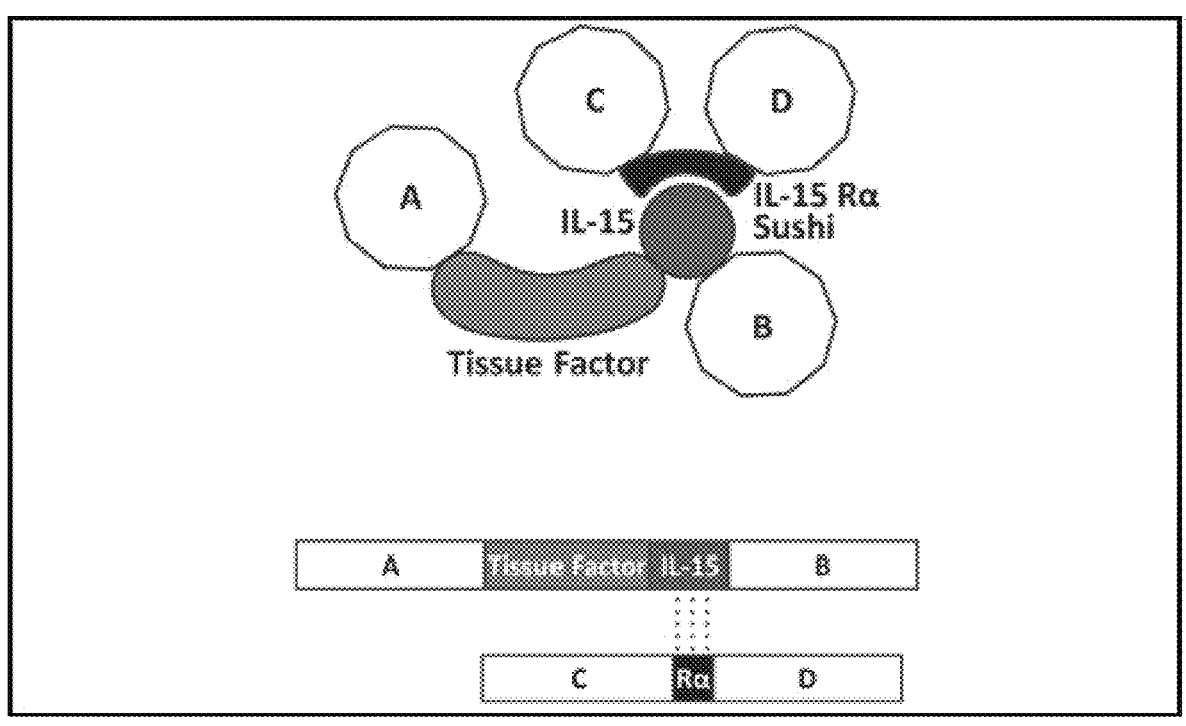
FIG. 1 shows exemplary diagrams for a multi-chain chimeric polypeptide: (i) a first chimeric polypeptide including a first target-binding domain (A), a soluble tissue factor domain, a first domain of an affinity pair of domains (soluble interleukin IL-15), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides.
Figure 2:
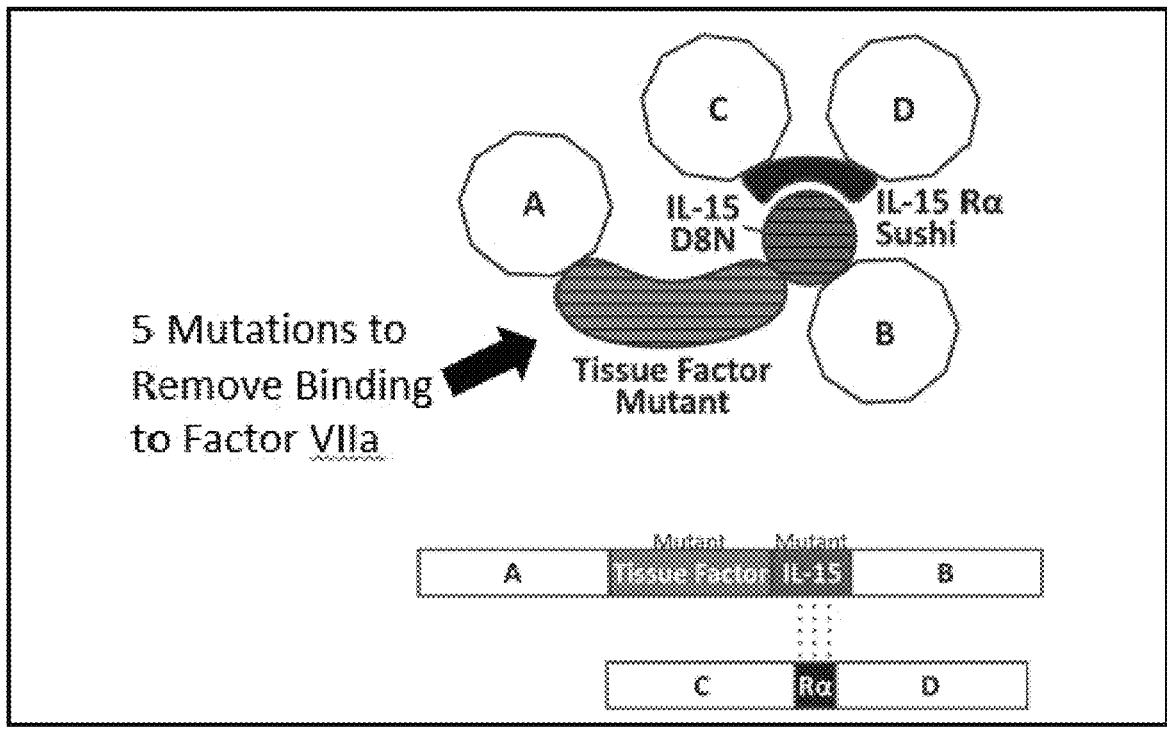
FIG. 2 shows exemplary diagrams for a multi-chain chimeric polypeptide: (i) a first chimeric polypeptide including a first target-binding domain (A), a soluble tissue factor domain including five amino acid substitutions in order to remove binding of the soluble tissue factor domain to FVIIa, a first domain of an affinity pair of domains (soluble interleukin IL-15 including a D8N or D8A amino acid substitution), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides. In other embodiments of any of the multi-chain chimeric polypeptides described herein the soluble tissue factor domain can comprise or consists of a soluble wildtype human tissue factor domain (comprising or consisting of a contiguous sequence within wildtype human tissue factor).

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750, amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary multi-chain chimeric polypeptides provided herein are depicted in FIGS. 1 and 2.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping 1 sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile^{-154}$-$Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from Asp58 onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding.

Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                    (SEQ ID NO: 1)
SGTTNTVAAYNLTWKSTNFKTILEWEPKPVNQVYTVQIST

KSGDWKSKCFYTTDTECDLTDEIVKDVKQTYLARVFSYPA

GNVESTGSAGEPLYENSPEFTPYLETNLGQPTIQSFEQVG

TKVNVTVEDERTLVRRNNTFLSLRDVFGKDLIYTLYYWKS

SSSGKKTAKTNTNEFLIDVDKGENYCFSVQAVIPSRTVNR

KSTDSPVECMGQEKGEFRE

Exemplary Nucleic Acid Encoding Soluble
Human Tissue Factor Domain
                                    (SEQ ID NO: 9)
AGCGGCACAACCAACACAGTCGCTGCCTATAACCTCACTT

GGAAGAGCACCAACTTCAAAACCATCCTCGAATGGGAACC

CAAACCCGTTAACCAAGTTTACACCGTGCAGATCAGCACC

AAGTCCGGCGACTGGAAGTCCAAATGTTTCTATACCACCG

ACACCGAGTGCGATCTCACCGATGAGATCGTGAAAGATGT

GAAACAGACCTACCTCGCCCGGGTGTTTAGCTACCCCGCC

GGCAATGTGGAGAGCACTGGTTCCGCTGGCGAGCCTTTAT

ACGAGAACAGCCCCGAATTTACCCCTTACCTCGAGACCAA

TTTAGGACAGCCCACCATCCAAAGCTTTGAGCAAGTTGGC

ACAAAGGTGAATGTGACAGTGGAGGACGAGCGGACTTTAG

TGCGGCGGAACAACACCTTTCTCAGCCTCCGGGATGTGTT
```

-continued

CGGCAAAGATTTAATCTACACACTGTATTACTGGAAGTCC

TCTTCCTCCGGCAAGAAGACAGCTAAAACCAACACAAACG

AGTTTTTAATCGACGTGGATAAAGGCGAAAACTACTGTTT

CAGCGTGCAAGCTGTGATCCCCTCCCGGACCGTGAATAGG

AAAAGCACCGATAGCCCCGTTGAGTGCATGGGCCAAGAAA

AGGGCGAGTTCCGGGAG

Exemplary Mutant Soluble Human Tissue Factor
Domain
(SEQ ID NO: 10)
SGTTNTVAAYNLTWKSTNFATALEWEPKPVNQVYTVQIST

KSGDWKSKCFYTTDTECALTDEIVKDVKQTYLARVFSYPA

GNVESTGSAGEPLYENSPEFTPYLETNLGQPTIQSFEQVG

TKVNVTVEDERTLVARNNTALSLRDVFGKDLIYTLYYWKS

SSSGKKTAKTNTNEFLIDVDKGENYCFSVQAVIPSRTVNR

KSTDSPVECMGQEKGEFRE

Exemplary Mutant Soluble Human Tissue Factor
Domain
(SEQ ID NO: 11)
SGTTNTVAAYNLTWKSTNFATALEWEPKPVNQVYTVQIST

KSGDAKSKCFYTTDTECALTDEIVKDVKQTYLARVFSYPA

GNVESTGSAGEPLAENSPEFTPYLETNLGQPTIQSFEQVG

TKVNVTVEDERTLVARNNTALSLRDVFGKDLIYTLYYWKS

SSSGKKTAKTNTNEFLIDVDKGENYCFSVQAVIPSRTVNR

KSTDSPVECMGQEKGEFRE

Exemplary Soluble Mouse Tissue Factor Domain
(SEQ ID NO: 12)
agipekafnltwistdfktilewqpkptnytytvqisdrs rnwknkcfsttdtecdltdeivkdvtwayeakvlsvprrn svhgdgdqlvihgeeppftnapkflpyrdtnlgqpviqqf eqdgrklnvvvkdsltlvrkngtfltlrqvfgkdlgyiit yrkgsstgkktnitntnefsidveegvsycffvqamifsr ktnqnspgsstvcteqwksflge Exemplary Soluble Rat Tissue Factor Domain
(SEQ ID NO: 13)
agtppgkafnltwistdfktilewqpkptnytytvqisdr srnwkykctgttdtecdltdeivkdvnwtyearvlsvpwr nsthgketlfgthgeeppftnarkflpyrdtkigqpviqk yeqggtklkvtvkdsftlvrkngtfltlrqvfgndlgyil tyrkdsstgrktntthtneflidvekgvsycffaqavifs rktnhkspesitkcteqwksvlge In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1, 10, 11, 12, or 13. In some embodiments, a soluble tissue factor domain can include a sequence of SEQ ID NO: 1, 10, 11, 12, or 13, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 10 or SEQ ID NO: 11.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 9.

In some embodiments, the soluble tissue factor domain can have a total length of about amino acids to about 220 amino acids, about 20 amino acids to about 215 amino acids, about amino acids to about 210 amino acids, about 20 amino acids to about 205 amino acids, about amino acids to about 200 amino acids, about 20 amino acids to about 195 amino acids, about amino acids to about 190 amino acids, about 20 amino acids to about 185 amino acids, about amino acids to about 180 amino acids, about 20 amino acids to about 175 amino acids, about amino acids to about 170 amino acids, about 20 amino acids to about 165 amino acids, about amino acids to about 160 amino acids, about 20 amino acids to about 155 amino acids, about amino acids to about 150 amino acids, about 20 amino acids to about 145 amino acids, about amino acids to about 140 amino acids, about 20 amino acids to about 135 amino acids, about amino acids to about 130 amino acids, about 20 amino acids to about 125 amino acids, about amino acids to about 120 amino acids, about 20 amino acids to about 115 amino acids, about amino acids to about 110 amino acids, about 20 amino acids to about 105 amino acids, about amino acids to about 100 amino acids, about 20 amino acids to about 95 amino acids, about amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., *Protein Engineering, Design & Selection* 27(10):325-330, 2014; Priyanka et al., *Protein Sci.* 22(2):153-167, 2013. In some examples, the linker sequence is a synthetic linker sequence.

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 3). In some embodiments, the linker sequence can be encoded by a nucleic acid comprising or consisting of:

(SEQ ID NO: 14)
GGCGGTGGAGGATCCGGAGGAGGTGGCTCCGGCGGCGGAGGATCT.

In some embodiments, the linker sequence can comprise or consist of: GGGSGGGS (SEQ ID NO: 15).

Target-Binding Domains

In some embodiments of any of the multi-chain chimeric polypeptides described herein, the first target-binding domain, the second target-binding domain, and/or the additional one or more target-binding domains can be an antigen-binding domain that binds specifically to a ligand of TGF-βRII (e.g., any of the exemplary antigen-binding domains described herein or known in the art) or a soluble interleukin or cytokine receptor that binds specifically to a ligand of TGF-βRII (e.g., any of the exemplary soluble interleukin receptors or soluble cytokine receptors described herein).

In some embodiments of any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids,

45

46 about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids; about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to a ligand of TGF-βRII with a dissociation equilibrium constant $(K_D)$ of less than $1{\times}10^{-7}$M, less than $1{\times}10^{-8}$ M, less than $1{\times}10^{-9}$M, less than $1{\times}10^{-10}$M, less than $1{\times}10^{-11}$ M, less than $1{\times}10^{-12}$ M, or less than $1{\times}10^{-13}$ M. In some embodiments, the antigen-binding protein construct provided herein can bind to an identifying antigen with a $K_D$ of about $1{\times}10^{-3}$ M to about $1{\times}10^{-5}$ M, about $1{\times}10^{-4}$ M to about $1{\times}10^{-6}$ M, about $1{\times}10^{-5}$M to about $1{\times}10^{-7}$ M, about $1{\times}10^{-6}$ M to about $1{\times}10^{-8}$ M, about $1{\times}10^{-7}$ M to about $1{\times}10^{-9}$M, about $1{\times}10^{-8}$ M to about $1{\times}10^{-10}$ M, or about $1{\times}10^{-9}$ M to about $1{\times}10^{-11}$ M (inclusive).

Any of the target-binding domains described herein can bind to a ligand of TGF-βRII (e.g., TGF-β) with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about nM to about 30 nM, and about 20 nM to about 25 nM).

Any of the target-binding domains described herein can bind to a ligand of TGFβRII with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the multi-chain chimeric polypeptides described herein, the first target-binding domain and the second target-binding domain bind specifically to the same antigen. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of any of the multi-chain chimeric polypeptides described herein, the first target-binding domain and the second target-binding domain bind specifically to different antigens.

In some embodiments of any of the multi-chain chimeric polypeptides described herein, one or both of the first target-binding domain and the second target-binding domain is an antigen-binding domain. In some embodiments of any of the multi-chain chimeric polypeptides described herein, the first target-binding domain and the second target-binding domain are each antigen-binding domains.

In some embodiments of any of the multi-chain chimeric polypeptides described herein, the antigen-binding domain includes or is a scFv or a single domain antibody (e.g., a VHH or a VNAR domain).

In some examples, an antigen-binding domain (e.g., any of the antigen-binding domains described herein) can bind specifically to a ligand of TGF-βRII (see, e.g., antigen-binding domains that can bind specifically to TGF-β described in US 2021/0061897, US 2020/0399358, US 2020/0392221, US 2019/0315850, US 2019/0092846, US 2021/0403545, US 2021/0355204, and US 2019/0177406, each of which is herein incorporated by reference).

The antigen-binding domains present in any of the multi-chain chimeric polypeptides described herein are each independently selected from the group consisting of: a VHH domain, a VNAR domain, and a scFv. In some embodiments, any of the antigen-binding domains described herein is a BiTe, a (scFv)2, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Inmmunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldennans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, the antigen-binding domains in the multi-chain chimeric polypeptides described herein are both VHH domains, or at least one antigen-binding domain is a VHH domain. In some embodiments, the antigen-binding domains in the multi-chain chimeric polypeptides described herein are both VNAR domains, or at least one antigen-binding domain is a VNAR domain. In some embodiments, the antigen-binding domains in the multi-chain chimeric polypeptides described herein are both scFv domains, or at least one antigen-binding domain is a scFv domain.

In some embodiments, two or more of polypeptides present in the multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')$_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a ImmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')$_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes the constant domain of the light chain and the first constant domain (CHI) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, *Nature Reviews Drug Discovery* 13:799-801, 2014. In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Receptor

In some embodiments of any of the multi-chain chimeric polypeptides described herein, one or both of the first target-binding domain and the second target-binding domain is a soluble interleukin receptor, a soluble cytokine receptor or a ligand receptor. In some embodiments, the soluble receptor is a soluble TGF-β receptor II (TGF-β RII) (see, e.g., those described in Yung et al., *Am. J. Resp. Crit. Care Med.* 194(9):1140-1151, 2016) or a soluble TGF-βRIII (see, e.g., those described in Heng et al., *Placenta* 57:320, 2017). In some embodiments, one or both of the first target-binding domain and the second target-binding domain is a soluble TGF-β receptor II (TGF-βRII). In some embodiments, the first target-binding domain and the second target-binding domain are a soluble TGF-βRII.

In some embodiments, the first target-binding domain comprises a first sequence that is at least 80%, at least 85%, at least 90%, at least 92%, at least 94%, at least 95%, at least 96%, at least 98%, or at least 99% identical to SEQ ID NO: 2 and a second sequence that is at least 80%, at least 85%, at least 90%, at least 92%, at least 94%, at least 95%, at least 96%, at least 98%, or at least 99% identical to SEQ ID NO: 2, wherein the first and second sequence are separated by a linker. In some embodiments, the first target-binding domain comprises a first sequence of SEQ ID NO: 2 and a second sequence of SEQ ID NO: 2.

In some embodiments, the first target-binding domain comprises a sequence that is at least 80%, at least 85%, at least 90%, at least 92%, at least 94%, at least 95%, at least 96%, at least 98%, or at least 99% identical to SEQ ID NO: 4. In some embodiments, the first target-binding domain comprises a sequence of SEQ ID NO: 4.

In some embodiments, the second target-binding domain comprises a first sequence that is at least 80%, at least 85%, at least 90%, at least 92%, at least 94%, at least 95%, at least 96%, at least 98%, or at least 99% identical to SEQ ID NO: 2 and a second sequence that is at least 80%, at least 85%, at least 90%, at least 92%, at least 94%, at least 95%, at least 96%, at least 98%, or at least 99% identical to SEQ ID NO: 2, wherein the first and second sequence are separated by a linker. In some embodiments, the second target-binding domain comprises a first sequence of SEQ ID NO: 2 and a second sequence of SEQ ID NO: 2.

In some embodiments, the second target-binding domain comprises a sequence that is at least 80%, at least 85%, at least 90%, at least 92%, at least 94%, at least 95%, at least 96%, at least 98%, or at least 99% identical to SEQ ID NO: 4. In some embodiments, the second target-binding domain comprises a sequence of SEQ ID NO: 4.

Additional examples of soluble interleukin receptors and soluble cytokine receptors are known in the art.

Additional Target-Binding Domains

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art)

of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide.

In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA*. 103: 6841-6846, 2006; Sharkey et al., *Cancer Res*. 68:5282-5290, 2008; Rossi et al., *Trends Pharmacol* Sci. 33:474-481, 2012) or SNARE modules based on interactions of the proteins syntaxin, synaptotagmin, synaptobrevin, and SNAP25 (Deyev et al., *Nat Biotechnol*. 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about to 45 amino acids in length, about 10 to 40 amino acids in length, about 10 to 35 amino acids in length, about 10 to 30 amino acids in length, about 10 to 25 amino acids in length, about 10 to amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSR-ERYICNSGFKRKAGTSSLTECVLNKATNVAHWTTPS LKCIR (SEQ ID NO: 16). In some embodiments, a sushi domain from an alpha chain of IL15Rα can be encoded by a nucleic acid including

```
                                    (SEQ ID NO: 17)
ATTACATGCCCCCCTCCCATGAGCGTGGAGCACGCCGACA

TCTGGGTGAAGAGCTATAGCCTCTACAGCCGGGAGAGGTA

TATCTGTAACAGCGGCTTCAAGAGGAAGGCCGGCACCAGC

AGCCTCACCGAGTGCGTGCTGAATAAGGCTACCAACGTGG

CTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDAT-LYTESDVHPSCKVTAMKCFLLELQVISLESGDASIHD TVENLIILANNSLSSNGNVTESGCKECEELEEKNIKE-FLQSFVHIVQMFINTS (SEQ ID NO: 18). In some embodiments, a soluble IL-15 can be encoded by a nucleic acid including the sequence of

```
                                    (SEQ ID NO: 19)
AACTGGGTGAACGTCATCAGCGATTTAAAGAAGATCGAAG

ATTTAATTCAGTCCATGCATATCGACGCCACTTTATACAC

AGAATCCGACGTGCACCCCTCTTGTAAGGTGACCGCCATG

AAATGTTTTTTACTGGAGCTGCAAGTTATCTCTTTAGAGA

GCGGAGACGCTAGCATCCACGACACCGTGGAGAATTTAAT

CATTTTAGCCAATAACTCTTTATCCAGCAACGGCAACGTG

ACAGAGTCCGGCTGCAAGGAGTGCGAAGAGCTGGAGGAGA

AGAACATCAAGGAGTTTCTGCAATCCTTTGTGCACATTGT

CCAGATGTTCATCAATACCTCC.
```

In some embodiments, a soluble IL-15 can include a D8N amino acid substitution. In some embodiments, the soluble IL-15 with D8N mutant (IL15D8N) can include a sequence that is at least 70% identical, at least 75% identical, at least 80% identical, at least 85% identical, at least 90% identical, at least 92% identical, at least 94% identical, at least 95% identical, at least 96% identical, at least 98% identical, at least 99% identical, or 100% identical to NWVNVISNLK-KIEDLIQSMHIDATLYTESDVHPSCKVTAMKCFL- LELQVISLESGDASIH       DTVENLIILANNSLSSNG-
NVTESGCKECEELEEKNIKEFLQSFVHIVQMFINTS
(SEQ ID NO: 62). In some embodiments, the soluble IL-15
with D8N mutant (IL15D8N) (e.g., SEQ ID NO: 62) can be
encoded by a nucleic acid including the sequence of:

```
                                   (SEQ ID NO: 63)
AACTGGGTGAATGTAATAAGTAATTTGAAAAAAATTGAAG

ATCTTATTCAATCTATGCATATTGATGCTACTTTATATAC

GGAAAGTGATGTTCACCCCAGTTGCAAAGTAACAGCAATG

AAGTGCTTTCTCTTGGAGTTACAAGTTATTTCACTTGAGT

CCGGAGATGCAAGTATTCATGATACAGTAGAAAATCTGAT

CATCCTAGCAAACAACAGTTTGTCTTCTAATGGGAATGTA

ACAGAATCTGGATGCAAAGAATGTGAGGAACTGGAGGAAA

AAAATATTAAAGAATTTTTGCAGAGTTTTGTACATATTGT

CCAAATGTTCATCAACACTTCT.
```

Signal Sequence

In some embodiments, a multi-chain chimeric polypep-
tide includes a first chimeric polypeptide that includes a
signal sequence at its N-terminal end. In some embodiments,
a multi-chain chimeric polypeptide includes a second chi-
meric polypeptide that includes a signal sequence at its
N-terminal end. In some embodiments, both the first chi-
meric polypeptide of a multi-chain chimeric polypeptide and
a second chimeric polypeptide of the multi-chain chimeric
polypeptide include a signal sequence. As will be under-
stood by those of ordinary skill in the art, a signal sequence
is an amino acid sequence that is present at the N-terminus
of a number of endogenously produced proteins that directs
the protein to the secretory pathway (e.g., the protein is
directed to reside in certain intracellular organelles, to reside
in the cell membrane, or to be secreted from the cell). Signal
sequences are heterogeneous and differ greatly in their
primary amino acid sequences. However, signal sequences
are typically 16 to 30 amino acids in length and include a
hydrophilic, usually positively charged N-terminal region, a
central hydrophobic domain, and a C-terminal region that
contains the cleavage site for signal peptidase.

In some embodiments, a first chimeric polypeptide of a
multi-chain chimeric polypeptide, a second chimeric poly-
peptide of the multi-chain chimeric polypeptide, or both
includes a signal sequence having an amino acid sequence
MKWVTFISLLFLFSSAYS (SEQ ID NO: 20). In some
embodiments, a first chimeric polypeptide of a multi-chain
chimeric polypeptide, a second chimeric polypeptide of the
multi-chain chimeric polypeptide, or both includes a signal
sequence encoded by the nucleic acid sequence

```
                                   (SEQ ID NO: 21)
ATGAAATGGGTGACCTTTATTTCTTTACTGTTCCTCTTTA

GCAGCGCCTACTCC, (SEQ ID NO: 22)
ATGAAGTGGGTCACATTTATCTCTTTACTGTTCCTCTTCT

CCAGCGCCTACAGC,
or (SEQ ID NO: 23)
ATGAAATGGGTGACCTTTATTTCTTTACTGTTCCTCTTTA

GCAGCGCCTACTCC.
```

In some embodiments, a first chimeric polypeptide of a
multi-chain chimeric polypeptide, a second chimeric poly-
peptide of the multi-chain chimeric polypeptide, or both
includes a signal sequence having an amino acid sequence
MKCLLYLAFLFLGVNC (SEQ ID NO: 24). In some
embodiments, a first chimeric polypeptide of a multi-chain
chimeric polypeptide, a second chimeric polypeptide of the
multi-chain chimeric polypeptide, or both includes a signal
sequence having an amino acid sequence MGQIVTMFE-
ALPHIIDEVINIVIIVLIIITSIKAVYNFATCGILALVSFL-
FLAGRSCG (SEQ ID NO: 25). In some embodiments, a
first chimeric polypeptide of a multi-chain chimeric poly-
peptide, a second chimeric polypeptide of the multi-chain
chimeric polypeptide, or both includes a signal sequence
having      an      amino      acid      sequence
MPNHQSGSPTGSSDLLLSGKKQRPHLALRRKRRRE-
MRKINRKVRRMNLAPIKEKTAWQ       HLQALISE-
AEEVLKTSQTPQNSLTLFLALLSVLGPPVTG (SEQ ID
NO: 26). In some embodiments, a first chimeric polypeptide
of a multi-chain chimeric polypeptide, a second chimeric
polypeptide of the multi-chain chimeric polypeptide, or both
includes a signal sequence having an amino acid sequence
MDSKGSSQKGSRLLLLLVVSNLLLCQGVVS (SEQ ID
NO: 27). Those of ordinary skill in the art will be aware of
other appropriate signal sequences for use in a first chimeric
polypeptide and/or a second chimeric polypeptide of multi-
chain chimeric polypeptides described herein.

In some embodiments, a first chimeric polypeptide of a
multi-chain chimeric polypeptide, a second chimeric poly-
peptide of the multi-chain chimeric polypeptide, or both
includes a signal sequence that is about 10 to 100 amino
acids in length. For example, a signal sequence can be about
10 to 100 amino acids in length, about 15 to 100 amino acids
in length, about 20 to 100 amino acids in length, about 25 to
100 amino acids in length, about 30 to 100 amino acids in
length, about 35 to 100 amino acids in length, about 40 to
100 amino acids in length, about 45 to 100 amino acids in
length, about 50 to 100 amino acids in length, about 55 to
100 amino acids in length, about 60 to 100 amino acids in
length, about 65 to 100 amino acids in length, about 70 to
100 amino acids in length, about 75 to 100 amino acids in
length, about 80 to 100 amino acids in length, about 85 to
100 amino acids in length, about 90 to 100 amino acids in
length, about 95 to 100 amino acids in length, about 10 to 95
amino acids in length, about 10 to 90 amino acids in length,
about 10 to 85 amino acids in length, about 10 to 80 amino
acids in length, about 10 to 75 amino acids in length, about
10 to 70 amino acids in length, about 10 to 65 amino acids
in length, about 10 to 60 amino acids in length, about 10 to
55 amino acids in length, about 10 to 50 amino acids in
length, about 10 to 45 amino acids in length, about 10 to 40
amino acids in length, about to 35 amino acids in length,
about 10 to 30 amino acids in length, about 10 to 25 amino
acids in length, about 10 to 20 amino acids in length, about
10 to 15 amino acids in length, about 20 to amino acids in
length, about 30 to 40 amino acids in length, about 40 to 50
amino acids in length, about 50 to 60 amino acids in length,
about 60 to 70 amino acids in length, about 70 to 80 amino
acids in length, about 80 to 90 amino acids in length, about
90 to 100 amino acids in length, about 20 to 90 amino acids
in length, about 30 to 80 amino acids in length, about 40 to
70 amino acids in length, about 50 to 60 amino acids in
length, or any range in between. In some embodiments, a
signal sequence is about 10, 15, 20, 25, 30, 35, 40, 45, 50,
55, 60, 65, 70, 75, 80, 85, 90, 95, or 100 amino acids in
length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLY-LAFLFLGVNC (SEQ ID NO: 28) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 29), a calmodulin-tag (KRRWKKNFIAVSAANRFKKISSSGAL; SEQ ID NO: 30), a polyglutamate tag (EEEEEE; SEQ ID NO: 31), an E-tag (GAPVPYPDPLEPR; SEQ ID NO: 32), a FLAG-tag (DYKDDDDK; SEQ ID NO: 33), an HA-tag, a peptide from hemagglutinin (YPYDVPDYA; SEQ ID NO: 34), a his-tag (HHHHH (SEQ ID NO: 35); HHHHHH (SEQ ID NO: 36); HHHHHHH (SEQ ID NO: 37); HHHHHHHH (SEQ ID NO: 38); HHHHHHHHH (SEQ ID NO: 39); or HHHHHHHHHH (SEQ ID NO: 40)), a myc-tag (EQKLI-SEEDL; SEQ ID NO: 41), NE-tag (TKENPRSNQEE-SYDDNES; SEQ ID NO: 42), S-tag, (KETAAAKFER-QHMDS; SEQ ID NO: 43), SBP-tag (MDEKTTGWRGGHVVEGLAGELEQLRAR-LEHHPGQREP; SEQ ID NO: 44), Softag 1 (SLAEL-LNAGLGGS; SEQ ID NO: 45), Softag 3 (TQDPSRVG; SEQ ID NO: 46), Spot-tag (PDRVRAVSHWSS; SEQ ID NO: 47), Strep-tag (WSHPQFEK; SEQ ID NO: 48), TC tag (CCPGCC; SEQ ID NO: 49), Ty tag (EVHTNQDPLD; SEQ ID NO: 50), V5 tag (GKPIPNPLLGLDST; SEQ ID NO: 51), VSV-tag (YTDIEMNRLGK; SEQ ID NO: 52), and Xpress tag (DLYDDDDK; SEQ ID NO: 53). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide. In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about to 45 amino acids in length, about 10 to 40 amino acids in length, about 10 to 35 amino acids in length, about 10 to 30 amino acids in length, about 10 to 25 amino acids in length, about 10 to amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 54) can include one or more additional amino acids (e.g., at the N-terminus and/or the C-terminus of the peptide tag), while still retaining the ability to be bound by an antibody.

Exemplary Multi-Chain Chimeric Polypeptides

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 3).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 2)
IPPHVQKSVNNDMIVTDNNGAVKFPQLCKFCDVRFSTCDN

QKSCMSNCSITSICEKPQEVCVAVWRKNDENITLETVCHD

PKLPYHDFILEDAASPKCIMKEKKKPGETFFMCSCSSDEC

NDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 2)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 55)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 56)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 4)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 57)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 6)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 58)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG
```

-continued

```
GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 7)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical to:

```
                                      (SEQ ID NO: 59)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG
```

-continued

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide
can include a sequence that is at least 80% identical (e.g., at
least 82% identical, at least 84% identical, at least 86%
identical, at least 88% identical, at least 90% identical, at
least 92% identical, at least 94% identical, at least 96%
identical, at least 98% identical, at least 99% identical, or
100% identical) to:

(SEQ ID NO: 5)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IR.

In some embodiments, a second chimeric polypeptide is
encoded by a sequence that is at least 80% identical (e.g., at
least 82% identical, at least 84% identical, at least 86%
identical, at least 88% identical, at least 90% identical, at
least 92% identical, at least 94% identical, at least 96%
identical, at least 98% identical, at least 99% identical, or
100% identical) to:

(SEQ ID NO: 60)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.

In some embodiments, a second chimeric polypeptide can
include a sequence that is at least 80% identical (e.g., at least
82% identical, at least 84% identical, at least 86% identical,
at least 88% identical, at least 90% identical, at least 92%
identical, at least 94% identical, at least 96% identical, at
least 98% identical, at least 99% identical, or 100% identi-
cal) to:

(SEQ ID NO: 8)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 61)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.
```

In some embodiments, the second chimeric polypeptide can include a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

```
                                        (SEQ ID NO: 64)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD
```

-continued

```
IWVKSYSLYSRERYICNSGFKRKAGTSSLTECVLNKATNVAHWTTPSLKC

IR.
```

In some embodiments, a second chimeric polypeptide is encoded by a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

```
                                        (SEQ ID NO: 65)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.
```

In some embodiments, the second chimeric polypeptide can include a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

```
                                        (SEQ ID NO: 66)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT
```

-continued

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

(SEQ ID NO: 67)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.

In some embodiments, a first chimeric polypeptide can include a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

(SEQ ID NO: 68)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISNLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

(SEQ ID NO: 69)
ATCCCACCGCACGTTCAGAAGTCGGTGAATAACGACATGATAGTCACTGA

CAACAACGGTGCAGTCAAGTTTCCACAACTGTGTAAATTTTGTGATGTGA

GATTTTCCACCTGTGACAACCAGAAATCCTGCATGAGCAACTGCAGCATC

ACCTCCATCTGTGAGAAGCCACAGGAAGTCTGTGTGGCTGTATGGAGAAA

GAATGACGAGAACATAACACTAGAGACAGTTTGCCATGACCCCAAGCTCC

CCTACCATGACTTTATTCTGGAAGATGCTGCTTCTCCAAAGTGCATTATG

AAGGAAAAAAAAAAGCCTGGTGAGACTTTCTTCATGTGTTCCTGTAGCTC

TGATGAGTGCAATGACAACATCATCTTCTCAGAAGAATATAACACCAGCA

ATCCTGACGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACTCAGGCACTACAAATACTGTGGCAGCATATAATTTAACT

TGGAAATCAACTAATTTCAAGACAATTTTGGAGTGGGAACCCAAACCCGT

CAATCAAGTCTACACTGTTCAAATAAGCACTAAGTCAGGAGATTGGAAAA

GCAAATGCTTTTACACAACAGACACAGAGTGTGACCTCACCGACGAGATT

-continued

GTGAAGGATGTGAAGCAGACGTACTTGGCACGGGTCTTCTCCTACCCGGC

AGGGAATGTGGAGAGCACCGGTTCTGCTGGGGAGCCTCTGTATGAGAACT

CCCCAGAGTTCACACCTTACCTGGAGACAAACCTCGGACAGCCAACAATT

CAGAGTTTTGAACAGGTGGGAACAAAAGTGAATGTGACCGTAGAAGATGA

ACGGACTTTAGTCAGAAGGAACAACACTTTCCTAAGCCTCCGGGATGTTT

TTGGCAAGGACTTAATTTATACACTTTATTATTGGAAATCTTCAAGTTCA

GGAAAGAAAACAGCCAAAACAAACACTAATGAGTTTTTGATTGATGTGGA

TAAAGGAGAAAACTACTGTTTCAGTGTTCAAGCAGTGATTCCCTCCCGAA

CAGTTAACCGGAAGAGTACAGACAGCCCGGTAGAGTGTATGGGCCAGGAG

AAAGGGGAATTCAGAGAAAACTGGGTGAATGTAATAAGTAATTTGAAAAA

AATTGAAGATCTTATTCAATCTATGCATATTGATGCTACTTTATATACGG

AAAGTGATGTTCACCCCAGTTGCAAAGTAACAGCAATGAAGTGCTTTCTC

TTGGAGTTACAAGTTATTTCACTTGAGTCCGGAGATGCAAGTATTCATGA

TACAGTAGAAAATCTGATCATCCTAGCAAACAACAGTTTGTCTTCTAATG

GGAATGTAACAGAATCTGGATGCAAAGAATGTGAGGAACTGGAGGAAAAA

AATATTAAAGAATTTTTGCAGAGTTTTGTACATATTGTCCAAATGTTCAT

CAACACTTCT.

In some embodiments, a first chimeric polypeptide can include a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

(SEQ ID NO: 70)
MGVKVLFALICIAVAEAIPPHVQKSVNNDMIVTDNNGAVKFPQLCKFCDV

RFSTCDNQKSCMSNCSITSICEKPQEVCVAVWRKNDENITLETVCHDPKL

PYHDFILEDAASPKCIMKEKKKPGETFFMCSCSSDECNDNIIFSEEYNTS

NPDGGGGSGGGGSGGGGSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDSGTTNTVAAYNLTWKSTNFKTILEWEPKPVNQVYTVQISTKSGDWK

SKCFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLRDV

FGKDLIYTLYYWKSSSSGKKTAKTNTNEFLIDVDKGENYCFSVQAVIPSR

TVNRKSTDSPVECMGQEKGEFRENWVNVISNLKKIEDLIQSMHIDATLYT

ESDVHPSCKVTAMKCFLLELQVISLESGDASIHDTVENLIILANNSLSSN

GNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 85% identical, at least 86% identical, at least 88% identical, at least 90% identical, at least 92% identical, at least 94% identical, at least 95% identical, at least 96% identical, at least 98% identical, at least 99% identical, or 100% identical) to:

(SEQ ID NO: 71)
ATGGGAGTGAAAGTTCTTTTTGCCCTTATTTGTATTGCTGTGGCCGAGGC

CATCCCACCGCACGTTCAGAAGTCGGTGAATAACGACATGATAGTCACTG

ACAACAACGGTGCAGTCAAGTTTCCACAACTGTGTAAATTTTGTGATGTG

AGATTTTCCACCTGTGACAACCAGAAATCCTGCATGAGCAACTGCAGCAT

CACCTCCATCTGTGAGAAGCCACAGGAAGTCTGTGTGGCTGTATGGAGAA

AGAATGACGAGAACATAACACTAGAGACAGTTTGCCATGACCCCAAGCTC

CCCTACCATGACTTTATTCTGGAAGATGCTGCTTCTCCAAAGTGCATTAT

GAAGGAAAAAAAAAGCCTGGTGAGACTTTCTTCATGTGTTCCTGTAGCT

CTGATGAGTGCAATGACAACATCATCTTCTCAGAAGAATATAACACCAGC

AATCCTGACGGAGGTGGCGGATCCGGAGGTGGAGGTTCTGGTGGAGGTGG

GAGTATTCCTCCCCACGTGCAGAAGAGCGTGAATAATGACATGATCGTGA

CCGATAACAATGGCGCCGTGAAATTTCCCCAGCTGTGCAAATTCTGCGAT

GTGAGGTTTTCCACCTGCGACAACCAGAAGTCCTGTATGAGCAACTGCTC

CATCACCTCCATCTGTGAGAAGCCTCAGGAGGTGTGCGTGGCTGTCTGGC

GGAAGAATGACGAGAATATCACCCTGGAAACCGTCTGCCACGATCCCAAG

CTGCCCTACCACGATTTCATCCTGGAAGACGCCGCCAGCCCTAAGTGCAT

CATGAAAGAGAAAAAGAAGCCTGGCGAGACCTTTTTCATGTGCTCCTGCA

GCAGCGACGAATGCAACGACAATATCATCTTTAGCGAGGAATACAATACC

AGCAACCCCGACTCAGGCACTACAAATACTGTGGCAGCATATAATTTAAC

TTGGAAATCAACTAATTTCAAGACAATTTTGGAGTGGGAACCCAAACCCG

TCAATCAAGTCTACACTGTTCAAATAAGCACTAAGTCAGGAGATTGGAAA

AGCAAATGCTTTTACACAACAGACACAGAGTGTGACCTCACCGACGAGAT

TGTGAAGGATGTGAAGCAGACGTACTTGGCACGGGTCTTCTCCTACCCGG

CAGGGAATGTGGAGAGCACCGGTTCTGCTGGGGAGCCTCTGTATGAGAAC

TCCCCAGAGTTCACACCTTACCTGGAGACAAACCTCGGACAGCCAACAAT

TCAGAGTTTTGAACAGGTGGGAACAAAAGTGAATGTGACCGTAGAAGATG

AACGGACTTTAGTCAGAAGGAACAACACTTTCCTAAGCCTCCGGGATGTT

TTTGGCAAGGACTTAATTTATACACTTTATTATTGGAAATCTTCAAGTTC

AGGAAAGAAAACAGCCAAAACAAACACTAATGAGTTTTTGATTGATGTGG

ATAAAGGAGAAAACTACTGTTTCAGTGTTCAAGCAGTGATTCCCTCCCGA

ACAGTTAACCGGAAGAGTACAGACAGCCCGGTAGAGTGTATGGGCCAGGA

GAAAGGGGAATTCAGAGAAAACTGGGTGAATGTAATAAGTAATTTGAAAA

AAATTGAAGATCTTATTCAATCTATGCATATTGATGCTACTTTATATACG

GAAAGTGATGTTCACCCCAGTTGCAAAGTAACAGCAATGAAGTGCTTTCT

CTTGGAGTTACAAGTTATTTCACTTGAGTCCGGAGATGCAAGTATTCATG

ATACAGTAGAAAATCTGATCATCCTAGCAAACAACAGTTTGTCTTCTAAT

GGGAATGTAACAGAATCTGGATGCAAAGAATGTGAGGAACTGGAGGAAAA

AAATATTAAAGAATTTTTGCAGAGTTTTGTACATATTGTCCAAATGTTCA

TCAACACTTCT.

Compositions/Kits

Also provided herein are compositions (e.g., pharmaceutical compositions) that include at least one of any multi-chain chimeric polypeptides, any of the cells, or any of the nucleic acids described herein. In some embodiments, the compositions include at least one of any of the multi-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the multi-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Nucleic Acids/Vectors

Also provided herein are nucleic acids that encode any of the multi-chain chimeric polypeptides described herein. In some embodiments, a first nucleic acid can encode the first chimeric polypeptide and a second nucleic acid can encode the second chimeric polypeptide. In some embodiments, a single nucleic acid can encode both the first chimeric polypeptide and the second chimeric polypeptide.

Also provided herein are vectors that include any of the nucleic acids encoding any of the multi-chain chimeric polypeptides described herein. In some embodiments, a first vector can include a nucleic acid encoding the first chimeric polypeptide and a second vector can include a nucleic acid encoding the second chimeric polypeptide. In some embodiments, a single vector can include a first nucleic acid encoding the first chimeric polypeptide and a second nucleic acid encoding the second chimeric polypeptide.

Any of the vectors described herein can be an expression vector. For example, an expression vector can include a promoter sequence operably linked to the sequence encoding the first chimeric polypeptide and the second chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the multi-chain chimeric polypeptides described herein.

Cells

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides). Also provided herein are cells (e.g., any of the exemplary cells described herein or known in the art) comprising any of the nucleic acids described herein that encode any of the first chimeric polypeptides described herein. Also provided are cells (e.g., any of the exemplary cells described herein or known in the art) comprising any of the nucleic acids described herein that encode any of the second chimeric polypeptides described herein.

Also provided herein are cells (e.g., any of the exemplary cells described herein or known in the art) that include any of the vectors described herein that encode any of the multi-chain chimeric polypeptides described herein (e.g., encoding both the first and second chimeric polypeptides). Also provided herein are cells (e.g., any of the exemplary cells described herein or known in the art) that include any of the vectors described herein that encode any of the first chimeric polypeptides described herein. Also provided herein are cells (e.g., any of the exemplary cells described herein or known in the art) that include any of the vectors described herein that encode any of the second chimeric polypeptides described herein).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Multi-Chain Chimeric Polypeptides

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are method of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein.

Methods of Reducing the Level of Neuroinflammation

Also provided herein are methods of reducing the level of neuroinflammation in a tissue of a subject in need thereof that include: administering to the subject a therapeutically effective amount of a multi-chain chimeric polypeptide (e.g., any of the exemplary multi-chain chimeric polypeptides described herein) comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

In some embodiments, the level of neuroinflammation can be measured by molecular imaging (e.g., positron emission tomography (PET)), monitoring microglial activation, or astrocytic responses (e.g., immunohistochemistry, immuno-cytochemistry), or magnetic resonance methods (e.g., magnetic resonance imaging (MRI) or magnetic resonance spectroscopy (MRS)). In some embodiments, the level of neuroinflammation can be measured by determining cerebrospinal fluid (CSF) levels of biomarkers reflecting microglia and astrocyte activation, neuroinflammation, and cerebrovascular changes. In some embodiments, a neuroinflammatory biomarker can include interleukin (IL)-6, IL-7, IL-8, IL-15, interferon-γ-induced protein 10 (IP-10), monocyte chemoattractant protein 1 (MCP-1), intercellular adhesion molecule 1 (ICAM-1), vascular adhesion molecule 1 (VCAM-1), placental growth factor (PlGF), YK1-40, and fms-related tyrosine kinase 1 (Flt-1). In some embodiments, the levels of biomarkers can be measured by using an ultrasensitive Mesoscale Discovery immunoassay and/or a customized V-PLEX kit. In some embodiments, the levels of biomarkers can be measured by using ELISA kits. Additional methods for measuring the level of inflammation are known in the art.

In some embodiments, the methods described herein can provide for about a 1% to about a 99% reduction (e.g., about a 1% to about a 95% reduction, about a 1% to about a 90% reduction, about a 1% to about a 85% reduction, about a 1% to about a 80% reduction, about a 1% to about a 75% reduction, about a 1% to about a 70% reduction, about a 1% to about a 65% reduction, about a 1% to about a 60% reduction, about a 1% to about a 55% reduction, about a 1% to about a 50% reduction, about a 1% to about a 45% reduction, about a 1% to about a 40% reduction, about a 1% to about a 35% reduction, about a 1% to about a 30% reduction, about a 1% to about a 25% reduction, about a 1% to about a 20% reduction, about a 1% to about a 15% reduction, about a 1% to about a 10% reduction, about a 1% to about a 5% reduction, about a 5% to about a 99% reduction, about a 5% to about a 95% reduction, about a 5% to about a 90% reduction, about a 5% to about a 85% reduction, about a 5% to about a 80% reduction, about a 5% to about a 75% reduction, about a 5% to about a 70% reduction, about a 5% to about a 65% reduction, about a 5% to about a 60% reduction, about a 5% to about a 55% reduction, about a 5% to about a 50% reduction, about a 5% to about a 45% reduction, about a 5% to about a 40% reduction, about a 5% to about a 35% reduction, about a 5% to about a 30% reduction, about a 5% to about a 25% reduction, about a 5% to about a 20% reduction, about a 5% to about a 15% reduction, about a 5% to about a 10% reduction, about a 10% to about a 99% reduction, about a 10% to about a 95% reduction, about a 10% to about a 90% reduction, about a 10% to about a 85% reduction, about a 10% to about a 80% reduction, about a 10% to about a 75% reduction, about a 10% to about a 70% reduction, about a 10% to about a 65% reduction, about a 10% to about a 60% reduction, about a 10% to about a 55% reduction, about a 10% to about a 50% reduction, about a 10% to about a 45% reduction, about a 10% to about a 40% reduction, about a 10% to about a 35% reduction, about a 10% to about a 30% reduction, about a 10% to about a 25% reduction, about a 10% to about a 20% reduction, about a 10% to about a 15% reduction, about a 15% to about a 99% reduction, about a 15% to about a 95% reduction, about a 15% to about a 90% reduction, about a 15% to about a 85% reduction, about a 15% to about a 80% reduction, about a 15% to about a 75% reduction, about a 15% to about a 70% reduction, about a 15% to about a 65% reduction, about a 15% to about a 60% reduction, about a 15% to about a 55% reduction, about a 15% to about a 50% reduction, about a 15% to about a 45% reduction, about a 15% to about a 40% reduction, about a 15% to about a 35% reduction, about a 15% to about a 30% reduction, about a 15% to about a 25% reduction, about a 15% to about a 20% reduction, about a 20% to about a 99% reduction, about a 20% to about a 95% reduction, about a 20% to about a 90% reduction, about a 20% to about a 85% reduction, about a 20% to about a 80% reduction, about a 20% to about a 75% reduction, about a 20% to about a 70% reduction, about a 20% to about a 65% reduction, about a 20% to about a 60% reduction, about a 20% to about a 55% reduction, about a 20% to about a 50% reduction, about a 20% to about a 45% reduction, about a 20% to about a 40% reduction, about a 20% to about a 35% reduction, about a 20% to about a 30% reduction, about a 20% to about a 25% reduction, about a 25% to about a 99% reduction, about a 25% to about a 95% reduction, about a 25% to about a 90% reduction, about a 25% to about a 85% reduction, about a 25% to about a 80% reduction, about a 25% to about a 75% reduction, about a 25% to about a 70% reduction, about a 25% to about a 65% reduction, about a 25% to about a 60% reduction, about a 25% to about a 55% reduction, about a 25% to about a 50% reduction, about a 25% to about a 45% reduction, about a 25% to about a 40% reduction, about a 25% to about a 35% reduction, about a 25% to about a 30% reduction, about a 30% to about a 99% reduction, about a 30% to about a 95% reduction, about a 30% to about a 90% reduction, about a 30% to about a 85% reduction, about a 30% to about a 80% reduction, about a 30% to about a 75% reduction, about a 30% to about a 70% reduction, about a 30% to about a 65% reduction, about a 30% to about a 60% reduction, about a 30% to about a 55% reduction, about a 30% to about a 50% reduction, about a 30% to about a 45% reduction, about a 30% to about a 40% reduction, about a 30% to about a 35% reduction, about a 35% to about a 99% reduction, about a 35% to about a 95% reduction, about a 35% to about a 90% reduction, about a 35% to about a 85% reduction, about a 35% to about a 80% reduction, about a 35% to about a 75% reduction, about a 35% to about a 70% reduction, about a 35% to about a 65% reduction, about a 35% to about a 60% reduction, about a 35% to about a 55% reduction, about a 35% to about a 50% reduction, about a 35% to about a 45% reduction, about a 35% to about a 40% reduction, about a 40% to about a 99% reduction, about a 40% to about a 95% reduction, about a 40% to about a 90% reduction, about a 40% to about a 85% reduction, about a 40% to about a 80% reduction, about a 40% to about a 75% reduction, about a 40% to about a 70% reduction, about a 40% to about a 65% reduction, about a 40% to about a 60% reduction, about a 40% to about a 55% reduction, about a 40% to about a 50% reduction, about a 40% to about a 45% reduction, about a 45% to about a 99% reduction, about a 45% to about a 95% reduction, about a 45% to about a 90% reduction, about a 45% to about a 85% reduction, about a 45% to about a 80% reduction, about a 45% to about a 75% reduction, about a 45% to about a 70% reduction, about a 45% to about a 65% reduction, about a 45% to about a 60% reduction, about a 45% to about a 55% reduction, about a 45% to about a 50% reduction, about a 50% to about a 99% reduction, about a 50% to about a 95% reduction, about a 50% to about a 90% reduction, about a 50% to about a 85% reduction, about a 50% to about a 80% reduction, about a 50% to about a 75% reduction, about a 50% to about a 70% reduction, about a 50% to about a 65% reduction, about a 50% to about a 60% reduction, about a 50% to about a 55% reduction, about a 55% to about a 99% reduction, about a 55% to about a 95% reduction, about a 55% to about a 90% reduction, about a 55% to about a 85% reduction, about a 55% to about a 80% reduction, about a 55% to about a 75% reduction, about a 55% to about a 70% reduction, about a 55% to about a 65% reduction, about a 55% to about a 60% reduction, about a 60% to about a 99% reduction, about a 60% to about a 95% reduction, about a 60% to about a 90% reduction, about a 60% to about a 85% reduction, about a 60% to about a 80% reduction, about a 60% to about a 75% reduction, about a 60% to about a 70% reduction, about a 60% to about a 65% reduction, about a 65% to about a 99% reduction, about a 65% to about a 95% reduction, about a 65% to about a 90% reduction, about a 656/o to about a 85% reduction, about a 65% to about a 80% reduction, about a 65% to about a 75% reduction, about a 65% to about a 70% reduction, about a 70% to about a 99% reduction, about a 70% to about a 95% reduction, about a 70% to about a 90% reduction, about a 70% to about a 85% reduction, about a 70% to about a 80% reduction, about a 70% to about a 75% reduction, about a 75% to about a 99% reduction, about a 75% to about a 95% reduction, about a 75% to about a 90% reduction, about a 75% to about a 85% reduction, about a 75% to about a 80% reduction, about a 80% to about a 99% reduction, about a 80% to about a 95% reduction, about a 80% to about a 90% reduction, about a 80% to about a 85% reduction, about a 85% to about a 99% reduction, about a 85% to about a 95% reduction, about a 85% to about a 90% reduction, about a 90% to about a 99% reduction, about a 90% to about a 95% reduction, or about a 95% to about a 99% reduction) in neuroinflammation, e.g., as compared to the level of neuroinflammation in the subject prior to administration of the multi-chain chimeric polypeptide.

Methods of Treating a Neuroinflammatory Disorder

Also provided herein are methods of treating a neuroinflammatory disorder in a subject that include: administering to the subject a therapeutically effective amount of a multi-chain chimeric polypeptide (e.g., any of the exemplary multi-chain chimeric polypeptides described herein) comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

In some embodiments, the subject has been diagnosed or identified as having a neuroinflammatory disease. In some embodiments, the neuroinflammatory disease is selected from the group consisting of: Alzheimer's disease (AD), Parkinson's disease (βD), multiple sclerosis (MS), schizophrenia, autism, depression, fibromyalgia, Huntington's disease, amyotrophic lateral sclerosis (ALS), acute disseminated encephalomyelitis (ADEM), acute optic neuritis (AON), transverse myelitis, neuromyelitis optica (NMO), Lewy body dementia (LBD), and sarcopenia.

In some embodiments, successful treatment of a neuroinflammatory disorder can be determined by assessing improvement in one or more neuroinflammation symptoms (e.g., fatigue, reduced brain endurance, major depressive disorders, anxiety, lethargy, loss of appetite, dementia, delirium, seizures, difficulty speaking, tremors or trembling, and involuntary twitching). In some embodiments, successful treatment of Alzheimer's disease can be determined by using PET scans or analysis of cerebrospinal fluid. In some embodiments, successful treatment of Parkinson's disease (βD) can be determined by using a rating scale (e.g., Hoehn and Yahr stages, the Unified Parkinson's Disease Rating Scale) to assess the progression of the disease. In some embodiments, Hoehn and Yahr stages can be used to describe the progression of motor symptoms in βD. In some embodiments, the Unified Parkinson's Disease Rating Scale can be used to describe the progression of non-motor symptoms, including mental functioning, mood and social interaction, cognitive difficulties, ability to carry out daily activities, and treatment complications. In some embodiments, successful treatment of multiple sclerosis (MS) can be determined by using MRI to identify imaging biomarkers (e.g., lesion delineation, T1 weighted gadolinium-enhanced (Gd+ T1) lesion, T2 weighted lesion detection, Combined unique active (CUA) magnetic resonance imaging (MRI) lesions, changes in lesion count and lesion volume, detection of central vein lesions, changes in brain volume, or diffusion measures around lesions) that reflect pathological progress in MS. In some embodiments, successful treatment of acute disseminated encephalomyelitis (ADEM) can be determined by using MRI to identify imaging biomarkers (e.g., large (greater than 1 to 2 cm) multifocal, hyperintense, bilateral, asymmetric lesions in the supra-/infratentorial white matter on T2-weighted or MRI FLAIR images, wherein the lesions can be seen in gray matter, especially basal ganglia and thalamus. In some embodiments, successful treatment of acute optic neuritis (AON) can be determined by using MRI to identify imaging biomarkers (e.g., gadolinium enhancement of the optic nerve). In some embodiments, successful treatment of transverse myelitis can be determined by using MRI to identify imaging biomarkers (e.g., gadolinium-enhancing lesions on MRI spreading over one or more segments). In some embodiments, successful treatment of Huntington's disease can be determined by using a rating scale (e.g., the Unified Huntington's Disease Rating Scale total motor scale (UHDRS-TMS)) to assess the progression of the disease.

Methods of Reducing the Rate of Progression of a Neuroinflammatory Disease

Also provided herein are methods of reducing the rate of progression of a neuroinflammatory disorder in a subject that include: administering to the subject a therapeutically effective amount of a multi-chain chimeric polypeptide (e.g., any of the exemplary multi-chain chimeric polypeptides described herein) comprising: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein: the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

In some embodiments, the subject has been diagnosed or identified as having a neuroinflammatory disease. In some embodiments, the neuroinflammatory disease is selected from the group consisting of: Alzheimer's disease (AD), Parkinson's disease (βD), multiple sclerosis (MS), schizophrenia, autism, depression, fibromyalgia, Huntington's disease, amyotrophic lateral sclerosis (ALS), acute disseminated encephalomyelitis (ADEM), acute optic neuritis (AON), transverse myelitis, neuromyelitis optica (NMO), Lewy body dementia (LBD), and sarcopenia.

In some embodiments, progression of a neuroinflammatory disorder can be determined by assessing the progression in one or more neuroinflammation symptoms (e.g., brain fatigue, reduced brain endurance, depression, lethargy, loss of appetite, dementia, delirium, seizures, difficulty speaking, tremors or trembling, and involuntary twitching). In some embodiments, progression of Alzheimer's disease can be determined by using PET scans or analysis of cerebrospinal fluid. In some embodiments, progression of Parkinson's disease (βD) can be determined by using a rating scale (e.g., Hoehn and Yahr stages, the Unified Parkinson's Disease Rating Scale) to assess the progression of the disease. In some embodiments, Hoehn and Yahr stages can be used to describe the progression of motor symptoms in βD. In some embodiments, the Unified Parkinson's Disease Rating Scale can be used to describe the progression of non-motor symptoms, including mental functioning, mood and social interaction, cognitive difficulties, ability to carry out daily activities, and treatment complications. In some embodiments, progression of multiple sclerosis (MS) can be determined by using MRI to identify imaging biomarkers (e.g., lesion delineation, T1 weighted gadolinium-enhanced (Gd+ Ti) lesion, T2 weighted lesion detection, Combined unique active (CUA) magnetic resonance imaging (MRI) lesions, changes in lesion count and lesion volume, detection of central vein lesions, changes in brain volume, or diffusion measures around lesions) that reflect pathological progression in MS. In some embodiments, progression of acute disseminated encephalomyelitis (ADEM) can be determined by using MRI to identify imaging biomarkers (e.g., large (greater than 1 to 2 cm) multifocal, hyperintense, bilateral, asymmetric lesions in the supra-/infratentorial white matter on T2-weighted or MRI FLAIR images, wherein the lesions can be seen in gray matter, especially basal ganglia and thalamus). In some embodiments, progression of acute optic neuritis (AON) can be determined by using MRI to identify imaging biomarkers (e.g., gadolinium enhancement of the optic nerve). In some embodiments, progression of transverse myelitis can be determined by using MRI to identify imaging biomarkers (e.g., gadolinium-enhancing lesions on MRI spreading over one or more segments). In some embodiments, progression of Huntington's disease can be determined by using a rating scale (e.g., the Unified Huntington's Disease Rating Scale total motor scale (UHDRS-TMS)) to assess the progression of the disease.

In some embodiments, the methods described herein can provide for about a 1% to about a 99% reduction (e.g., about a 1% to about a 95% reduction, about a 1% to about a 90% reduction, about a 1% to about a 85% reduction, about a 1% to about a 80% reduction, about a 1% to about a 75% reduction, about a 1% to about a 70% reduction, about a 1% to about a 65% reduction, about a 1% to about a 60% reduction, about a 1% to about a 55% reduction, about a 1% to about a 50% reduction, about a 1% to about a 45% reduction, about a 1% to about a 40% reduction, about a 1% to about a 35% reduction, about a 1% to about a 30% reduction, about a 1% to about a 25% reduction, about a 1% to about a 20% reduction, about a 1% to about a 15% reduction, about a 1% to about a 10% reduction, about a 1% to about a 5% reduction, about a 5% to about a 99% reduction, about a 5% to about a 95% reduction, about a 5% to about a 90% reduction, about a 5% to about a 85% reduction, about a 5% to about a 80% reduction, about a 5% to about a 75% reduction, about a 5% to about a 70% reduction, about a 5% to about a 65% reduction, about a 5% to about a 60% reduction, about a 5% to about a 55% reduction, about a 5% to about a 50% reduction, about a 5% to about a 45% reduction, about a 5% to about a 40% reduction, about a 5% to about a 35% reduction, about a 5% to about a 30% reduction, about a 5% to about a 25% reduction, about a 5% to about a 20% reduction, about a 5% to about a 15% reduction, about a 5% to about a 10% reduction, about a 10% to about a 99% reduction, about a 10% to about a 95% reduction, about a 10% to about a 90% reduction, about a 10% to about a 85% reduction, about a 10% to about a 80% reduction, about a 10% to about a 75% reduction, about a 10% to about a 70% reduction, about a 10% to about a 65% reduction, about a 10% to about a 60% reduction, about a 10% to about a 55% reduction, about a 10% to about a 50% reduction, about a 10% to about a 45% reduction, about a 10% to about a 40% reduction, about a 10% to about a 35% reduction, about a 10% to about a 30% reduction, about a 10% to about a 25% reduction, about a 10% to about a 20% reduction, about a 10% to about a 15% reduction, about a 15% to about a 99% reduction, about a 15% to about a 95% reduction, about a 15% to about a 90% reduction, about a 15% to about a 85% reduction, about a 15% to about a 80% reduction, about a 15% to about a 75% reduction, about a 15% to about a 70% reduction, about a 15% to about a 65% reduction, about a 15% to about a 60% reduction, about a 15% to about a 55% reduction, about a 15% to about a 50% reduction, about a 15% to about a 45% reduction, about a 15% to about a 40% reduction, about a 15% to about a 35% reduction, about a 15% to about a 30% reduction, about a 15% to about a 25% reduction, about a 15% to about a 20% reduction, about a 20% to about a 99% reduction, about a 20% to about a 95% reduction, about a 20% to about a 90% reduction, about a 20% to about a 85% reduction, about a 20% to about a 80% reduction, about a 20% to about a 75% reduction, about a 20% to about a 70% reduction, about a 20% to about a 65% reduction, about a 20% to about a 60% reduction, about a 20% to about a 55% reduction, about a 20% to about a 50% reduction, about a 20% to about a 45% reduction, about a 20% to about a 40% reduction, about a 20% to about a 35% reduction, about a 20% to about a 30% reduction, about a 20% to about a 25% reduction, about a 25% to about a 99% reduction, about a 25% to about a 95% reduction, about a 25% to about a 90% reduction, about a 25% to about a 85% reduction, about a 25% to about a 80% reduction, about a 25% to about a 75% reduction, about a 25% to about a 70% reduction, about a 25% to about a 65% reduction, about a 25% to about a 60% reduction, about a 25% to about a 55% reduction, about a 25% to about a 50% reduction, about a 25% to about a 45% reduction, about a 25% to about a 40% reduction, about a 25% to about a 35% reduction, about a 25% to about a 30% reduction, about a 30% to about a 99% reduction, about a 30% to about a 95% reduction, about a 30% to about a 90% reduction, about a 30% to about a 85% reduction, about a 30% to about a 80% reduction, about a 30% to about 75% reduction, about a 30% to about a 70% reduction, about a 30% to about a 65% reduction, about a 30% to about a 60% reduction, about a 30% to about a 55% reduction, about a 30% to about a 50% reduction, about a 30% to about a 45% reduction, about a 30% to about a 40% reduction, about a 30% to about a 35% reduction, about a 35% to about a 99% reduction, about a 35% to about a 95% reduction, about a 35% to about a 90% reduction, about a 35% to about a 85% reduction, about a 35% to about a 80% reduction, about a 35% to about a 75% reduction, about a 35% to about a 70% reduction, about a 35% to about a 65% reduction, about a 35% to about a 60% reduction, about a 35% to about a 55% reduction, about a 35% to about a 50% reduction, about a 35% to about a 45% reduction, about a 35% to about a 40% reduction, about a 40% to about a 99% reduction, about a 40% to about a 95% reduction, about a 40% to about a 90% reduction, about a 40% to about a 85% reduction, about a 40% to about a 80% reduction, about a 40% to about a 75% reduction, about a 40% to about a 70% reduction, about a 40% to about a 65% reduction, about a 40% to about a 60% reduction, about a 40% to about a 55% reduction, about a 40% to about a 50% reduction, about a 40% to about a 45% reduction, about a 45% to about a 99% reduction, about a 45% to about a 95% reduction, about a 45% to about a 90% reduction, about a 45% to about a 85% reduction, about a 45% to about a 80% reduction, about a 45% to about a 75% reduction, about a 45% to about a 70% reduction, about a 45% to about a 65% reduction, about a 45% to about a 60% reduction, about a 45% to about a 55% reduction, about a 45% to about a 50% reduction, about a 50% to about a 99% reduction, about a 50% to about a 95% reduction, about a 50% to about a 90% reduction, about a 50% to about a 85% reduction, about a 50% to about a 80% reduction, about a 50% to about a 75% reduction, about a 50% to about a 70% reduction, about a 50% to about a 65% reduction, about a 50% to about a 60% reduction, about a 50% to about a 55% reduction, about a 55% to about a 99% reduction, about a 55% to about a 95% reduction, about a 55% to about a 90% reduction, about a 55% to about a 85% reduction, about a 55% to about a 80% reduction, about a 55% to about a 75% reduction, about a 55% to about a 70% reduction, about a 55% to about a 65% reduction, about a 55% to about a 60% reduction, about a 60% to about a 99% reduction, about a 60% to about a 95% reduction, about a 60% to about a 90% reduction, about a 60% to about a 85% reduction, about a 60% to about a 80% reduction, about a 60% to about a 75% reduction, about a 60% to about a 70% reduction, about a 60% to about a 65% reduction, about a 65% to about a 99% reduction, about a 65% to about a 95% reduction, about a 65% to about a 90% reduction, about a 65% to about a 85% reduction, about a 65% to about a 80% reduction, about a 65% to about a 75% reduction, about a 65% to about a 70% reduction, about a 70% to about a 99% reduction, about a 70% to about a 95% reduction, about a 70% to about a 90% reduction, about a 70% to about a 85% reduction, about a 70% to about a 80% reduction, about a 70% to about a 75% reduction, about a 75% to about a 99% reduction, about a 75% to about a 95% reduction, about a 75% to about a 90% reduction, about a 75% to about a 85% reduction, about a 75% to about a 80% reduction, about a 80% to about a 99% reduction, about a 80% to about a 95% reduction, about a 80% to about a 90% reduction, about a 80% to about a 85% reduction, about a 85% to about a 99% reduction, about a 85% to about a 95% reduction, about a 85% to about a 90% reduction, about a 90% to about a 99% reduction, about a 90% to about a 95% reduction, or about a 95% to about a 99% reduction) in the rate of progression of a neuroinflammatory disease, e.g., as compared to the rate of progression in a similar subject not administered a treatment or administered a different treatment.

EXAMPLES

The invention is further described in the following examples, which do not limit the scope of the invention described in the claims.

Example 1. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides includes a first chimeric polypeptide that includes a soluble tissue factor domain covalently linked a first target-binding domain and a first domain of an affinity pair of domains. The second chimeric polypeptide in each of the two multi-chain chimeric polypeptides includes a second domain of the affinity pair of domains, and a second target-binding domain.

Description of logic underlying construction of multi-chain chimeric polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 1 and FIG. 2) possess functional scFvs or cytokines, in vitro binding assays were performed. The data from the aforementioned assays were consistent with the purified first chimeric polypeptides having the expected biological activities (e.g. scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connecter linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties and activities.

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are stable. These multi-chain chimeric polypeptides are structurally intact and frilly biologically active when they are incubated in human serum at 37° C. for 72 hours.

Characterization of Propensity of Described Chimeric Polypeptides to Aggregate

Both purified multi-chain chimeric polypeptides developed do not form aggregates when stored at 4° C. in PBS.

Characterization of Viscosity of Described Chimeric Polypeptides

There is no viscosity issue when the multi-chain chimeric polypeptides are formulated at a concentration as high as 50 mg/mL in PBS.

Additional Applications of the Multi-Chain Chimeric Polypeptide Platform

The data from these studies show that the platform technologies described herein can be utilized to create molecules that could be fused to target-binding domains derived from antibodies, in any of the formats as described herein including, without limitation, adhesion molecules, receptors, cytokines, ligands, and chemokines. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 2: TGFRt15-TGFRs Fusion Protein Generation and Characterization

Figure 3:
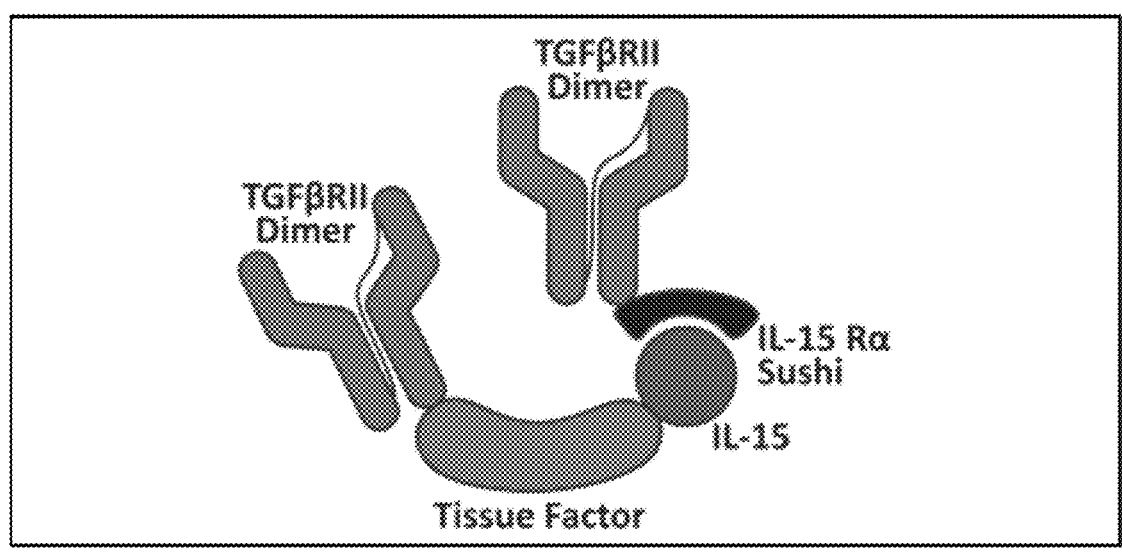
FIG. 3 shows a schematic of the TGFRt15-TGFRs construct.
Figure 4:
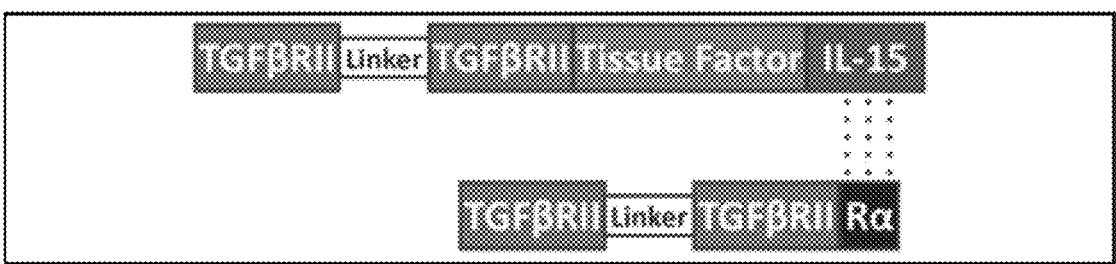
FIG. 4 shows an additional schematic of the TGFRt15-TGFRs construct.

A fusion protein complex was generated comprising of TGFβ Receptor II/IL-15RαSu and TGFβ Receptor II/TF/IL-15 fusion proteins (FIG. 3 and FIG. 4). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

(SEQ ID NO: 59)

(Signal peptide)
ATGAAGTGGGTGACCTTCATCAGCCTGCTGTTCCTGTTCTCCAGCGCCTACTCC (Two Human TGFβ Receptor II fragments)
ATCCCCCCCCATGTGCAAAAGAGCGTGAACAACGATATGATCGTGACCGACAACAA

CGGCGCCGTGAAGTTTCCCCAGCTCTGCAAGTTCTGCGATGTCAGGTTCAGCACCTG

-continued

CGATAATCAGAAGTCCTGCATGTCCAACTGCAGCATCACCTCCATCTGCGAGAAGCC

CCAAGAAGTGTGCGTGGCCGTGTGGCGGAAAAATGACGAGAACATCACCCTGGAGA

CCGTGTGTCACGACCCCAAGCTCCCTTATCACGACTTCATTCTGGAGGACGCTGCCT

CCCCCAAATGCATCATGAAGGAGAAGAAGAAGCCCGGAGAGACCTTCTTTATGTGT

TCCTGTAGCAGCGACGAGTGTAACGACAACATCATCTTCAGCGAAGAGTACAACAC

CAGCAACCCTGATGGAGGTGGCGGATCCGGAGGTGGAGGTTCTGGTGGAGGTGGGA

GTATTCCTCCCCACGTGCAGAAGAGCGTGAATAATGACATGATCGTGACCGATAAC

AATGGCGCCGTGAAATTTCCCCAGCTGTGCAAATTCTGCGATGTGAGGTTTTCCACC

TGCGACAACCAGAAGTCCTGTATGAGCAACTGCTCCATCACCTCCATCTGTGAGAAG

CCTCAGGAGGTGTGCGTGGCTGTCTGGCGGAAGAATGACGAGAATATCACCCTGGA

AACCGTCTGCCACGATCCCAAGCTGCCCTACCACGATTTCATCCTGGAAGACGCCGC

CAGCCCTAAGTGCATCATGAAAGAGAAAAAGAAGCCTGGCGAGACCTTTTTCATGT

GCTCCTGCAGCAGCGACGAATGCAACGACAATATCATCTTTAGCGAGGAATACAAT

ACCAGCAACCCCGAC (Human Tissue Factor 219)
AGCGGCACAACCAACACAGTCGCTGCCTATAACCTCACTTGGAAGAGCACCAACTT

CAAAACCATCCTCGAATGGGAACCCAAACCCGTTAACCAAGTTTACACCGTGCAGA

TCAGCACCAAGTCCGGCGACTGGAAGTCCAAATGTTTCTATACCACCGACACCGAGT

GCGATCTCACCGATGAGATCGTGAAAGATGTGAAACAGACCTACCTCGCCCGGGTG

TTTAGCTACCCCGCCGGCAATGTGGAGAGCACTGGTTCCGCTGGCGAGCCTTTATAC

GAGAACAGCCCCGAATTTACCCCTTACCTCGAGACCAATTTAGGACAGCCCACCATC

CAAAGCTTTGAGCAAGTTGGCACAAAGGTGAATGTGACAGTGGAGGACGAGCGGAC

TTTAGTGCGGCGGAACAACACCTTTCTCAGCCTCCGGGATGTGTTCGGCAAAGATTT

AATCTACACACTGTATTACTGGAAGTCCTCTTCCTCCGGCAAGAAGACAGCTAAAAC

CAACACAAACGAGTTTTTAATCGACGTGGATAAAGGCGAAAACTACTGTTTCAGCGT

GCAAGCTGTGATCCCCTCCCGGACCGTGAATAGGAAAAGCACCGATAGCCCCGTTG

AGTGCATGGGCCAAGAAAAGGGCGAGTTCCGGGAG (Human IL-15)
AACTGGGTGAACGTCATCAGCGATTTAAAGAAGATCGAAGATTTAATTCAGTCCATG

CATATCGACGCCACTTTATACACAGAATCCGACGTGCACCCCTCTTGTAAGGTGACC

GCCATGAAATGTTTTTTACTGGAGCTGCAAGTTATCTCTTTAGAGAGCGGAGACGCT

AGCATCCACGACACCGTGGAGAATTTAATCATTTTAGCCAATAACTCTTTATCCAGC

AACGGCAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATCAATACCTCC.

The amino acid sequence of TGFβ Receptor II/TF/IL-15 fusion protein (including the leader sequence) is as follows:

(SEQ ID NO: 7)
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

-continued
KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

-continued

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(SEQ ID NO: 61)
(Signal peptide)
ATGAAGTGGGTGACCTTCATCAGCCTGCTGTTCCTGTTCTCCAGCGCCTA

CTCC (Two human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.

The amino acid sequence of the two TGFβ Receptor II/IL-15RαSu construct (including signal peptide sequence) is as follows:

(SEQ ID NO: 8)
(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKA

TNVAHWTTPSLKCIR.

In some cases, the leader peptide is cleaved from the intact polypeptide to generate the mature form that may be soluble or secreted.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF IgG1 affinity and other chromatography methods.

Effect of TGFRt15-TGFRs on TGFβ1 Activity in HEK-Blue TGFβ Cells

Figure 5:
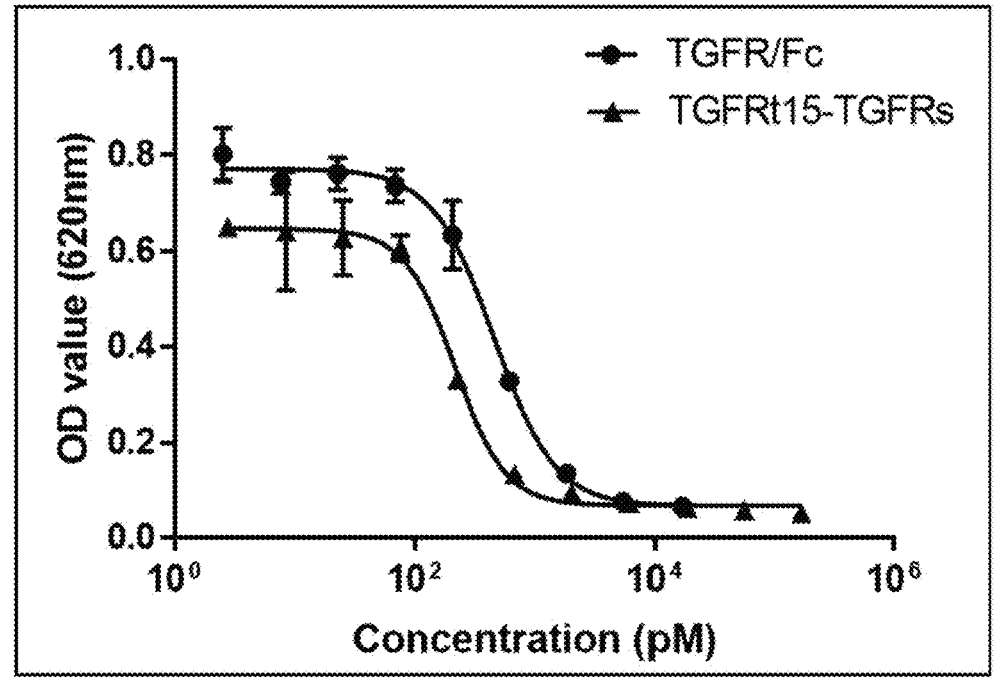
FIG. 5 shows results of TGFβ1 inhibition by TGFRt15-TGFRs and TGFR-Fc.

To evaluate the activity of TGFβRII in TGFRt15-TGFRs, the effect of TGFRt15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1x glutamine, 1x anti-anti, and 2× gluta-mine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-TGFRs or TGFR-Fc (R&D Systems) prepared at a 1:3 serial dilution was then added to the plate to reach a total volume of 200 μL. After 24 hrs of incubation at 37° C., 40 μL of induced HEK-Blue TGF$ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβI in HEK-Blue TGFβ cells (FIG. 5).

The IL-15 in TGFRt15-TGFRs Promotes IL-2Rβ and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 6). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 5, TGFRt15-TGFRs and IL-15 promoted 32Dβ cell proliferation, with the $EC_{50}$ of TGFRt15-TGFRs and IL-15 being 1901 pM and 10.63 pM, respectively.

Figure 7B:
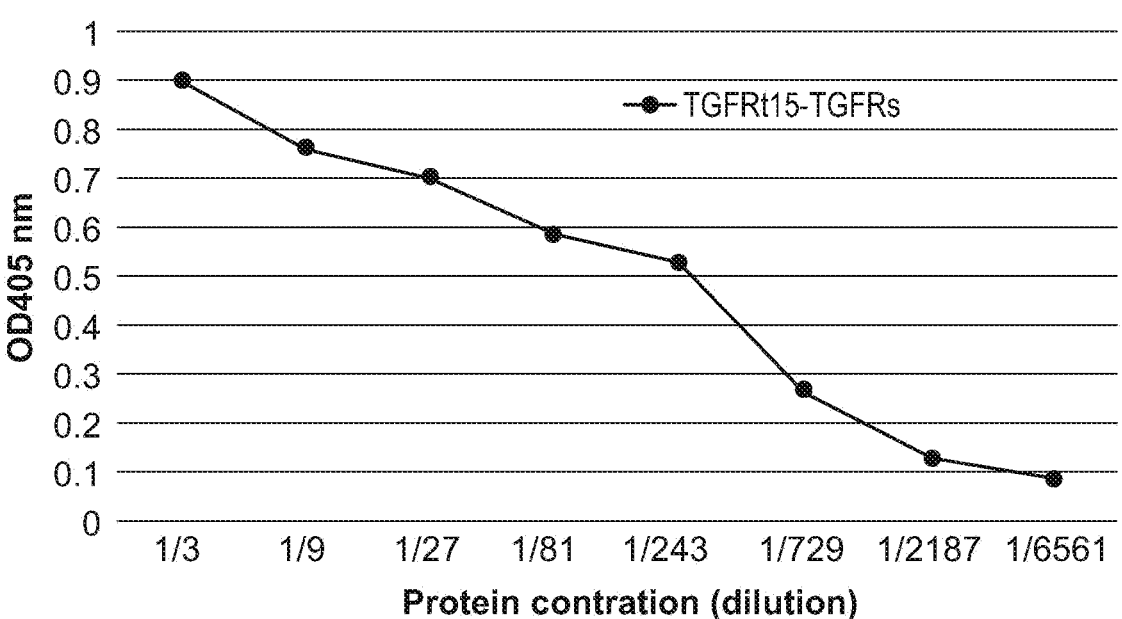

Detection of IL-15 and TGFβRII Domains in TGFRt15-TGFRs with Corresponding Antibodies Using ELISA A 96-well plate was coated with 100 μL (8 pg/mL) of anti-TF IgG1 in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFβRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 7A and 7B, the IL-15 and TGFβ RII domains in TGFRt15-TGFRs were detected by the individual antibodies.

Figure 8:
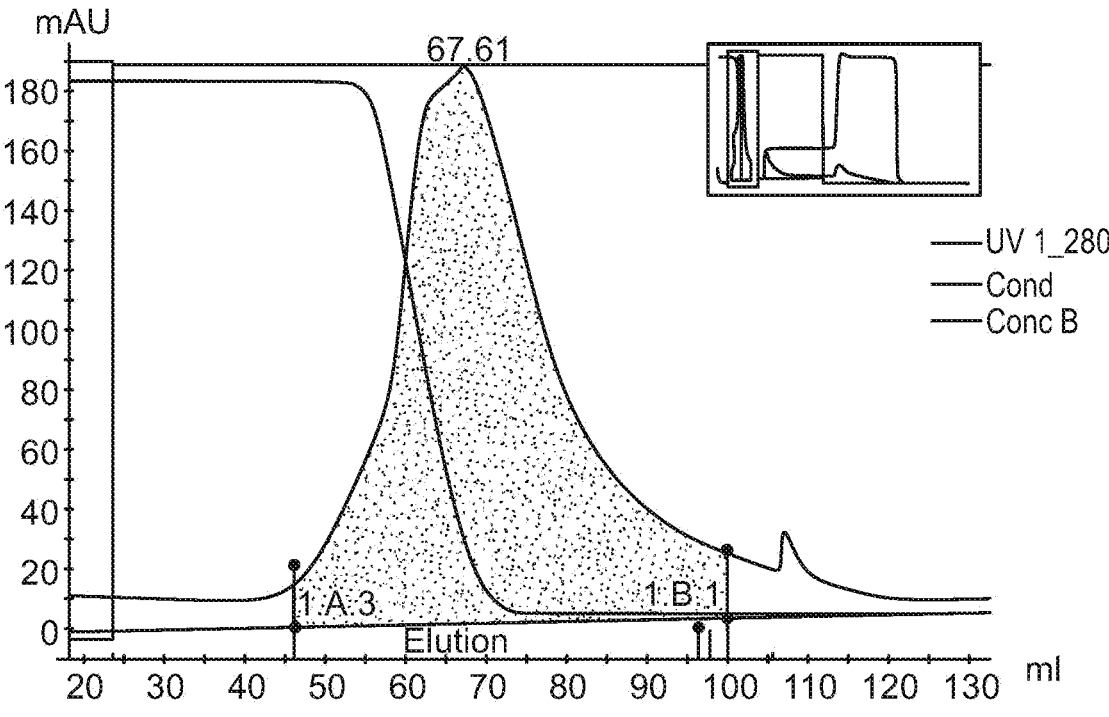
FIG. 8 is a line graph showing the chromatographic profile of TGFRt15-TGFRs protein containing cell culture supernatant following binding and elution on anti-TF antibody resin.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 8, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 9:
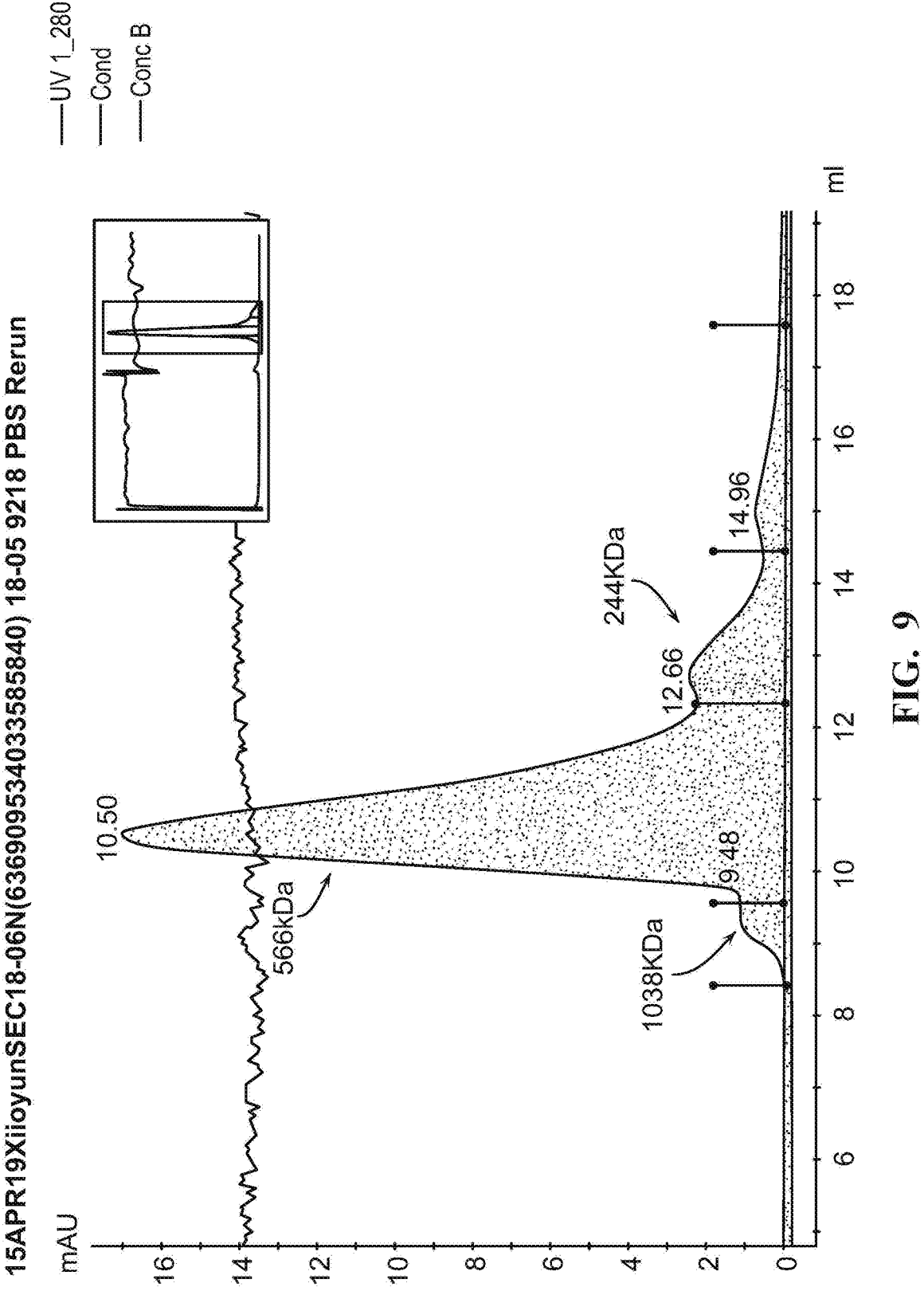
FIG. 9 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 9. The SEC results showed four protein peaks for TGFRt15-TGFRs.

Reduced SDS-PAGE Analysis of TGFRt15-TGFRs

To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 10:
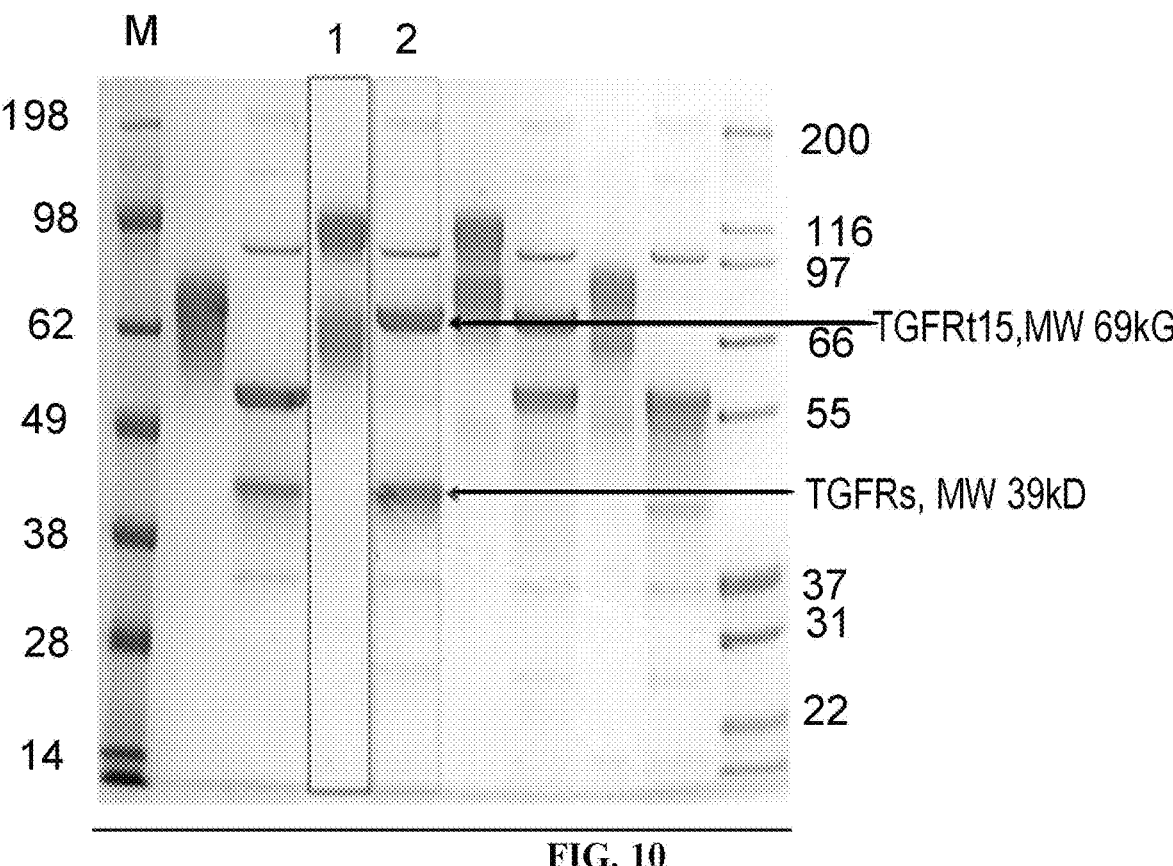
FIG. 10 shows TGFRt15-TGFRs before and after deglycosylation as analyzed by reduced SDS-PAGE.

To verify that the TGFRt15-TGFRs protein undergoes glycosylation after translation in CHO cells, a deglycosylation experiment was conducted using the Protein Deglycosylation Mix II kit from New England Biolabs and the manufacturer's instructions. FIG. 10 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL/6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 11A:
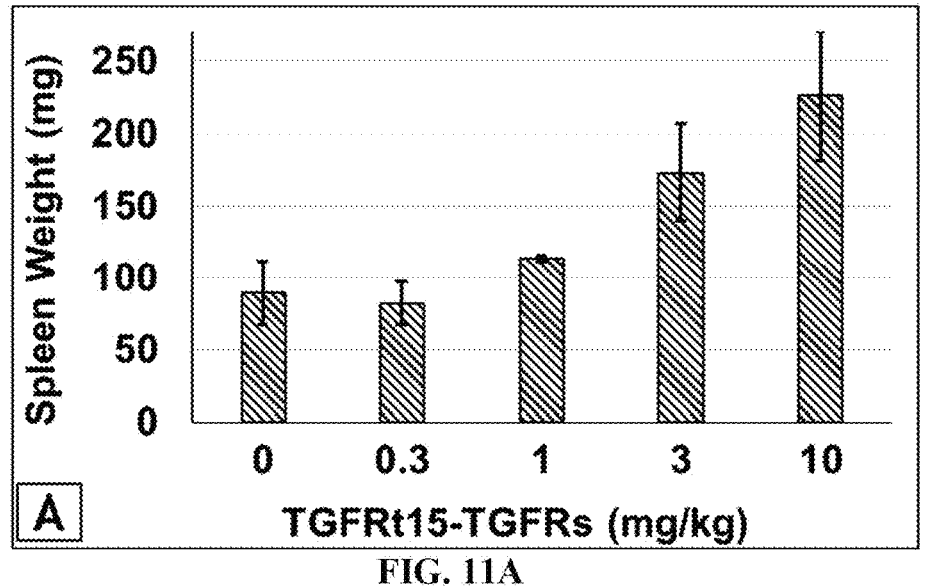
FIGS. 11A and 11B show spleen weight and the percentages of immune cell types in TGFRt15-TGFRs-treated and control-treated mice.
Figure 11B:
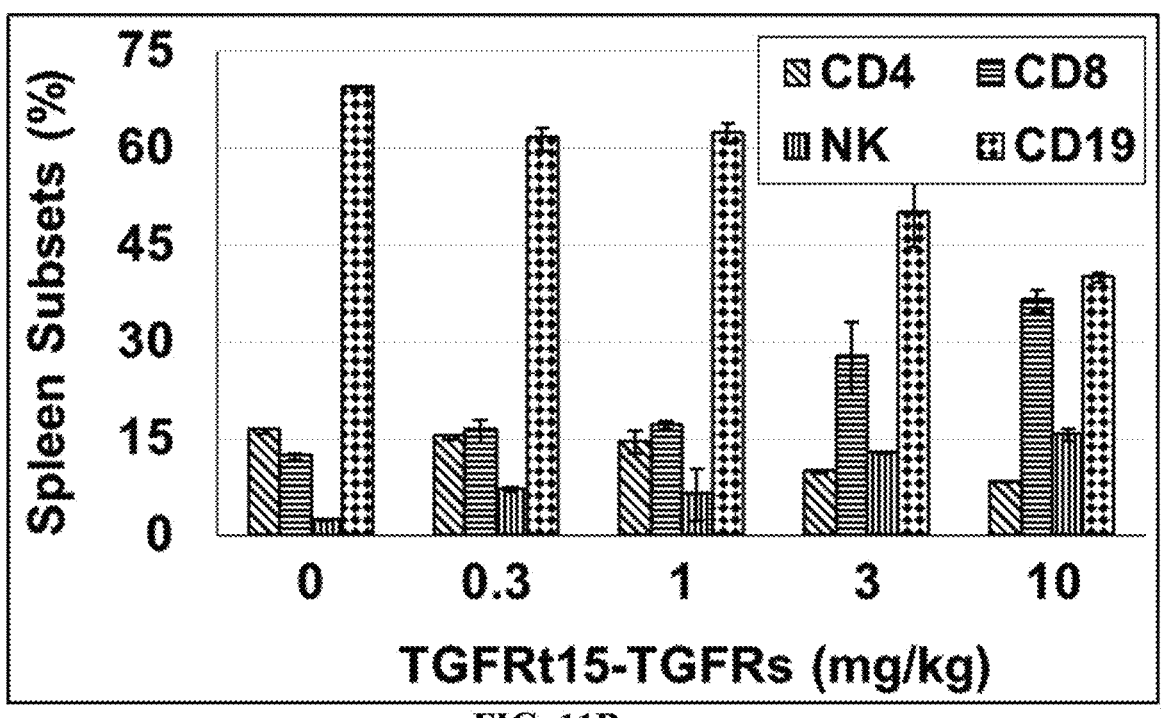

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 11A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of CD4+ T cells, CD8+ T cells, NK cells, and CD19+ B cells present in the spleen of control-treated and TGFRt15-TGFRs-treated mice were evaluated. As shown in FIG. 11B, in the spleens of mice treated with TGFRt15-TGFRs, the percentages of CD8+ T cells and NK cells both increased with increasing dosage of TGFRt15-TGFRs. Specifically, the percentages of CD8+ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular CD8+ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 12A:
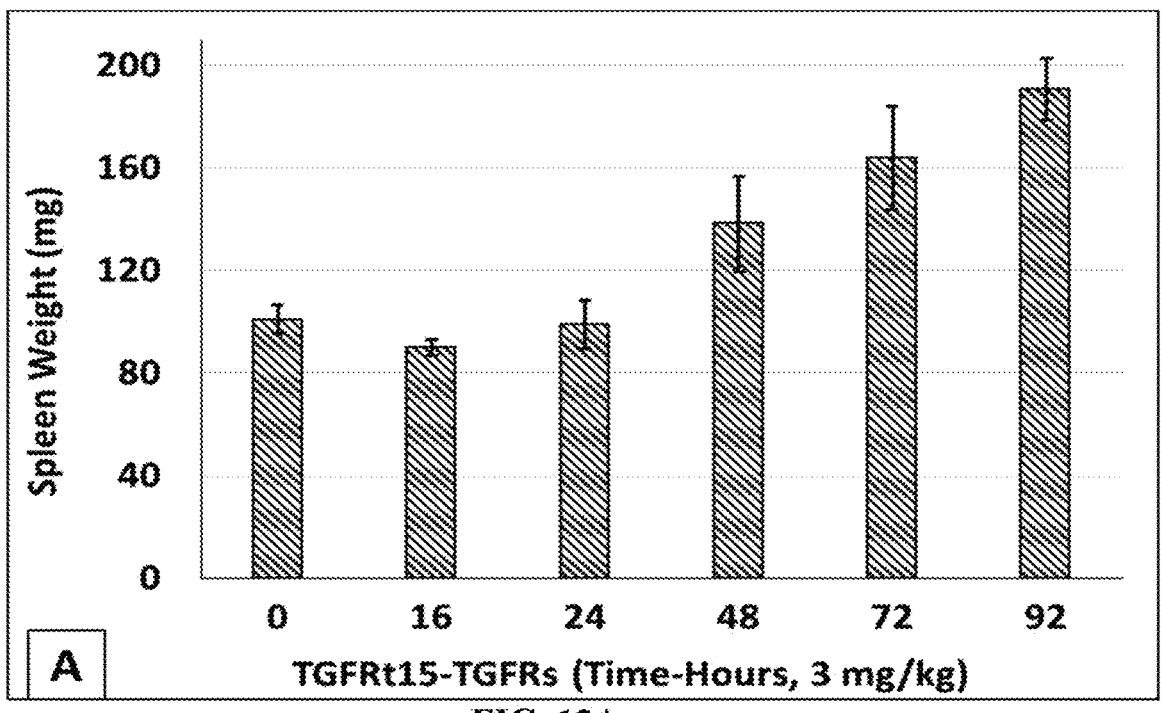
FIGS. 12A and 12B show the spleen weight and immunostimulation over 92 hours in mice treated with TGFRt15-TGFRs.
Figures 12B, 13A:
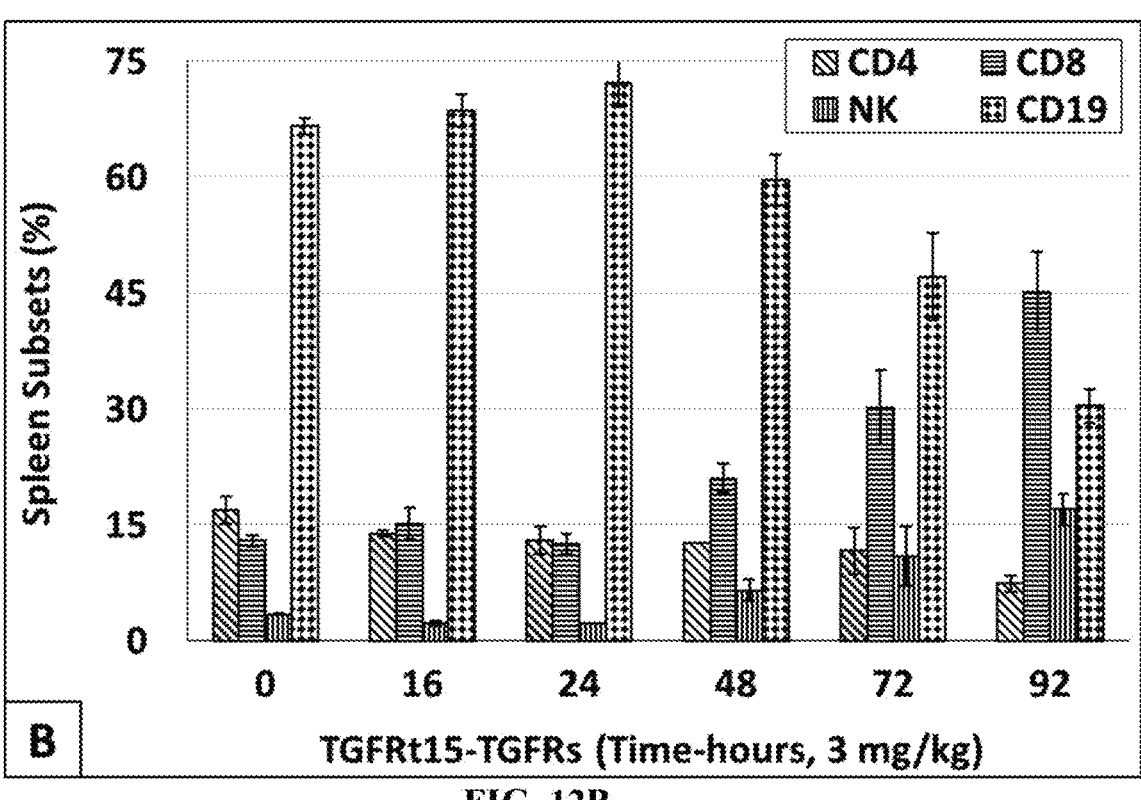
FIGS. 13A and 13B show Ki67 and Granzyme B expression in mice treated with TGFRt15-TGFRs over time.
Figures 13B, 14:
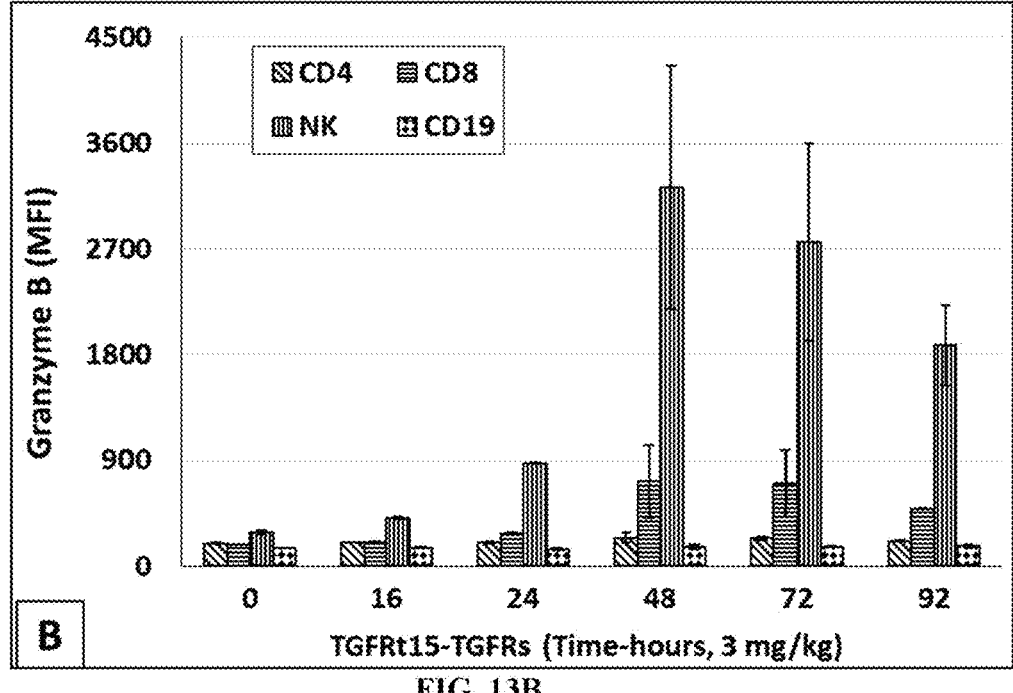
FIG. 14 shows enhancement of cytotoxicity of splenocytes by TGFRt15-TGFRs in C57BL/6 Mice.

The mouse splenocytes were prepared in order to evaluate the immunostimulatory activity of TGFRt15-TGFRs over time in mice. As shown in FIG. 12A, the spleen weight in mice treated with TGFRt15-TGFRs increased 48 hours posttreatment and continued to increase over time. In addition, the percentages of CD4$^+$ T cells, CD8$^+$ T cells, NK cells, and CD19$^+$ B cells present in the spleen of control-treated and TGFRt15-TGFRs-treated mice were evaluated. As shown in FIG. 12B, in the spleens of mice treated with TGFRt15-TGFRs, the percentages of CD8$^+$ T cells and NK cells both increased at 48 hours after treatment and were higher and higher overtime after the single dose treatment. These results further demonstrate that TGFRt15-TGFRs is able to stimulate immune cells in the spleen, in particular CD8$^+$ T cells and NK cells. Furthermore, the dynamic proliferation of immune cells based on K67 expression of splenocytes and cytotoxicity potential based on granzyme B expression were evaluated in splenocytes isolated from mice following a single dose (3 mg/kg) of TGFRt15-TGFRs. As shown in FIGS. 13A and 13B, in the spleens of mice treated with TGFRt15-TGFRs, the expression of Ki67 and granzyme B by NK cells increased at 24 hours after treatment and its expression of CD8$^+$ T cells and NK cells both increased at 48 hours and later time points after the single dose treatment. These results demonstrate that TGFRt15-TGFRs not only increases the numbers of CD8$^+$ T cells and NK cells but also enhance the cytotoxicity of these cells. The single dose treatment of TGFRt15-TGFRs led CD8' T cells and NK cells to proliferate for at least 4 days.

The cytotoxicity of the splenocytes from TGFRt15-TG-FRs-treated mice against tumor cells was also evaluated. Mouse Moloney leukemia cells (Yac-1) were labeled with CellTrace Violet and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 14, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 15:
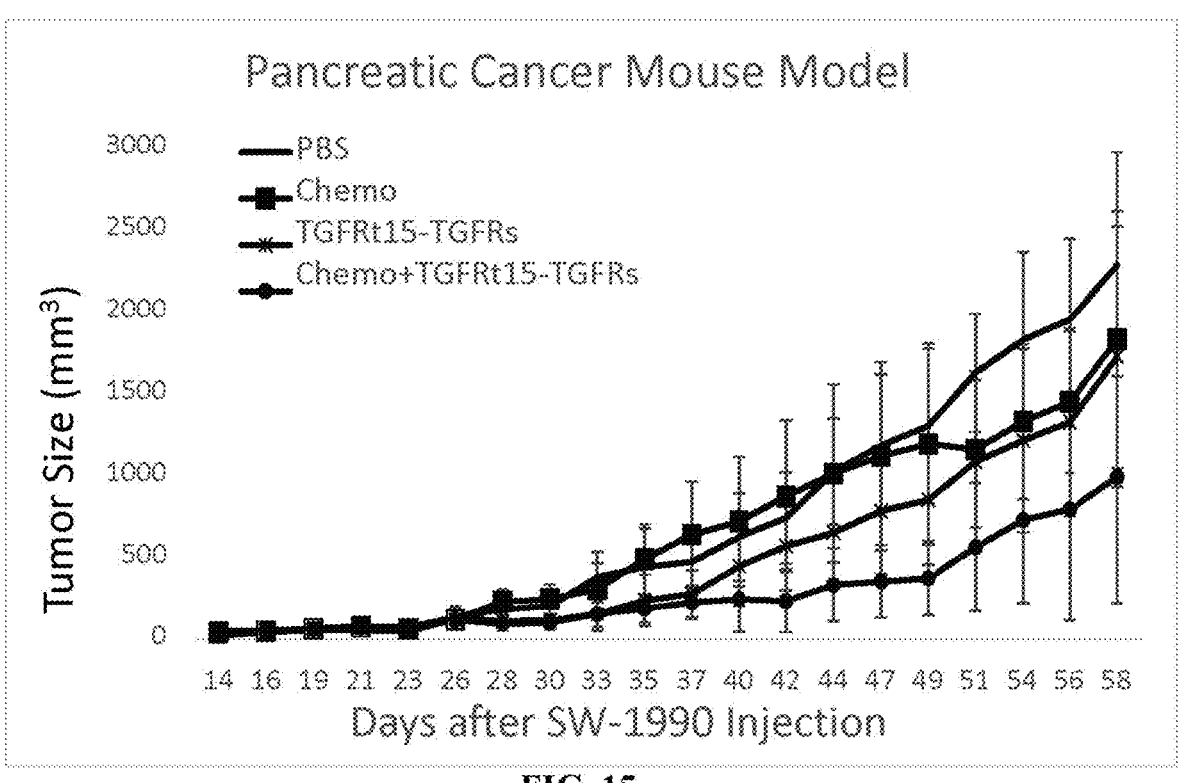
FIG. 15 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, 2×10$^6$ cells/mouse, in 100 μL HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 15).

In Vitro Senescent B16F10 Melanoma Model

Figure 16:
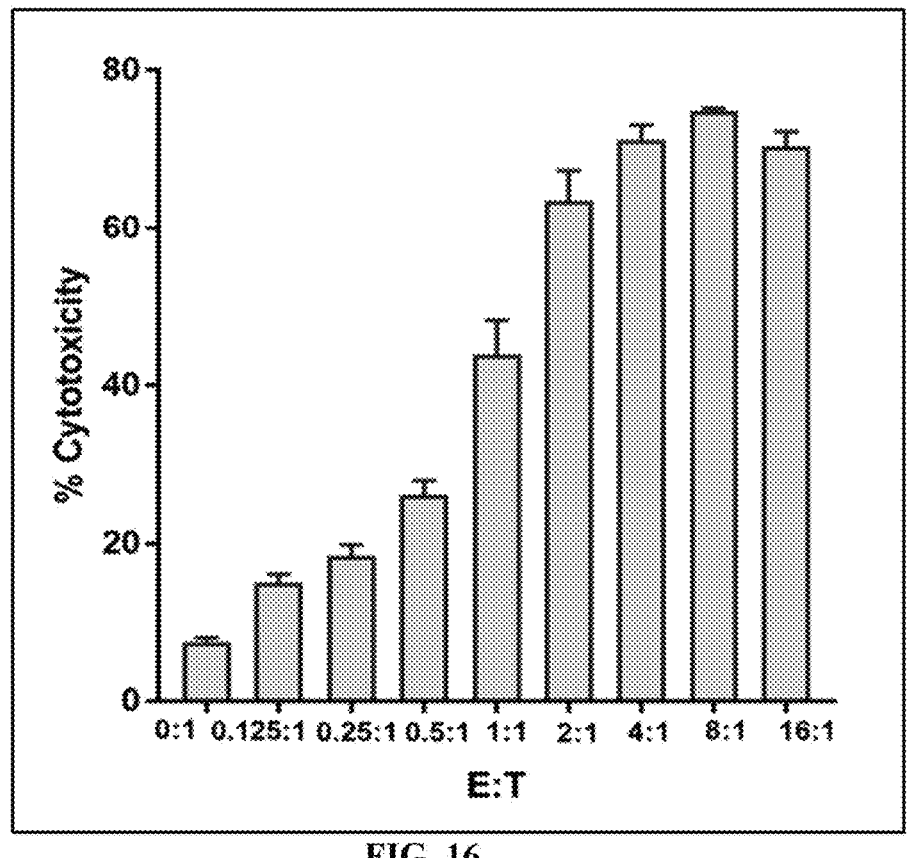
FIG. 16 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with Cell-Trace violet and incubated for 16 hrs with different E:T ratio of in vitro 2t2-activated mouse NK cells (isolated from spleen of C57BL/6 mice injected with TGFRt15-TGFRs10 mg/kg for 4 days). The cells were trypsinized, washed and resuspended in complete media containing propidium iodide (PI) solution. The cytotoxicity was assessed by flow cytometry (FIG. 16).

Example 3: Stimulation of NK Cells In Vivo by TGFRt15-TGFRs

Figure 17A:
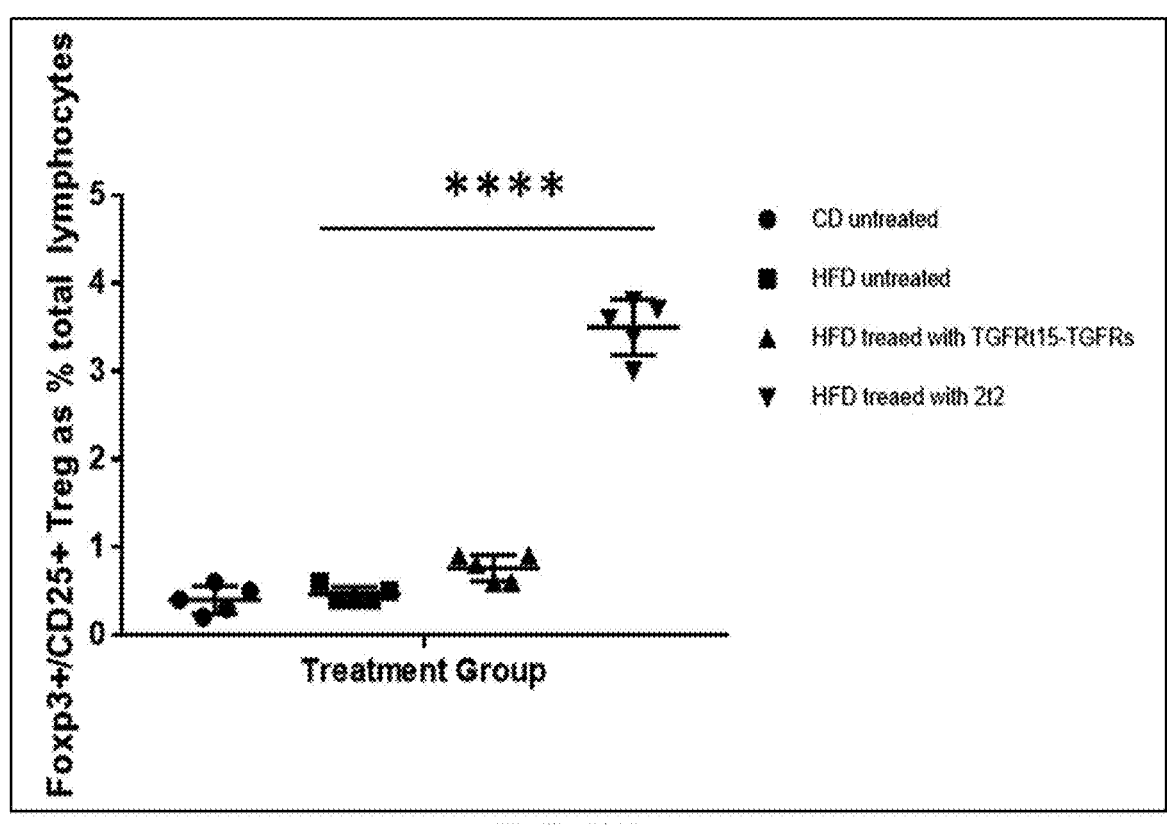
FIGS. 17A-17C show in vivo stimulation of Tregs, NK cells, and CD8+ T cells in ApoE−/− mice fed with a Western diet and treated with TGFRt15-TGFRs.
Figure 17B:
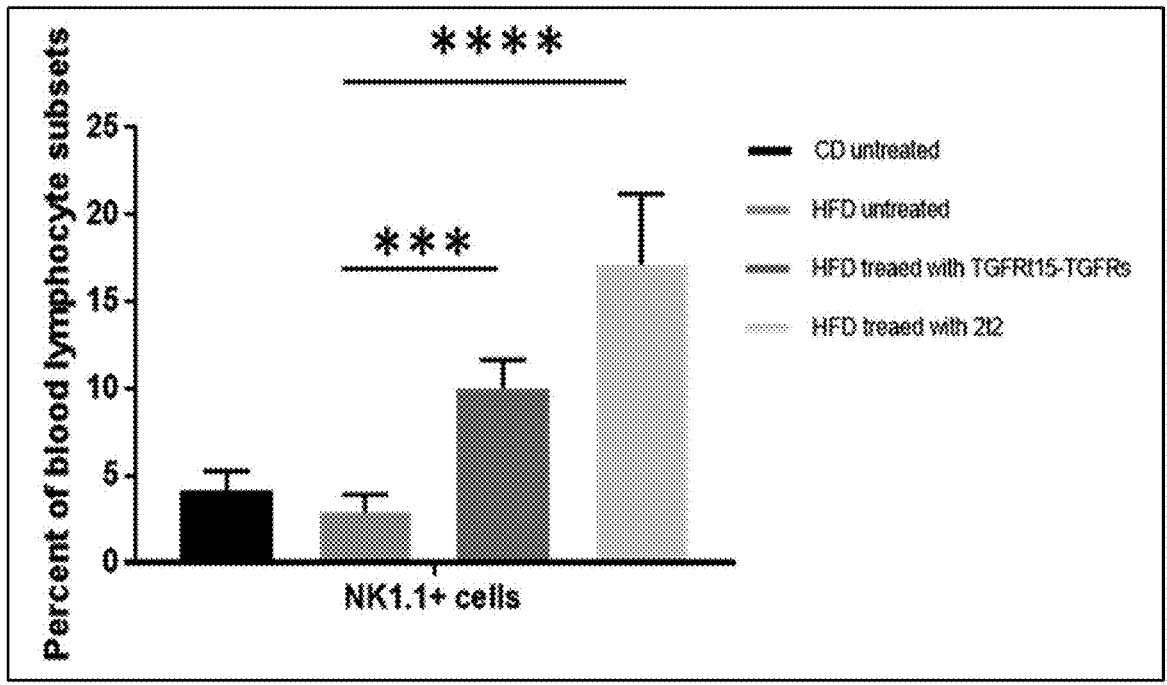
Figure 17C:
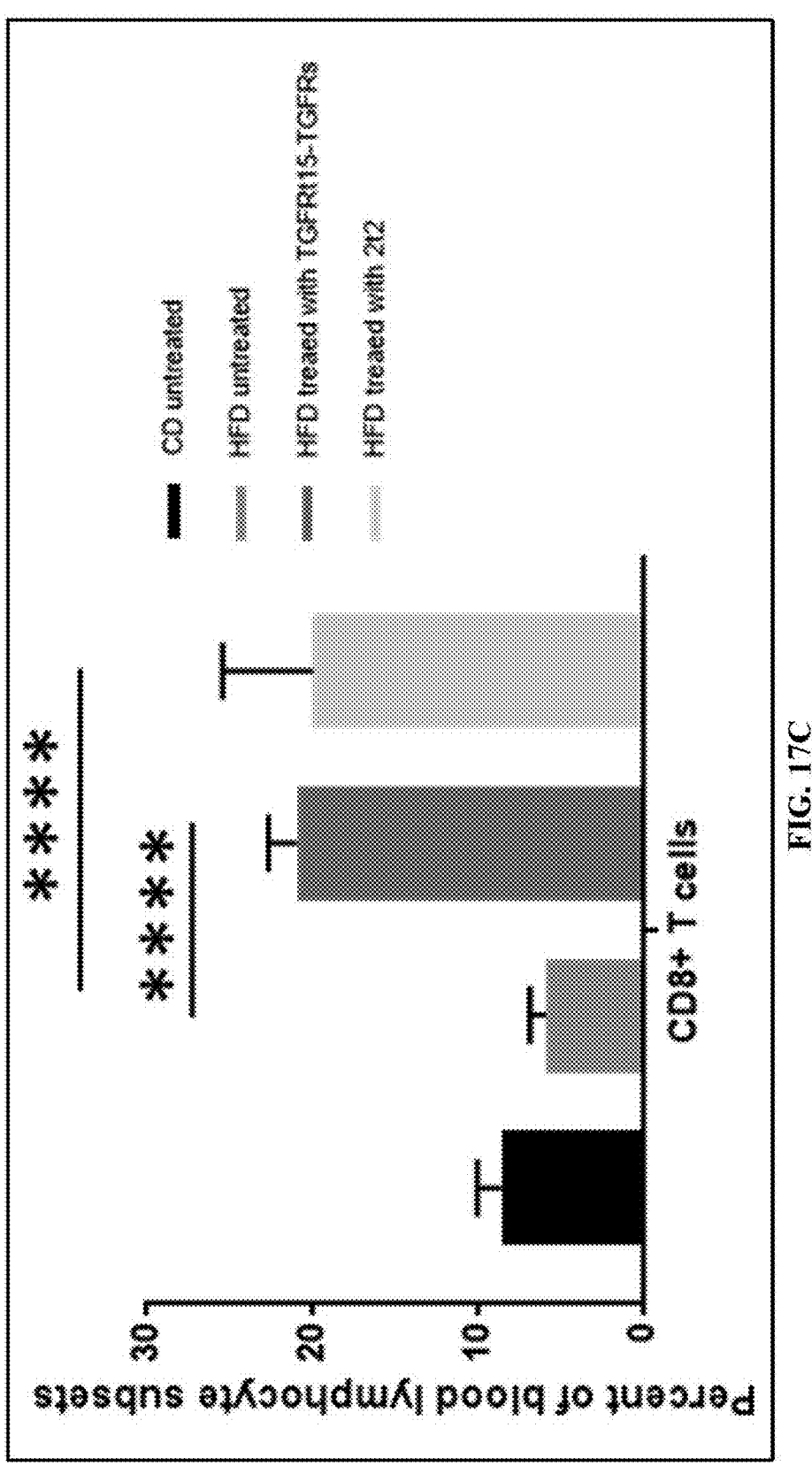

A set of experiments was performed to determine the effect of the TGFRt15-TGFRs construct on immune stimulation in ApoE$^{-/-}$ mice fed with a Western diet. In these experiments, 6-week-old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post treatment, mice were fasted for 16 hours and then blood samples were collected through retro-orbital venous plexus puncture. The blood was mixed with 10 μL 0.5 M EDTA, and 20 μL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4° C. in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 μL with 1× permeabilization buffer. Anti-Foxp3 antibody was added to the cells, and the cells were incubated for 30 minutes at room temperature. Permeabilization buffer (200 L) was added to the cells, and the cells were centrifuged at 300-400×g for 5 minutes at room temperature. The cells were resuspended in flow cytometry staining buffer and analyzed on a flow cytometer. FIGS. 17A-17C show that treatment with TGFRt15-TGFRs increased the percentage of NK cells and CD8$^+$ T cells in ApoE$^{-/-}$ mice fed with Western diet.

Example 4: Induction of Proliferation of Immune Cells In Vivo

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.1, 0.3, 1, 3, and 10 mg/kg. The treated mice were euthanized 4 days post-treatment.

Figure 18A:
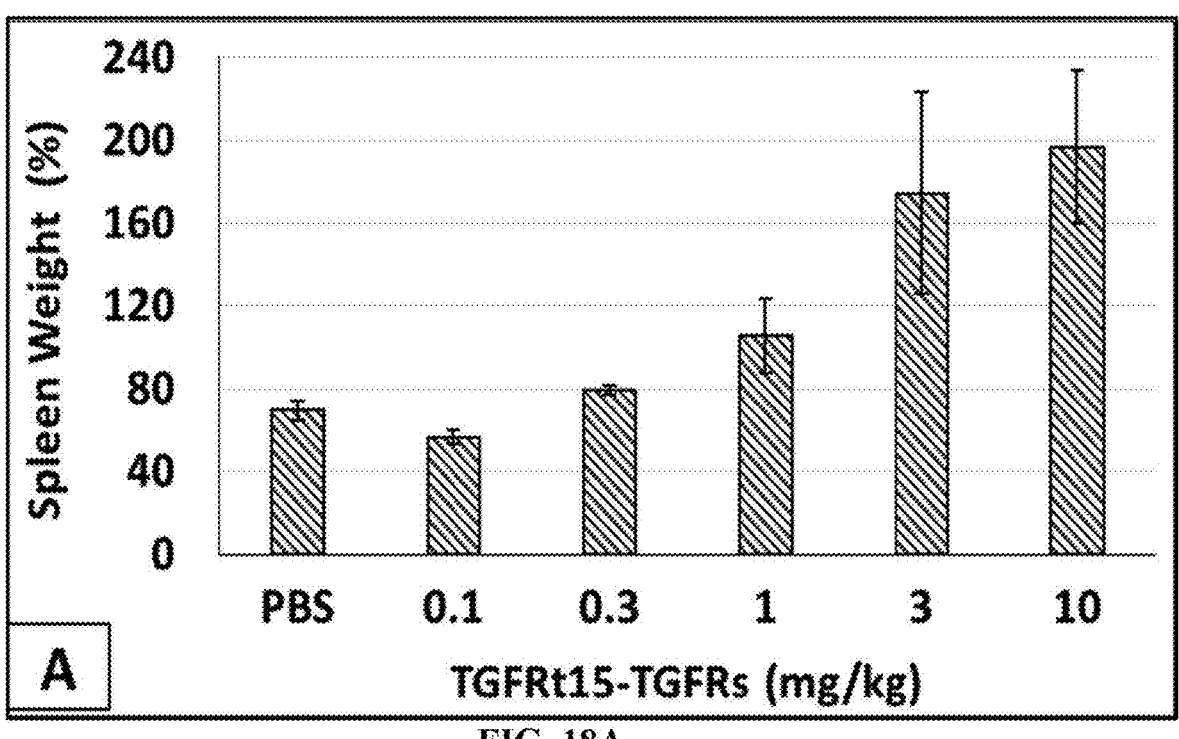
Figure 18B:
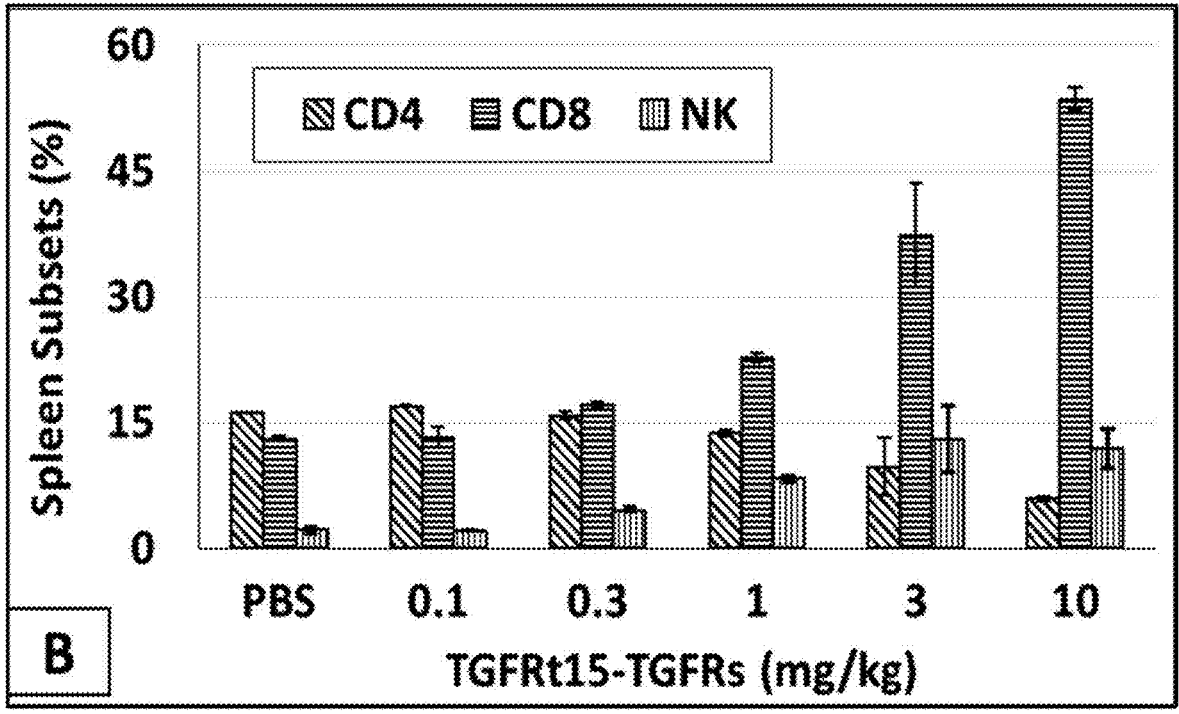

Spleen weight was measured and splenocyte suspensions were prepared. The splenocyte suspensions were stained with conjugated anti-CD4, anti-CD8, and anti-NK1.1 (NK) antibodies. The cells were additionally stained for proliferation marker Ki67. FIG. 18A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs was higher as compared to mice treated with just the control solution. The percentages of CD8$^+$ T cells and NK cells both increased with increasing dosage of TGFRt15-TGFRs (FIG. 18B). Finally, TGFRt15-TGFRs significantly upregulated expression of cell proliferation marker Ki67 in both CD8$^+$ T cells and NK cells at all doses of TGFRt15-TGFRs tested (FIG. 18C). These results demonstrate that TGFRt15-TGFRs treatment induced proliferation of both CD8+ T cells and NK cells in C57BL/6 mice.

Figure 19A:
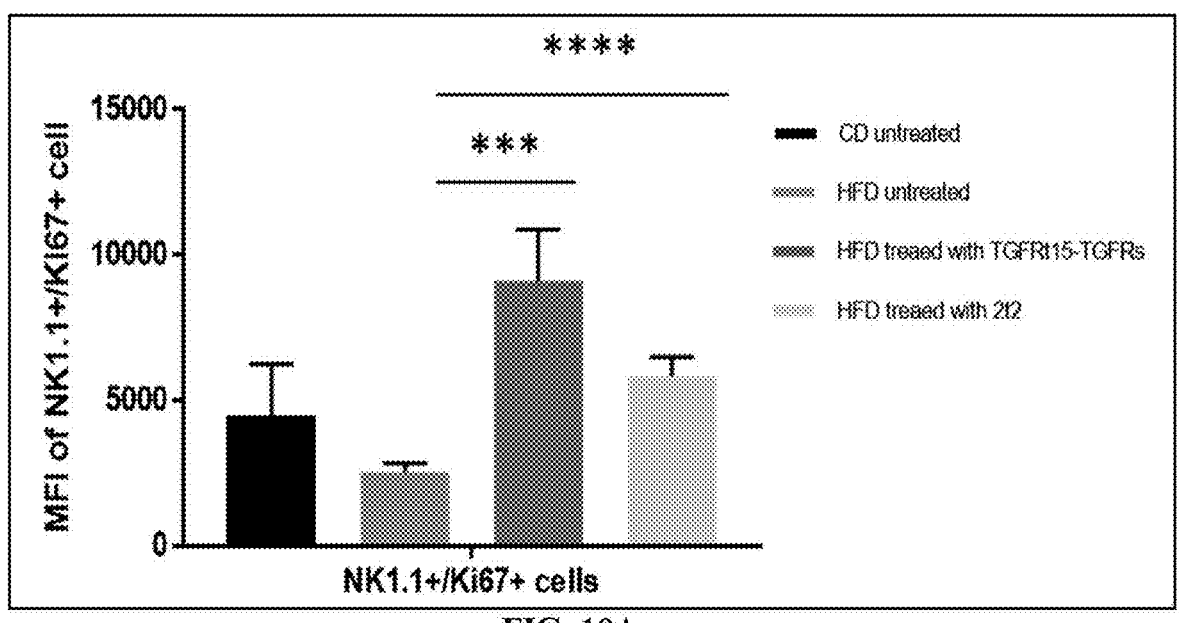
FIGS. 19A and 19B show in vivo induction of proliferation of NK cells and CD8+ T cells in ApoE−/− mice fed with a Western diet and treated with TGFRt15-TGFRs.
Figure 19B:
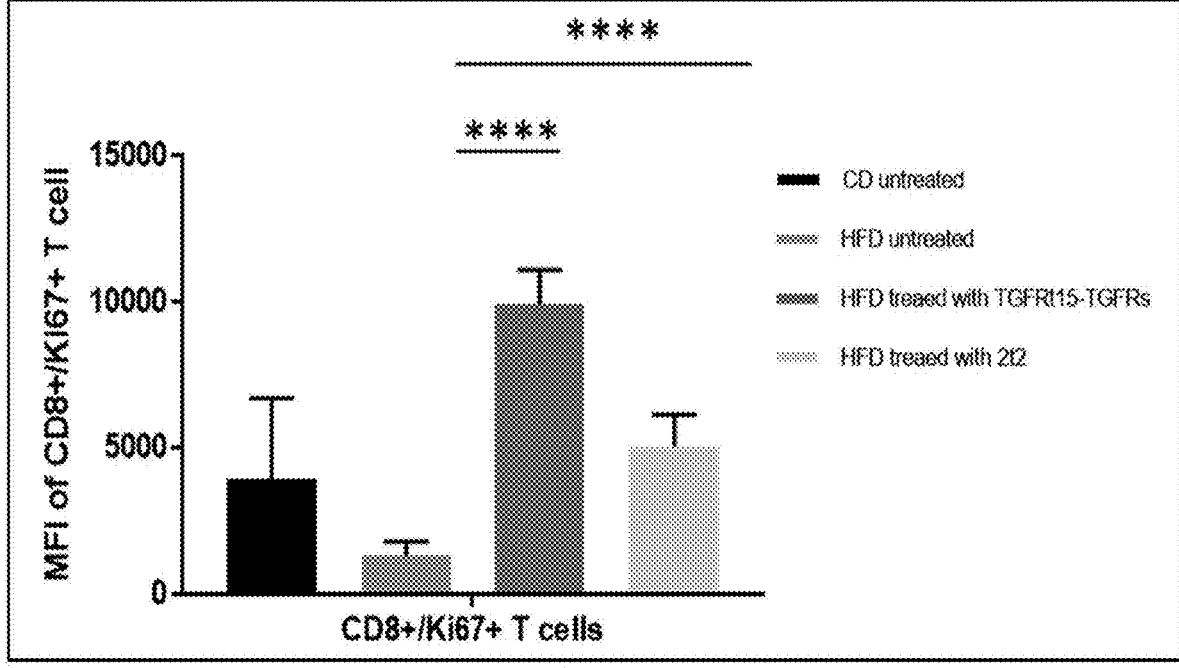

A set of experiments was performed to determine the effect of the TGFRt15-TGFRs construct on immune stimulation in ApoE$^{-/-}$ mice fed with a Western diet. In these experiments, 6-week-old female B6.129P2-ApoE$^{tm1 Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with TGFRt15-TGFRs at 3 mg/kg. Three days post-treatment, the mice were fasted for 16 hours and then blood samples were collected through retro-orbital venous plexus puncture. The blood was mixed with 10 μL 0.5 M EDTA and 20 μL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. As described in FIGS. 19A and 19B, treatment of ApoE$^1$ mice with TGFRt15-TGFRs induced proliferation (Ki67-positive staining) in NK and CD8$^+$ T cells.

Figures 20A, 20B:
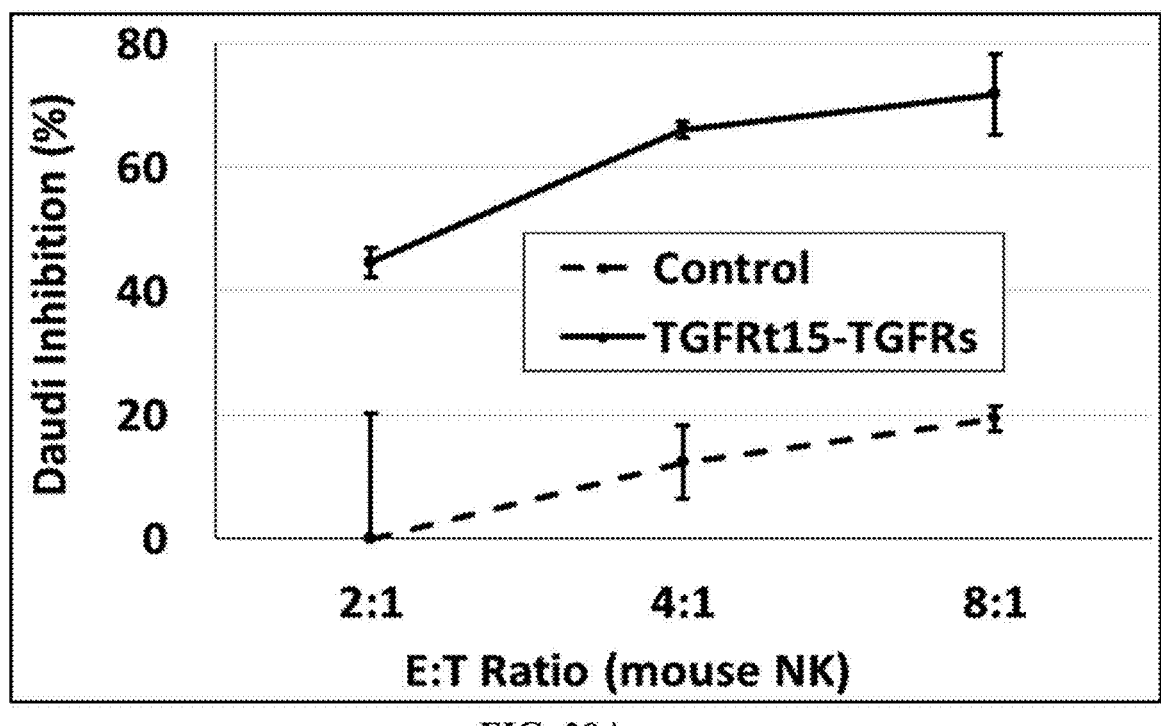
FIGS. 20A and 20B show enhancement of cytotoxicity of NK cells following treatment of NK cells with TGFRt15-TGFRs.

Example 5: NK-Mediated Cytotoxicity Following Treatment with Multi-Chain Construct A set of experiments was performed to determine if treatment of NK cells with TGFRt15-TGFRs enhanced cytotoxicity of NK cells. In these experiments, Human Daudi B lymphoma cells were labeled with CellTrace Violet (CTV) and used as tumor target cells. Mouse NK effector cells were isolated with NK1.1-positive selection using a magnetic cell sorting method (Miltenyi Biotec) of C57BL/6 female mouse spleens 4 days post TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Human Daudi B lymphoma cells) were mixed with effector cells (either mouse NK effector cells or human NK effector cells) in the presence of 50 nM TGFRt15-TGFRs or in the absence of TGFRt15-TGFRs (control) and incubated at 37° C. for 44 hours for mouse NK cells and for 20 hours for human NK cells. Target cell (Daudi) viability was assessed by analysis of propidium iodide-positive, CTV-labeled cells using flow cytometry. The percentage of Daudi inhibition was calculated using the formula (1-viable tumor cell number in experimental sample/viable tumor cell number in the sample without NK cells)×100. FIG. 20 shows that mouse (FIG. 20A) and human (FIG. 20B) NK cells had significantly stronger cytotoxicity against Daudi B cells following NK cell activation with TGFRt15-TGFRs than in the absence of TGFRt15-TGFRs activation.

Figure 21A:
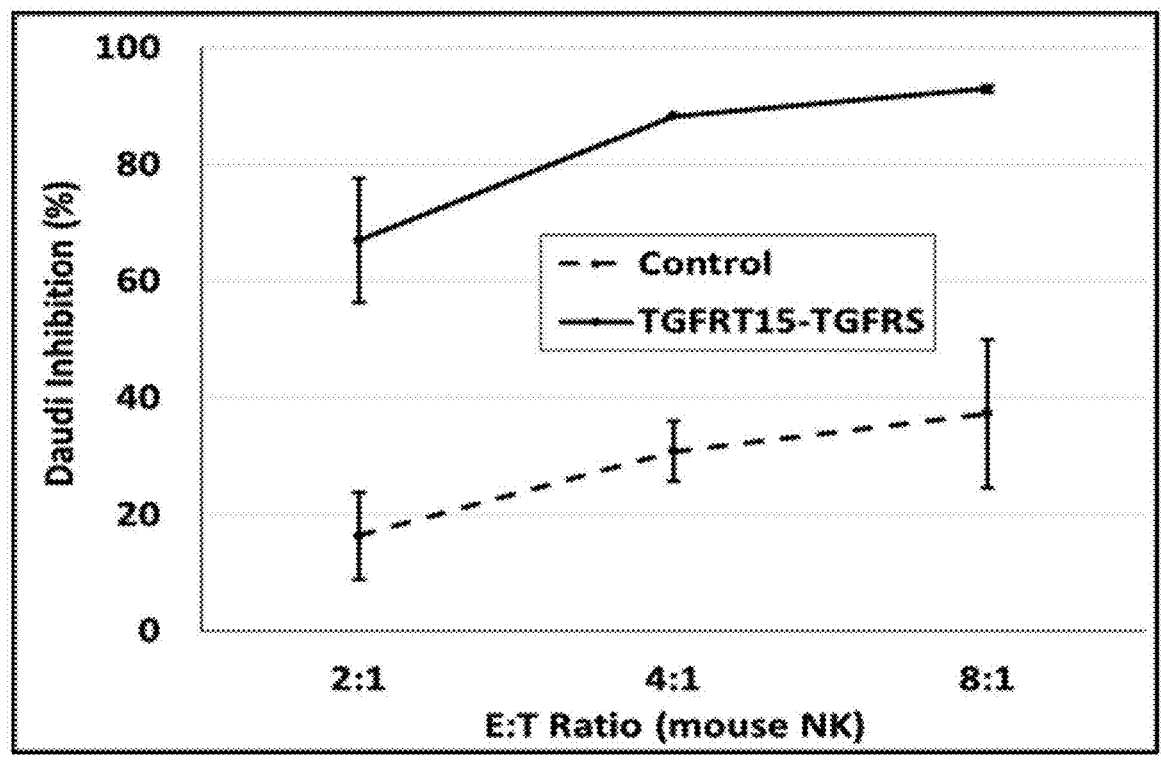
FIGS. 21A and 21B show enhancement of ADCC activity of NK cells following treatment of NK cells with TGFRt15-TGFRs.
Figure 21B:
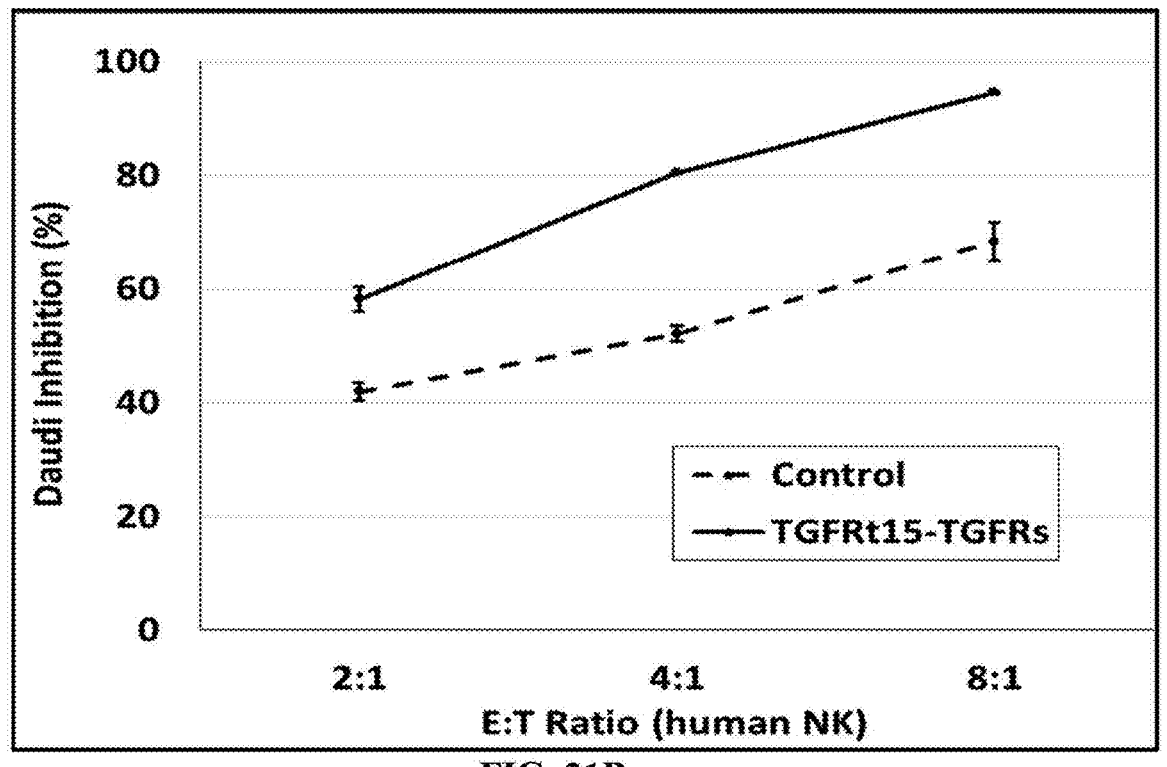

A set of experiments was performed to determine antibody-dependent cellular cytotoxicity (ADCC) of mouse and human NK cells following treatment with TGFRt15-TGFRs. In these experiments, human Daudi B lymphoma cells were labeled with CellTrace Violet (CTV) and used as tumor target cells. Mouse NK effector cells were isolated with NK1.1-positive selection using a magnetic cell sorting method (Miltenyi Biotec) of C57BL/6 female mouse spleens 4 days post-TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Daudi B cells) were mixed with effector cells (either mouse NK effector cells or human NK effector cells) in the presence of anti-CD20 antibody (10 nM Rituximab, Genentech) and in the presence of 50 nM TGFRt15-TGFRs, or in the absence of TGFRt15-TGFRs (control) and incubated at 37° C. for 44 hours for mouse NK cells and for 20 hours for human NK cells. The Daudi B cells express the CD20 targets for the anti-CD20 antibody. Target cell viability was assessed after incubation by analysis of propidium iodide-positive, CTV-labeled target cells using flow cytometry. The percentage of Daudi inhibition was calculated using the formula (1-viable tumor cell number in experimental sample/viable tumor cell number in the sample without NK cells)×100. FIG. 21 shows that mouse NK cells (FIG. 21A) and human NK cells (FIG. 21B) had stronger ADCC activity against Daudi B cells following NK cell activation with TGFRt15-TGFRs than in the absence of TGFRt15-TGFRs activation.

Example 6: Treatment of Cancer

Figure 22A:
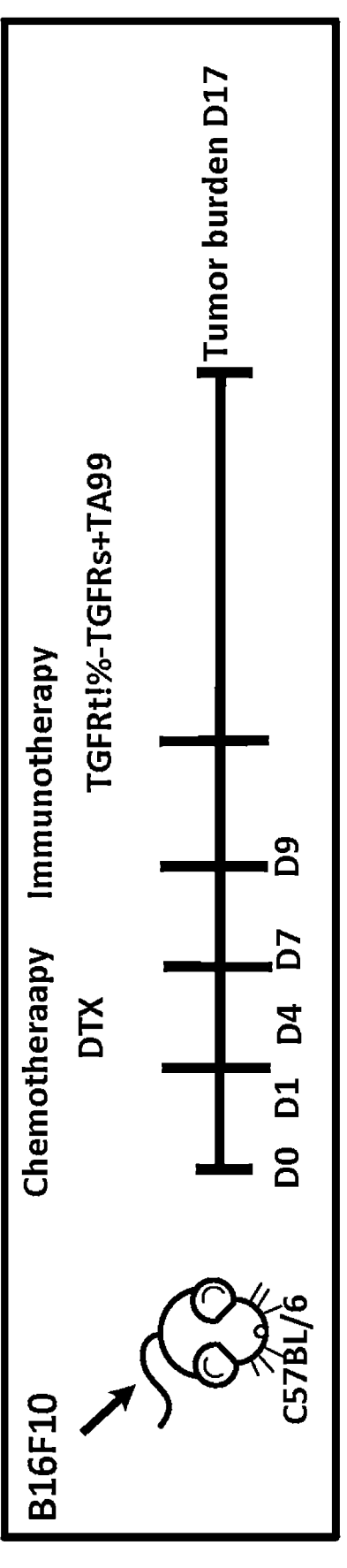
FIGS. 22A-22H show antitumor activity of TGFRt15-TGFRs plus anti-TRP1 antibody (TA99) in combination with chemotherapy in a melanoma mouse model.
Figure 22B:
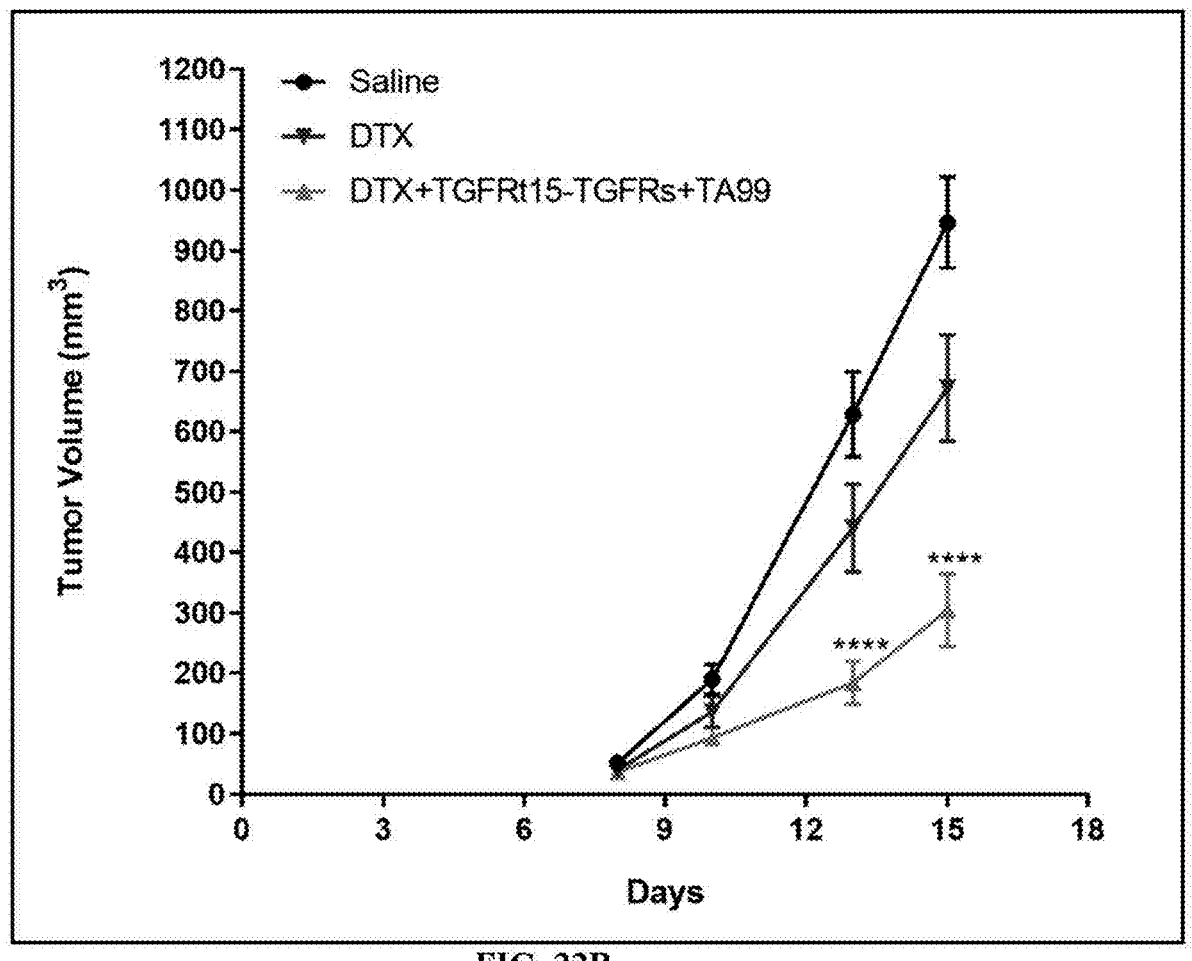

A set of experiments was performed to assess antitumor activity of TGFRt15-TGFRs plus anti-TRP1 antibody (TA99) in combination with chemotherapy in a melanoma mouse model. In these experiments, C57BL/6 mice were subcutaneously injected with 0.5×10$^6$ B16F10 melanoma cells. The mice were treated with three doses of chemotherapy docetaxel (10 mg/kg) (DTX) on day 1, day 4, and day 7, followed by treatment with single dose of combination immunotherapy TGFRt15-TGFRs (3 mg/kg)+anti-TRP1 antibody TA99 (200 μg) on day 9. FIG. 22A shows a schematic of the treatment regimen. Tumor growth was monitored by caliper measurement, and tumor volume was calculated using the formula V=(L×W$^2$)/2, where L is the largest tumor diameter and W is the perpendicular tumor diameter. FIG. 22B shows that treatment with DTX+TGFRt15-TGFRs+TA99 significantly reduced tumor growth compared to saline control and DTX treatment groups (N=10, ****p<0.001, Multiple t test analyses).

Figure 22C:
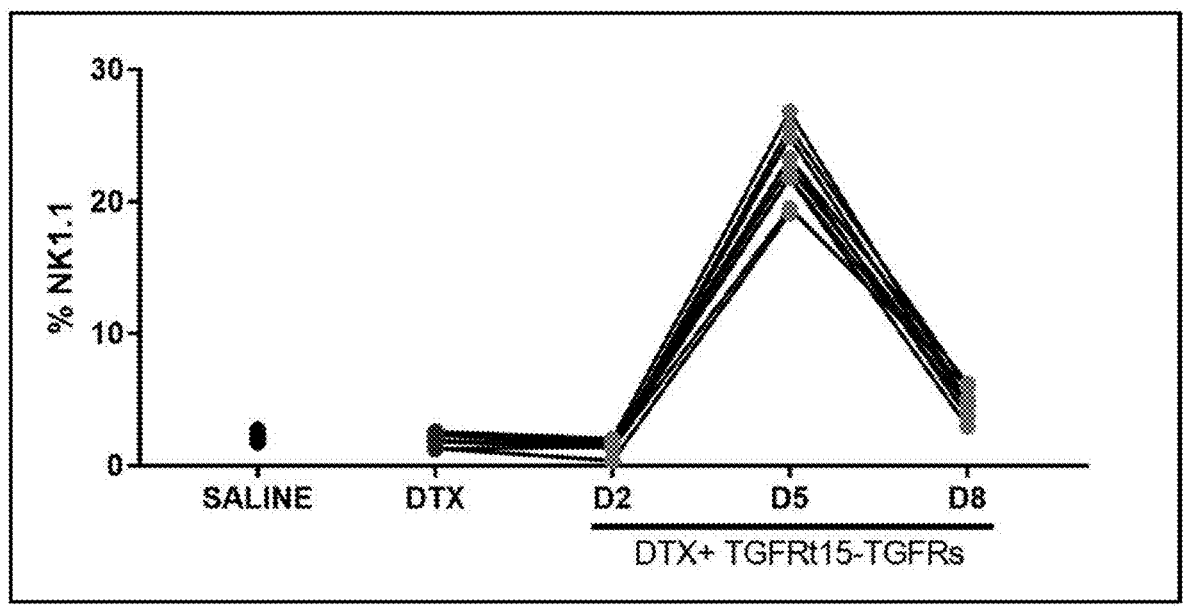
Figure 22D:
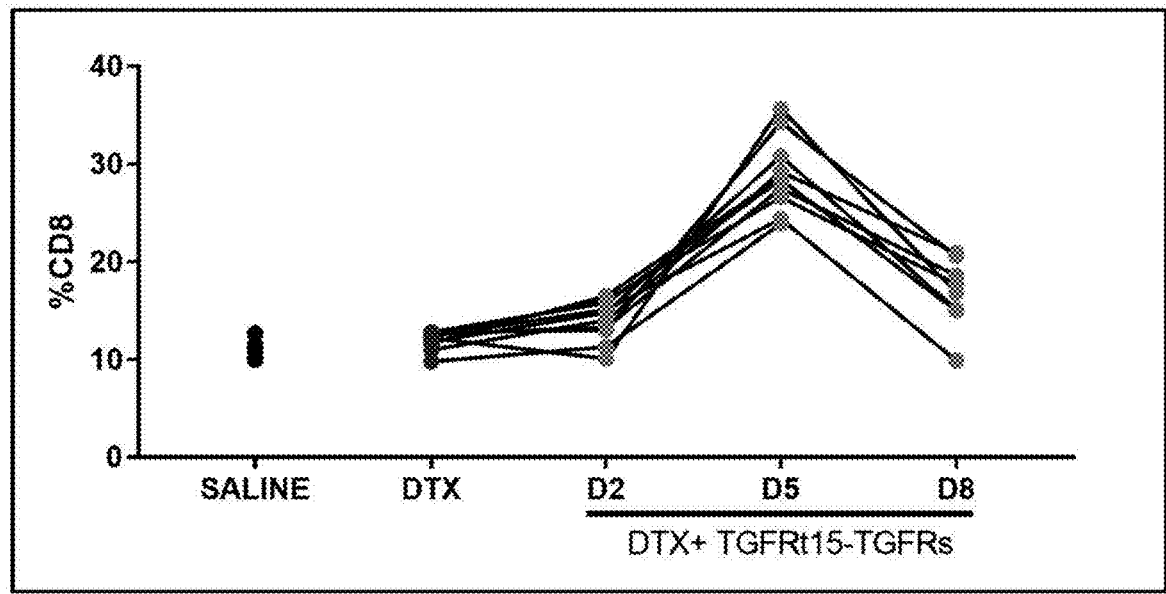
Figure 22E:
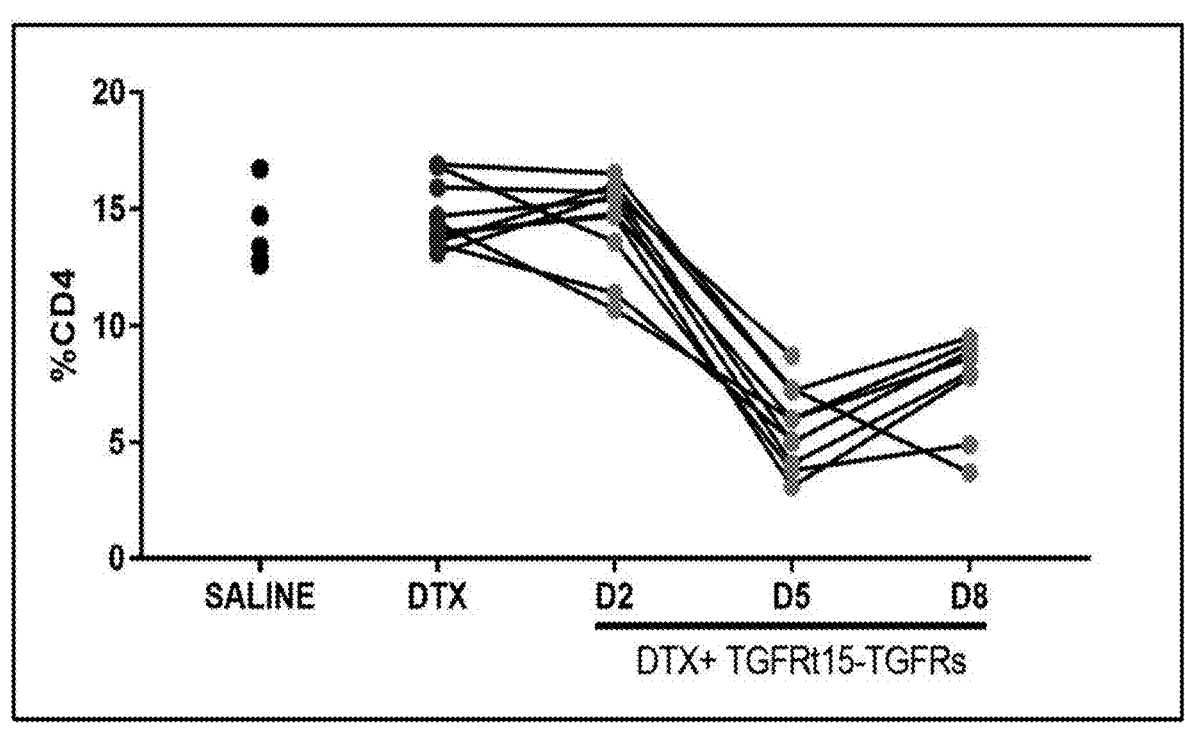

To assess immune cell subsets in the B16F10 tumor model, peripheral blood analysis was performed. In these experiments, C57BL/6 mice were injected with B16F10 cells and treated with DTX, DTX+TGFRt15-TGFRs+TA99, or saline. Blood was drawn from the submandibular vein of B16F10 tumor-bearing mice on days 2, 5, and 8 post-immunotherapy for the DTX+TGFRt15-TGFRs+TA99 group and day 11 post-tumor injection for the DTX and saline groups. RBCs were lysed in ACK lysis buffer and the lymphocytes were washed and stained with anti-NK1.1, anti-CD8, and anti-CD4 antibodies. The cells were analyzed by flow cytometry (Celesta-BD Bioscience). FIGS. 22C-22E show that DTX+TGFRt15-TGFRs+TA99 treatment induced an increase in the percentage of NK cells and CD8$^+$ T cells in the tumors compared to the saline and DTX treatment groups.

Figure 22F:
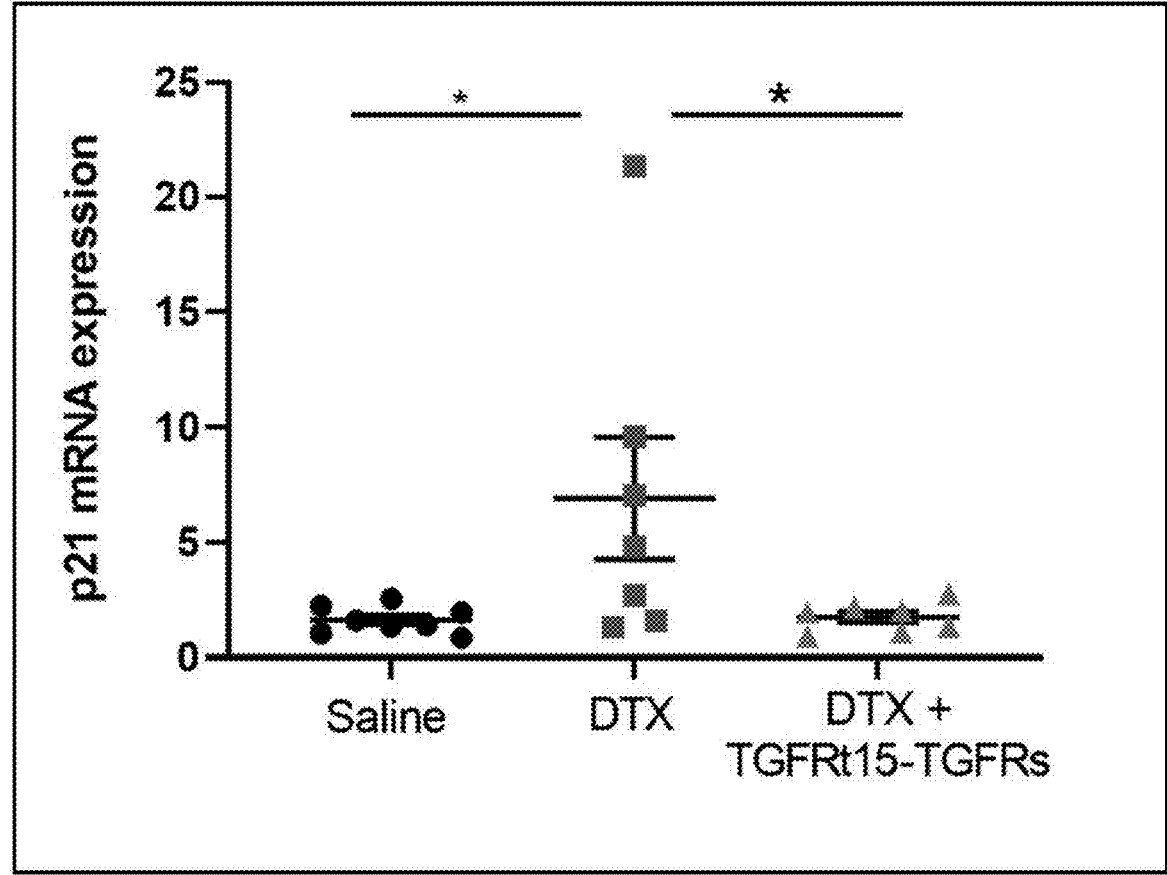
Figure 22G:
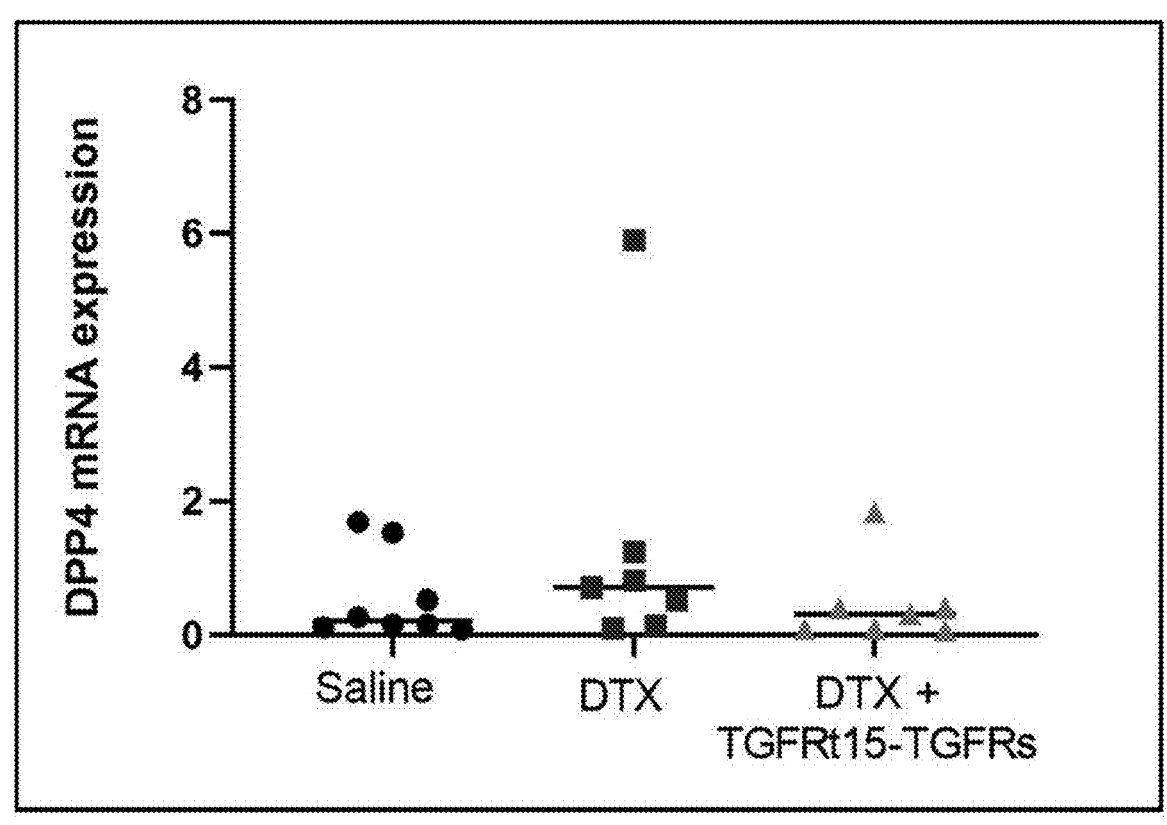
Figure 22H:
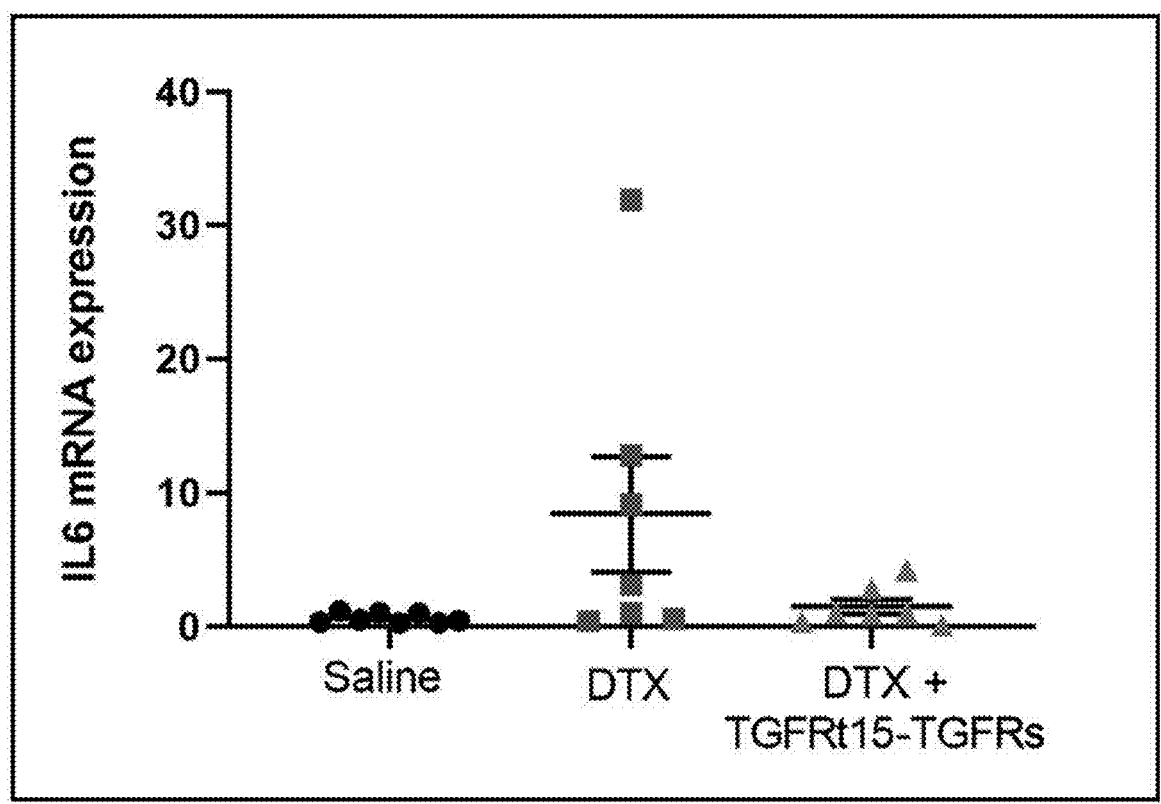
Figure 23A:
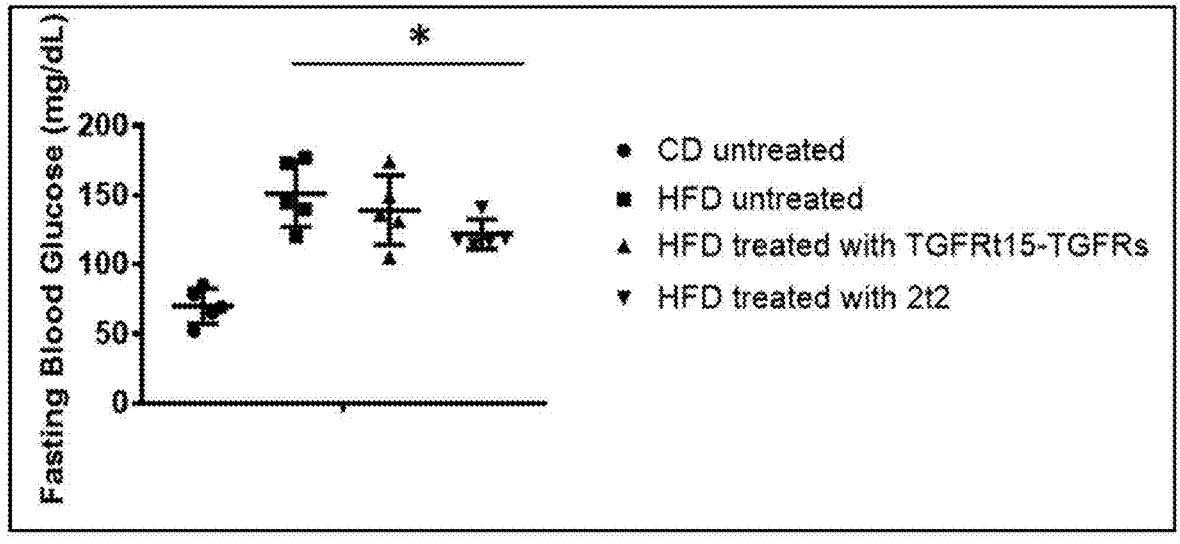
FIGS. 23A-23C show amelioration of the Western diet-induced hyperglycemia in ApoE−/− mice by TGFRt15-TGFRs.
Figure 23B:
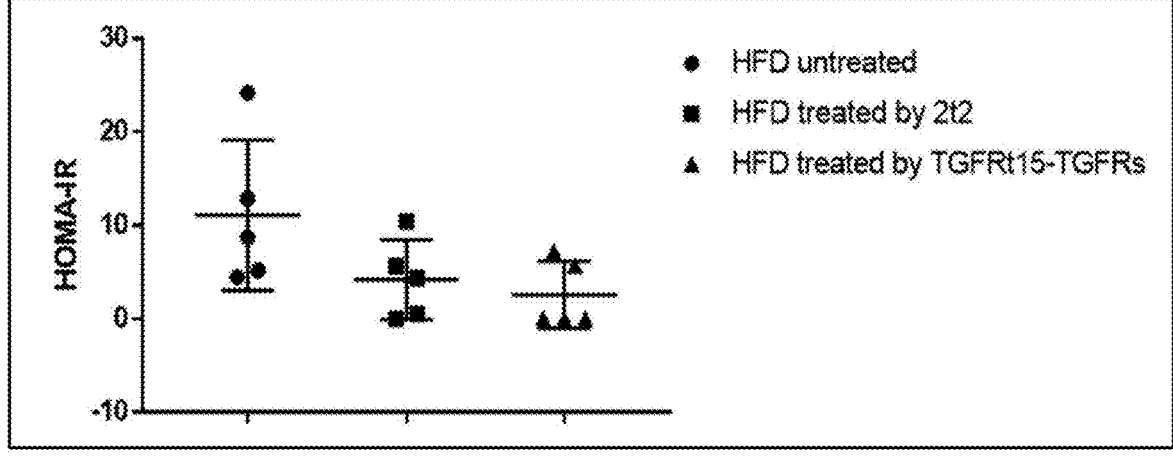
Figure 23C:
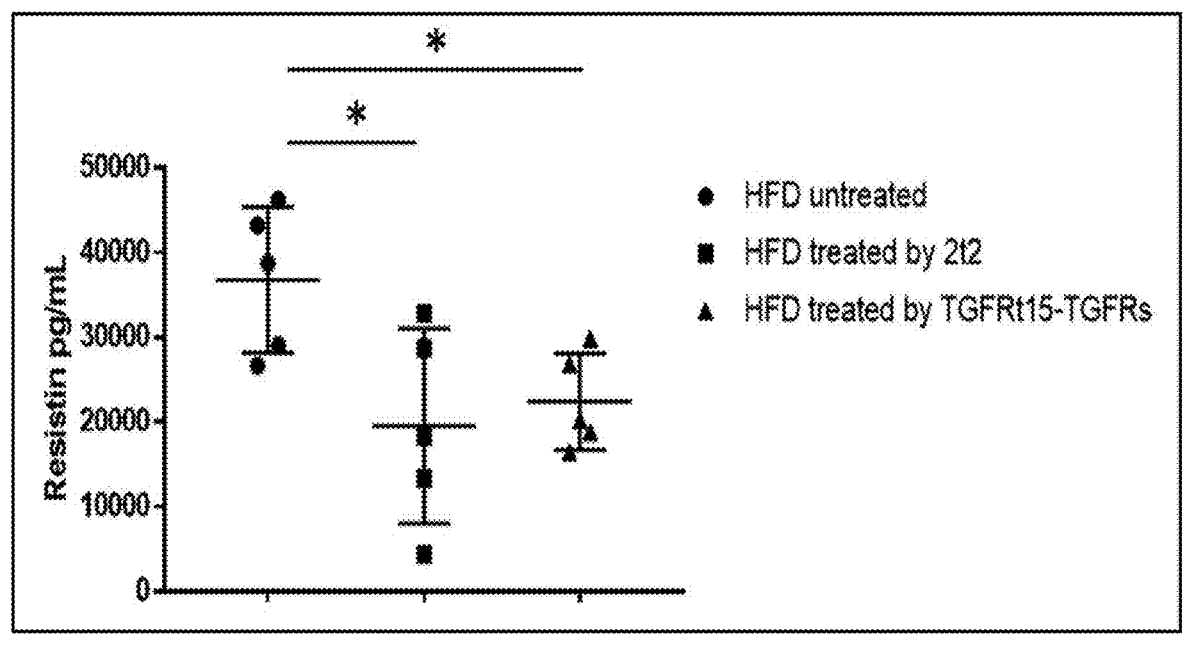

On day 17, total RNA was extracted from tumors of mice treated with saline, DTX or DTX+TGFRt15-TGFRs+TA99 using Trizol. Total RNA (1 pg) was used for cDNA synthesis using the QuantiTect Reverse Transcription Kit (Qiagen). Real-time PCR was carried out with CFX96 Detection System (Bio-Rad) using FAM-labeled predesigned primers for senescence cell markers, (F) p21 (G) DPP4 and (H) IL6. The housekeeping gene 18S ribosomal RNA was used as an internal control to normalize the variability in expression levels. The expression of each target mRNA relative to 18S rRNA was calculated based on Ct as $2^{-\Delta(\Delta Ct)}$, in which $\Delta Ct = Ct_{target} - Ct_{18S}$. The data is presented as fold-change as compared to saline control. FIG. 22F-22H show that DTX treatment induced an increase in senescent tumor cells that were subsequently reduced following treatment with TGFRt15-TGFRs+TA99 immunotherapy. A set of experiments was performed to investigate amelioration of Western diet-induced hyperglycemia in ApoE$^{-/-}$ mice by TGFRt15-TGFRs. In these experiments, 6-week-old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post-treatment, the mice were fasted for 16 hours and then blood samples were collected through retro-orbital venous plexus puncture. Blood glucose was detected with a glucose meter (OneTouch UltraMini) and GenUltimated test strips using a drop of fresh blood. As shown in FIG. 23A, TGFRt15-TGFRs treatment reduced hyperglycemia induced by the Western diet. The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 23B, TGFRt15-TGFRs treatment reduced insulin resistance compared to the untreated group.

Example 7: Upregulation of CD44 Memory T Cells

Figure 24:
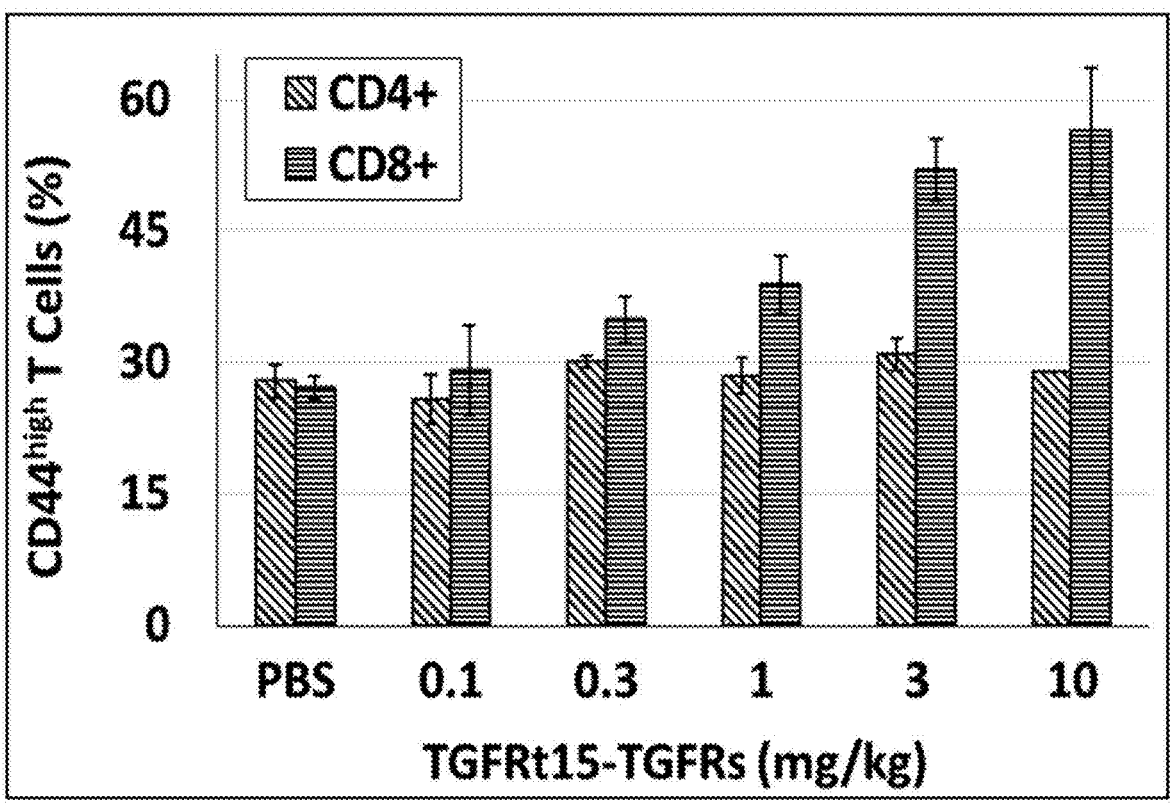
FIG. 24 shows upregulation of CD44hi memory T cells upon treatment with TGFRt15-TGFRs.

A set of experiments was performed to assess upregulation of CD44 memory T cells upon treatment with TGFRt15-TGFRs. In these experiments, C57BL/6 mice were subcutaneously treated with TGFRt15-TGFRs. The treated mice were euthanized and the single splenocyte suspensions were prepared 4 days (TGFRt15-TGFRs) following the treatment. The prepared splenocytes were stained with fluorochrome-conjugated anti-CD4, anti-CD8 and anti-CD44 antibodies and the percentages of CD44$^{high}$ T cells in CD4$^+$ T cells or CD8$^+$ T cells were analyzed by flow cytometry. The results show that TGFRt15-TGFRs upregulated expression of the memory marker CD44 on CD4$^+$ and CD8$^+$ T cells (FIG. 24). These findings indicate that TGFRt15-TGFRs was able to induce mouse T cells to differentiate into memory T cells.

Example 8. Generation of TGFRt15*-TGFRs

A fusion protein complex was generated comprising of TGFR/IL15RαSu and TGFR/TF/IL-15D8N fusion proteins. The human TGF-b receptor (TGFR), IL-15 alpha receptor sushi domain (IL15RaSu), tissue factor (TF) and IL-15 with D8N mutant (IL15D8N) sequences were obtained from the GenBank website and DNA fragments for these sequences were synthesized by Genewiz. Specifically, a construct was made linking the TGFR sequence to the N-terminus coding region of IL15RaSu and the TGFR sequence to the N-terminus of tissue factor 219 followed by the N-terminus coding region of IL-1D8N.

The nucleic acid sequence of the TGFR/IL15RαSu construct (including signal peptide sequence) is as follows:

```
                                    (SEQ ID NO: 61)
(Signal peptide)
ATGAAGTGGGTGACCTTCATCAGCCTGCTGTTCCTGTTCTCCAGCGCCTA

CTCC (Single chain Human TGF-beta Receptor II
homodimer)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Sushi domain of IL15 receptor alpha chain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.
```

The nucleic acid sequence of the TGFR/TF/IL15D8N construct (including signal peptide sequence) is as follows:

(SEQ ID NO: 71)
(Signal peptide)
ATGGGAGTGAAAGTTCTTTTTGCCCTTATTTGTATTGCTGTGGCCGAGGC

C (Single chain Human TGF-beta Receptor II
homodimer)
ATCCCACCGCACGTTCAGAAGTCGGTGAATAACGACATGATAGTCACTGA

CAACAACGGTGCAGTCAAGTTTCCACAACTGTGTAAATTTTGTGATGTGA

GATTTTCCACCTGTGACAACCAGAAATCCTGCATGAGCAACTGCAGCATC

ACCTCCATCTGTGAGAAGCCACAGGAAGTCTGTGTGGCTGTATGGAGAAA

GAATGACGAGAACATAACACTAGAGACAGTTTGCCATGACCCCAAGCTCC

CCTACCATGACTTTATTCTGGAAGATGCTGCTTCTCCAAAGTGCATTATG

AAGGAAAAAAAAAAGCCTGGTGAGACTTTCTTCATGTGTTCCTGTAGCTC

TGATGAGTGCAATGACAACATCATCTTCTCAGAAGAATATAACACCAGCA

ATCCTGACGGAGGTGGCGGATCCGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
TCAGGCACTACAAATACTGTGGCAGCATATAATTTAACTTGGAAATCAAC

TAATTTCAAGACAATTTTGGAGTGGGAACCCAAACCCGTCAATCAAGTCT

ACACTGTTCAAATAAGCACTAAGTCAGGAGATTGGAAAAGCAAATGCTTT

TACACAACAGACACAGAGTGTGACCTCACCGACGAGATTGTGAAGGATGT

GAAGCAGACGTACTTGGCACGGGTCTTCTCCTACCCGGCAGGGAATGTGG

AGAGCACCGGTTCTGCTGGGGAGCCTCTGTATGAGAACTCCCCAGAGTTC

ACACCTTACCTGGAGACAAACCTCGGACAGCCAACAATTCAGAGTTTTGA

ACAGGTGGGAACAAAAGTGAATGTGACCGTAGAAGATGAACGGACTTTAG

TCAGAAGGAACAACACTTTCCTAAGCCTCCGGGATGTTTTTGGCAAGGAC

TTAATTTATACACTTTATTATTGGAAATCTTCAAGTTCAGGAAAGAAAC

AGCCAAAACAAACACTAATGAGTTTTTGATTGATGTGGATAAAGGAGAAA

ACTACTGTTTCAGTGTTCAAGCAGTGATTCCCTCCCGAACAGTTAACCGG

AAGAGTACAGACAGCCCGGTAGAGTGTATGGGCCAGGAGAAAGGGGAATT

CAGAGAA (Human IL-15D8N)
AACTGGGTGAATGTAATAAGTAATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

-continued

CATCCTAGCAAACAACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCT.

The amino acid sequence of TGFR/IL15RαSu fusion
protein (including signal peptide sequence) is as follows:

(SEQ ID NO: 8)
(Signal peptide)
MKWVTFISLLFLFSSAYS (Single chain Human TGF-beta Receptor II
homodimer)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15 receptor α sushi domain)
ITCPPPMSVEHADIWVKSYSLYSRERYICNSGFKRKAGTSSLTECVLNKA

TNVAHWTTPSLKCIR.

The amino acid sequence of TGFR/TF/IL15D8N fusion
protein (including signal peptide sequence) is as follows:

(SEQ ID NO: 70)
(Signal peptide)
MGVKVLFALICIAVAEA (Single chain Human TGF-beta Receptor II
homodimer)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Tissue factor)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (IL-15D8N)
NWVNVISNLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

The TGFR/IL15RαSu and TGFR/TF/IL-15D8N con-
structs were cloned into a modified retrovirus expression
vectors as described previously (Hughes M S, Yu Y Y,
Dudley M E, Zheng Z, Robbins P F, Li Y, et al). The
expression vectors were transfected into CHO-K1 cells.
Co-expression of the two constructs in CHO-K1 cells allowed for formation and secretion of the soluble TGFR/ IL15RαSu-TGFR/TF/IL-15D8N protein complex (referred to as TGFRt15*-TGFRs), which can be purified by anti-TF antibody affinity.

Example 9: TGFRt15-TGFRs Treatment Enhances Immune-Mediated Biological Activities in Diabetic db/db Mice Five-week-old male db/db mice [BKS.Cg-Dock$^{7m}$+/+ Lepr$^{db}$/J (Wildtype for Dock7$^m$, Homozygous for Lepr$^{db}$), strain #000642] from Jackson Lab (Bar Harbor, ME) were fed with standard chow diet (Irradiated 2018 Teklad global 18% protein rodent diet, Envigo) and received drinking water ad libitum. Mice were divided into three groups as follows: PBS control group (n=6), TGFRt15-TGFRs group (n=6) and TGFRt15*-TGFRs group (n=6). Mice were treated subcutaneously with PBS, TGFRt15-TGFRs (3 mg/kg) and TGFRt15*-TGFRs (3 mg/kg). The mice were euthanized, and spleen was harvested and processed to a single cell suspension.

It was first evaluated whether metabolically dysfunctional db/db mice retained immune cell stimulatory capability following TGFRt15-TGFRs treatment. Mice were injected subcutaneously with 3 mg/kg of TGFRt15-TGFRs, TGFRt15*-TGFRs (a derivative of TGFRt15-TGFRs without IL-15 activity due to an IL-15D8N mutation), or PBS (negative control). Mice treated with TGFRt15-TGFRs, but not TGFRt15*-TGFRs or PBS, showed increased numbers of total splenic cells and higher percentages of CD3$^{30}$, CD8$^+$ T cells and NK cells, but not CD4$^+$ T cells, in the spleen (FIG. 25A-25E). These cells also expressed CD44, CD62L and CD127, markers of central and effector memory-cell phenotype (FIG. 25F-25G). TGFRt15-TGFRs treated splenocytes also showed significantly enhanced killing of NK-sensitive Yac1 cells (FIG. 25H) and increased interferon (IFN)-γ release by CD3$^+$ cells upon antigen-independent stimulation (FIG. 25I) compared to TGFRt15*-TGFRs treatment. Since metabolic pathways are linked to immune-cell fate decision and effector functions, the extracellular acidification rate (ECAR) and oxygen consumption rate (OCR) of splenocytes were further determined following TGFRt15-TGFRs treatment in db/db mice. Splenocytes from TGFRt15-TGFRs-treated mice on day (D)2 and D4 showed enhanced parameters of glycolysis and mitochondrial respiration (FIG. 25J, FIG. 32A-32D). These findings indicate that TGFRt15-TGFRs, but not TGFRt15*-TGFRs or PBS, was able to stimulate the NK and T cells in an IL-15 dependent manner in metabolically dysfunctional, type-2 diabetic db/db mice. TGFRt15-TGFRs-treated db/db mice also showed reduced plasma levels of TGFβ 1l and TGFβ2 (FIG. 25K).

Figure 26A:
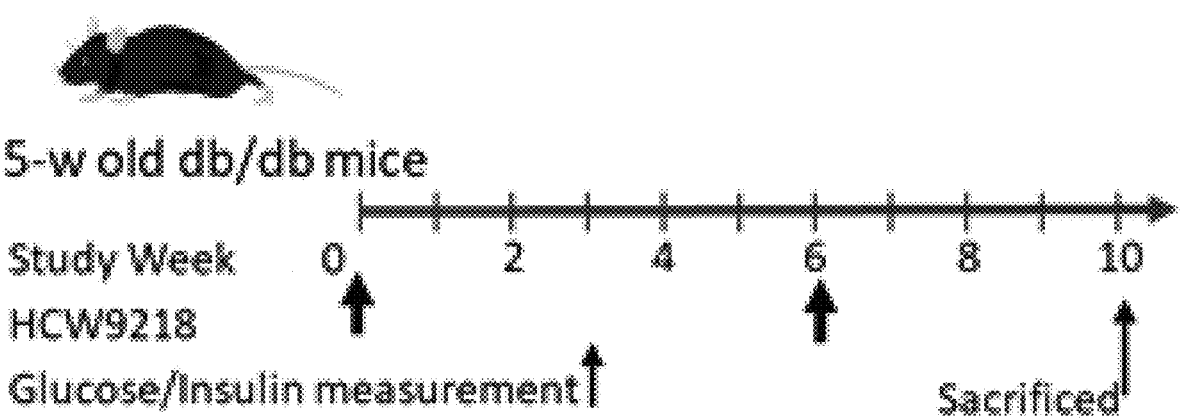
Figure 26B:
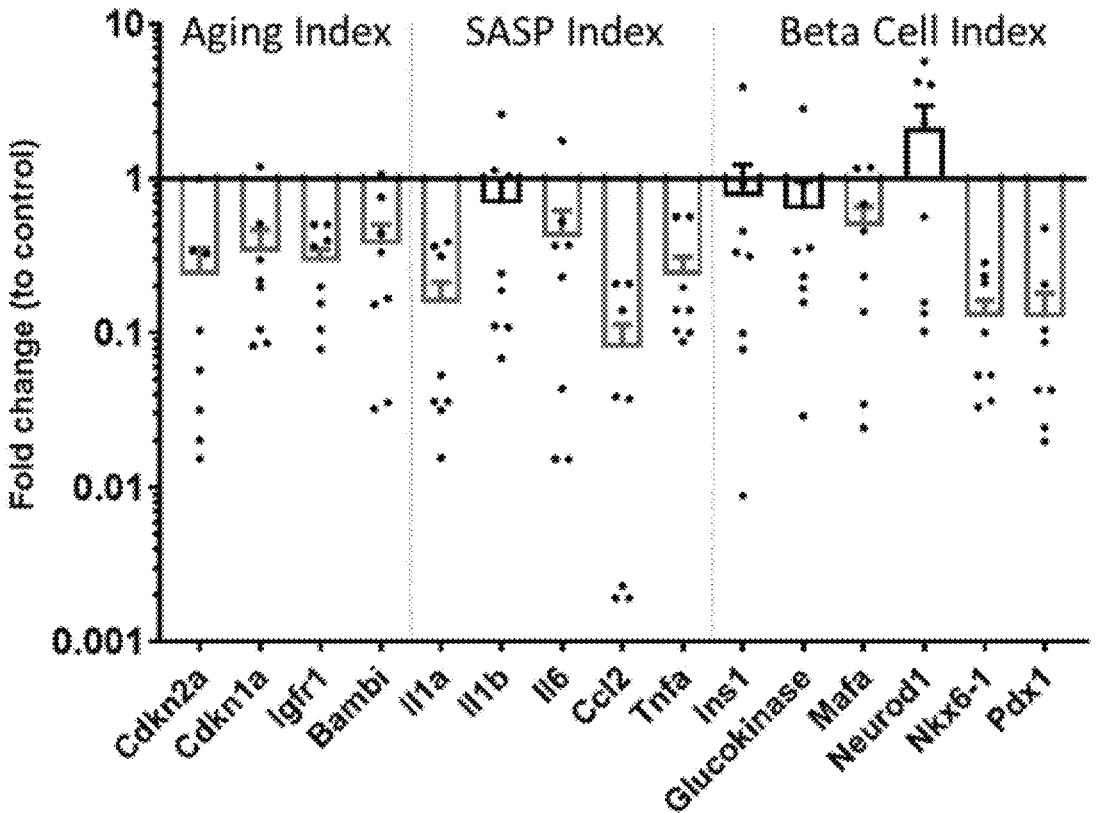
FIG. 26B shows expression of Aging, SASP, and β Cell index (related genes) in islet transcript was analyzed by quantitative PCR and normalized to control treatment.
Figure 26C:
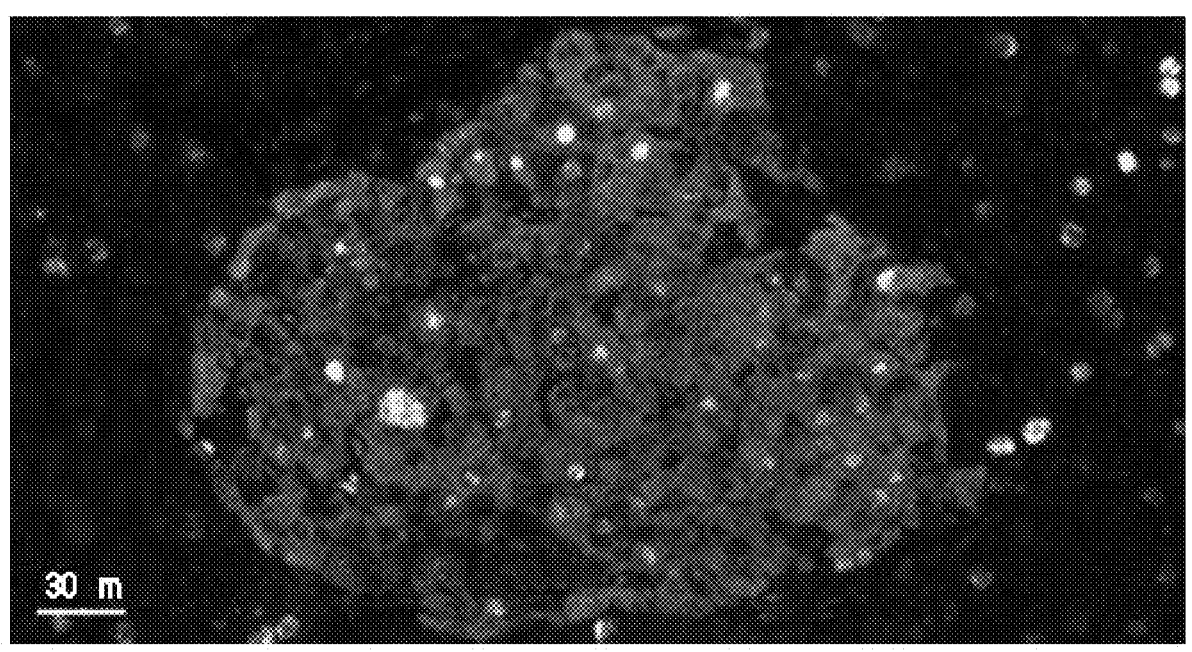
FIGS. 26C-26D show immunofluorescent staining of p21+ cells (yellow) and insulin+β islet cells (green) in pancreatic tissue sections.
Figure 26D:
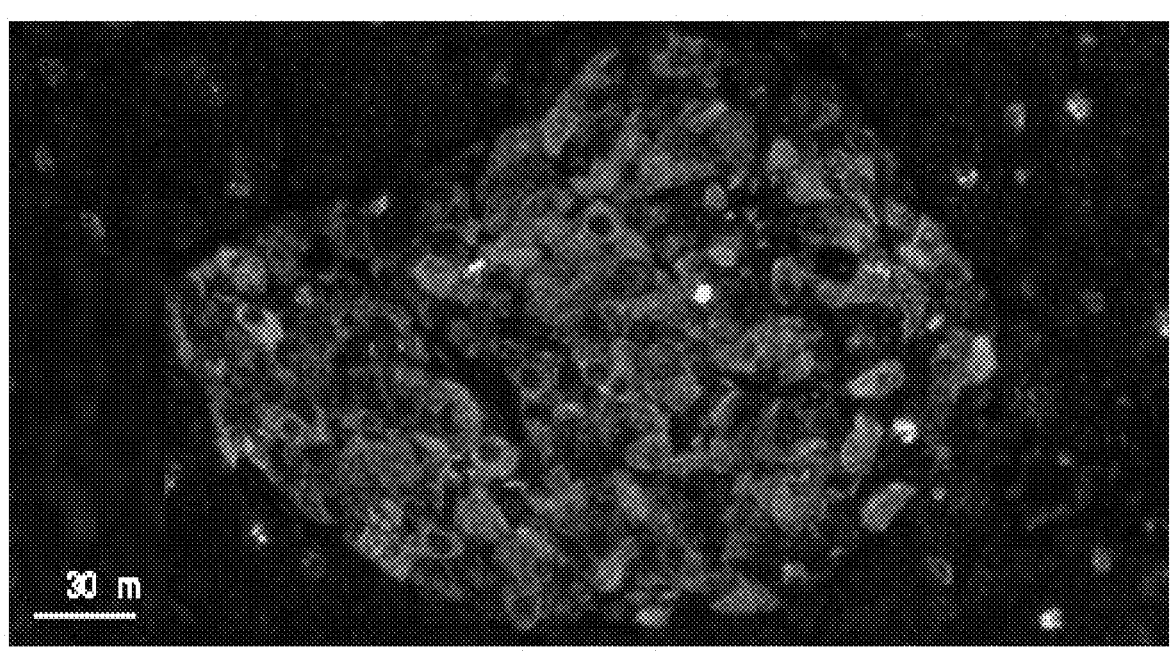
Figure 26E:
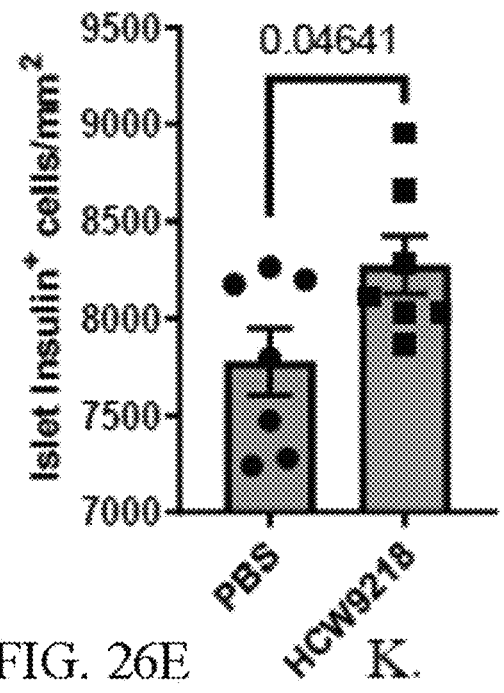
FIG. 26E shows number of insulin positive Islet cells in tissue section.
Figure 26F:
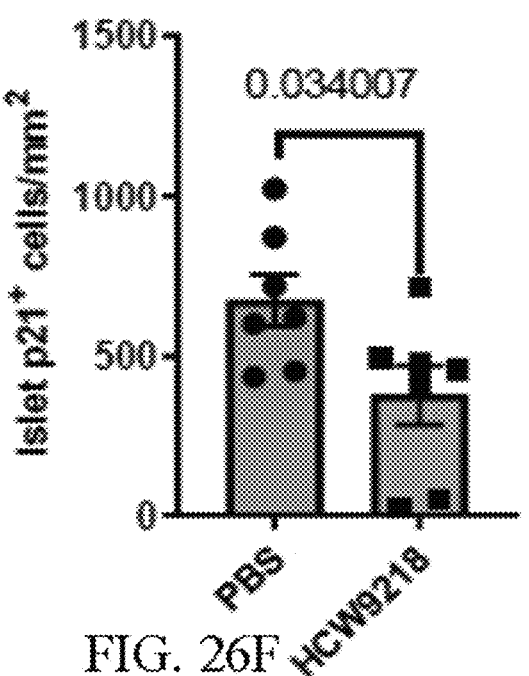
FIG. 26F shows number of p21+ senescence cells in 0 islet cells in tissue section.
Figure 26G:
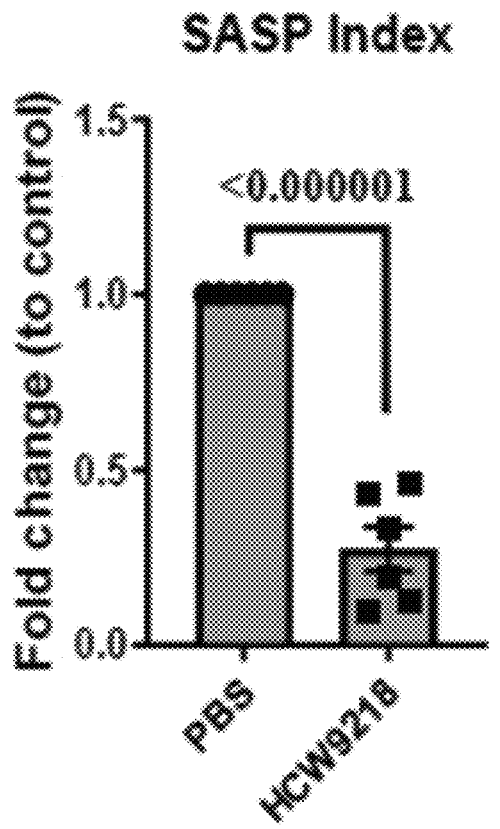
Figure 26H:
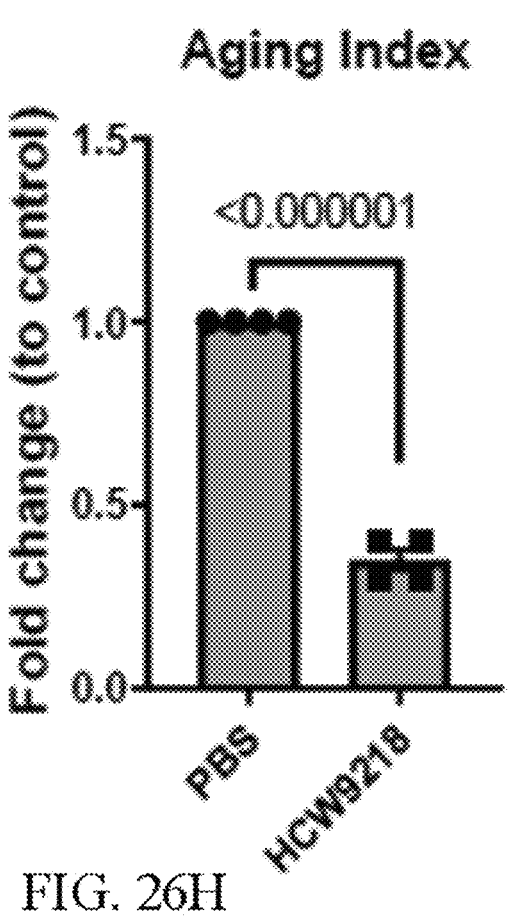

Example 10: TGFRt15-TGFRs Treatment Reduces Senescent Pancreatic β Islet Cells and SASP Factors and Improves Type-2 Diabetes Profile of db/db Mice Metabolic dysfunction induces senescence of pancreatic β cells and removal of these senescent β cells was shown to improve glucose metabolism and β cell functions while decreasing expression of markers of aging, senescence, and SASP. Thus, reducing the senescent cell burden may have the potential to prevent or alleviate type-2 diabetes (T2D). To assess whether TGFRt15-TGFRs treatment can remove senescent β cells, 5-week-old male db/db mice fed with a standard chow diet were subcutaneously administered TGFRt15-TGFRs (3 mg/kg or PBS (control group), with a second dose 6 weeks later (FIG. 26A). qRT-PCR analysis of pancreas showed that TGFRt15-TGFRs treatment reduced Cdkn1a and Cdkn2a expression, which encode cyclin-dependent kinase (CDK) inhibitors p21 and p16, respectively, as markers and effectors of β-islet cell senescence (FIG. 26B). Accumulation of p21$^+$ SNCs, which was observed in pancreatic islets of control db/db mice, was significantly reduced in TGFRt15-TGFRs-treated mice as analyzed by immunofluorescent staining of pancreatic sections (FIG. 26C-26D). The insulin-positive islet cells were significantly increased and p21$^+$ cells were significantly reduced in the pancreas of the TGFRt15-TGFRs treatment group compared to control mice (FIG. 26E-26F). In addition to Cdkn1a and Cdkn2a, expression of Igfr1, Bamb1, Il1a, Il6, Mcp1, and Tnfa were also lowered in the pancreas of TGFRt15-TGFRs-treated db/db mice compared to the PBS control group (FIG. 26B). Genes associated with the SASP Index and Aging Index were significantly reduced in the pancreas following TGFRt15-TGFRs treatment compared to controls (FIG. 26G-26H), whereas gene expression of the β-islet cell index was not significantly changed in TGFRt15-TGFRs vs. PBS-treated db/db mice (FIG. 26I). Collectively, these data suggest that TGFRt15-TGFRs has potent senolytic and senomorphic activities to reduce SNCs and SASP factors in db/db mice. In addition, it was found that the fasting glucose levels and the insulin resistance index (HOMA-IR) were significantly reduced following TGFRt15-TGFRs treatment compared to the PBS group (p=0.0051, FIG. 26J and p=0.04412, FIG. 26K). These results suggest that the reduction of senescent β-islet cells improves the healthy life span of T2D mice.

Figure 26L:
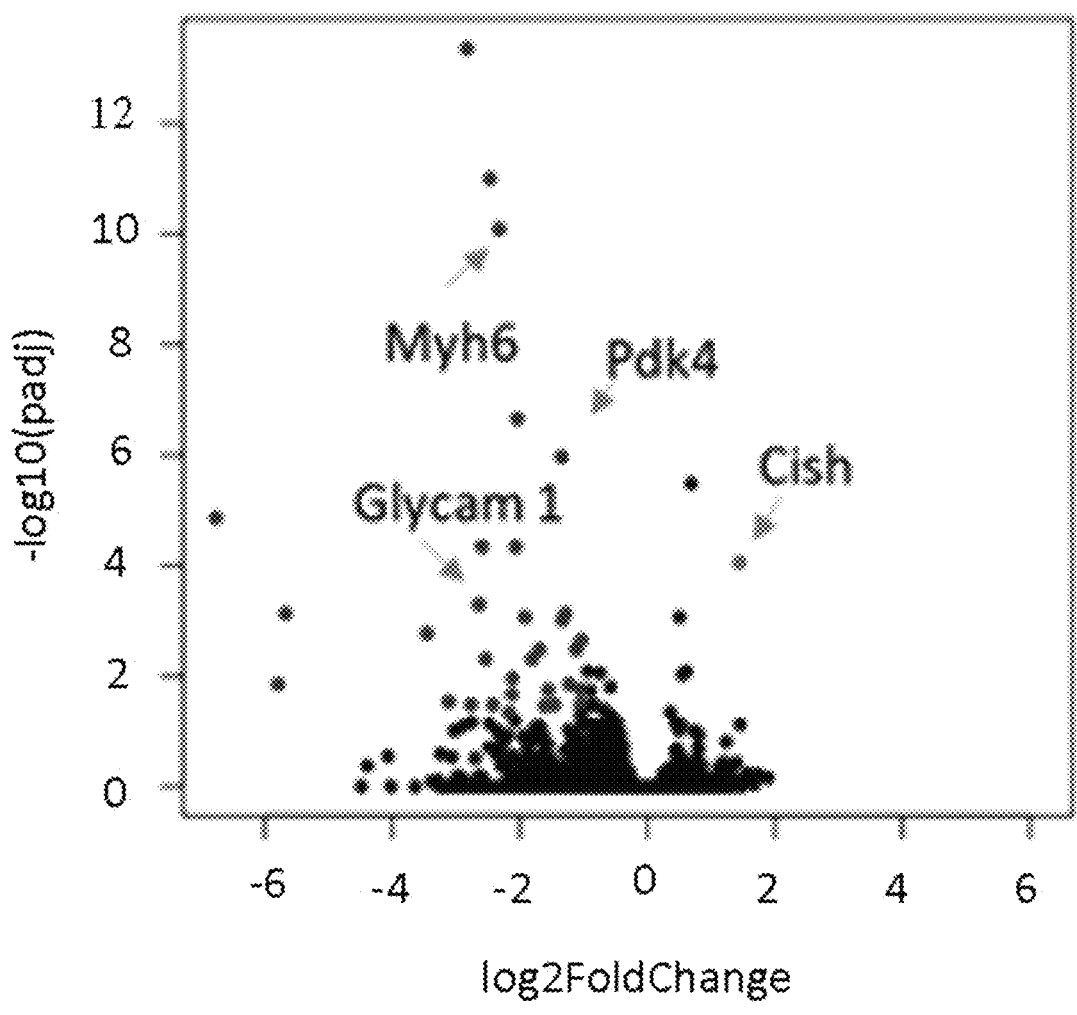
FIG. 26L shows Volcano plot for RNAseq analysis on the livers of db/db mice.
Figures 26M, 26N, 26O, 26P:
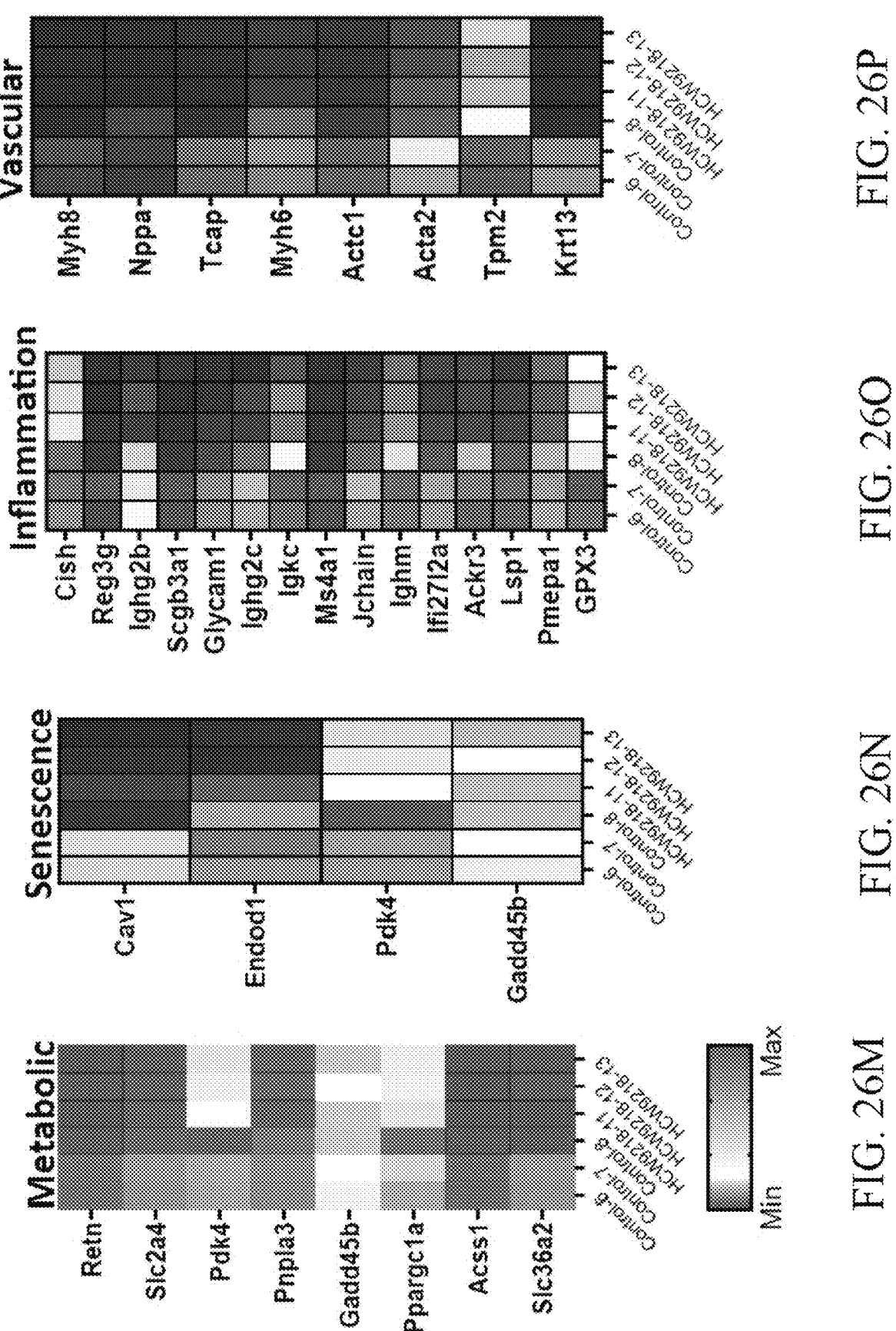

Since T2D is a metabolic disease and the liver is a key metabolic organ governing body energy metabolism, RNA-seq analysis on the livers of db/db mice was also performed following TGFRt15-TGFRs treatment. Of the differentially expressed liver genes, one was upregulated and 32 were downregulated which together could be grouped (by STRING) into 4 clusters based on function (FIG. 26L) (Table 1). Expression of 8 genes related to glucose, lipid, or amino acid metabolism were significantly reduced in the liver following TGFRt15-TGFRs treatment (FIG. 26M). Among this group, TGFRt15-TGFRs-mediated downregulation of resistin (Retn), previously found to be mainly synthesized in adipocytes, is particularly interesting. Resistin has been shown to induce insulin resistance in mice partially through toll-like receptor 4 signaling pathway and its downregulation by TGFRt15-TGFRs treatment could contribute to the reduction of insulin resistance (FIG. 26M). The expression of cellular senescence related genes, Cav1, Endod1, Pdk4, and Gadd45b, was also downregulated (FIG. 26N) suggesting TGFRt15-TGFRs treatment reduced senescent cell levels in livers. Fourteen pro-inflammation genes were downregulated and one gene was upregulated (Cish) (FIG. 26O) suggesting that TGFRt15-TGFRs treatment reduced liver inflammation. Expression of nine genes related to vascular regulation was also reduced (FIG. 26P). Since diabetes is known to induce vascular dysfunction and cellular senescence is implicated in this pathological process, this result further suggests that the reduction of SNCs and SASP in db/db mice could favorably impact vascular health in diabetes. Collectively, the results of this RNA-seq analysis support the hypothesis that TGFRt15-TGFRs treatment reduces the cellular senescence, SASP, and gluconeogenesis induced by metabolic dysfunction to improve glucose metabolism, metabolic homeostasis, and lower sterile inflammation in the livers of T2D db/db mice.

TABLE 1

| | | | | | | |
|---|---|---|---|---|---|---|
| Summary table of liver RNA Seq data showing 33 genes | | | | | | |
| Group | Regulation | ID | log2FC | pvalue | padj | Gene |
| Glucose regulation | Down | ENSMUSG00000012705 | −2.12306 | 5.09E−05 | 0.021507 | Retn |
| | Down | ENSMUSG00000018566 | −1.80962 | 7.35E−05 | 0.004942 | Slc2a4 |
| | Down | ENSMUSG00000019577 | −1.34542 | 3.76E−10 | 1.08E−06 | Pdk4 |
| | Down | ENSMUSG00000041653 | −1.32796 | 1.08E−05 | 0.000967 | Pnpla3 |
| | Down | ENSMUSG00000015312 | −1.04635 | 8.53E−05 | 0.032995 | Gadd45b |
| | Down | ENSMUSG00000029167 | −1.0363 | 2.79E−06 | 0.002228 | Ppargc1a |
| | Down | ENSMUSG00000027452 | −2.16447 | 0.000148 | 0.046106 | Acss1 |
| | Down | ENSMUSG00000020264 | −2.53609 | 7.57E−06 | 0.004942 | Slc36a2 |
| Senenscent cell regulation | Down | ENSMUSG00000007655 | −1.61384 | 0.000104 | 0.034636 | Cav1 |
| | Down | ENSMUSG00000037419 | −1.22862 | 2.82E−05 | 0.014052 | Endod1 |
| | Down | ENSMUSG00000019577 | −1.34542 | 3.76E−10 | 1.08E−06 | Pdk4 |
| | Down | ENSMUSG00000015312 | −1.04635 | 8.53E−05 | 0.032995 | Gadd45b |
| Inflammation regulation | Up | ENSMUSG00000032578 | 1.447471 | 6.18E−08 | 8.88E−05 | Clsh |
| | Down | ENSMUSG00000030017 | −3.11365 | 7.11E−05 | 0.029176 | Reg3g |
| | Down | ENSMUSG00000076613 | −2.82776 | 3.06E−18 | 4.40E−14 | Ighg2b |
| | Down | ENSMUSG00000064057 | −2.76399 | 9.05E−05 | 0.032995 | Scgb3a1 |
| | Down | ENSMUSG00000022491 | −2.63969 | 3.88E−07 | 0.000507 | Glycam1 |
| | Down | ENSMUSG00000076612 | −2.59181 | 2.27E−08 | 4.56E−05 | Ighg2c |
| | Down | ENSMUSG00000076609 | −2.46752 | 1.39E−15 | 9.97E−12 | Igkc |
| | Down | ENSMUSG00000024673 | −2.42377 | 8.34E−05 | 0.32995 | Ms4a1 |
| | Down | ENSMUSG00000067149 | −2.06336 | 2.86E−08 | 4.56E−05 | Jchain |
| | Down | ENSMUSG00000076617 | −2.03893 | 6.19E−11 | 2.22E−07 | Ighm |
| | Down | ENSMUSG00000079017 | −1.91748 | 8.57E−07 | 0.000856 | Ifi27l2a |
| | Down | ENSMUSG00000044337 | −1.68889 | 4.63E−06 | 0.003327 | Ackr3 |
| | Down | ENSMUSG00000018819 | −1.46106 | 9.06E−05 | 0.032995 | Lsp1 |
| | Down | ENSMUSG00000038400 | −1.11498 | 4.45E−06 | 0.003327 | Pmepa1 |
| | Down | ENSMUSG00000018339 | −1.04274 | 3.87E−05 | 0.017861 | Gpx3 |
| Vascular regulation | Down | ENSMUSG00000055775 | −5.78706 | 2.84E−05 | 0.014052 | Myh8 |
| | Down | ENSMUSG00000041616 | −5.67018 | 6.68E−07 | 0.000738 | Nppa |
| | Down | ENSMUSG00000007877 | −3.45345 | 2.00E−06 | 0.001691 | Tcap |
| | Down | ENSMUSG00000040752 | −2.32434 | 1.71E−14 | 8.20E−11 | Myh6 |
| | Down | ENSMUSG00000068614 | −2.11515 | 2.07E−05 | 0.011003 | Actc1 |
| | Down | ENSMUSG00000035783 | −1.5518 | 3.98E−05 | 0.017861 | Acta2 |
| | Down | ENSMUSG00000028464 | −1.28337 | 6.32E−07 | 0.000738 | Tpm2 |
| | Down | ENSMUSG00000044041 | −6.76486 | 6.73E−09 | 1.38E−05 | Krt13 |

Example 11: TGFRt15-TGFRs Stimulates Immune Cell Activities and Metabolic Functions while Reducing SASP and Cellular Senescence Markers in Naturally Aged Mice C57BL/6, 6 and 76-week-old mice were purchased from the Jackson Laboratory. Mice were housed in a controlled temperature and controlled light environment. Mice were divided into three groups as follows: Saline control group (n=6), TGFRt15-TGFRs group (n=6) and TGFRt15*-TG-FRs group (n=6). Mice were treated subcutaneously with PBS, TGFRt15-TGFRs (3 mg/kg) and TGFRt15*-TGFRs (3 mg/kg). The mice were euthanized, and spleen and liver were harvested and processed to a single cell suspension.

Although TGFRt15-TGFRs treatment has been shown to effectively reduce therapy-induced and metabolic dysfunction-induced SNCs and SASP in vivo, it is unknown whether TGFRt15-TGFRs could also eliminate the heterogenous population of SNCs generated and accumulated during natural aging. Heterogeneity of accumulated SNCs in the aging process is the result of poorly defined cell and tissue context-dependence inducers over time. Thus, studies to evaluate the senolytic and senomorphic activities of TGFRt15-TGFRs in naturally aged mice were also conducted.

Figure 27C:
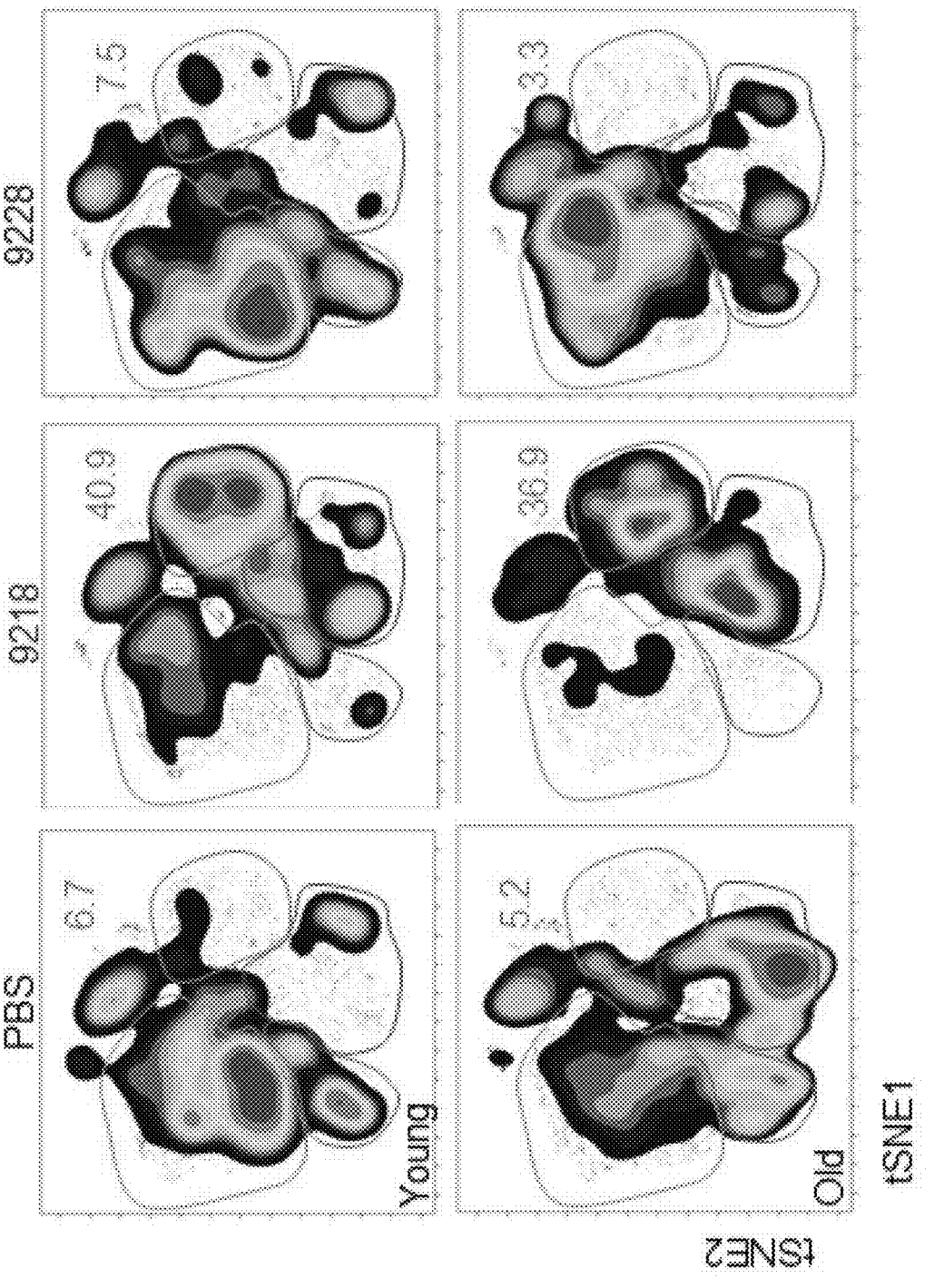
FIG. 27C shows representative viSNE plots colored by density from Livers harvested at day 4. Gates are colored by population and inset numbers represent frequency of I-ILC (ILC1 and NK cells).
Figures 33A, 33B:
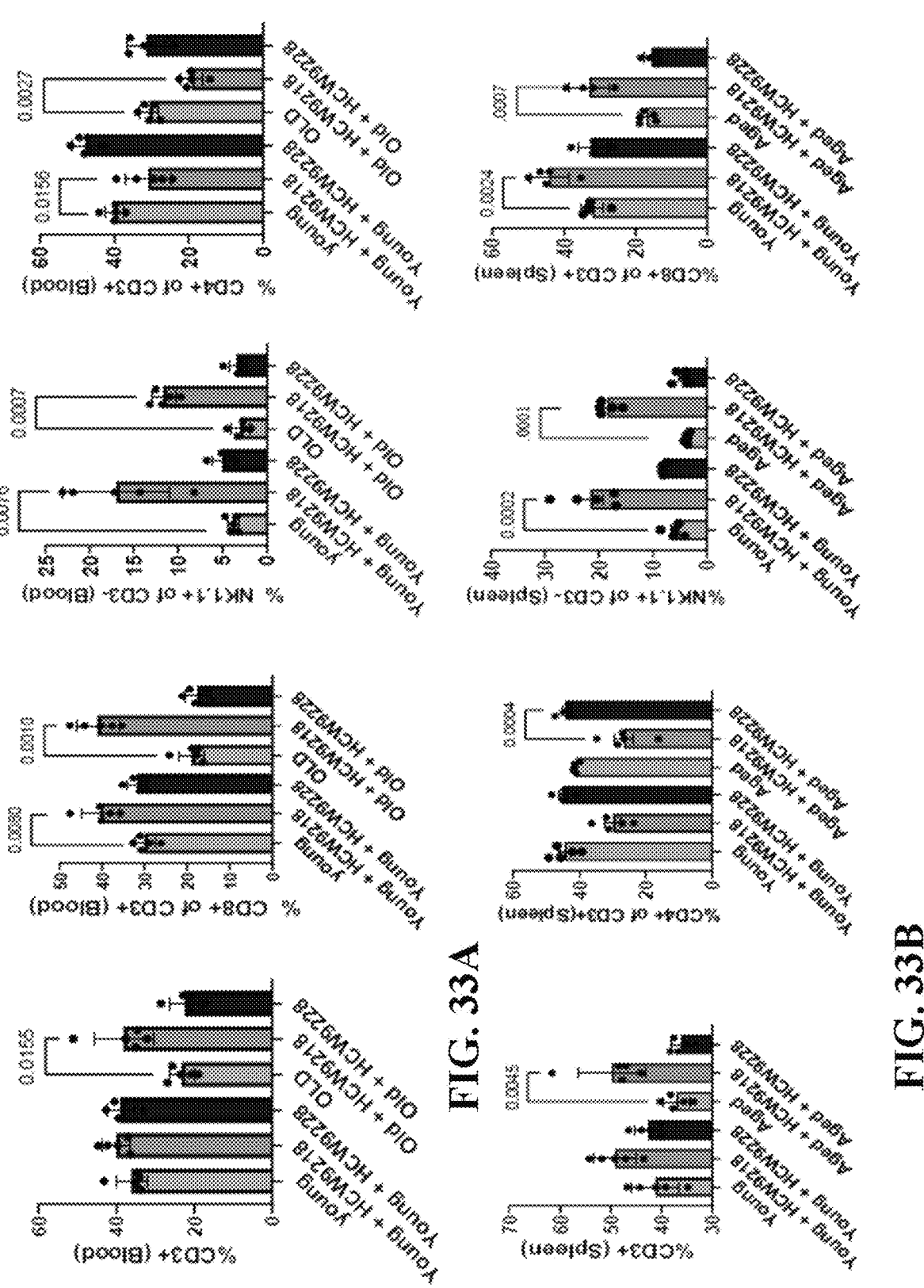
Figure 33C:
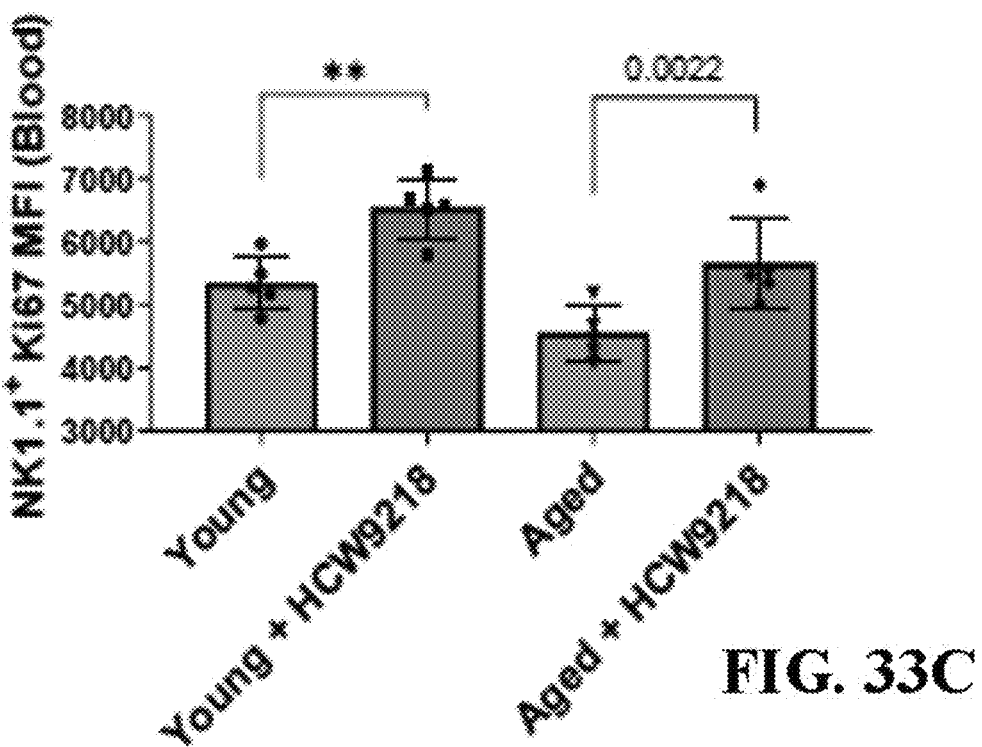
Figure 33D:
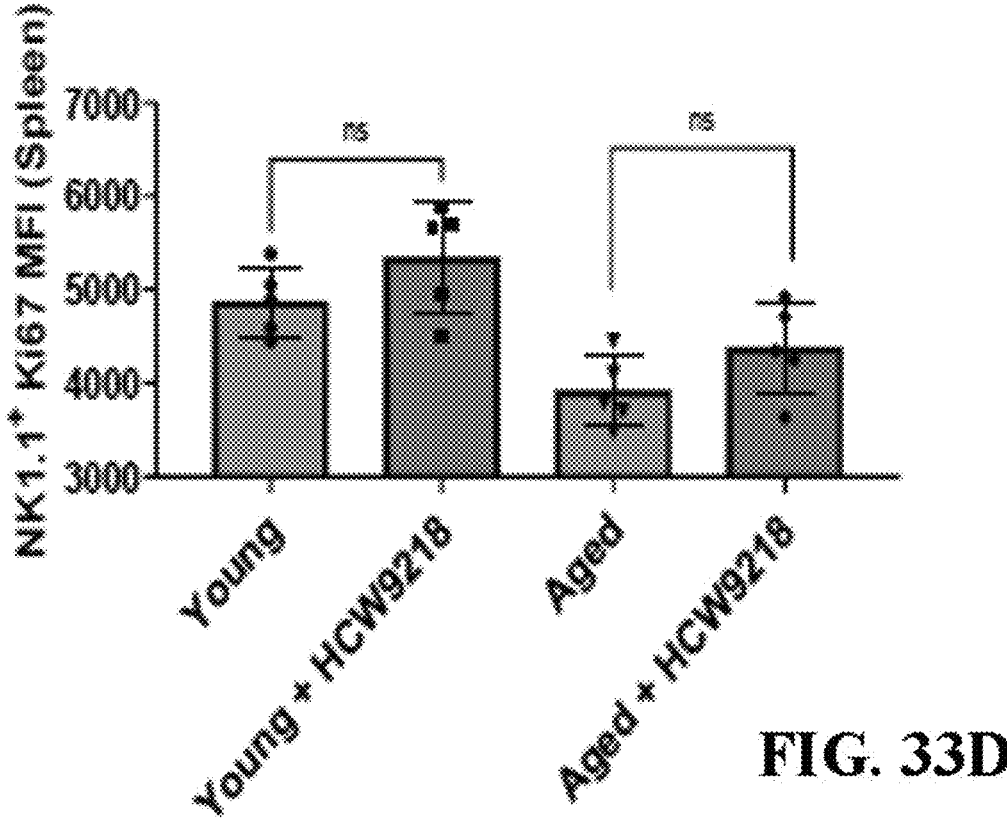
Figures 33E, 33F, 33G:
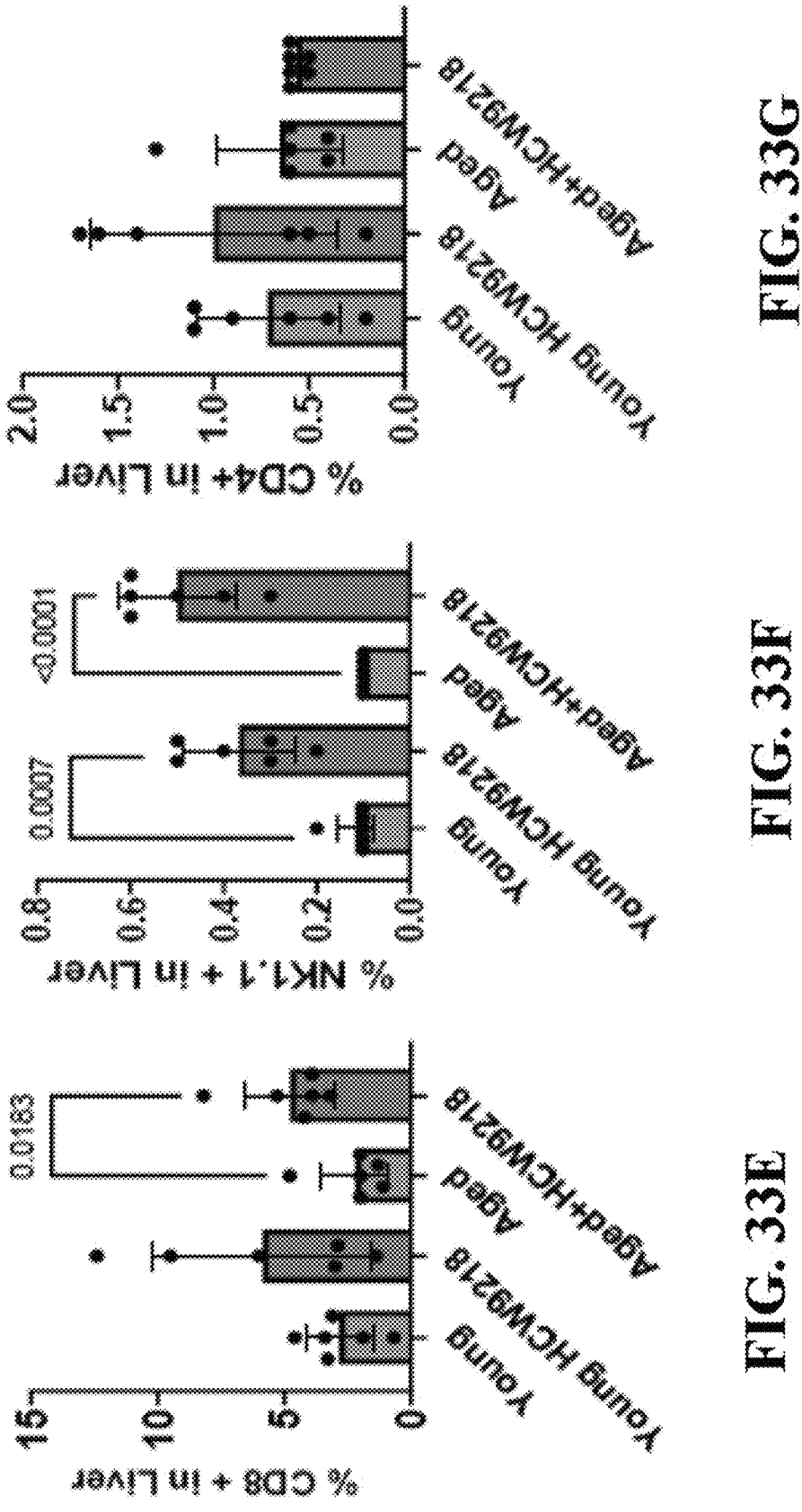

It was first evaluated whether TGFRt15-TGFRs exhibited immune cell stimulatory activity in aged mice which are reported to have immunosenescence. To determine the impact of TGFRt15-TGFRs on immune cells of aged and young mice, mass cytometry was performed utilizing an antibody panel that focuses on lymphocytes (B cells, CD4*, CD8+ T cells) and group 1 ILCs (NK cells and ILC1s). After a single injection of PBS (vehicle control), TGFRt15-TG-FRs, or TGFRt15*-TGFRs (IL-15 negative control), mononuclear cells were evaluated from the liver and spleen on either 4 day or 10 after treatment (FIG. 27A). Unbiased t-SNE based clustering identified lymphocyte annotated subsets (FIG. 27B), and density maps demonstrate a marked alteration in immune cell composition of the liver on day 4 (FIG. 27C). In liver, TGFRt15-TGFRs treatment significantly increased group 1 ILCs (FIG. 27D-27E) at day 4 and day 10 and NK cells (FIG. 27F-27G) at day 4 and day 10 in both aged and young mice. In spleen, total NK cells increased in both aged and young mice at day 4 and day 10 (FIG. 27H-27I). However, TGFRt15*-TGFRs did not induce any activation in NK or ILC1. Both liver NK cells and ILC1s showed evidence of TGFRt15-TGFRs-mediated activation with increased expression of Ki67 in the aged mice (FIG. 27J). In addition, total CD8+ T cells in liver and spleen in aged mice significantly increased in day 4 following TGFRt15-TGFRs treatment, compared to controls (FIG. 27K-27L). Liver CD4+ T cells in aged and young mice also increased at Day 4 following TGFRt15-TGFRs (FIG. 33J). There was no effect of TGFRt15-TGFRs on Treg frequency (FIG. 33K). These findings were further confirmed by flow cytometry analysis on immune cells from spleen and peripheral blood of TGFRt15-TGFRs-treated young and aged mice (FIG. 33A-33G).

Splenocytes from both young and aged mice treated with TGFRt15-TGFRs showed elevated glycolysis (FIG. 27M) and mitochondrial respiration rates (FIG. 27N) and enhanced killing of NK-sensitive Yac1 cells (FIG. 27O).

Splenocytes from aged mice showed increased IFN-$\gamma$ (FIG. 27P) and TNF$\alpha$ (FIG. 27Q) released by CD3$^+$ cells upon anti-CD3/anti-CD28 stimulation. The liver ILC-1 (Aged mice) and NK (young mice) granzyme B levels (FIG. 27R) were also upregulated by TGFRt15-TGFRs treatment.

Collectively, results provide evidence that TGFRt15-TG-FRs treatment could effectively stimulate and promote the proliferation of NK cells and CD8$^+$ T cells and improve the fitness (i.e., metabolic functions) of these immune cells in lymphoid tissue and liver of naturally aged mice.

Example 12: TGFRt15-TGFRs Reduces SNCs and SASP in Peripheral Organs

C57BL/6, 6-week and 76-week-old mice were purchased from the Jackson Laboratory. Mice were housed in a controlled temperature and controlled light environment. Mice were divided into three groups as follows: Saline control group (n=5), TGFRt15-TGFRs group (n=5) and TGFRt15*-TGFRs group (n=6). Mice were treated subcutaneously with PBS, TGFRt15-TGFRs (3 mg/kg) and TGFRt15*-TGFRs (3 mg/kg) at day 0 and day 60. The mice were euthanized at day 120, and spleen was harvested and processed to a single cell suspension.

Figure 28A:
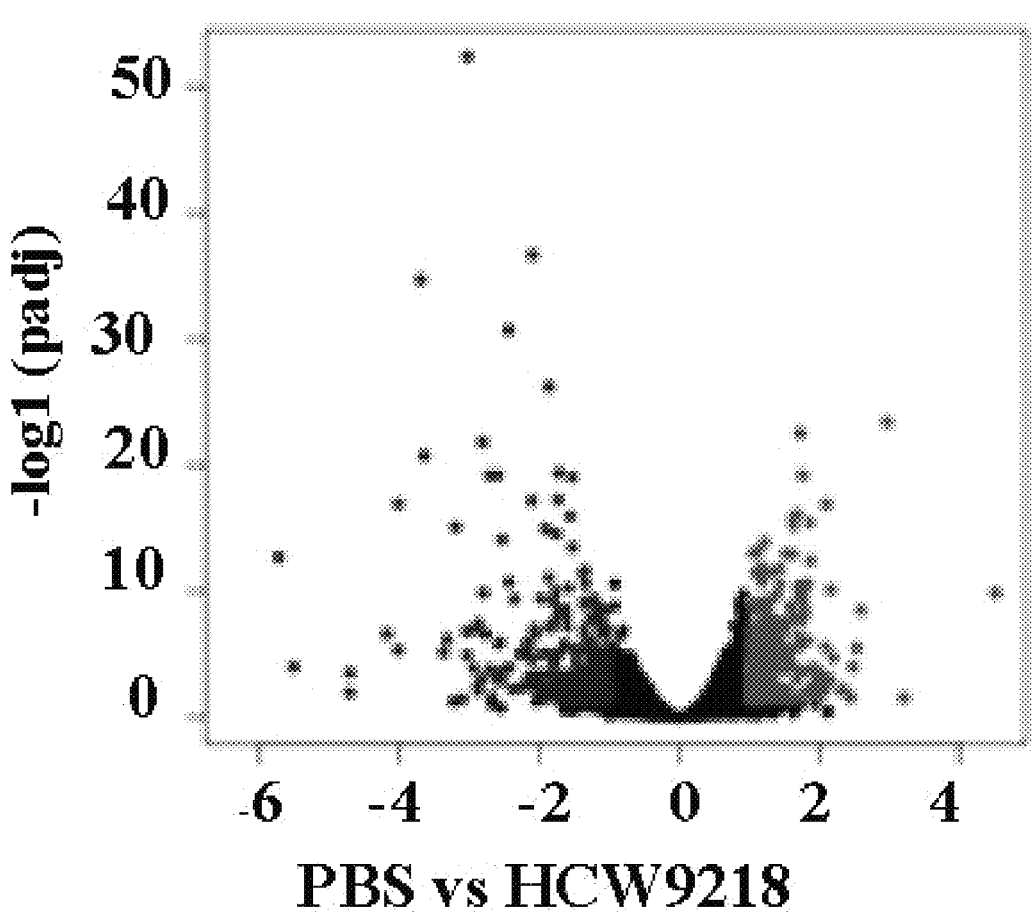
FIGS. 28A-28F show TGFRt15-TGFRs (HCW9218) reduces inflammation (SASP) and cellular senescence markers of chronologically aged mice in liver either after one or two subcutaneous doses of TGFRt15-TGFRs (HCW9218) or PBS.
Figure 28B:
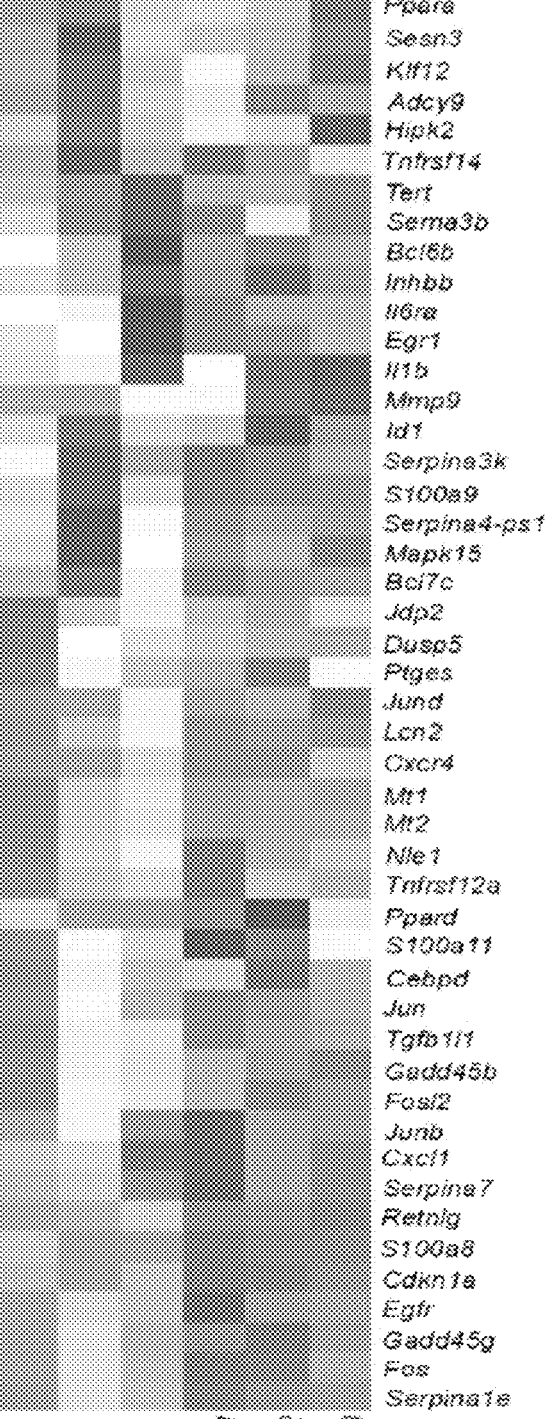
Figure 28C:
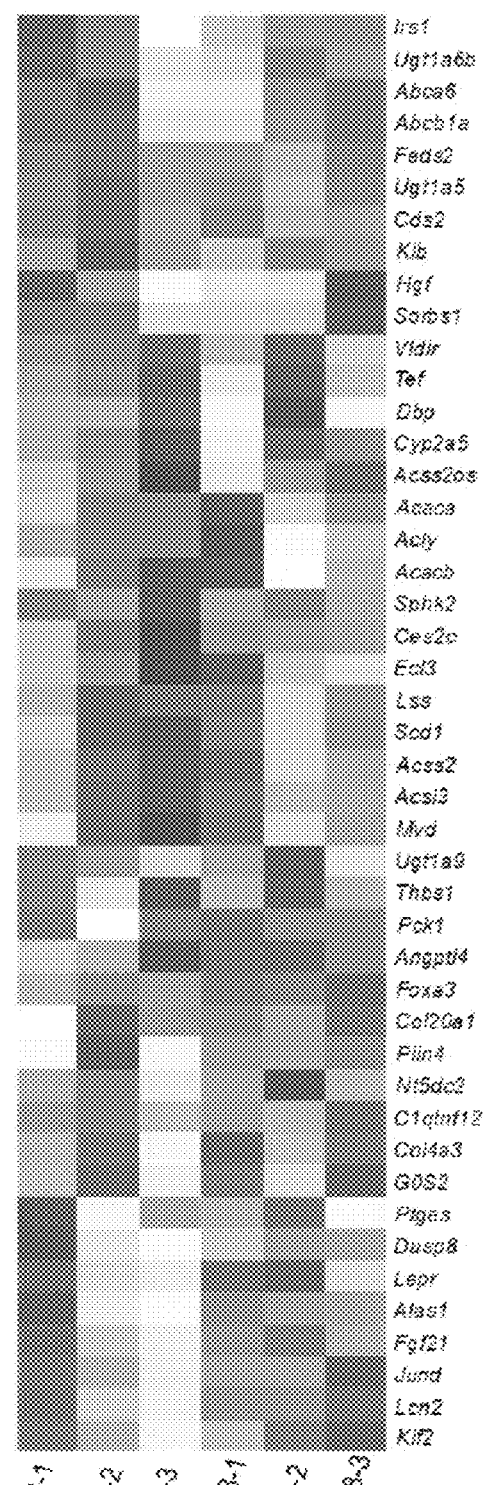
Figure 28D:
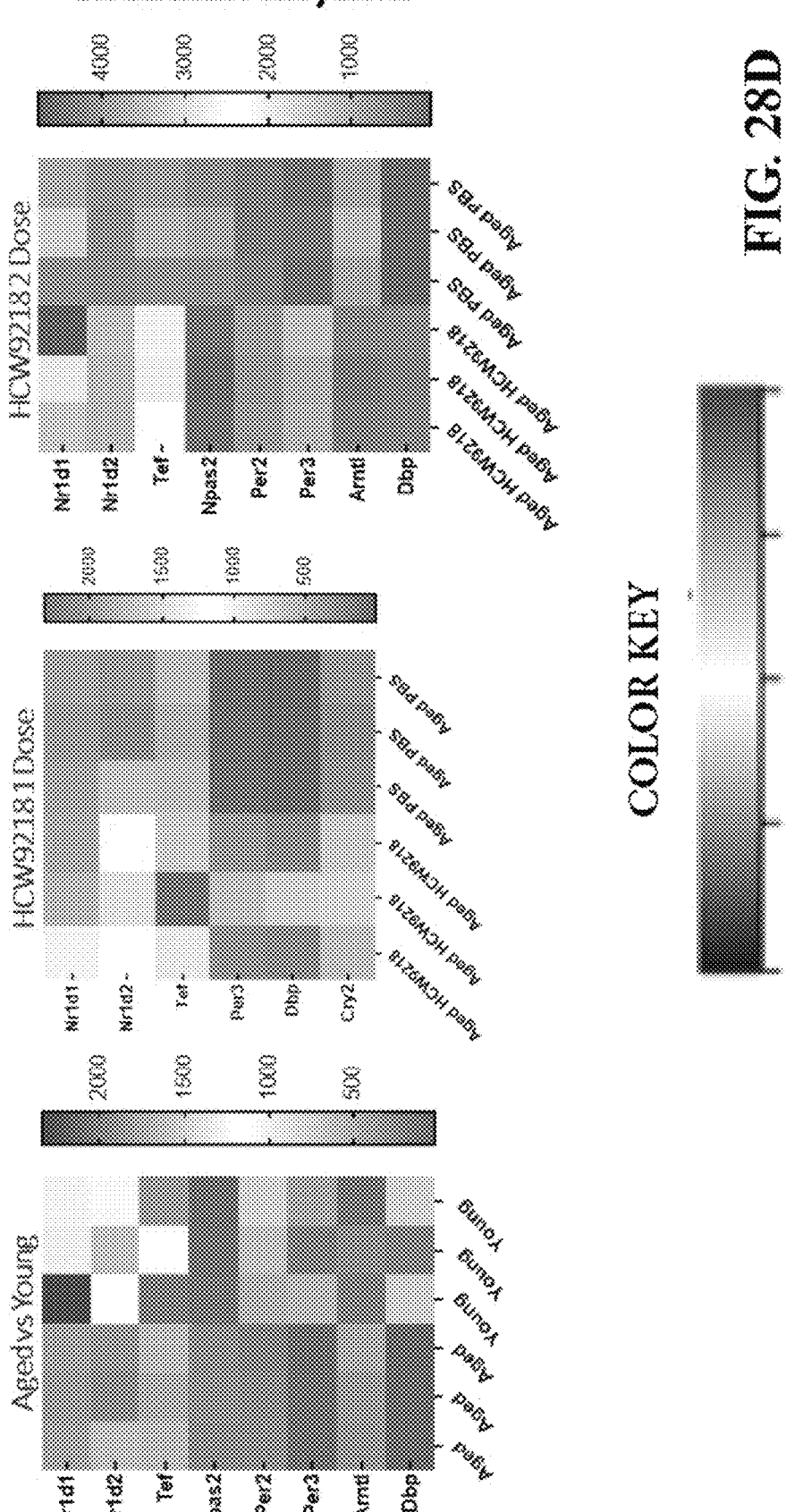

The long-term changes in expression of inflammation and senescence-associated genes in aged mice (76 weeks) receiving either one or two subcutaneous doses of TGFRt15-TGFRs (3 mg/kg) or PBS (control) were examined. RNA-seq analysis was performed on the liver isolated at 60 or 90 days after TGFRt15-TGFRs treatment to determine the global transcriptional changes. Significant differentially expressed genes were clustered by their gene ontology and the enrichment of gene ontology terms was tested using Fisher exact test (GeneSCF v1.1-p2). The liver of TGFRt15-TGFRs-treated aged mice showed dramatic changes in gene expression with a total of 539 differentially expressed mRNAs compared to PBS-treated mice (FIG. 28A). Significant downregulation (e.g., Cdkn1a, Nle1, Jund, Sema3b, Bcl6, Bcl7c, Gadd45$\beta$) or upregulation (e.g., Tert) expression of senescence and inflammation associated (SASP) genes (e.g., cytokines: Il6r$\alpha$, Il1$\alpha$, Il-6, Tnf$\alpha$, S100a8, S100a9, S100a11, Lcn2, Retnlg, Inhbb; chemokines: Cxcl1, Cxcr4, Mt1, and Mt2; metalloproteinases: Mmp9; gene expression and signaling pathways: e.g., Cebpd, Klf12, Egr1, Egfr, Gadd45$\beta$, Gadd45g, Ppara, Ppar$\beta$, Fos, Fosl2, Jun, Junb, Mapk15, Adcy9) were observed following TGFRt15-TGFRs treatment (FIG. 28B). TGFRt15-TGFRs treatment also upregulated important gene families associated with immune function and reduced transcripts involved with immune suppression (e.g., immune functions: Sucnr1, Lex-1, Slfn4, Ascc3, Lyst, Sesn and immune suppressions: Zc3h12d, Lax1, Socs2, Mat1) (FIG. 34A). Expression of gene sets associated with glucose and fatty acid metabolism (e.g., Angptl4, Gos2, C1qtnfl2, Fads2, Sorbs1, Zbtb16, Mvd, Scd1, Acaca, Acacb, Abcb1c, Abca6, Acly, Eci3, Ugt1a5, Ugta6, Ugta9, Acsl3, Lss, Acss2os, Plin4), fibrosis (e.g., Col4a3, Col20a1, Jund, Thbs1), and other liver functions (e.g., Dbp, Tef Acss2) were also altered with TGFRt15-TGFRs treatment (FIG. 28C). The RNA-seq analysis also found that transcripts of circadian molecular clock repressor genes (orchestrating circadian rhythms) were altered 60 days after TGFRt15-TGFRs treatment (FIG. 28D). Per, Cry, Nr1d1, Nr1d2, and Dbp (i.e., repressors) were upregulated by the TGFRt15-TGFRs treatment (FIG. 28D). Sixty days after two-dose TGFRt15-TGFRs treatment, the repressor genes were found to be upregulated similarly to a single-dose treatment, but the expression of the activator genes Arntl and Npas2 were now down regulated (FIG. 28D). TGFRt15-TGFRs treatment as either a single- or double dose regimen, appeared to reverse the expression pattern of these key circadian-rhythm genes of aged mice sixty days after treatment to that of young mice (FIG. 28D).

Figures 28E, 28F:
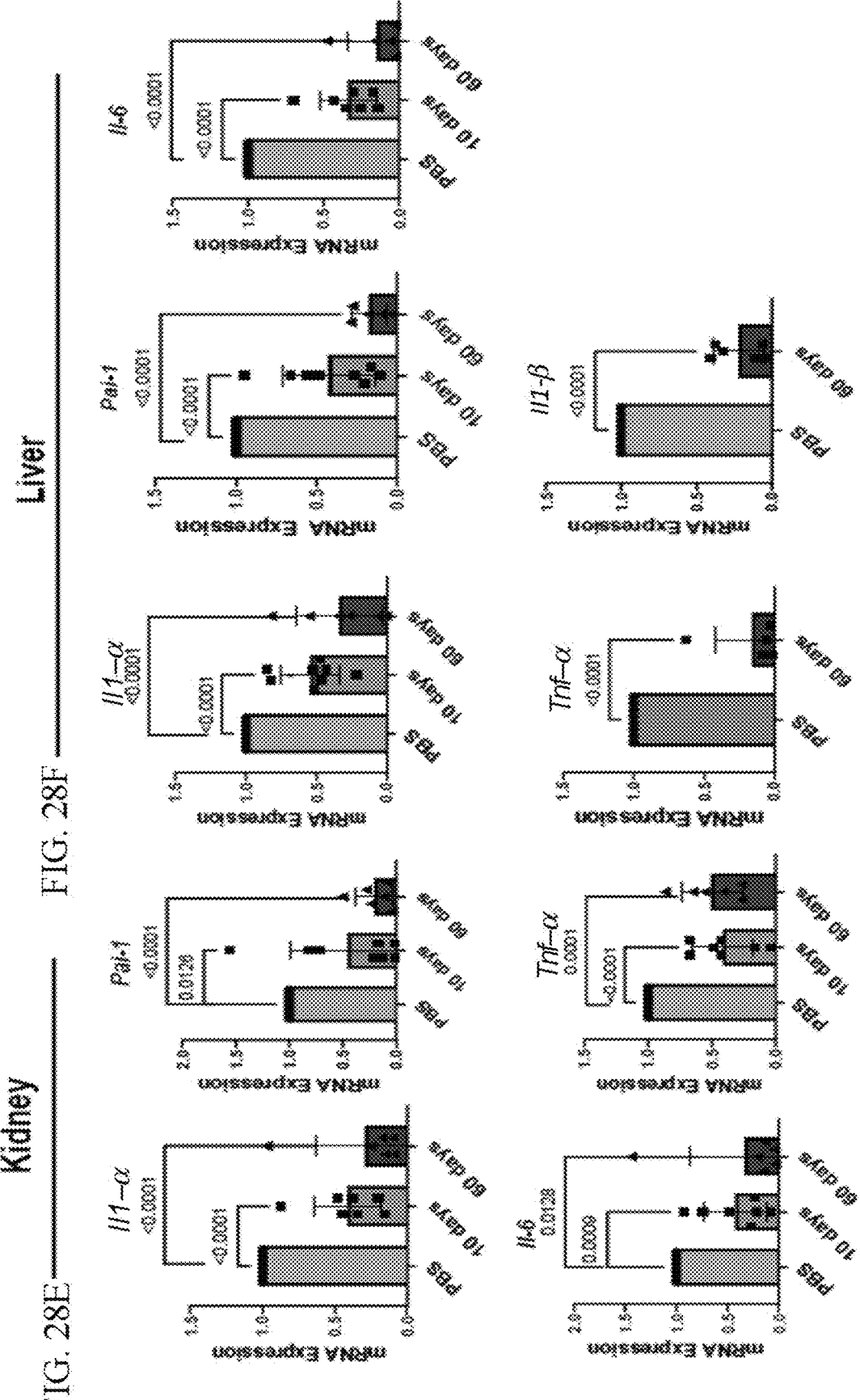
Figures 29G, 29H:
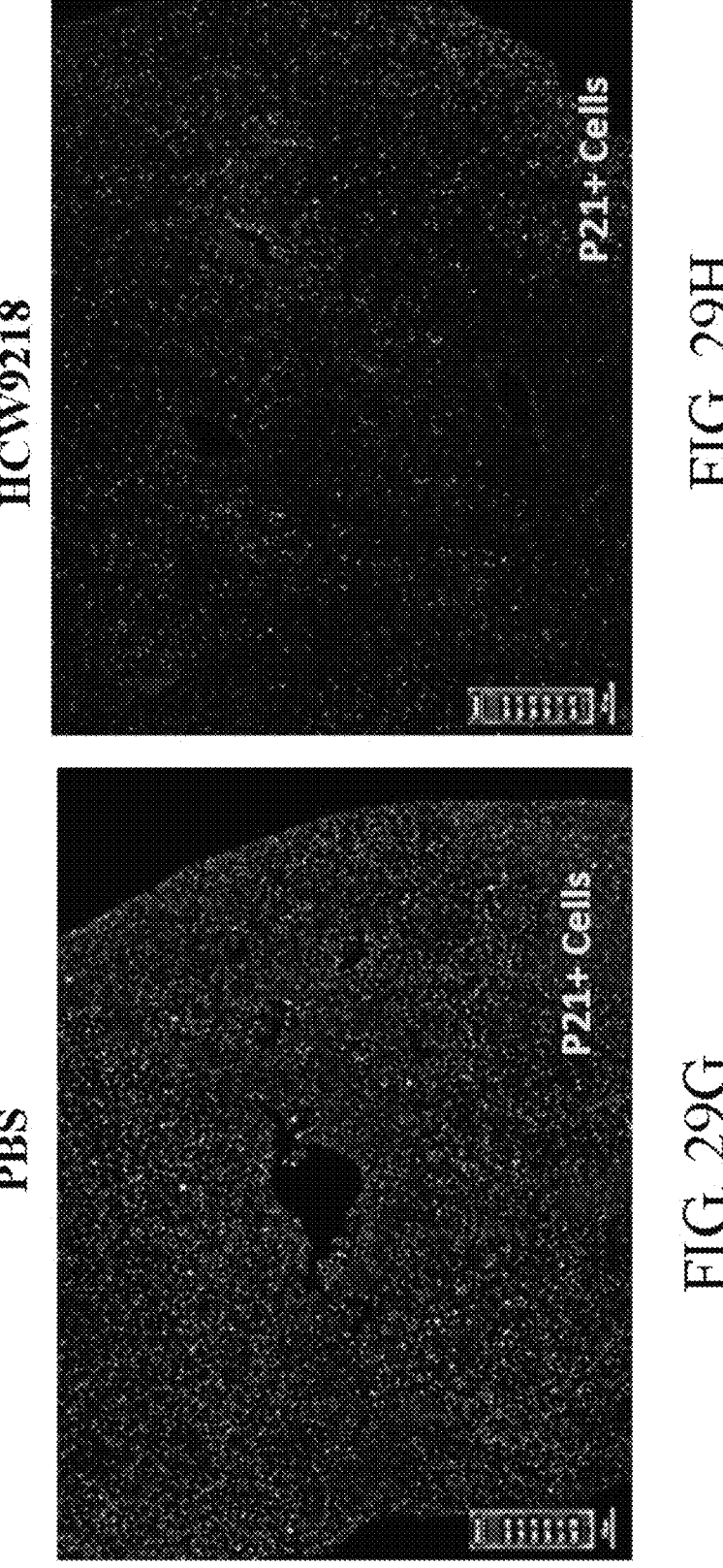

The impacts of TGFRt15-TGFRs treatment on cellular senescence and SASP in the peripheral organs of aged mice were further analyzed using qRT-PCR, ELISA and immunofluorescence studies (FIG. 29A). qRT-PCR analysis of kidney and liver of aged mice either 10 days or 60 days after a single-dose TGFRt15-TGFRs treatment showed a significant reduction in gene expression for the cellular senescence and SASP signature genes, PAI-1, Il1a, Il6, Il1$\beta$, and Tnfa (FIGS. 28E and 28F) compared to the PBS control mice. Two-dose TGFRt15-TGFRs treatment (FIG. 29A) also provided significant reduction in Il1a, Cdkn1a, PAI, Il1b, and Il6 transcripts in the liver at 120 days post-treatment initiation versus the control group (FIG. 29D). Reduction of liver IL-1$\alpha$, IL-6 and IL-8 were also observed at protein levels by ELISA (FIG. 29E). In a two-dose treatment regimen, it was also found that TGFRt15-TGFRs lowered biomarkers PAI-1 and fibronectin (FIG. 29F) suggesting that TGFRt15-TGFRs could reduce liver fibrosis in old mice, consistent with significant down-regulation of Col4a3 and Col20a1 expression observed in the above RNA-seq study. Immunofluorescence staining of aged mice liver sections confirmed accumulation of p21$^+$ SNCs which were reduced with TGFRt15-TGFRs treatment (FIGS. 29G and 29H).

Figure 29I:
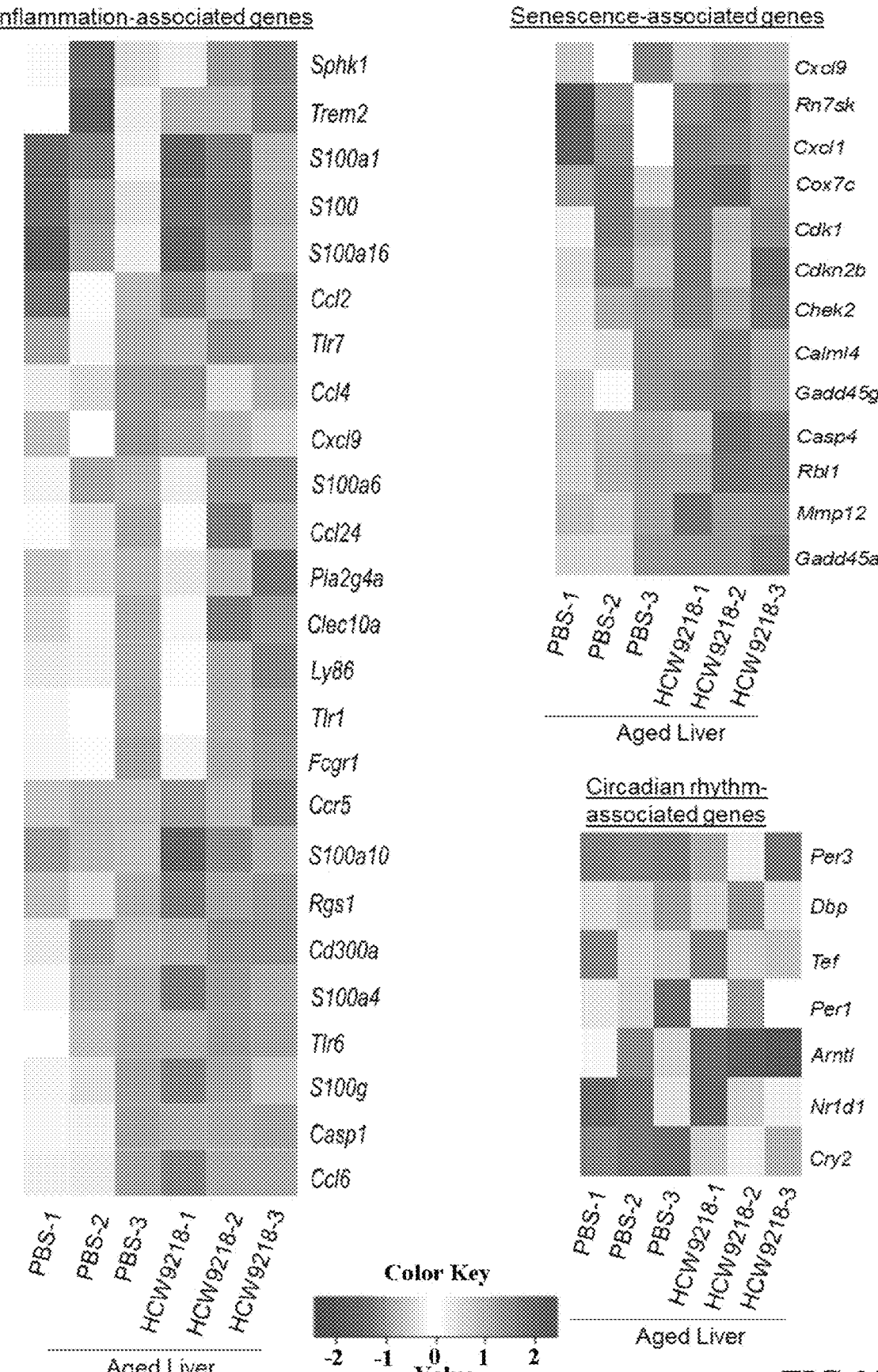

The durability of the senolytic and senomorphic activities of TGFRt15-TGFRs treatment on gene expression was further evaluated using RNA-seq analysis on liver of aged mice isolated at 120 days. Significant downregulation (e.g., Cdkn1a) or upregulation (e.g., Tert) of senescence and inflammation associated (SASP) genes (e.g., cytokine: 117, 1115, 1118, S100g, S100a1, S100a4, S100a6, S100a10, S100a16, S100g; chemokines: Ccl2, Ccl4, Ccl6, Ccl7, Ccl8, Ccl9, Ccl24, Ccl25, Ccl27, Cxcl1, Cxcl10, Cxcl11; metalloproteins: Mmp12, Mmp13, Mmp27; gene expression and signaling pathways: Klf1, Klf3, Klf7, Klf9, Klf13, Egr1, Ppara, Jun, Fosl2; Mapk3, Mapk6, Mapk7, Mapk9, Mapk12, Mapk15, Adcy1, Adcy3, Adcy5, Adcy6, Adcy9, Adcy10), and gene associated liver functions (e.g., Dbp, Tef) and immune stimulation (e.g., Lyst, Sesn2, Sesn3) was continuously observed following TGFRt15-TGFRs treatment (FIG. 29I). The RNA-seq analysis also found that transcripts of circadian molecular clock repressor genes, Per1, Per3, Cry2, Nr1d1, and Dbp, were still upregulated 120 days after TGFRt15-TGFRs treatment (FIG. 28D). However, following 120 days after two-dose TGFRt15-TGFRs treatment, the expression of the activator gene Arntl was upregulated and the effects on Npas2 expression became insignificant compared with the PBS treatment (FIG. 29I).

Beside gene expression signatures in solid peripheral organs, long lasting impact of TGFRt15-TGFRs in enhancement of splenocytes' glycolysis and mitochondrial respiration was also found which continued 60 days after treatment with the second dose (FIGS. 29B and 29C).

Figure 34C:
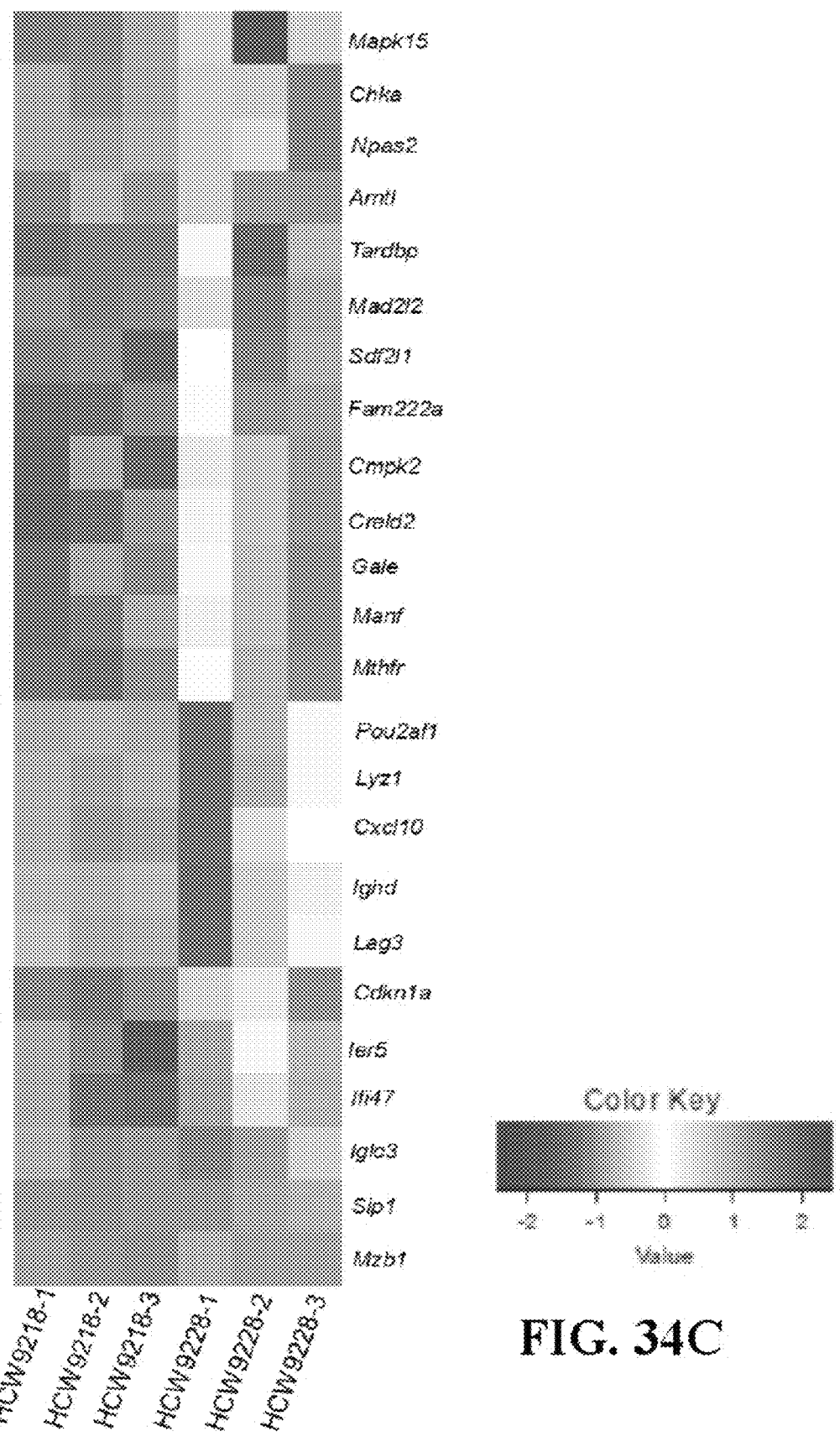

To further evaluate whether the TGF$\beta$RII component of TGFRt15-TGFRs exhibited senolytic and senomorphic function, young and aged mice were treated with a single-dose of TGFRt15*-TGFRs and conducted the RNA-seq analysis on the livers 10 days after treatment. As shown in FIG. 34B, TGFRt15*-TGFRs treatment could significantly lower the expression of Cdkn1a and many circadian clock genes in the liver. A comparison of impacts of TGFRt15-TGFRs and TGFRt15*-TGFRs 120 days after treatment was also performed (FIG. 34C). RNA-seq analysis on liver from treated mice showed that TGFRt15-TGFRs, but not TGFRt15*-TGFRs, maintained the downregulation of Cdkn1a expression and both treatments continued to upregulate the Tert gene expression compared with PBS treatment. TGFRt15*-TGFRs treatment significantly increased circadian molecular clock activator genes Arntl and Npas2 compared to TGFRt15-TGFRs-treated or the control group. Since TGFRt15*-TGFRs did not activate or promote proliferation of immune cells (FIG. 27A-27H), this suggests that direct neutralization of TGF-β by the TGFβRII component of TGFRt15-TGFRs may contribute to the senolytic and senomorphic activities of TGFRt15-TGFRs. This also suggests that the IL-15 component of TGFRt15-TGFRs provides long lasting senolytic activity.

Taken together, the data indicates that TGFRt15-TGFRs treatment durably reduces genes associated with SNCs and SASP, and enhances the immune-cell activities in naturally aged mice. It also suggests that TGFRt15-TGFRs treatment improves the metabolic function, fibrosis, and circadian rhythms of liver cells of naturally aged mice.

Example 13: TGFRt15-TGFRs Lowers Expression of Inflammatory Genes in the Central Nervous System The mouse hippocampus was harvested to evaluate changes in transcripts levels of the senescence marker IL1-β in hippocampus of aged mice after treatment with one dose of TGFRt15-TGFRs by quantitative PCR. C57BL/6, 76-week-old mice were purchased from the Jackson Laboratory. Mice were housed in a temperature and light controlled environment. Mice were treated with either PBS or one dose of TGFRt15-TGFRs (3 mg/kg). Mice were euthanized after day 60 of treatment, hippocampus were harvested and stored in liquid nitrogen in 1.7 mis Eppendorf tubes.

Figure 30A:
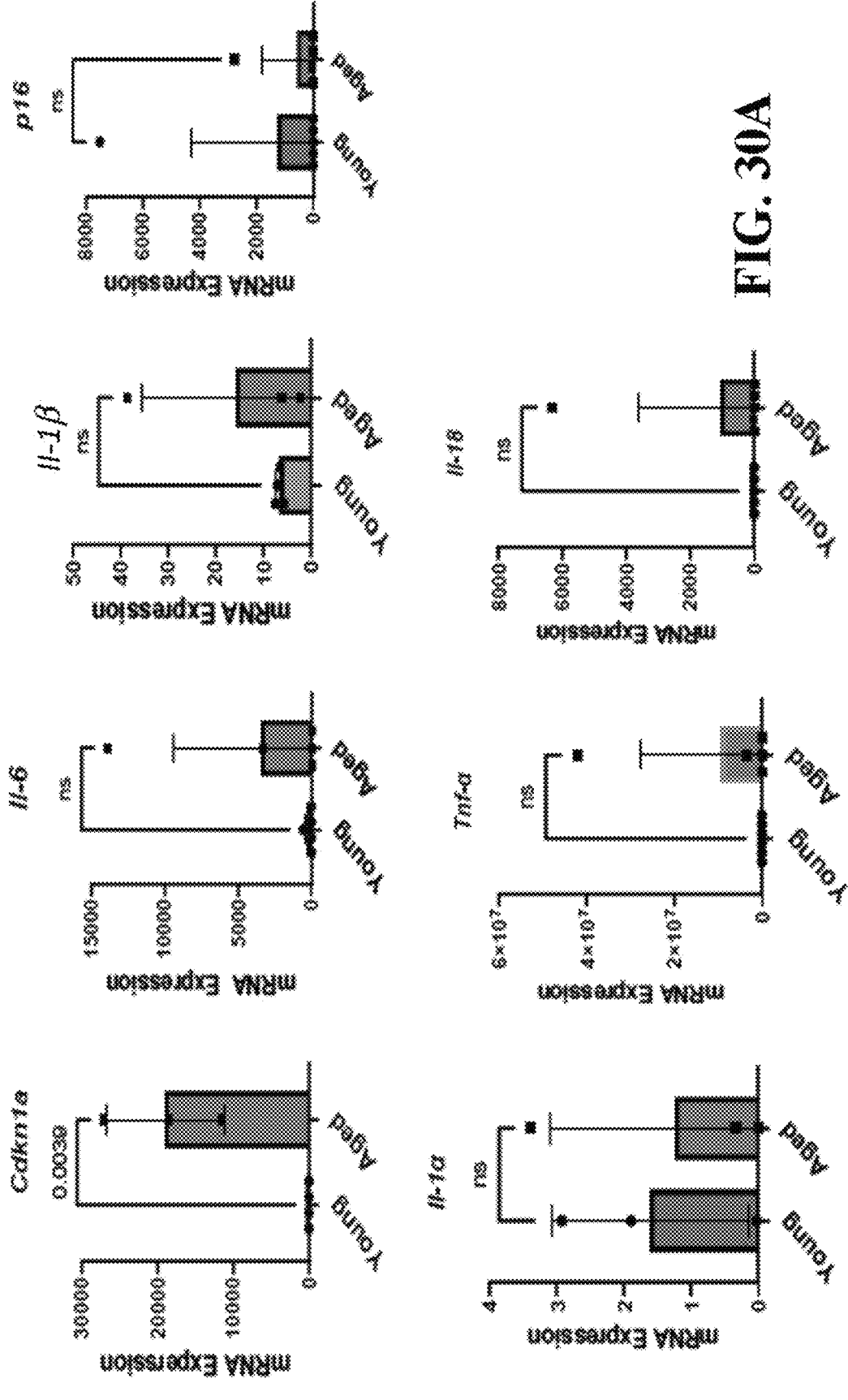
FIGS. 30A-30E show TGFRt15-TGFRs (HCW9218) reduces neuroinflammation and affects neuronal functions of the naturally aged mice.
Figure 30B:
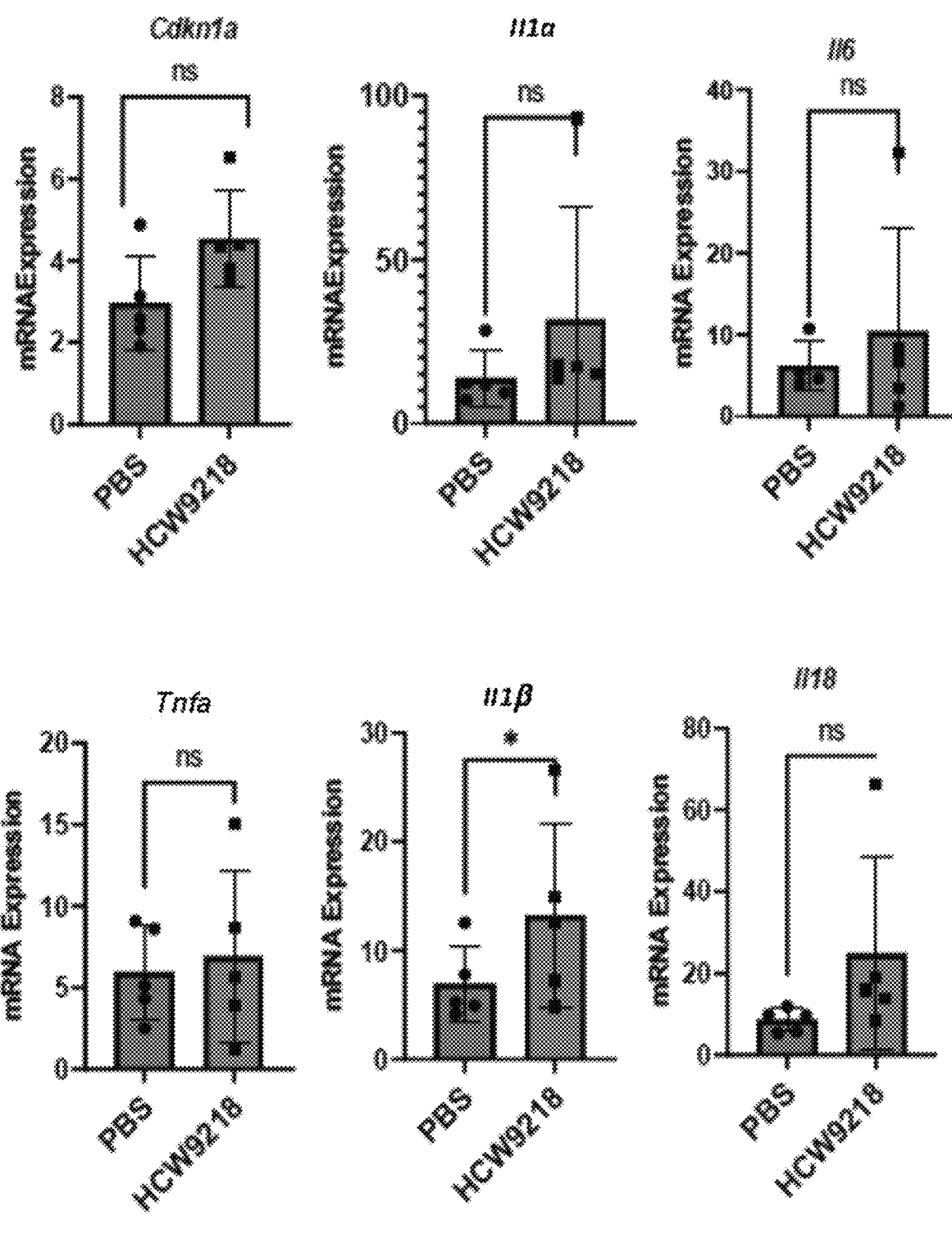

Neuroinflammation has been associated with several neurodegenerative disorders including Alzheimer's disease (AD), Down syndrome, and Parkinson's disease (PD), while it has been shown that accumulation of cellular senescence and SASP factors contributes to neuroinflammation in chronological aging. Moreover, clearance of SNCs in the hippocampus of the aged mice has been shown to alleviate cognitive dysfunction during the ageing process. Thus, qRT-PCR was first used to compare the expression levels of Cdkn1a (cellular senescence), Il-1α, Il-6 and Tnfα (SASP), Il-1β and IL-18 (NLRP3 Inflammasome) in hippocampus of naturally aged mice vs. young mice. Except for up-regulation of Cdkn1a, the expression of these genes was not significantly different in hippocampus of young vs. aged mice (FIG. 30A). Furthermore, qRT-PCR analysis at 60 days after the second dose of TGFRt15-TGFRs treatment similarly showed no significant difference in these cellular senescence-, SASP-, and inflammasome-related genes (FIG.

30B) in the hippocampus of naturally aged mice. This lack of TGFRt15-TGFRs treatment effects on expression of these genes by qRT-PCR was confirmed by RNA-seq analysis of hippocampus samples from aged mice.

Figure 30C:
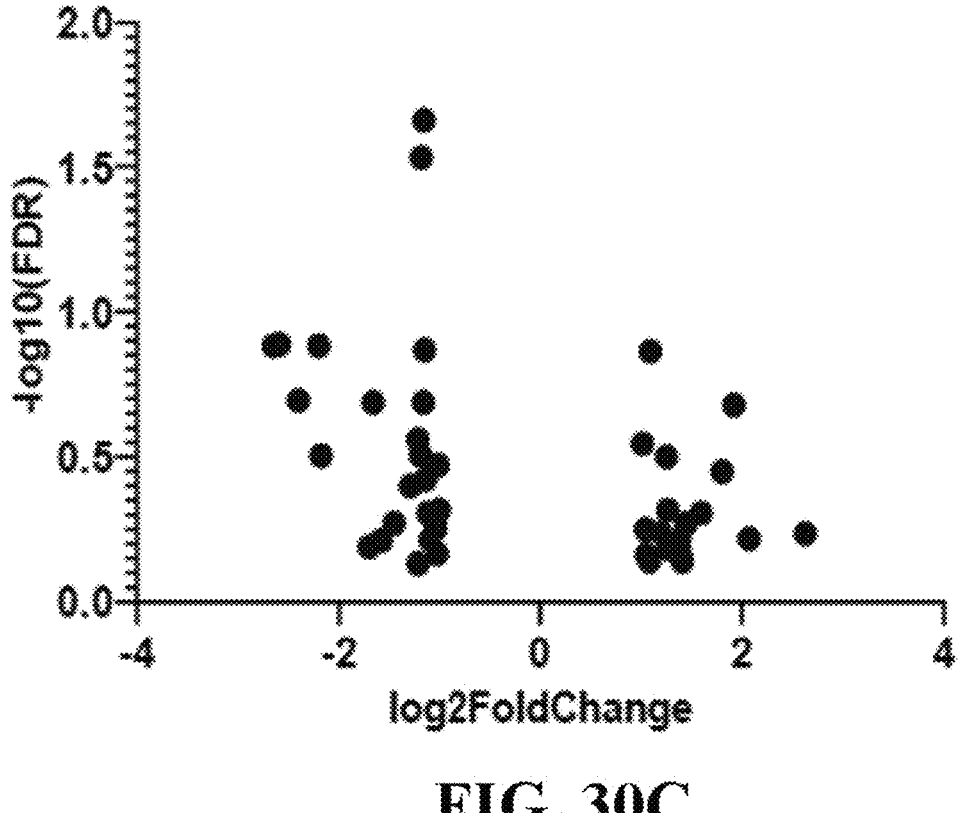
Figures 30D, 30E:
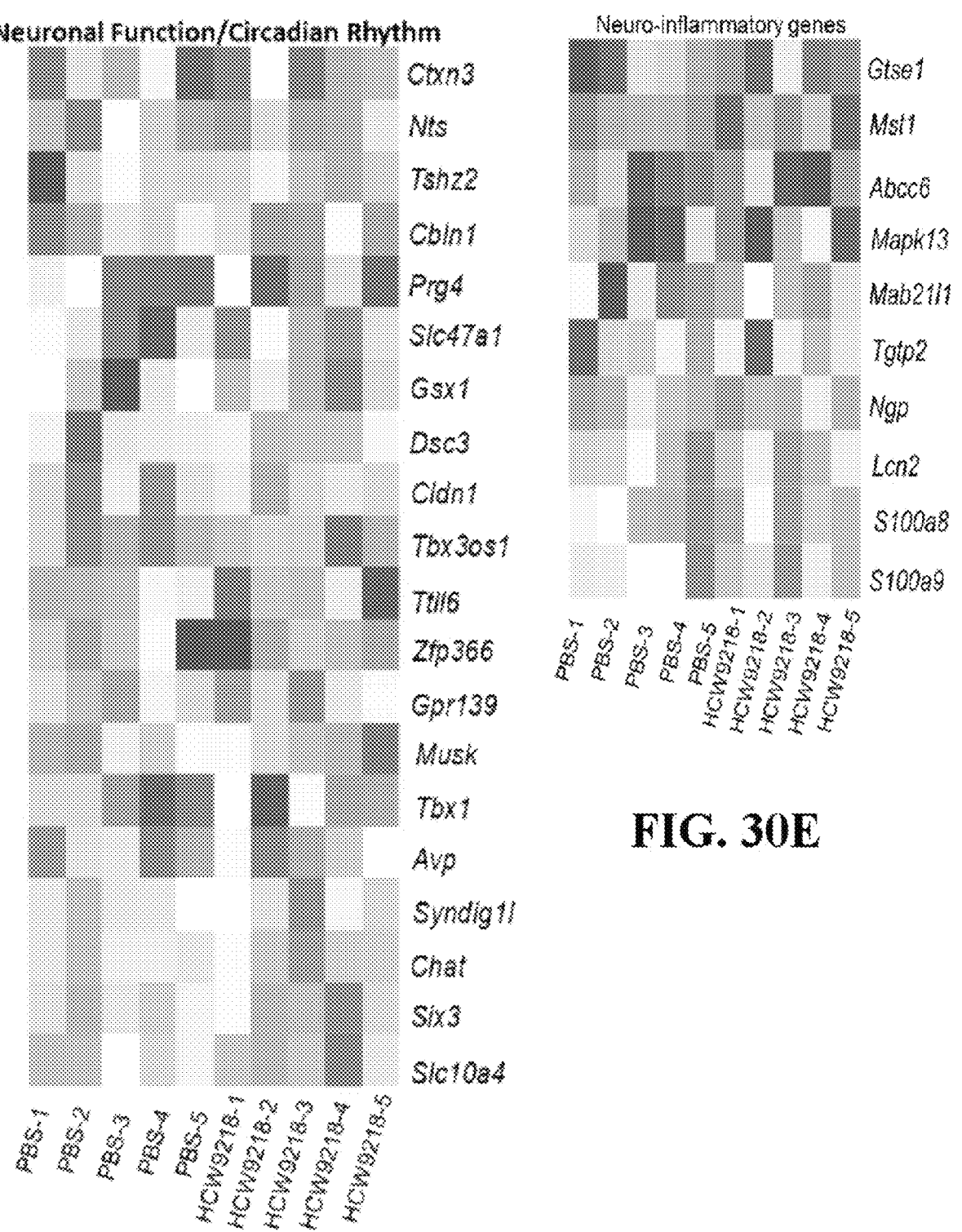

Despite the insensitivity of cellular senescence- and SASP-related genes in the hippocampus to TGFRt15-TGFRs treatment, RNA-seq analysis revealed the treatment causing significant changes in gene expression, with a total of 150 differentially expressed mRNAs in TGFRt15-TGFRs-treated vs. PBS-treated control mice (FIG. 30C). Clustering by gene ontology and enrichment of gene ontology terms using Fisher exact test (GeneSCF v1.1-p2), revealed significant downregulated expression of inflammation-associated genes (e.g., S100a8, S100a9, Lcn2, Mab21/1, Mapk13, Mst1, Ngp, and Tgtp2) following TGFRt15-TGFRs treatment (FIG. 30E), as well as upregulated transcripts for important gene families associated with neuronal functions and circadian rhythm (e.g., Six3) and reduced transcripts involved with immune suppression (e.g., immune functions: . . . ) (FIG. 30D). Thus, TGFRt15-TGFRs treatment may potentially reduce neuroinflammatory activity and affect neuronal function in the hippocampus of naturally aged mice in the absence of overt effects on cellular senescence and SASP (FIG. 30E).

Figure 35A:
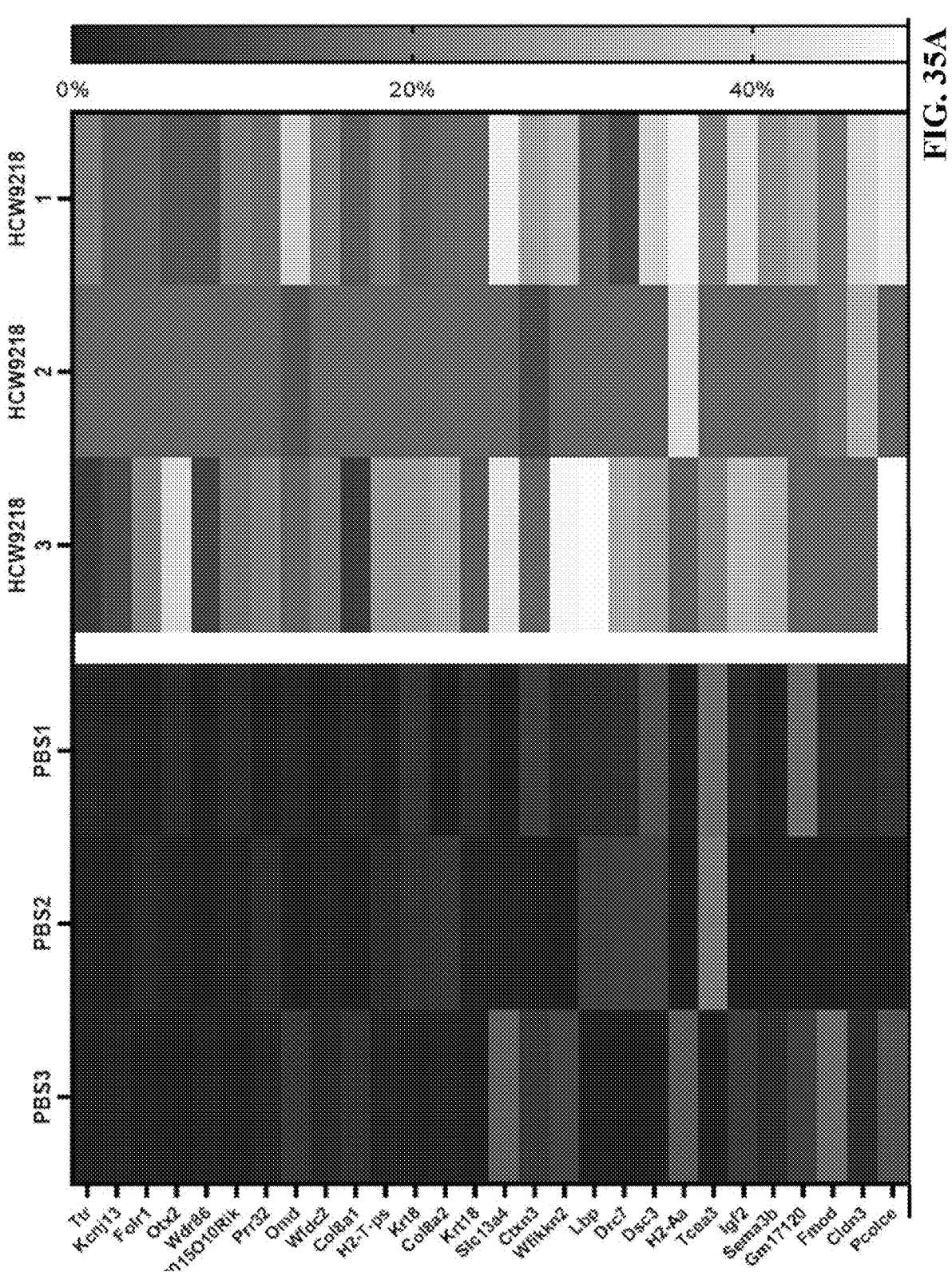
FIG. 35A shows heat maps of the differentially expressed Senescence, Inflammation and Circadian Rhythm associated genes associated genes in hippocampus after treatment with TGFRt15-TGFRs (HCW9218) compared to control treatment (adjusted p value<0.05).
Figure 35B:
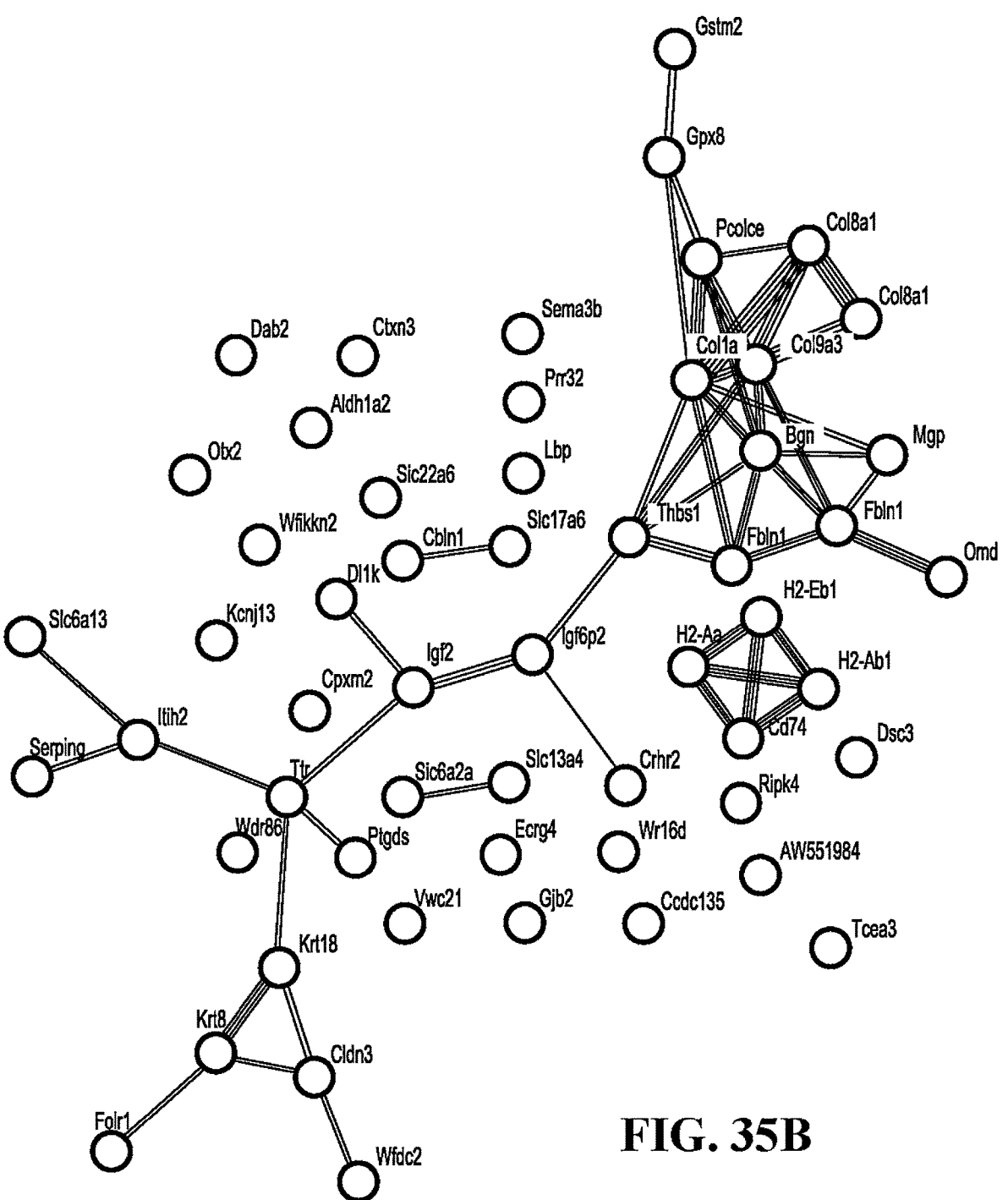
FIG. 35B shows string analysis of hippocampus differentially expressed hippocampus genes after TGFRt15-TGFRs (HCW9218) treatment at day 120.

The long-term impacts of TGFRt15-TGFRs and TGFRt15*-TGFRs treatment was further evaluated using RNA-seq analysis on hippocampus of aged mice isolated at 120 days after TGFRt15-TGFRs, TGFRt15*-TGFRs or PBS (control) treatment. RNA-seq analysis identified that the expression of 58 genes were significantly upregulated and none were significantly downregulated in TGFRt15-TGFRs-treated hippocampus compared to PBS control (Table 2 and FIG. 35A). There was also no significant difference in expression of genes between TGFRt15*-TGFRs and PBS treatment. When mapped via STRING (FIG. 35B), many of the genes with increased expression were connected and identified as having known interactions. The most highly increased gene transcript, Ttr (transthyretin), is known to inhibit amyloid-β (Aβ) which is a primary pathological protein associated with Alzheimer's Disease (AD). Genes associated with improved memory via preservation of hippocampal function (i.e., Kcnj13, Otx2, Folr1, Lbp, Slc13a4, Col8a1, Igf2), extracellular matrix (ECM) genes associated with learning and memory maintenance and/or improvement (i.e., Pcolce, Col1a2, Col8a1, Col8a2, Col9a3, Col1a2, Bgn, Mgp, Fmod, Thbs1, and Fbln1), and transporter genes (Slc6a13, Slc6a20a, Slc13a4, Sic17a6) were also increased with TGFRt15-TGFRs treatment. Collectively, the results indicate that TGFRt15-TGFRs, but not TGFRt15*-TGFRs, treatment has a broad and long-term indirect effect on expression of genes which are associated with overall health of the aged brain and hippocampus, with specific implications on memory, learning, and neurogenesis

TABLE 2

Table for differentially expressed Senescence, Inflammation and Circadian Rhythm associated genes associated genes in hippocampus after treatment with TGFRt15-TGFRs compared to control treatment.

| Gene.name | log2FoldChange | pvalue | padj | HCW92181 | HCW92182 |
|---|---|---|---|---|---|
| Tcea3 | 2.117802573 | 0.000126148 | 0.037293188 | 30.99895003 | 33.8342098 |
| Folr1 | 4.142743906 | 3.95E−09 | 7.96E−06 | 72.33088341 | 439.8447273 |
| Crhr2 | 1.487724754 | 3.91E−05 | 0.018186447 | 123.056438 | 254.269213 |
| Ripk4 | 1.605 787002 | 8.06E−05 | 0.028678142 | 42.2712955 | 50.23867515 |
| Fbln1 | 1.01161194 | 2.86E−10 | 8.65E−07 | 503.4980975 | 535.1956822 |
| Aldh1a2 | 1.911866095 | 2.01E−06 | 0.001821576 | 305.2926897 | 147.6401882 |
| Ptgds | 1.921373829 | 8.04E−06 | 0.00502576 | 31082.55326 | 9910.34 7633 |
| Lbp | 2.494640682 | 1.50E−06 | 0.001594808 | 146.5204911 | 711.5436848 |

TABLE 2-continued

Table for differentially expressed Senescence, Inflammation and Circadian Rhythm associated genes
associated genes in hippocampus after treatment with TGFRt15-TGFRs compared to control treatment.

| | | | | | |
|---|---|---|---|---|---|
| Wfdc2 | 3.389069785 | 4.09E−06 | 0.003087041 | 35.69576064 | 143.5390719 |
| Cfap52 | 1.940310769 | 0.000122939 | 0.037293188 | 66.69471067 | 123.0334902 |
| Gpx8 | 1.91279427 | 2.32E−05 | 0.012008616 | 71.39152128 | 207.1063751 |
| Otx2 | 3.756124879 | 7.59E−09 | 1.38E−05 | 72.33088341 | 520.841775 |
| Dab2 | 1.085939409 | 3.71E−06 | 0.002921345 | 257.3852215 | 411.136913 |
| Krt18 | 2.740044794 | 9.13E−05 | 0.030703035 | 46.96810611 | 218.384445 |
| Serping1 | 1.546970329 | 9.68E−05 | 0.031909635 | 317.5043973 | 193.777747 |
| Cd74 | 1.301790929 | 1.64E−06 | 0.001634952 | 198.2054078 | 195.8283052 |
| Slc22a6 | 1.79964986 | 6.61E−05 | 0.027884949 | 295.8990685 | 132.2610019 |
| 1500015O10Rik | 3.655552997 | 6.84E−10 | 1.55E−06 | 275.2331018 | 1242.638251 |
| Col9a3 | 1.952586216 | 1.06E−05 | 0.006223193 | 740.2173523 | 2946.652089 |
| Col1a2 | 1.443098253 | 6.87E−05 | 0.027985008 | 557.0417384 | 304.5078882 |
| Pcolce | 1.962310337 | 1.04E−10 | 5.60E−07 | 383.2597458 | 597.7377064 |
| Slc13a4 | 2.69817878 | 1.24E−07 | 5.60E−07 | 520.4066157 | 881.7400129 |
| Slc6a13 | 1.492872764 | 8.04E−05 | 0.028678142 | 386.0778322 | 147.6401882 |
| Mgp | 1.187109753 | 6.61E−05 | 0.027884949 | 913.0599827 | 412.1621921 |
| Slc17a6 | 1.77664616 | 9.98E−05 | 0.03231487 | 1099.053683 | 332.1904234 |
| Cpxm2 | 1.524887845 | 6.42E−05 | 0.027884949 | 150.2979395 | 242.9911431 |
| Bgn | 1.220294091 | 1.89E−11 | 1.72E−07 | 671.6439173 | 544.423194 |
| Cbln1 | 1.336480501 | 0.000128816 | 0.037293188 | 611.5247415 | 634.6477534 |
| Drc7 | 2.411311342 | 8.78E−05 | 0.030608427 | 106.1479198 | 726.9228711 |
| H2-Aa | 2.212473285 | 7.42E−08 | 0.000112165 | 73.27024553 | 82.02232678 |
| Slc6a20a | 1.691045824 | 1.99E−10 | 7.21E−07 | 590.8587748 | 433.6930528 |
| Prr32 | 3.591416208 | 9.90E−07 | 0.001163433 | 40.39257125 | 206.081096 |
| Itih2 | 1.954065756 | 7.37E−05 | 0.028678142 | 142.7830426 | 47.1628379 |
| AW551984 | 1.275287492 | 6.95E−05 | 0.027985008 | 205.7203047 | 212.2327705 |
| Igfbp2 | 1.26270498 | 0.000129576 | 0.037293188 | 1749.092271 | 3451.089399 |
| Thbs1 | 1.548992377 | 1.00E−07 | 0.000139947 | 84.54259099 | 96.37623396 |
| Gstm2 | 1.521550772 | 1.03E−08 | 1.70E−05 | 108.026644 | 100.4 773503 |
| Dlk1 | 1.40742654 | 3.07E−05 | 0.015034132 | 789.0641826 | 813.0463142 |
| Fmod | 1.991868085 | 1.97E−05 | 0.011184503 | 621.8577249 | 201.9799797 |
| Wfikkn2 | 2.495017245 | 6.46E−12 | 1.17E−07 | 131.5106971 | 170.1963281 |
| Vwc2l | 1.682900344 | 6.94E−06 | 0.00449164 | 406.7437989 | 241.965864 |
| Gjb2 | 1.349242446 | 0.000140133 | 0.039701366 | 247.9916002 | 136.3621183 |
| Omd | 3.399659129 | 0.000161715 | 0.045111047 | 37.57448489 | 8.202232678 |
| Igf2 | 2.082853419 | 3.78E−10 | 9.79E−07 | 2980.596014 | 6169.104253 |
| Krt8 | 2.806083905 | 9.14E−05 | 0.030703035 | 28.18086366 | 157.892979 |
| Wdr86 | 3.708698825 | 1.71E−06 | 0.001634952 | 79.84578038 | 579.2826829 |
| Col8a2 | 2.768012512 | 9.56E−07 | 0.001163433 | 139.9649562 | 687.9622658 |
| Sema3b | 2.07313979 | 1.03E−06 | 0.001163433 | 218.8713745 | 636.6983116 |
| Dsc3 | 2.249539984 | 2.06E−05 | 0.011330663 | 93.93621221 | 137.3873974 |
| H2-Eb1 | 1.45479799 | 2.67E−05 | 0.013428098 | 93.93621221 | 98.42679213 |
| Ttr | 5.561855342 | 2.23E−06 | 0.001925183 | 28550.03298 | 137693.9558 |
| Col8a1 | 3.379125962 | 3.2SE−05 | 0.015498322 | 92.05 748797 | 614.1421717 |
| Ctxn3 | 2.582699856 | 0.000175023 | 0.04666928 | 110.844 7304 | 46.13755881 |
| Cldn3 | 1.975405524 | 0.000111764 | 0.03555271 | 26.30213942 | 42.03644247 |
| H2-T-ps | 3.28733405 | 0.000124611 | 0.037293188 | 15.02979395 | 68.69369868 |
| H2-Ab1 | 1.531800651 | 7.57E−05 | 0.028678142 | 84.54259099 | 101.5026294 |
| Kcnj13 | 4.904349065 | 6.65E−06 | 0.004464225 | 113.6628168 | 768.9593135 |
| Gm17120 | 2.031545333 | 0.000174484 | 0.04666928 | 26.30213942 | 31.78365163 |

| Gene.name | HCW92183 | PBS1 | PBS2 | PBS3 |
|---|---|---|---|---|
| Tcea3 | 30.1794686 | 8.600057354 | 9.445304027 | 3.539884614 |
| Folr1 | 103.4725607 | 8.600057354 | 16.7916516 | 9.439638972 |
| Crhr2 | 268.1663864 | 92.68950704 | 74.51295399 | 62.53760819 |
| Ripk4 | 56.04763703 | 12.42230507 | 17.84112983 | 18.87927794 |
| Fbln1 | 544.9554862 | 268.5129018 | 291.7549466 | 224.1914256 |
| Aldh1a2 | 442.3451969 | 68.80045883 | 78.7108669 | 90.8565251 |
| Ptgds | 37508.80324 | 6589.555057 | 5107.810522 | 9027.834722 |
| Lbp | 371.63894 71 | 72.62270655 | 93.40356205 | 51.91801435 |
| Wfdc2 | 32.76631088 | 5.73337157 | 6.296869352 | 8.2596841 |
| Cfap52 | 108.6461887 | 25.80017206 | 40.92965079 | 10.61959384 |
| Gpx8 | 112.9575454 | 40.13360099 | 29.38539031 | 34.21869127 |
| Otx2 | 215.5678347 | 27.71129592 | 18.89060805 | 12.97950359 |
| Dab2 | 305.244054 | 150.0232227 | 146.9269515 | 161.6538174 |
| Krt18 | 41.38902427 | 19.11123857 | 13.64321693 | 12.97950359 |
| Serping1 | 459.5906236 | 155.7565943 | 102.8488661 | 73.15720203 |
| Cd74 | 306.1063253 | 83.04501161 | 92.35408382 | 107.3758933 |
| Slc22a6 | 319.9026667 | 57.3337157 | 46.17704191 | 112.0957128 |
| 1500015O10Rik | 255.2323163 | 62.11152534 | 44.07808546 | 34.21809127 |
| Col9a3 | 1151.132237 | 465.3586591 | 392.5048563 | 391.7450173 |
| Col1a2 | 653.6016749 | 174.8678329 | 125.937387 | 257.230162 |
| Pcolce | 338.0103649 | 108.9340598 | 87.1066927 | 142.7745395 |
| Slc13a4 | 542.3686722 | 60.20040148 | 69.26556287 | 171.0934564 |
| Slc6a13 | 375.9503038 | 107.022936 | 99.7004314 | 116.8155323 |
| Mgp | 793.2896318 | 310.5576267 | 307.49712 | 312.6880409 |

TABLE 2-continued

Table for differentially expressed Senescence, Inflammation and Circadian Rhythm associated genes
associated genes in hippocampus after treatment with TGFRt15-TGFRs compared to control treatment.

| | | | | |
|---|---|---|---|---|
| Slc17a6 | 625.1467207 | 254.1794729 | 111.2446919 | 234.8110194 |
| Cpxm2 | 100.8857467 | 48.73365834 | 65.06764997 | 57.8177887 |
| Bgn | 628.5958061 | 307.6909409 | 230.885 2096 | 252.5103425 |
| Cbln1 | 344.9085356 | 150.9787847 | 174.2133854 | 305.6083117 |
| Drc7 | 246.6096029 | 68.80045883 | 90.25512737 | 43.65833025 |
| H2-Aa | 121.5802588 | 16.24455278 | 15.74217338 | 28.31891692 |
| Slc6a20a | 757.0742356 | 193.0235095 | 146.9269515 | 212.3918769 |
| Prr32 | 48.28719498 | 5.73337157 | 10.49478225 | 8.2595841 |
| Itih2 | 135.3766002 | 25.80017206 | 23.0885 2096 | 35.39864614 |
| AW551984 | 135.3766002 | 58.28927762 | 101.7993879 | 68.43738255 |
| Igfbp2 | 1391.705941 | 867.6502309 | 1038.983443 | 840.1278685 |
| Thbs1 | 96.57438996 | 29.62241978 | 35.68225966 | 29.49887179 |
| Gstm2 | 112.0952741 | 38.22247713 | 34.63278143 | 38.93851076 |
| Dlk1 | 871.7563236 | 154.8010324 | 398.8017256 | 379.9454686 |
| Fmod | 669.9848303 | 105.1118121 | 88.15617092 | 182.8930051 |
| Wfikkn2 | 100.0234753 | 21.97792435 | 18.89060805 | 30.67882666 |
| Vwc2l | 162.9692831 | 81.2227639 | 70.31504109 | 101.4 761189 |
| Gjb2 | 324.2140234 | 85.04501161 | 83.95825802 | 109.735803 |
| Omd | 55.18536569 | 2.866685785 | 2.098956451 | 4.719819486 |
| Igf2 | 2582.50266 | 932.628442 | 772.4159738 | 1064.319294 |
| Krt8 | 46.5626523 | 13.377867 | 12.5937387 | 7.079729229 |
| Wdr86 | 61.22126506 | 17.200114 71 | 17.84112983 | 20.05923282 |
| Col8a2 | 225.0528195 | 38.22247713 | 70.31504109 | 46.01823999 |
| Sema3b | 249.1964169 | 85.04501161 | 81.85930157 | 95.57634459 |
| Dsc3 | 44.83810962 | 24.84461013 | 20.98956451 | 11.79954871 |
| H2-Eb1 | 170.7297251 | 44.91141063 | 44.07808546 | 43.65833025 |
| Ttr | 8006.189382 | 2274.237389 | 581.4109368 | 833.0481393 |
| Col8a1 | 51.73628033 | 23.88904821 | 13.64321693 | 35.39864614 |
| Ctxn3 | 346.6330782 | 35.35579135 | 15.74217338 | 33.0387364 |
| Cldn3 | 51.73628033 | 10.51118121 | 9.445304027 | 10.61959384 |
| H2-T-ps | 19.83224079 | 2.866685785 | 4.197912901 | 3.539864614 |
| H2-Ab1 | 185.3883379 | 40.13360099 | 47.22652014 | 41.2984205 |
| Kcnj13 | 75.87987782 | 11.46674314 | 5.247391126 | 15.33941333 |
| Gm17120 | 31.90403954 | 9.555619283 | 5.247391126 | 7.079729229 |

Studies were also conducted to examine whether TGFRt15-TGFRs passes through the blood brain barrier (BBB) to directly modulate the resident immune cells in the CNS for its anti-neuroinflammation activities. Seven-, 73-, or 105-week-old C57BL/J mice (n=3/group) received subcutaneous injections of either PBS (control group) or TGFRt15-TGFRs (3 mg/kg) (treatment group). Mice were euthanized the following day and brain cryosections were processed for immunohistochemical staining with a human-specific anti-tissue factor (TF) antibody HCW9101 (FIG. 36A-36C); human TF is a component of the TGFRt15-TGFRs fusion protein complex. No detectable TGFRt15-TGFRs was found in brain sections of 7-, 73-, or 105-week-old mice treated with either TGFRt15-TGFRs or PBS. As a positive control, anti-TF antibody could positively stain human brain tissues (FIG. 36D). These results indicate that TGFRt15-TGFRs does not pass through the BBB, including that of aging brains, even though BBB integrity of aged mice is expected to be compromised. Based on these findings, it is not believed that TGFRt15-TGFRs acts directly on the resident immune cells in the CNS. Rather, it functions primarily as a peripheral immune-senolytic and immune-senomorphic agent that, when administered subcutaneously, also affects the CNS via an indirect mechanism.

Example 14: TGFRt15-TGFRs and
TGFRt15*-TGFRs Support Maintenance of
Physical Performance in Naturally Aged Mice C57BL/6, 76-week-old mice were purchased from the Jackson Laboratory. Mice were housed in a controlled temperature and controlled light environment. Mice were divided into three groups as follows: Saline control group (n=5), TGFRt15-TGFRs group (n=5) and TGFRt15*-TGFRs group (n=6). Mice were treated subcutaneously with PBS, TGFRt15-TGFRs (3 mg/kg) and TGFRt15*-TGFRs (3 mg/kg). The aged C57Bl/6 mice were housed in the behavior room on a reversed 12 h light/dark cycle (7 AM-7 PM) for behavior experiments. Mice were moved to the behavior room 10 days prior to beginning of behavioral experiments to acclimate to the change in light cycle and were handled for at least 5-10 minutes daily to help reduce the stress of handling during behavioral experiments. The behavior room was maintained at a temperature of between 20° C.-23.8° C., and consistent white noise was used in the behavior room to reduce stress and maintain a constant ambient environment. Mice were given ad libitum access to food and water, and all behavioral experiments were performed between the hours of 9 AM and 5 PM. Unless otherwise stated, all tests were run in red light at approximately 3-4 lux.

Grip Strength

Using the Ugo Basile Grip Strength Meter (Stoelting, Item: 57107) with the grid for combined front and hind limb grip strength, objective neuromuscular performance was measured in terms of peak force generated (gf) and amount of time to hold the peak force (peak force time(s)). Mice were measured for five (5) repetitions each timepoint to determine an average for each mouse, and the average for each mouse was used as the score for that trial. Calculations were completed via GraphPad Prism 9.3.1.

Rotarod

The Ugo Basile Mouse Rota-Rod (Stoelting, Item: 57624) apparatus was used to measure motor performance, coordination, and learning. Prior to running tests, mice were placed on the device and allowed to acclimate and explore by walking at 5 RPM for 5 minutes. On testing days, mice were placed on the rotarod at 5 RPM. Once all mice were placed in their lanes (total of 5 mice per group), the test was started. Speed was increased from 5 RPM to 50 RPM over 300 seconds (5 minutes). Time and speed for each mouse was collected when either a mouse dropped from the rod or made one full rotation gripping the rod. Once the test ended for all mice running together, mice were removed, placed back in home cage, and the apparatus was cleaned with 70% EtOH. The test was then repeated for the next group, and this process was repeated for a total of three (3) times per group per time point, providing a 10-15-minute break for each group between each run. All times and speeds for all repetitions for each group were combined to determine average latency to fall and speed (RPM) for each timepoint. Calculations were completed via GraphPad Prism 9.3.1.

Open Field

Open field experiments were setup, video was recorded, and behavior scored via Novus EthoVision XT (v15.0.1416). The open field apparatus consisted of a black acrylic box (40 cm×40 cm×30 cm) with a gray base (MazeEngineers, Conduct Science). Tests were run in a combination of indirect red and white (3200K, 10%) light at a total of approximately 16 lux inside the open field apparatus. Mice were placed in the center of the apparatus and allowed to explore freely for ten (10) minutes. Distance travelled and speed were measured. All mice were allowed a single exploration of the open field at each time point. Calculations were completed via GraphPad Prism 9.3.1.

Figures 37A, 37B, 37C:
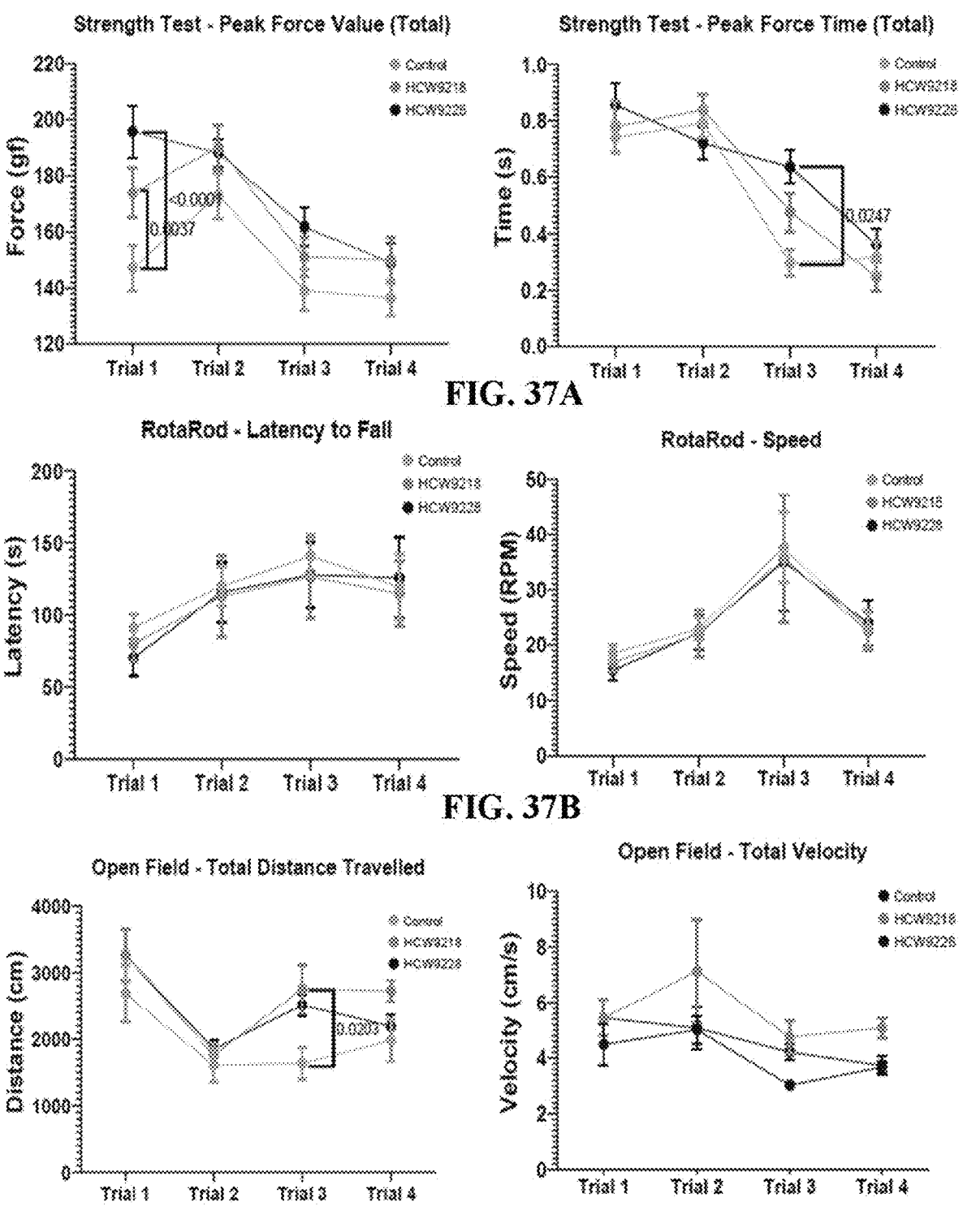
FIGS. 37A-37C show behavioral study indicate minimal acute significant performance maintenance by both TGFRt15-TGFRs (HCW9218) and TGFRt15*-TGFRs (HCW9228) in naturally aged mice.

A battery of behavioral tests, consisting of a grip strength, rotarod, and open field tests were used to evaluate whether TGFRt15-TGFRs and TGFRt15*-TGFRs treatment could support maintenance of physical performance (i.e., strength, coordination, and ambulation) of naturally aged mice. Aged C57BL/6 mice (N=5) were either treated with TGFRt15-TGFRs, TGFRt15*-TGFRs, or PBS (negative control), tests were conducted at four timepoints: 30 days post dose 1 (Trial 1), 3-6 days post dose 2 (Trial 2), 30 days post dose 2 (Trial 3), and 60 days post dose 2 (Trial 4). While results showed a minimal acute effect of application of TGFRt15-TGFRs and TGFRt15*-TGFRs on performance (FIG. 37A-37C), there were significant results in maintenance of performance across time for two of the three tests. Grip strength (FIG. 31A) indicated a significant treatment effect with both TGFRt15-TGFRs (p=0.0037) and TGFRt15*-TGFRs (p<0.0001) treatment maintaining grip strength (peak force) over time compared to PBS treatment. There was also a significant maintenance in the amount of time that mice treated with TGFRt15*-TGFRs were able to maintain the peak grip level versus PBS controls (p=0.0358). The rotarod test, which focused on motor learning and coordination (FIG. 31B), showed no significant differences in the ability to remain on the rotating rod ($F_{(2, 48)}$=02391, p=0.7882) or the maximum rotation speed attained ($F_{(2, 48)}$=0.08336, p=0.2394) among the treatment groups. Although these results indicated no change to coordination or motor learning capability, all groups improved in performance over time, indicating motor learning capability was the same across groups. In the open field test (FIG. 31C), which allowed the mice to freely explore their environment while measuring ambulation, TGFRt15-TGFRs treatment had a significant maintenance of distance travelled (p=0.0064), while TGFRt15*-TGFRs treatment had a nearly significant result (p=0.0566) compared to PBS treatment. Likewise, there was a significant treatment main effect on speed (total velocity) over PBS control; TGFRt15-TGFRs, but not TGFRt15*-TGFRs, treatment was identified as having a significant difference in speed (p=0.0111). Collectively, the results suggested that both TGFRt15-TGFRs and TGFRt15*-TGFRs treatments provided a better overall support in neuromuscular and motor performance compared to PBS over a long period of time in naturally aged mice.

Figures 31A, 31B, 31D, 32C:
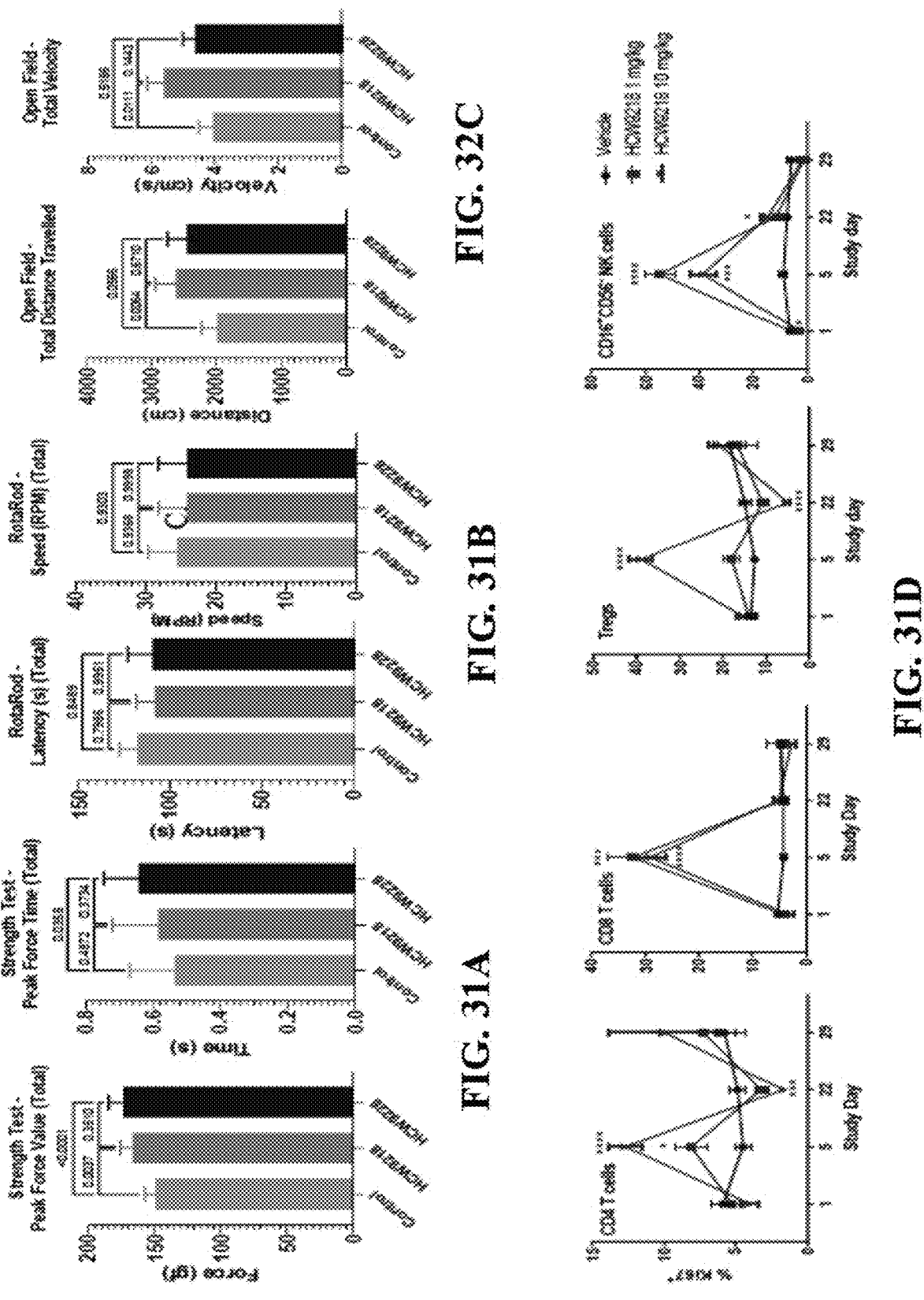
Figures 31E, 31F, 31G, 31H, 31I:
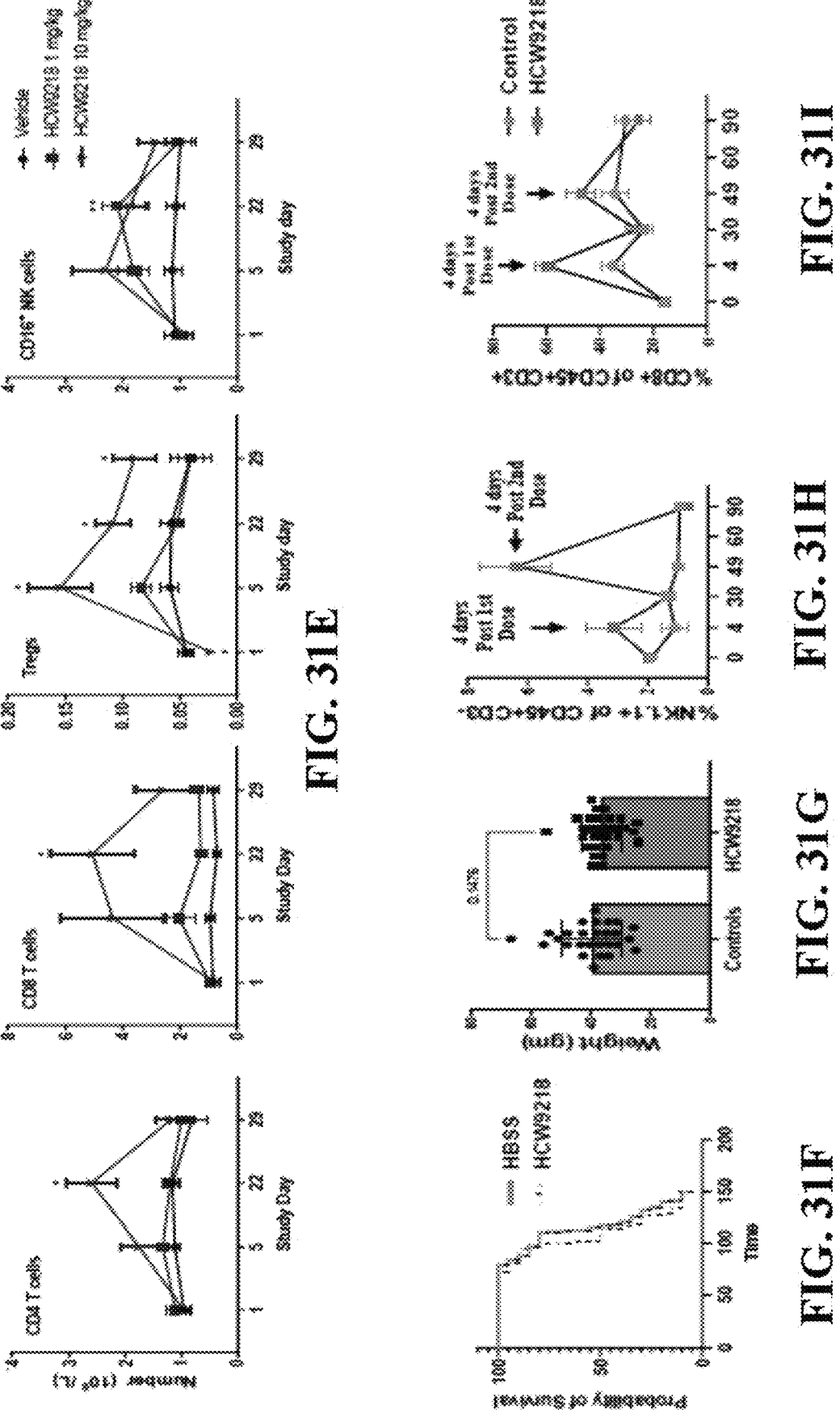
Figure 32A:
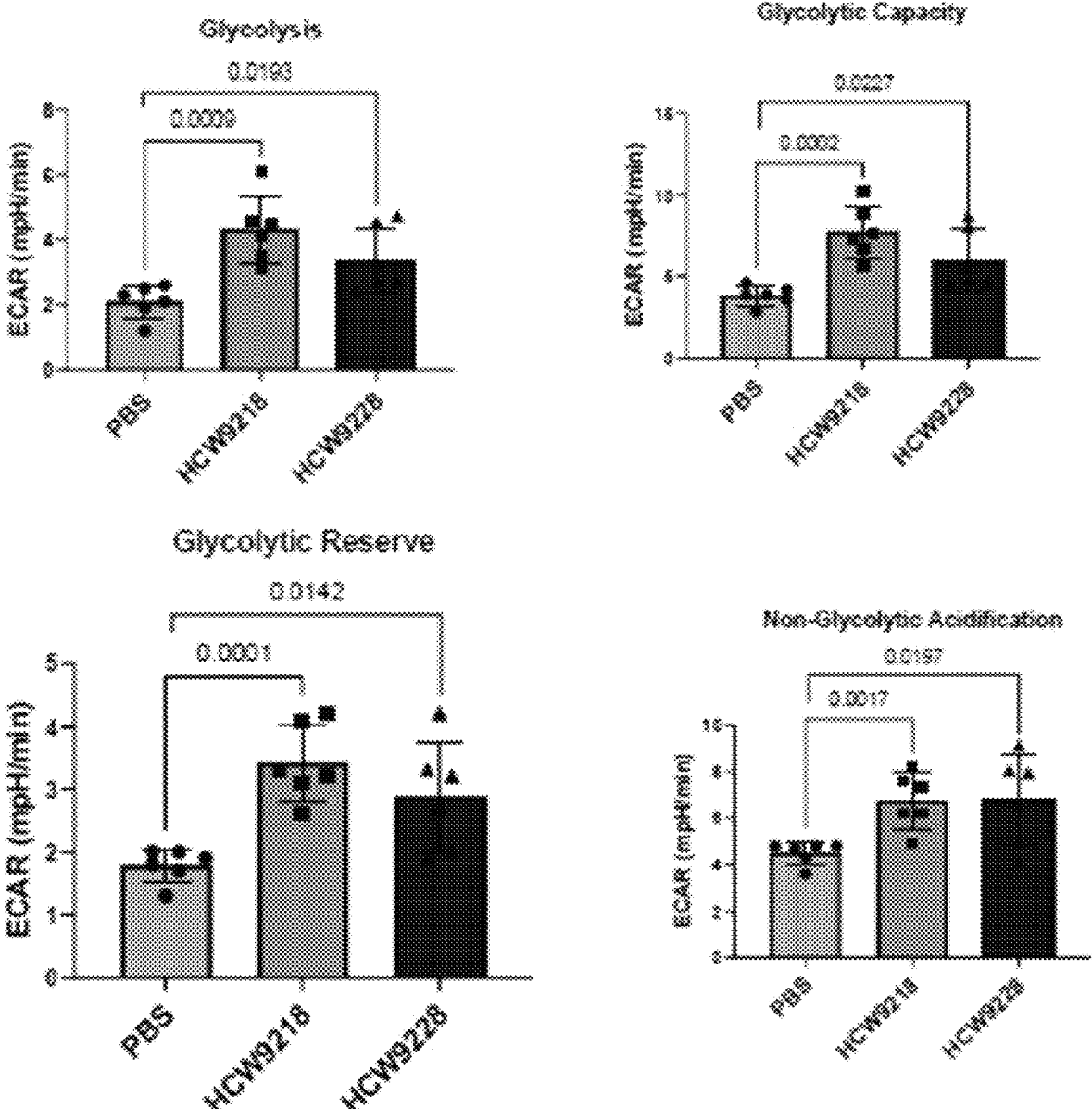
FIGS. 32A-32D show metabolic activities of splenocytes Day 2 and Day 4 in naturally aged mice.
Figure 32B:
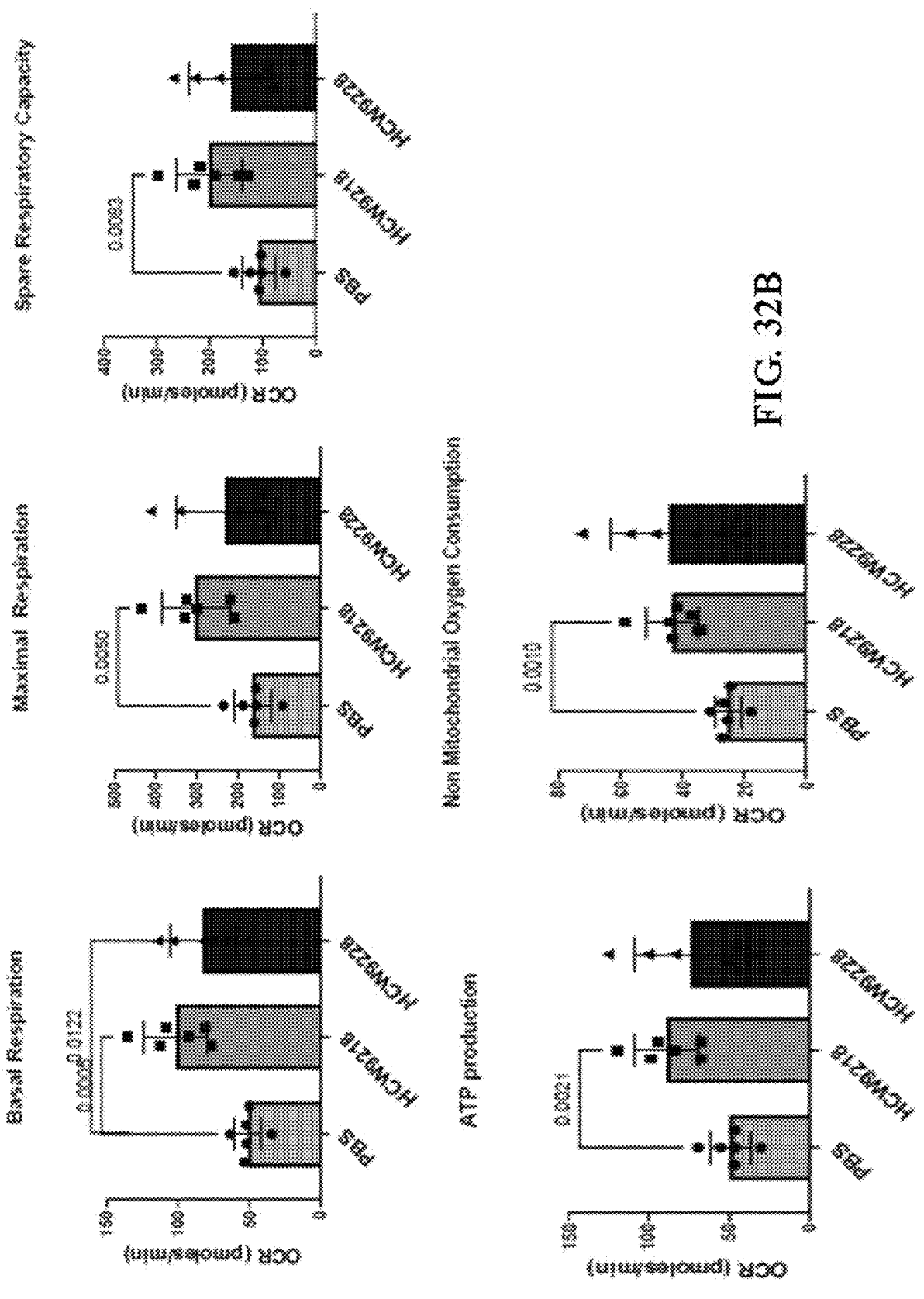
Figures 32C, 32D:
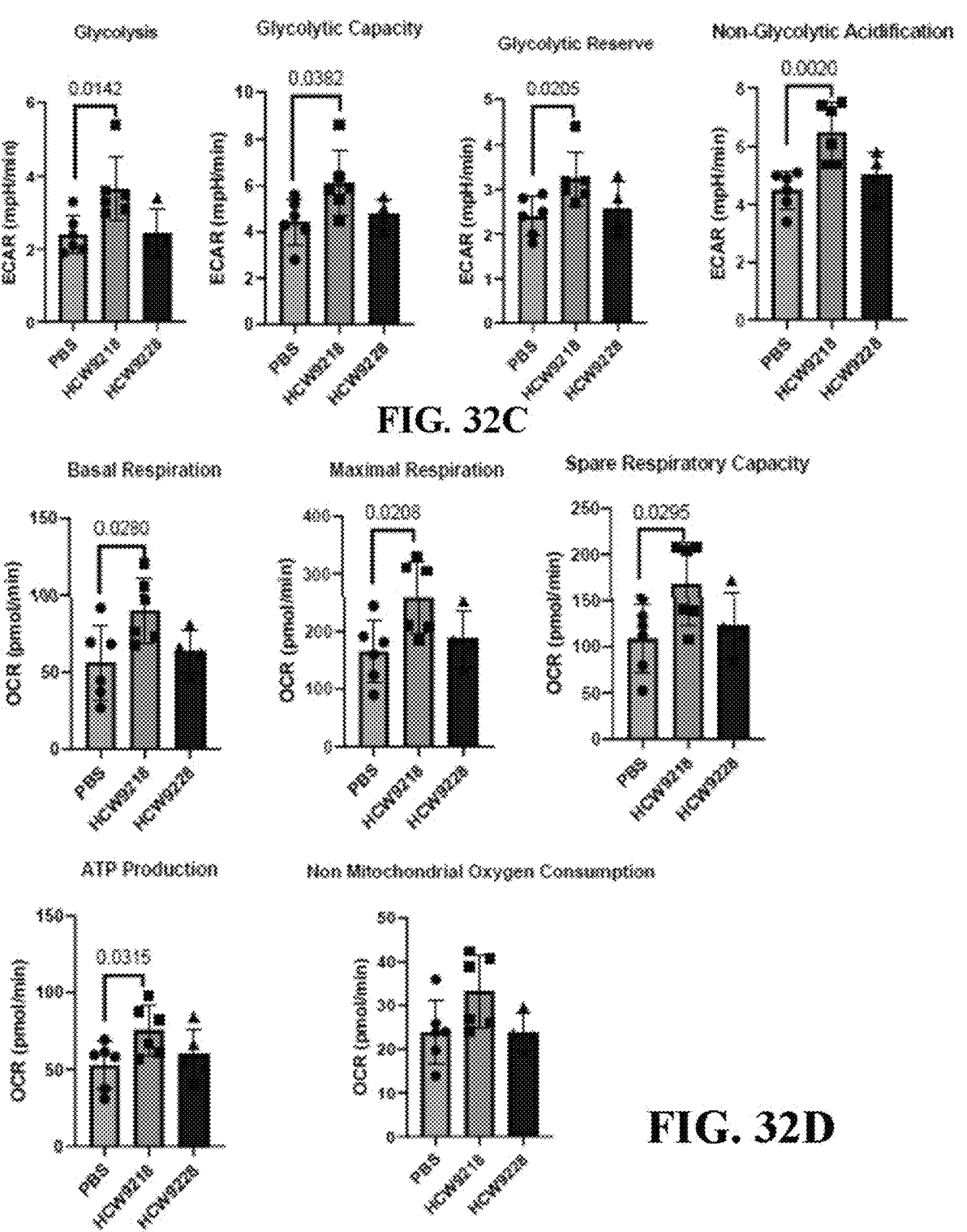

Example 15: Safety and Tolerability of TGFRt15-TGFRs in Mice and Non-Human Primates Considering the diverse physiological roles of SNCs in tissue homeostasis, the potential adverse effects of their removal must be considered. Thus, short-term and long-term toxicity studies of TGFRt15-TGFRs treatment were conducted in mice and non-human primates. Administration of TGFRt15-TGFRs at 5 to 100 mg/kg in two doses on days 1 and 15 was well tolerated in a GLP toxicity study in C57BL/6 mice with no observed mortality and no test article related changes in clinical signs or clinical pathology. In a GLP toxicology study in cynomolgus monkeys, s.c. administration of TGFRt15-TGFRs at 1 to 10 mg/kg in two doses on days 1 and 15 was also well tolerated. There was no test article related changes in clinical signs, body weight, ophthalmology, ECG, blood pressure, or gross pathology. Dose-dependent increases of MCP-1 and decreases of TGFβ1 and TGFβ2 in the serum were observed. Immunophenotyping indicated that TGFRt15-TGFRs induced dose-dependent increases in the percentage of Ki67$^+$ cells and absolute cell numbers of CD4$^+$, CD8$^+$, Treg and CD16$^+$ NK cells (FIGS. 31D and 31E). There was no observed adverse effect of multidose s.c. TGFRt15-TGFRs administration in cynomolgus monkeys even at a dose level as high as 10 mg/kg.

Pharmacokinetic analysis showed a half-life of 12 to 21 hours for 1 to 10 mg/kg s.c. TGFRt15-TGFRs in cynomolgus monkeys. The results also confirm that exposures to TGFRt15-TGFRs increased serum levels in a dose-dependent manner with no apparent accumulation of TGFRt15-TGFRs following repeated dosing at 14-day intervals. While the serum Cmax levels were low, the findings were consistent with the results reported in nonclinical and clinical studies of other IL-15 therapies where the Cmax observed for s.c. administration was ~200-fold less than that for the i.v. route, suggesting s.c. bioavailability (based on $AUC_{0-t}$) of ~3%. Thus, s.c. administration was found to be advantageous in reducing IL-15-related constitutional adverse events while maintaining immunostimulatory activity.

The activity and tolerability of TGFRt15-TGFRs was also assessed in naturally aged C57BL/6 mice. Mice (76-week-old) treated s.c. with 3 mg/kg TGFRt15-TGFRs (N=20) or PBS (control; N=20) were observed weekly for changes body weight and overall survival (FIGS. 31G and 31F). In subsequent studies, 90-week-old mice were treated with two s.c. 3 mg/kg doses of TGFRt15-TGFRs 45 days apart. Blood was drawn at various time points to assess immune cell subset frequencies. As expected, TGFRt15-TGFRs treatment mediated significant increases in the percentage of CD8$^+$ T cells and NK cells in the blood which returned to baseline 4 weeks post treatment (FIG. 31H-31I).

Overall, TGFRt15-TGFRs treatment was well tolerated by mice and non-human primates at dose levels significantly higher than the therapeutic level (3 mg/kg) that were employed in this study. There was also no long-term overt adverse effect of TGFRt15-TGFRs treatment observed on the health span of naturally aged mice.

Example 16. Study of TGFRt15-TGFRs
(HCW9218) in Chemically-Induced Parkinson's
Disease Mouse Model Animals Twenty male C57Bl/6J mice from Jackson Laboratory (Stock No. 000664) at 24-weeks-old were purchased for this experiment. Once received, mice were randomly assigned to one of two experimental groups: Untreated (PQ/HBSS) (n=10) or Treated (PQ/HCW9218) (n=10). All mice were kept in the behavior room under temperature control between 20° C. and 22.2° C., on a reverse light/dark cycle of 12 hours of dark during the day, 12 hours of light at night. A white noise machine was used to create a consistent ambient environment. Mice had ad libitum access to food and water. All experiments were run between 9 AM and 5 PM each time, and only one test per day.

Experimental Design

To study the effect of TGFRt15-TGFRs (HCW9218) on the treatment of pre-clinical or prodromal Parkinson's Disease, a chemically induced model was selected using the herbicide paraquat via intranasal application in a thermo-sensitive hydrogel as previously described (Chen et al., *Neurol. Res.* 43(4):267-277, 2021). Briefly, a thermosensitive hydrogel composed of poloxamer 407 and poloxamer 188 were combined in water with paraquat dichloride hydrate (Sigma-Aldrich No. 36541) (PQ). The resulting PQ gel was used at 7.5 mg/kg of PQ per dose, equating to approximately 5 μL of hydrogel applied intranasally to each mouse for a total of 5 doses over 14 days. At the end of 14 days, a battery of behavioral tests was run to assess motor skill, consisting of Rotarod, Open Field, and Pole Test. The same tests were run every 30 days thereafter. Mice receiving the treatment of TGFRt15-TGFRs (HCW9218) were given two doses 30 days apart at 3 mg/kg subcutaneously, while the untreated mice received two doses of HBSS subcutaneously at the same volume as if it were TGFRt15-TGFRs. Behavior tests were continued until behavioral changes were observed between the two groups at 150 days post dose two of treatment. At 60 days post dose 2, half of each group were sacrificed, with half of each brain processed for lysate and half drop-fixed and processed for pathology. At 180 Days post dose 2, the remaining mice were sacrificed and prepared the same as before. A total of seven timepoints for behavior were collected: Pre-treatment, 30 Days Post Dose 1, 30 Days Post Dose 2, 60 Days Post Dose 2, 90 Days Post Dose 2, 120 Days Post Dose 2, and 150 Days Post Dose 2.

Behavior

Rotarod. The rotarod test was conducted using the Ugo Basile Mouse Rotarod apparatus (Stoelting, Item: 57624). Training on the apparatus consisted of allowing the mice five minutes to walk on the apparatus at 10 rpm, with no change in speed. Mice were replaced on the rod each time they fell during the five-minute training round. After a single training/acclimation round, mice were allowed to rest for 30 minutes. For testing purposes, mice were placed on the rotarod apparatus at 10 RPM and allowed a total of 300 seconds to walk on the apparatus as the speed increased from 10 RPM to 40 RPM; mice completed three rounds of measure at each timepoint with no less than 20 minutes of rest between rounds. The apparatus was cleaned between each round with 70% EtOH. All measures were collected at the end of all rounds per timepoint and analyzed using GraphPad Prism 9.5.1.

Open Field. The open field apparatus consisted of a black opaque acrylic box with a gray base, 40 cm×40 cm×30 cm purchased from Maze Engineers, Conduct Science. Noldus EthoVisionXT (v15.0.1416) was used to setup and record the video and behavioral measures. Indirect red light with direct white light (3200k, 10%) at a total of approximately 16 lux inside the apparatus was used consistently. Mice were placed in the middle of the apparatus and allowed to freely explore for ten (10) minutes. All mice were allowed a single round of exploration at each timepoint. All data was collected and analyzed using GraphPad Prism 9.5.1.

Pole Test. As previously described (Matsuura et al., *J. Neurosci. Methods* 73(1):45-48, 1997), a rough, unfinished wooden dowel of approximately 9.5 mm diameter and approximately 50 cm length was inserted to a heavy base. A piece of square cardboard was tacked to the top to stop mice from climbing up. The base with the pole attached was placed in the home cage and covered with bedding for the duration of testing of all mice. For testing, mice were placed at the top of the pole, face up, just beneath the cardboard. Mice were allowed a total of 120 seconds to turn and descend the pole. The time taken to turn was measured and the total time to descend. If mice were unable to turn or fell from the pole at any time during the test, then the full 120 seconds was assigned as the time for both measures. Mice repeated the test 3 times each in succession before moving to the next mouse. All mice completed this test at each time point. All data was analyzed using GraphPad Prism 9.5.1.

Pathology

All tissue for pathology was processed as Formalin Fixed Paraffin-Embedded (FFPE). At the time of sacrifice, half of the brain was placed in a 15 ml tube with 4% paraformaldehyde (PFA) for at least 24 hours. Tubes were transferred after 24 hours to University of Miami for embedding in paraffin, cutting, and mounting to slides. Brains were sliced coronally at 5 μm.

Immunohistochemical Tissue Staining. All immunohistochemical staining was completed using Proteintech IHCEasy kits. Specific kits used were the IHCeasy IBA1 Ready-To-Use IHC Kit (Proteintech, Cat No. KHC0056) and IHCeasy Alpha Synuclein Ready-To-Use IHC Kit (Proteintech, Cat No. KHC0290). Quantification was completed using FIJI and analysis was completed using GraphPad Prism 9.5.1.

Immunofluorescent Tissue Staining. Immunofluorescence was completed using Proteintech FlexAble antibody labeling kits: FlexAble CoraLite488 Antibody Labeling Kit for Rabbit IgG (Proteintech, Cat No. KFA001), FlexAble CoraLite Plus 555 Antibody Labeling Kit for Rabbit IgG (Proteintech, Cat No. KFA002), and FlexAble CoraLite Plus 647 Antibody Labeling Kit for Rabbit IgG (Proteintech, Cat No. KFA003). Primary antibodies used include α-synuclein (Proteintech, 10842-1-AP) and IBA1 (Proteintech, 10904-1-AP). DAPI counterstain used was by Invitrogen (ThermoFisher Scientific, Catalog Number: D1306). Quantification was completed using FIJI and analysis was completed using GraphPad Prism 9.5.1.

Western Blot

Half brains harvested were placed in 2-mL bead mill tubes with 1.4 mm ceramic beads (ThermoFisher Scientific, Catalog No.: 15-340-153), in RIPA buffer (ThermoFisher Scientific, Catalog No.: 89901) with HALT Protease Inhibitor Cocktail (ThermoFisher Scientific, Catalog No.: 78429) on ice. Brains were homogenized in the bead mill at 4.85 m/s for 20 seconds. All tubes were then immediately centrifuged at 20000×g for 20 minutes at 4° C. After centrifuging, the supernatant was transferred to 1.7 ml tubes. Protein content was measured using Pierce Rapid Gold BCA Protein Assay Kit (ThermoFisher Scientific, Catalog No. A53225). After measurement, 500 μL of all samples were prepared at 2 mg/mL protein concentration for Western Blots using Li-Cor 4× Protein Sample Loading Buffer for Western Blots (Li-Cor, P/N: 928-40004). Samples were run on 8% precast SurePage gels (GenScript, Cat No.: M00656) in Invitrogen NuPage MES buffer (ThermoFisher Scientific, Catalog No.: NP0002) for approximately 22 minutes. Gels were transferred to PVDF membranes (Millipore Immobilon FL PVDF Membrane, Li-Cor, P/N: 926-32099) in Invitrogen NuPage Transfer Buffer (ThermoFisher Scientific, Catalog No. NP0006) for 1 hour at room temperature. After transfer, membranes were rinsed three times for ten minutes each in Li-Cor Intercept TBS Blocking Buffer (Li-Cor, P/N: 927-6001), followed by blocking for one hour of blocking in the same buffer. Primary antibodies were prepared in Li-Cor Intercept T20 (TBS) Antibody Diluent (Li-Cor, P/N: 927-65001) and after blocking were placed on the membranes overnight on a rocker at 4° C. Primary antibodies used include α-synuclein (Abcam, ab155038) and p16 (Abcam, ab51243). The next day, the primary antibodies were removed, and the membranes washed three times for ten minutes each in fresh Li-Cor Intercept T20 (TBS) Antibody Diluent. Li-Cor fluorescent secondary antibodies were prepared in Li-Cor Intercept (TBS) Antibody Diluent and placed on the membranes on a rocker for one hour at room temperature. After one-hour, secondary antibodies were removed and the membranes washed with Li-Cor Intercept T20 (TBS) Antibody Diluent three times for ten minutes each, followed by a final wash in Li-Cor Intercept TBS Buffer to remove the T20. Immediately after the final wash, membranes were imaged using the Li-Cor Odyssey XF imager with ImageStudio. Quantification of images was completed using FIJI and analysis was completed using GraphPad Prism 9.5.1.

Results

Performance Maintained or Improved Over Time in TGFRt15-TGFRs (HCW9218)-Treated Mice.

Figure 38A:
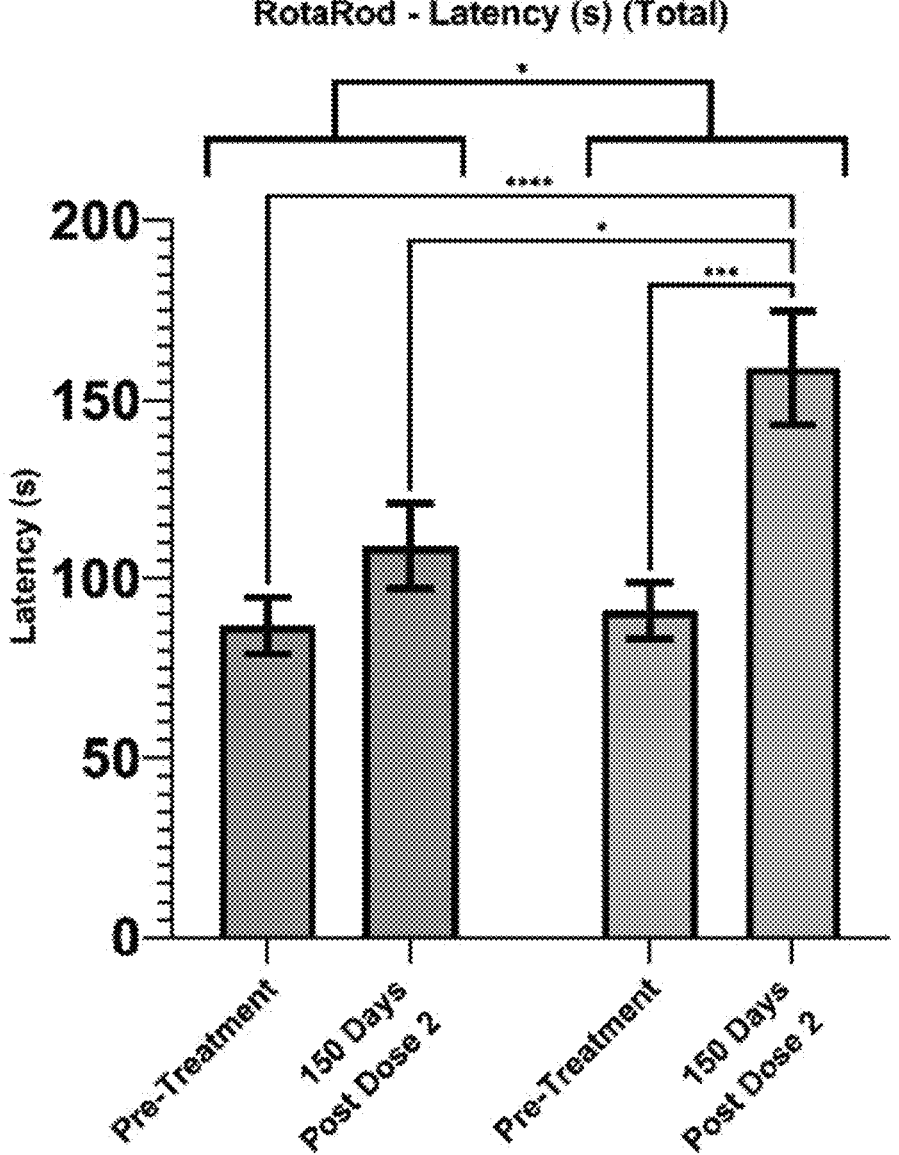
FIG. 38A is a graph showing the latency (s) in a Rotarod test performed in a chemically-induced Parkinson's disease mouse model untreated or treated with TGFRt15-TGFRs (HCW9218) as described in Example 16.

In the rotarod test, mice treated with TGFRt15-TFFRs (HCW9218) showed a significant improvement overall in how long they were able to stay on the apparatus from pre-treatment to 150 days post dose 2 (p<0.0001), while untreated mice at 150 days post dose 2 were not able to stay on the apparatus significantly more (p=0.4346); the difference between treated and untreated mice at 150 days post dose 2 was also significantly different (p=0.0263) (FIG. 38A). Overall, there was also a significant difference between the treated and untreated mice when looking at pre-treatment and 150 days post dose two combined (p=0.0120). There were no significant differences in max speed on rotarod overall (p=0.4124).

Figure 38B:
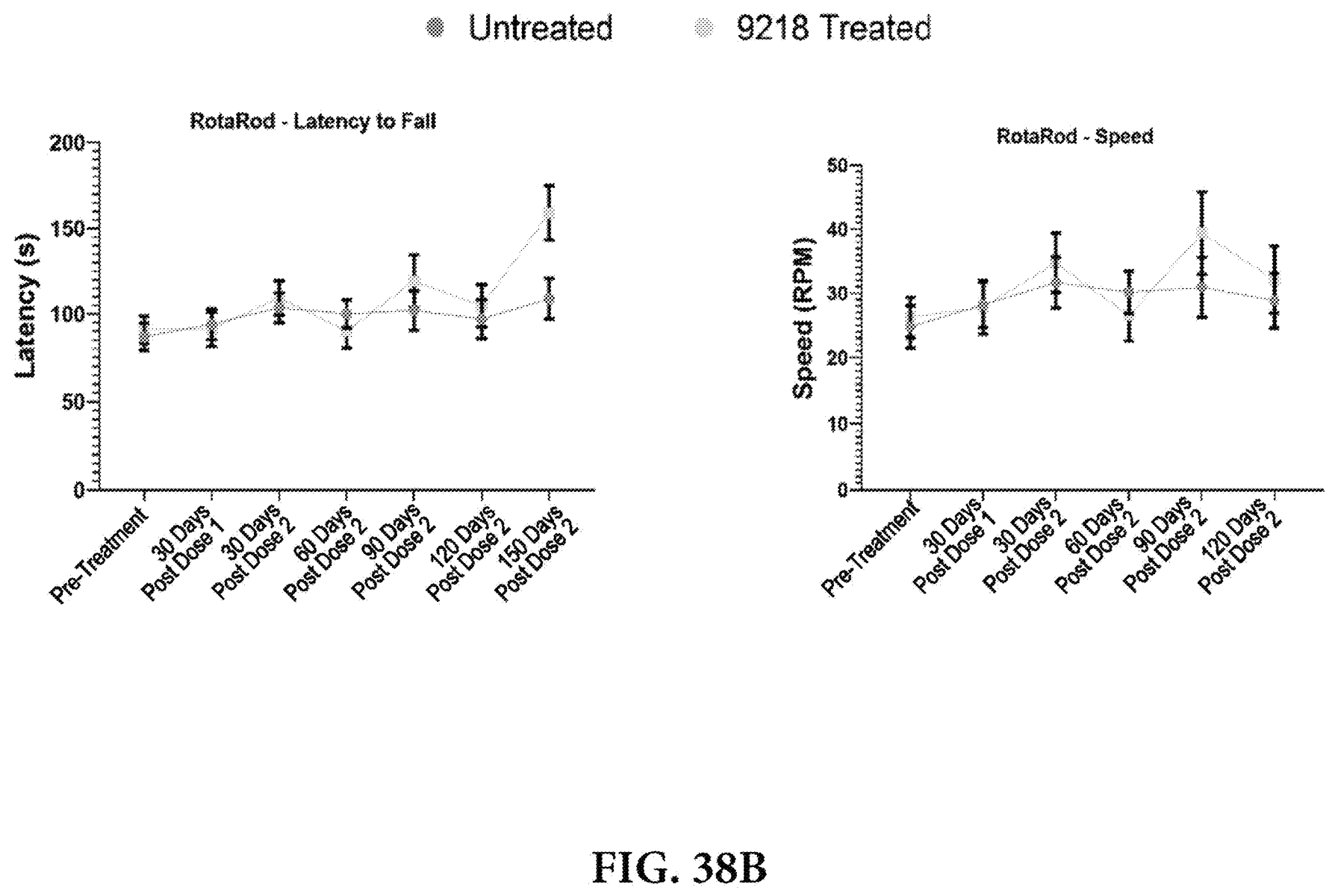
Figure 39:
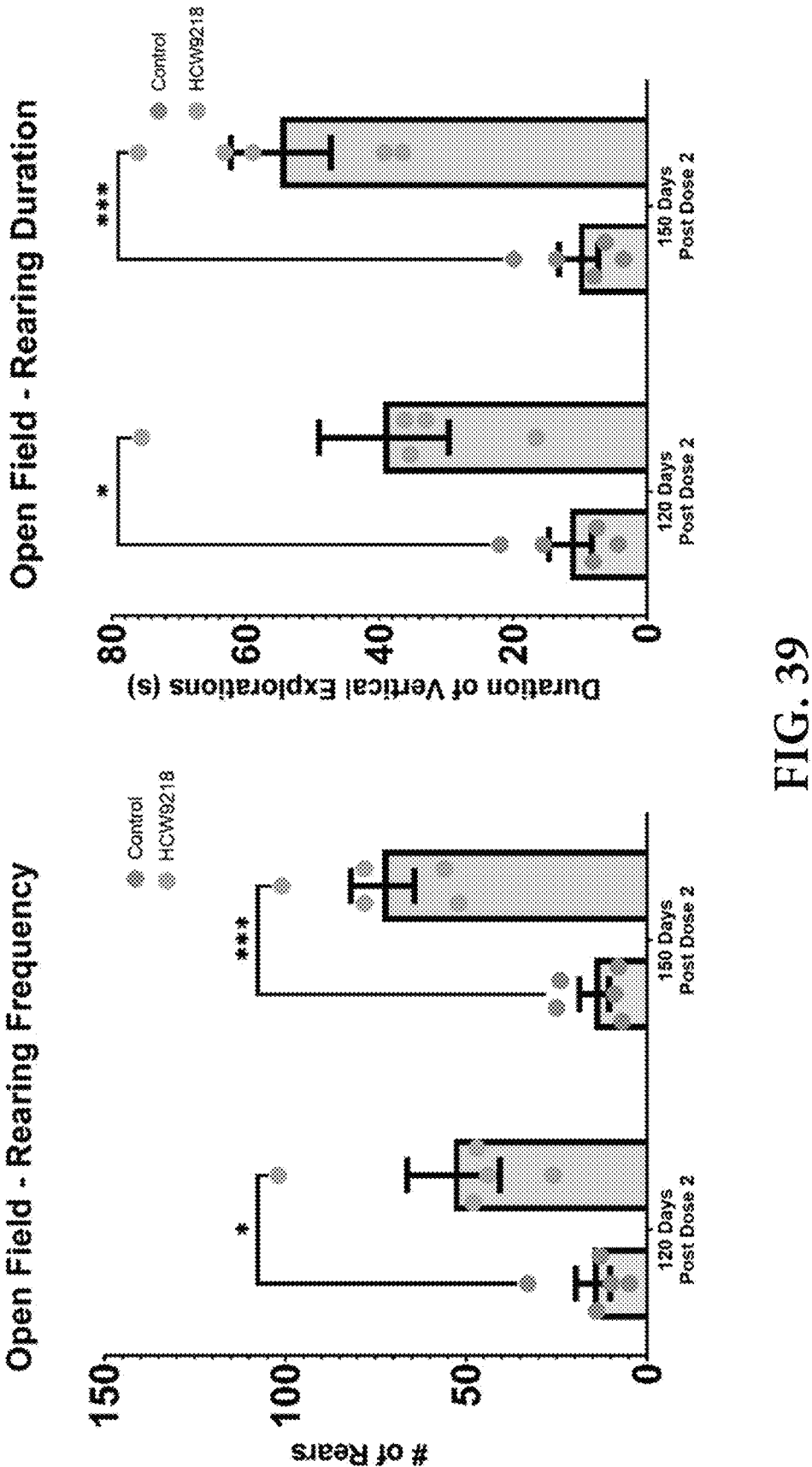
FIG. 39 is a graph showing the rearing frequency (left graph) and a graph showing rearing duration (right graph) in an open field in a chemically-induced Parkinson's disease mouse model untreated or treated with TGFRt15-TGFRs (HCW9218) as described in Example 16.

In the Open Field test, TGFRt15-TGFRs (HCW9218)-treated mice travelled significantly further overall (p<0.0001) and travelled at a significantly higher speed overall (p=0.0005) than the untreated mice (FIG. 38B). In measures of vertical exploration, specifically how many times mice raised up on hind legs to explore vertically and how long on average they maintained the raised position, TGFRt15-TGFRs-treated mice raised up significantly more (p<0.0001) and remained raised up for significantly longer on average (p<0.0001) (FIG. 39). Together, these results indicate substantial differences in physical performance of the TGFRt15-TGFRs-treated mice.

The pole test is generally a sensitive test that requires coordination and strength. For this test, lower scores are better, as it demonstrates less time to turn around and descend the apparatus. TGFRt15-TGFRs-treated mice reduced the time to turn (p=0.0882) and the total time to descend (p=0.0825) over time compared to the untreated mice but did not achieve significant difference in either measure.

α-Synuclein Aggregation Reduced in TGFRt15-TGFRs (HCW9218)-Treated Mice.

Figure 40:
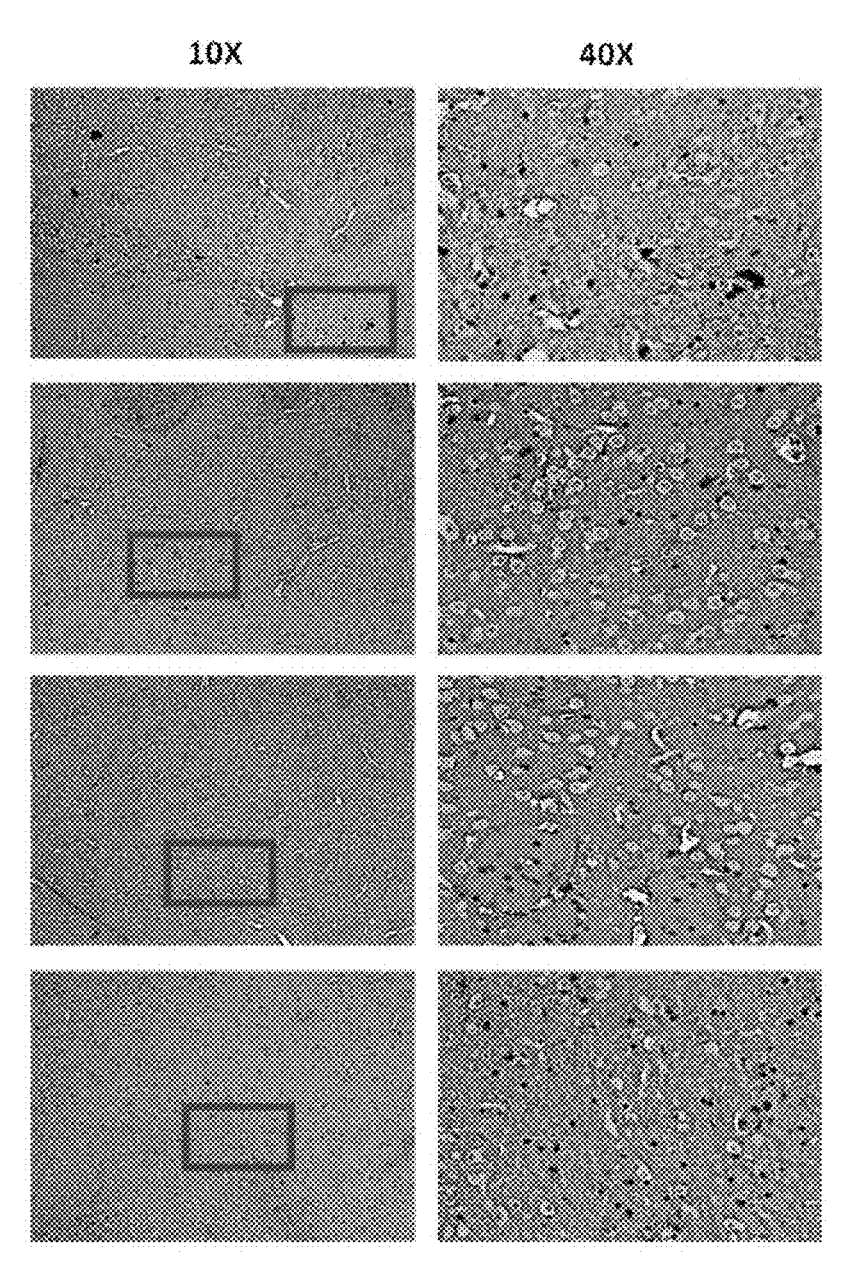
FIG. 40 is a set of anti-alpha synuclein-stained striatum formalin-fixed paraffin-embedded tissue sections from a chemically-induced Parkinson's disease mouse model untreated or treated with TGFRt15-TGFRs (HCW9218) as described in Example 16.
Figure 41:
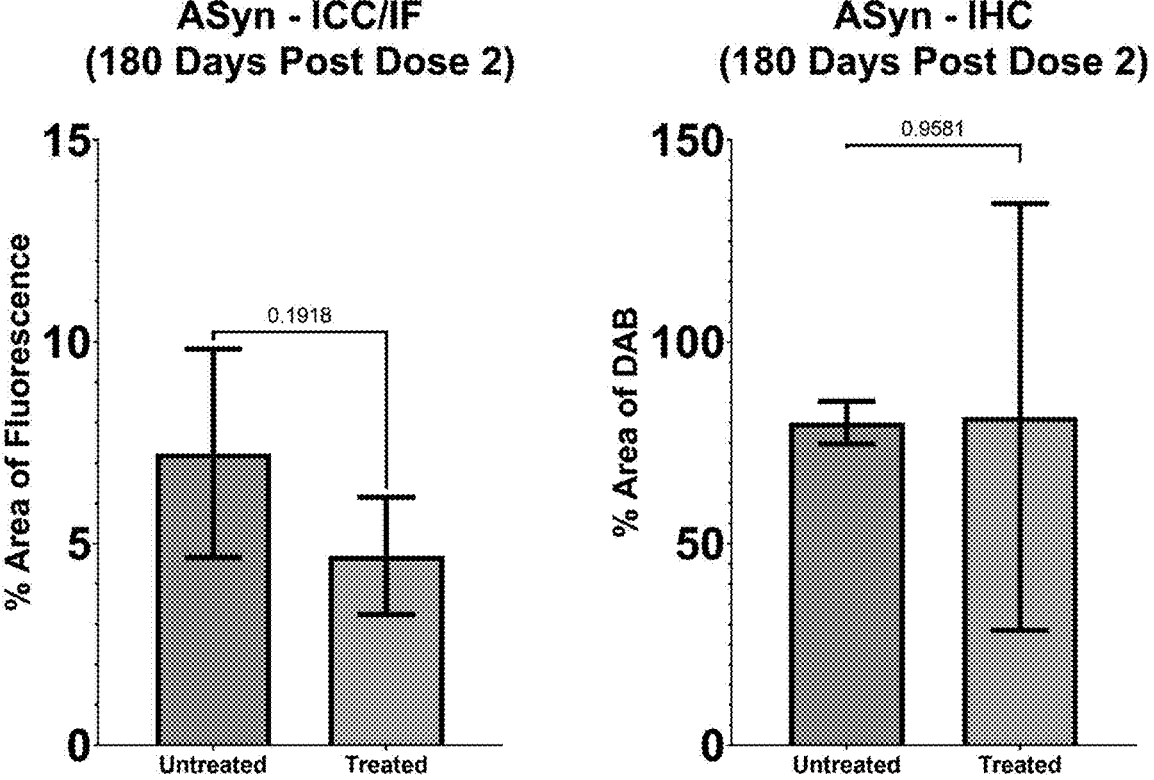
FIG. 41 is a graph showing the percentage of the area of fluorescence for formalin-fixed paraffin-embedded tissue sections immunohistochemically-stained for alpha-sy-nuclein from a chemically-induced Parkinson's disease mouse model untreated or treated with TGRFt15-TGFRs (HCW9218) as described in Example 16 (left graph) and a graph showing the percentage of the area of DAB (3,3'-diaminobenzidine) for formalin-fixed paraffin-embedded tissue sections immunohistochemically-stained for alpha-sy-nuclein from a chemically-induced Parkinson's disease mouse model untreated or treated with TGRFt15-TGFRs (HCW9218) as described in Example 16 (right graph).
Figure 44:
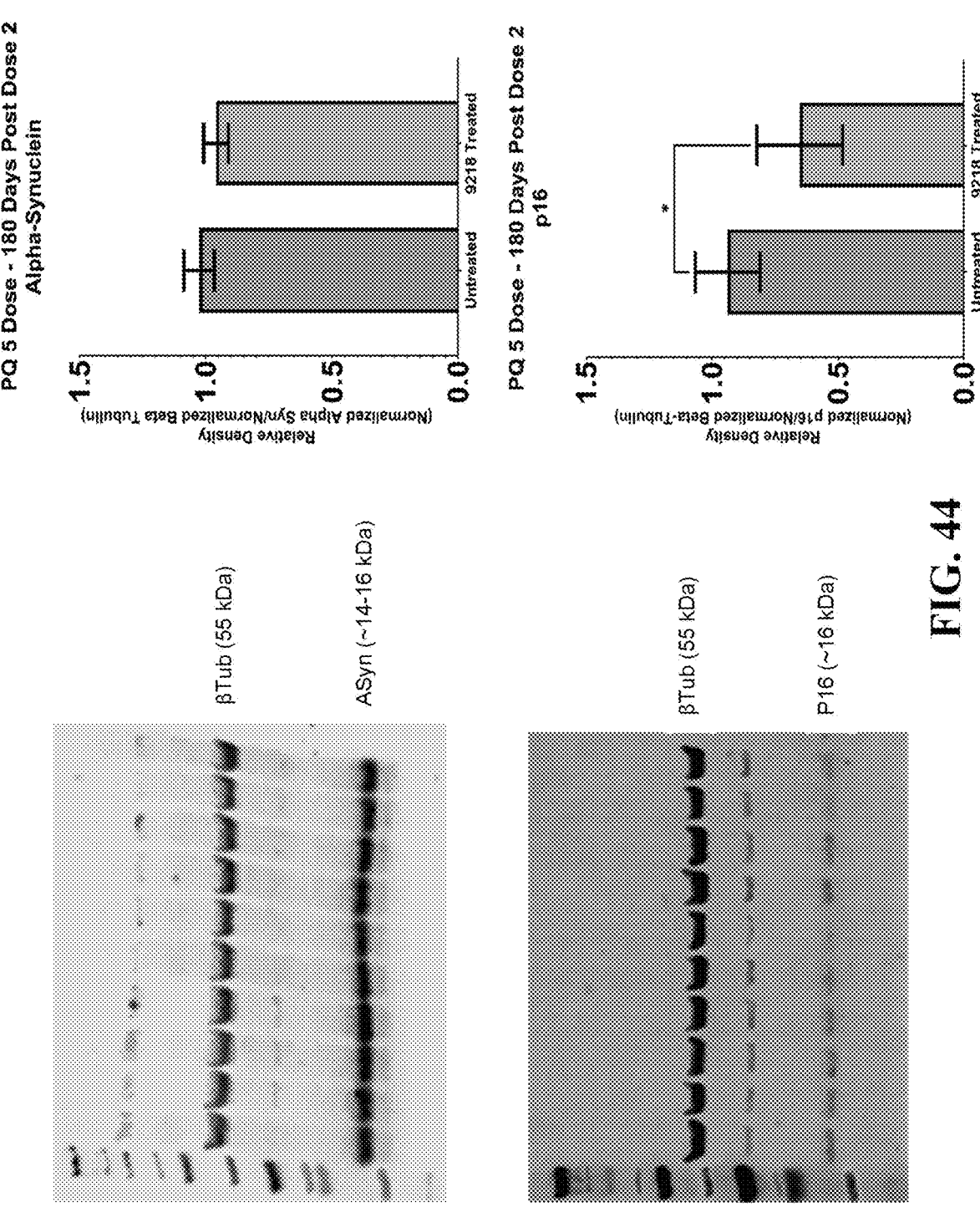
FIG. 44 are two Western blots and graphs showing the level of expression or normalized expression of alpha-synuclein (top Western blot and graph) and P16 (bottom Western blot and graph) in brain samples from a chemically-induced Parkinson's disease mouse model untreated or treated with TGFRt15-TGFRs (HCW9218) as described in Example 16.

IHC staining showed no significant decrease in overall α-synuclein, (FIGS. 40 & 41), but did show what appear to be aggregates in the untreated samples with little to no aggregation in TGFRt15-TGFRs-treated mice. Immunofluorescence showed a decrease in total α-synuclein, but it did not reach significance (p=0.1918) (FIG. 41). Western Blots also showed a reduction in ASyn but did not reach significance (p=0.0897) (FIG. 44).

TGFRt15-TGFRs (HCW9218)-Treated Mice have Healthier, Less Activated Microglia.

Figure 42:
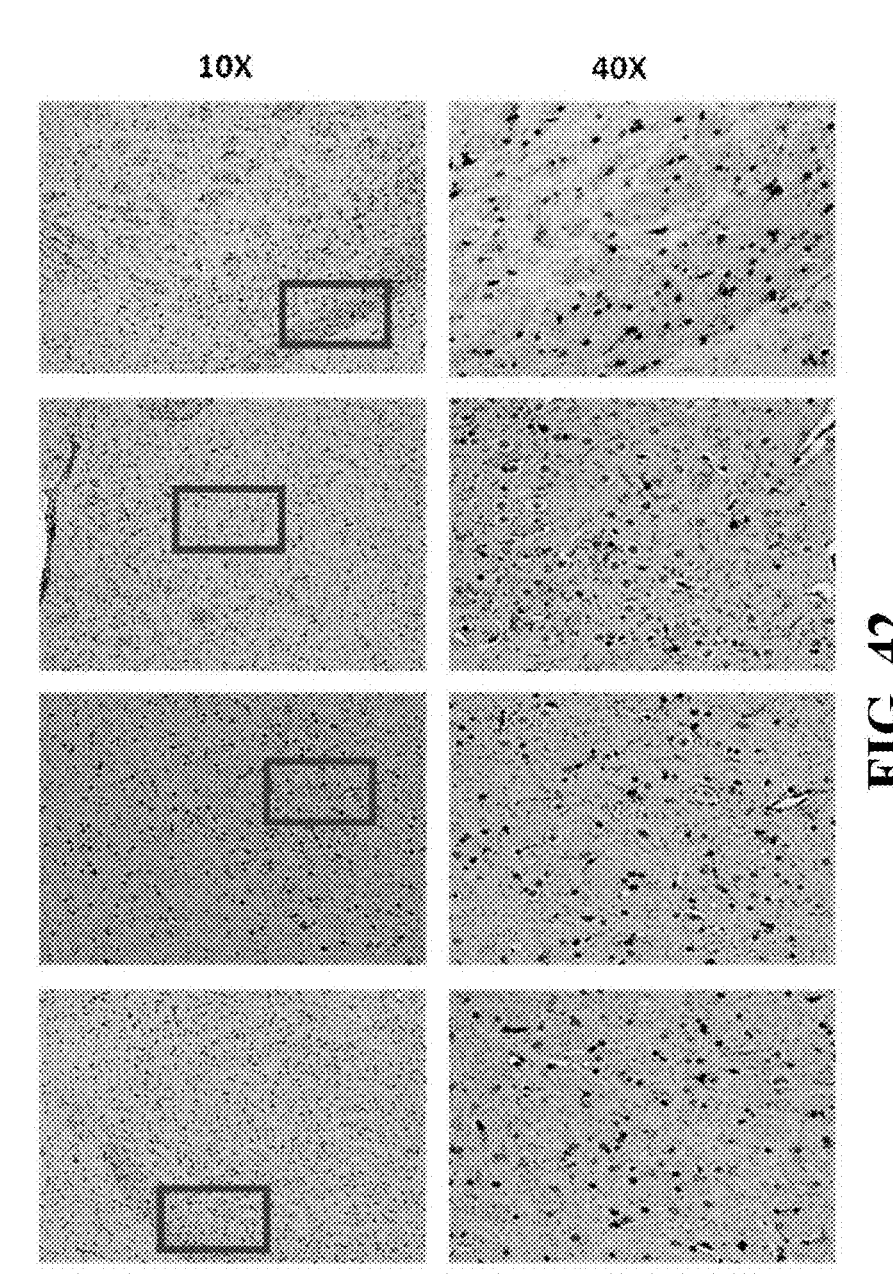
FIG. 42 is a set of anti-ionized calcium-binding adaptor molecule 1 (IBA1)-stained striatum formalin-fixed paraffin-embedded tissue sections from a chemically-induced Parkinson's disease mouse model untreated or treated with TGFRt15-TGFRs (HCW9218) as described in Example 16.
Figure 43:
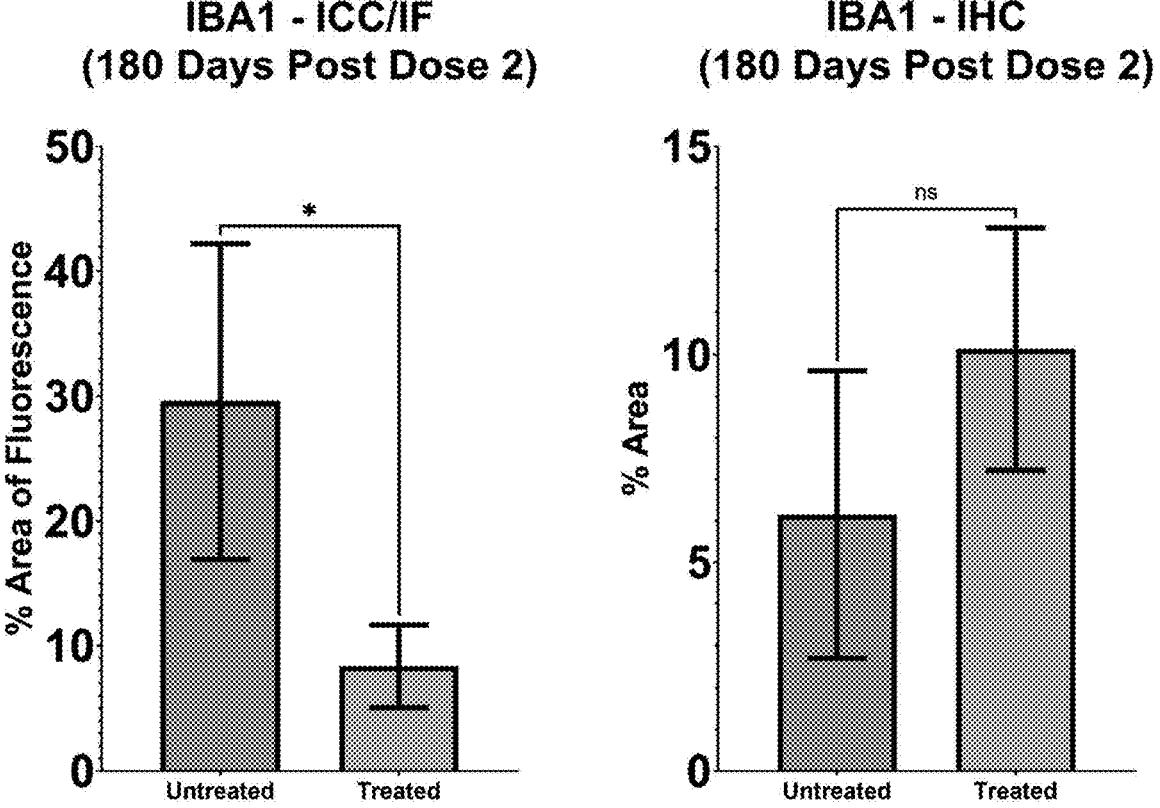
FIG. 43 is a graph showing the percentage of the area of fluorescence for formalin-fixed paraffin-embedded tissue sections immunohistochemically-stained for IBA1 from a chemically-induced Parkinson's disease mouse model untreated or treated with TGRFt15-TGFRs (HCW9218) as described in Example 16 (left graph) and a graph showing the percentage of the area for formalin-fixed paraffin-embedded tissue sections immunohistochemically-stained for alpha-synuclein from a chemically-induced Parkinson's disease mouse model untreated or treated with TGRFt15-TGFRs (HCW9218) as described in Example 16 (right graph).

IHC staining appears to show more dystrophic microglia in untreated mice (FIGS. 42 & 43), but did not measure significantly less IBA1 staining (p=0.2774). Immunofluorescence, however, showed a significant decrease in IBA1 in TGFRt15-TGFRs (HCW9218)-treated mice (p=0.0395).

Senescence Reduced in the Brain Via TGFRt15-TGFRs (HCW9218).

Western blots demonstrated a significant reduction in p16 (p=0.0171) (FIG. 44) in brains of mice treated with TGFRt15-TGFRs (HCW9218). This indicates a reduction in a protein responsible for maintenance of cellular senescence.

What is claimed is:

1. A method of reducing the level of neuroinflammation in a tissue of a subject in need thereof, the method comprising administering to the subject a therapeutically effective amount of a multi-chain chimeric polypeptide comprising:
  (a) a first chimeric polypeptide comprising:
    (i) a first target-binding domain comprising a sequence that is at least 90% identical to SEQ ID NO: 2;
    (ii) a soluble tissue factor domain comprising a sequence that is at least 90% identical to SEQ ID NO: 1; and
    (iii) a first domain of a pair of affinity domains comprising a sequence that is at least 90% identical to SEQ ID NO: 18;
  (b) a second chimeric polypeptide comprising:
    (i) a second domain of a pair of affinity domains comprising a sequence that is at least 90% identical to SEQ ID NO: 16; and
    (ii) a second target-binding domain comprising a sequence that is at least 90% identical to SEQ ID NO: 2,
  wherein:
  the first chimeric polypeptide and the second chimeric polypeptide associate through the binding of the first domain and the second domain of the pair of affinity domains; and
  the first target-binding domain and the second target-binding domain each bind specifically to a ligand of TGF-β receptor II (TGF-βRII).

2. The method of claim 1, wherein the first target-binding domain and the soluble tissue factor domain directly abut each other in the first chimeric polypeptide.

3. The method of claim 1, wherein the first chimeric polypeptide further comprises a linker sequence between the first target-binding domain and the soluble tissue factor domain in the first chimeric polypeptide.

4. The method of claim 1, wherein the soluble tissue factor domain and the first domain of the pair of affinity domains directly abut each other in the first chimeric polypeptide.

5. The method of claim 1, wherein the first chimeric polypeptide further comprises a linker sequence between the soluble tissue factor domain and the first domain of the pair of affinity domains in the first chimeric polypeptide.

6. The method of claim 1, wherein the second domain of the pair of affinity domains and the second target-binding domain directly abut each other in the second chimeric polypeptide.

7. The method of claim 1, wherein second chimeric polypeptide further comprises a linker sequence between the second domain of the pair of affinity domains and the second target-binding domain in the second chimeric polypeptide.

8. The method of claim 1, wherein the soluble tissue factor domain is a soluble human tissue factor domain.

9. The method of claim 8, wherein the soluble human tissue factor domain comprises the sequence of SEQ ID NO: 1.

10. The method of claim 1, wherein the first target-binding domain comprises a first sequence that is at least 90% identical to SEQ ID NO: 2 and a second sequence that is at least 90% identical to SEQ ID NO: 2, wherein the first and second sequence are separated by a linker.

11. The method of claim 10, wherein the linker comprises a sequence of SEQ ID NO: 3.

12. The method of claim 1, wherein the first target-binding domain comprises a sequence that is at least 90% identical to SEQ ID NO: 4.

13. The method of claim 1, wherein the first chimeric polypeptide comprises a sequence that is at least 90% identical to SEQ ID NO: 6.

14. The method of claim 13, wherein the first chimeric polypeptide comprises the sequence of SEQ ID NO: 6.

15. The method of claim 14, wherein the first chimeric polypeptide comprises the sequence of SEQ ID NO: 7.

16. The method of claim 1, wherein the second target-binding domain comprises a first sequence that is at least 90% identical to SEQ ID NO: 2 and a second sequence that is at least 90% identical to SEQ ID NO: 2, wherein the first and second sequence are separated by a linker.

17. The method of claim 16, wherein the linker comprises a sequence of SEQ ID NO: 3.

18. The method of claim 1, wherein the second target-binding domain comprises a sequence that is at least 90% identical to SEQ ID NO: 4.

19. The method of claim 1, wherein the second chimeric polypeptide comprises a sequence that is at least 90% identical to SEQ ID NO: 5.

20. The method of claim 19, wherein the second chimeric polypeptide comprises a sequence of SEQ ID NO: 8.

21. The method of claim 1, wherein the tissue is one or more of the brain, spinal cord, skeletal muscle, or optic nerve.

22. The method of claim 1, wherein the subject has been diagnosed or identified as having a neuroinflammatory disease.

23. The method of claim 22, wherein the neuroinflammatory disease is selected from the group consisting of: Alzheimer's disease (AD), Parkinson's disease (PD), multiple sclerosis (MS), schizophrenia, autism, depression, major depressive disorder (MDD), dysthymia, bipolar disorders, mood disorders, anxiety, fibromyalgia, Huntington's disease, amyotrophic lateral sclerosis (ALS), acute disseminated encephalomyelitis (ADEM), acute optic neuritis (AON), transverse myelitis, neuromyelitis optica (NMO), Lewy body dementia (LBD), and sarcopenia.

24. The method of claim 1, wherein the subject has been identified as having an increased risk of developing a neuroinflammatory disease.

25. A method of treating a neuroinflammatory disorder in a subject, the method comprising administering to the subject a therapeutically effective amount of a multi-chain chimeric polypeptide comprising:

(a) a first chimeric polypeptide comprising:

(i) a first target-binding domain comprising a sequence that is at least 90% identical to SEQ ID NO: 2;

(ii) a soluble tissue factor domain comprising a sequence that is at least 90% identical to SEQ ID NO: 1; and (iii) a first domain of a pair of affinity domains comprising a sequence that is at least 90% identical to SEQ ID NO: 18;

(b) a second chimeric polypeptide comprising:

(i) a second domain of a pair of affinity domains comprising a sequence that is at least 90% identical to SEQ ID NO: 16; and (ii) a second target-binding domain comprising a sequence that is at least 90% identical to SEQ ID NO: 2, wherein:

the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

26. A method of maintaining and/or improving learning and memory in a subject, the method comprising administering to the subject a therapeutically effective amount of a multi-chain chimeric polypeptide comprising:

(a) a first chimeric polypeptide comprising:

(i) a first target-binding domain comprising a sequence that is at least 90% identical to SEQ ID NO: 2;

(ii) a soluble tissue factor domain comprising a sequence that is at least 90% identical to SEQ ID NO: 1; and (iii) a first domain of a pair of affinity domains comprising a sequence that is at least 90% identical to SEQ ID NO: 18;

(b) a second chimeric polypeptide comprising:

(i) a second domain of a pair of affinity domains comprising a sequence that is at least 90% identical to SEQ ID NO: 16; and (ii) a second target-binding domain comprising a sequence that is at least 90% identical to SEQ ID NO: 2, wherein:

the first chimeric polypeptide and the second chimeric polypeptide associate through the binding of the first domain and the second domain of the pair of affinity domains; and the first target-binding domain and the second target-binding domain each bind specifically to a ligand of TGF-β receptor II (TGF-βRII).

* * * * *